(12) United States Patent
Bodil van Niel et al.

(10) Patent No.: US 9,115,101 B2
(45) Date of Patent: Aug. 25, 2015

(54) ARYL SULTAM DERIVATIVES AS RORC MODULATORS

(71) Applicant: Genentech, Inc., South San Francisco, CA (US)

(72) Inventors: Monique Bodil van Niel, Harlow (GB); Benjamin Fauber, San Francisco, CA (US); Simon Gaines, Harlow (GB); Alberto Gobbi, San Francisco, CA (US); Olivier Rene, San Francisco, CA (US); David Vesey, Harlow (GB); Stuart Ward, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 89 days.

(21) Appl. No.: 13/939,962

(22) Filed: Jul. 11, 2013

(65) Prior Publication Data

US 2014/0031330 A1 Jan. 30, 2014

Related U.S. Application Data

(60) Provisional application No. 61/670,519, filed on Jul. 11, 2012, provisional application No. 61/788,430, filed on Mar. 15, 2013, provisional application No. 61/837,461, filed on Jun. 20, 2013.

(51) Int. Cl.

| C07D 417/10 | (2006.01) |
|---|---|
| C07D 417/12 | (2006.01) |
| C07D 417/14 | (2006.01) |
| C07D 279/02 | (2006.01) |
| C07D 281/02 | (2006.01) |
| C07D 291/02 | (2006.01) |
| C07D 295/185 | (2006.01) |
| C07D 491/10 | (2006.01) |
| C07D 513/10 | (2006.01) |
| A61K 31/541 | (2006.01) |
| A61P 19/02 | (2006.01) |
| C07D 451/14 | (2006.01) |
| C07D 471/04 | (2006.01) |
| C07D 471/08 | (2006.01) |
| C07D 471/10 | (2006.01) |
| C07D 487/04 | (2006.01) |
| C07D 487/08 | (2006.01) |
| C07D 275/02 | (2006.01) |
| C07D 498/10 | (2006.01) |
| C07D 515/12 | (2006.01) |

(52) U.S. Cl.
CPC .......... *C07D 295/185* (2013.01); *C07D 275/02* (2013.01); *C07D 279/02* (2013.01); *C07D 281/02* (2013.01); *C07D 291/02* (2013.01); *C07D 417/10* (2013.01); *C07D 417/12* (2013.01); *C07D 417/14* (2013.01); *C07D 451/14* (2013.01); *C07D 471/04* (2013.01); *C07D 471/08* (2013.01); *C07D 471/10* (2013.01); *C07D 487/04* (2013.01); *C07D 487/08* (2013.01); *C07D 491/10* (2013.01); *C07D 498/10* (2013.01); *C07D 513/10* (2013.01); *C07D 515/12* (2013.01)

(58) Field of Classification Search
CPC .. A61K 31/541; C07D 417/10; C07D 417/12; C07D 417/14; C07D 279/02; C07D 281/02; C07D 291/02; C07D 491/10; C07D 513/10
USPC ......... 514/222.2, 211.01, 372, 211.15, 222.5, 514/254.04, 326, 327; 544/3, 367; 546/209, 546/216; 548/206; 540/544
See application file for complete search history.

(56) References Cited

U.S. PATENT DOCUMENTS

2012/0135997 A1 5/2012 Kato et al.

FOREIGN PATENT DOCUMENTS

| EP | 2 368 886 A1 | 9/2011 |
|---|---|---|
| WO | 2012/064744 A2 | 5/2012 |
| WO | 2013/160418 A1 | 10/2013 |

OTHER PUBLICATIONS

Klotz et al., "A Convenient Synthesis of 5-Substituted Tetrahydro-1,4,3-oxathiazine 4,4-Dioxides" Heterocycles 36(4):733-42 ( 1993).

*Primary Examiner* — Sreeni Padmanabhan
*Assistant Examiner* — Irina Neagu
(74) *Attorney, Agent, or Firm* — Robert C. Hall

(57) ABSTRACT

Compounds of the formula I:

or pharmaceutically acceptable salts thereof,
wherein m, n, p, q, r, A, W, $X^1$, $X^2$, $X^3$, $X^4$, Y, Z, $R^1$, $R^2$, $R^3$, $R^4$, $R^5$, $R^6$, $R^7$, $R^8$, $R^9$, $R^{10}$, $R^{11}$, and $R^{12}$ are as defined herein. Also disclosed are methods of making the compounds and using the compounds for treatment of inflammatory diseases such as arthritis.

21 Claims, No Drawings

ARYL SULTAM DERIVATIVES AS RORC MODULATORS

CROSS REFERENCE TO RELATED APPLICATIONS

This application claims the benefit of priority of U.S. Provisional Patent Application Ser. No. 61/670,519 filed Jul. 11, 2012, U.S. Provisional Patent Application Ser. No. 61/788,430 filed Mar. 15, 2013 and U.S. Provisional Patent Application Ser. No. 61/837,461 filed Jun. 20, 2013, the disclosures of which are incorporated herein by reference in their entirety.

FIELD OF THE INVENTION

The invention pertains to compounds that modulate the function of retinoid-receptor related orphan receptor RORc (RORγ) and use of such compounds for treatment of autoimmune diseases

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, irritable bowel disease, psoriasis, psoriatic arthritis and spondyloarthridities.

SUMMARY OF THE INVENTION

The invention provides compounds of the formula I:

I or a pharmaceutically acceptable salt thereof, wherein:
m is 0 or 1;
n is 0 or 1;
p is from 0 to 3;
q is 0, 1 or 2;
r is from 1 to 3;
A is: a bond; $-(CR_jR_k)_t-$; $-C(O)-(CR_jR_k)_t-$; $-(CR_jR_k)_t-C(O)-$; $-NR^a-(CR_jR_k)_t-$; $-(CR_jR_k)_t-NR^a-$; $-C(O)NR^a-(CR_jR_k)_t-$; $-(CR_jR_k)_t-NR^aC(O)-$; $-O-(CR_jR_k)_t-$; $-(CR_jR_k)_t-O-$; $-S-(CR_jR_k)_t-$; $-(CR_jR_k)_t-S-$; $-SO_2-(CR_jR_k)_t-$; or $-(CR_jR_k)_t-SO_2-$;

t is from 0 to 4;
W is: $-CR^bR^c-$; $-O-$; $-S-$; $-SO_2-$; or $-NR^d-$;
one of $X^1$, $X^2$, $X^3$ and $X^4$ is N and the others are $CR^e$; or two of $X^1$, $X^2$, $X^3$ and $X^4$ are N and the others are $CR^e$; or three of $X^1$, $X^2$, $X^3$ and $X^4$ are N and the other is $CR^e$; or each of $X^1$, $X^2$, $X^3$ and $X^4$ is $CR^e$;
Y is: $-O-$; $-S-$; $SO_2-$; $-CR^fR^g-$; or $-NR^h-$;
Z is: CH; or N;
$R^1$, $R^2$, $R^3$, $R^4$, $R^5$, $R^6$, $R^7$ and $R^8$ each independently is: hydrogen; or $C_{1-6}$alkyl which may be unsubstituted or substituted one or more times with halo;
or $R^3$ and $R^4$ together with the atom to which they are attached may form an ethylene group;
or $R^3$ and $R^4$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
or $R^5$ and $R^6$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
or $R^7$ and $R^8$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
or one of $R^3$ and $R^4$ together with one of $R^5$ and $R^6$ and the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
or one of $R^5$ and $R^6$ together with one of $R^7$ and $R^8$ and the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
each $R^9$ is independently: $C_{1-6}$alkyl; halo; $C_{1-6}$alkoxy; or cyano; wherein the $C_{1-6}$alkyl moieties may be unsubstituted or substituted one or more times with halo;
$R^{10}$ is: hydrogen; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; halo; or $C_{1-6}$alkyl which may be unsubstituted or substituted one or more times with halo or oxo;
$R^{11}$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; $C_{1-6}$alkyl-sulfonylamino; $C_{1-6}$alkyl-sulfonylamino-$C_{1-6}$alkyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; or $C_{1-6}$alkyl which may be unsubstituted or substituted one or more times with halo or oxo;
$R^{12}$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; or $C_{1-6}$alkyl which may be unsubstituted or substituted one or more times with halo or oxo;

or $R^{10}$ and $R^{11}$ together with the atoms to which they are attached may form a three, four, five, six or seven membered saturated or partially saturated ring that may optionally include one or two heteroatoms selected from —O—, —$NR^a$- or —S—, and which may be optionally substituted one or more times with $R^i$;

$R^a$, $R^b$, $R^c$ and $R^d$ each independent is: hydrogen; or $C_{1-6}$alkyl which may be unsubstituted or substituted one or more times with halo;

or $R^b$ and $R^c$ together with the atoms to which they are attached may form a three, four, five, six or seven membered saturated or partially saturated ring that may optionally include one or two heteroatoms selected from —O—, —$NR^a$- or —S—, and which may be optionally substituted one or more times with $R^i$;

or one of $R^b$ and $R^c$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;

or one of $R^b$ and $R^c$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;

each $R^e$ is independently: hydrogen; $C_{1-6}$alkyl; halo; $C_{1-6}$alkoxy; or cyano; wherein the $C_{1-6}$alkyl moieties may be unsubstituted or substituted one or more times with halo;

$R^f$ is: hydrogen; halo; or $C_{1-6}$alkyl which may be unsubstituted or substituted one or more times with halo;

$R^g$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; aminocarbonyl-$C_{1-6}$alkyl; N—$C_{1-6}$alkyl-aminocarbonyl-$C_{1-6}$alkyl; N,N-di-$C_{1-6}$alkyl-aminocarbonyl-$C_{1-6}$alkyl; $C_{1-6}$alkoxy-carbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N—$C_{1-6}$alkyl-sulfonylaminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; amino; N—$C_{1-6}$alkyl-amino; N,N-di-$C_{1-6}$alkyl-amino; halo-$C_{1-6}$alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;

or $R^f$ and $R^g$ together with the atoms to which they are attached may form a four, five, six or seven membered saturated or partially saturated ring that may optionally include one or two heteroatoms selected from —O—, —$NR^a$— or —S—, and which may be optionally substituted one or more times with $R^i$;

$R^h$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N—($C_{1-6}$alkyl-sulfonyl) aminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; aminocarbonyl-$C_{1-6}$alkyl; N—$C_{1-6}$alkyl-aminocarbonyl-$C_{1-6}$alkyl; N,N-di-$C_{1-6}$alkyl-aminocarbonyl-$C_{1-6}$alkyl; $C_{1-6}$alkoxy-carbonyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;

or $R^h$ and one of $R^{10}$ and $R^{11}$ together with the atoms to which they are attached may form a four, five, six or seven membered aromatic, partially saturated or unsaturated ring that may optionally include one or two additional heteroatom selected from —O—, —$NR^a$— or —S—, and which may be optionally substituted one or more times with $R^i$—;

or one of $R^f$ and $R^g$ and one of $R^{10}$ and $R^{11}$ together with the atoms to which they are attached may form a three, four, five, six or seven membered aromatic, partially saturated or unsaturated ring that may optionally include an additional heteroatom selected from —O—, —$NR^a$— or —S—, and which may be optionally substituted one or more times with $R^i$;

$R^i$ is: $C_{1-6}$alkyl; halo; oxo; hydroxy; acetyl; $C_{1-6}$alkyl-carbonyl; amino-carbonyl; hydroxy-$C_{1-6}$alkyl; cyano; heteroaryl; or $C_{1-6}$alkoxy; wherein the $C_{1-6}$alkyl moieties may be unsubstituted or substituted one or more times with halo; and $R^j$ and $R^k$ each independent is: hydrogen; or $C_{1-6}$alkyl which may be unsubstituted or substituted one or more times with halo.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —SO₂—R, wherein R is alkyl as defined herein.

"Alkylsulfonylalkyl means a moiety of the formula —R'—SO₂—R" where R' is alkylene and R" is alkyl as defined herein.

"Alkylsulfonylalkoxy" means a group of the formula —O—R—SO₂—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-$C_{1-6}$alkyl-aminocarbonyl" means a group of the formula —C(O)—NRR' wherein R and R' are alkyl as defined herein.

"Aminosulfonyl" means a group of the formula —SO₂—NH₂.

"N-alkylaminosulfonyl" means a group of the formula —SO₂—NHR wherein R is alkyl as defined herein.

"N,N-dialkylaminosulfonyl" means a group of the formula —SO₂—NRR' wherein R and R' are alkyl as defined herein.

"Alkylsulfonylamino" means a group of the formula —NR'—SO₂—R wherein R id alkyl and R' is hydrogen or alkyl as defined herein.

"N-(alkylsulfonyl)-aminoalkyl" means a group of the formula —R—NH—SO₂—R' wherein R is alkylene and R' is alkyl as defined herein.

"N-(Alkylsulfonyl)aminocarbonyl" means a group of the formula —C(O)—NH—SO₂—R wherein wherein R is alkyl as defined herein.

"N-(Alkylsulfonyl)-N-alkylaminocarbonyl" means a group of the formula —C(O)—NR—SO₂—R' wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like.

"Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO₂—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"N-Alkylacetimidamidyl" means a group of the formula

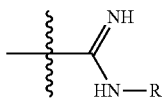

wherein R is alkyl as defined herein.

"N,N'-Dialkylacetimidamidyl" means a group of the formula

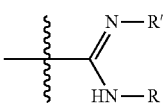

wherein R and R' are both alkyl as defined herein.

"N'-Alkoxyacetimidamidyl" means a group of the formula

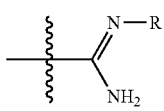

wherein R is alkoxy as defined herein.

"N'-Alkoxy-N-alkyl-acetimidamidyl" means a group of the formula

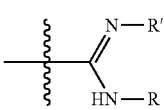

wherein R is alkyl and R' is alkoxy as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO₂—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof "Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —SO₂—R wherein R is cycloalkyl as defined herein.

"Cycloalkylalkylsulfonyl" means a group of the formula —SO₂—R wherein R is cycloalkylalkyl as defined herein.

"N'-Cyanoacetimidamidyl" means a group of the formula

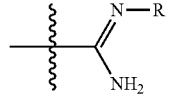

wherein R is cyano or nitrile.

"N'-Cyano-N-alkylacetimidamidyl" means a group of the formula

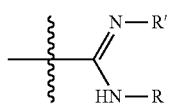

wherein R is alkyl as defined herein and R' is cyano or nitrile.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"N' hydroxyacetimidamidyl" means a group of the formula

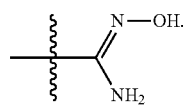

"N'-hydroxy-N-alkyl-acetimidamidyl" means a group of the formula

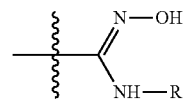

wherein R is alkyl as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"2-Nitro-1-N-alkylamino-vinyl" means a group of the formula

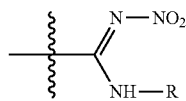

wherein R is alkyl as defined herein.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Gastrointestinal disorder" ("GI disorder") refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of the formula I:

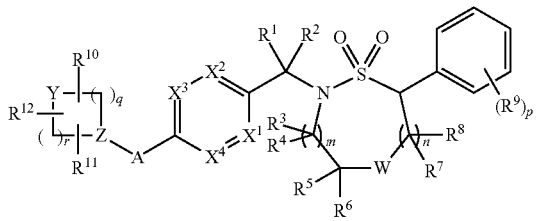

I or a pharmaceutically acceptable salt thereof, wherein:
m is 0 or 1;
n is 0 or 1;
p is from 0 to 3;
q is 0, 1 or 2;

r is from 1 to 3;

A is: a bond; —(CR$_j$R$_k$)$_t$—; —C(O)—(CR$_j$R$_k$)$_t$—; —(CR$_j$R$_k$)$_t$—C(O)—; —NR$^a$—(CR$_j$R$_k$)$_t$—; —(CR$_j$R$_k$)$_t$—NR$^a$—; —C(O)NR$^a$—(CR$_j$R$_k$)$_t$—; —(CR$_j$R$_k$)$_t$—NR$^a$C(O)—; —O—(CR$_j$R$_k$)$_t$—; —(CR$_j$R$_k$)$_t$—O—; —S—(CR$_j$R$_k$)$_t$—; —(CR$_j$R$_k$)$_t$—S—; —SO$_2$—(CR$_j$R$_k$)$_t$—; or —(CR$_j$R$_k$)$_t$—SO$_2$—;

t is from 0 to 4;

W is: —CR$^b$R$^c$—; —O—; —S—; —SO$_2$—; or —NR$^d$—;

one of $X^1$, $X^2$, $X^3$ and $X^4$ is N and the others are CR$^e$; or two of $X^1$, $X^2$, $X^3$ and $X^4$ are N and the others are CR$^e$; or three of $X^1$, $X^2$, $X^3$ and $X^4$ are N and the other is CR$^e$; or each of $X^1$, $X^2$, $X^3$ and $X^4$ is CR$^e$;

Y is: —O—; —S—; SO$_2$—; —CR$^f$R$^g$—; or —NR$^h$—;

Z is: CH; or N;

$R^1$, $R^2$, $R^3$, $R^4$, $R^5$, $R^6$, $R^7$ and $R^8$ each independently is: hydrogen; or $C_{1-6}$alkyl which may be unsubstituted or substituted one or more times with halo;

or $R^3$ and $R^4$ together with the atom to which they are attached may form an ethylene group;

or $R^3$ and $R^4$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or $R^5$ and $R^6$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or $R^7$ and $R^8$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of $R^3$ and $R^4$ together with one of $R^5$ and $R^6$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of $R^5$ and $R^6$ together with one of $R^7$ and $R^8$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

each $R^9$ is independently: $C_{1-6}$alkyl; halo; $C_{1-6}$alkoxy; or cyano; wherein the $C_{1-6}$ alkyl moieties may be unsubstituted or substituted one or more times with halo;

$R^{10}$ is: hydrogen; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; halo; or $C_{1-6}$alkyl which may be unsubstituted or substituted one or more times with halo or oxo;

$R^{11}$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; $C_{1-6}$alkyl-sulfonylamino; $C_{1-6}$alkyl-sulfonylamino-$C_{1-6}$alkyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl;

N—C$_{1-6}$alkoxy-aminocarbonyl; or C$_{1-6}$alkyl which may be unsubstituted or substituted one or more times with halo or oxo;

R$^{12}$ is: hydrogen; halo; carboxy; C$_{1-6}$alkyl-carbonyl; C$_{1-6}$alkoxy-carbonyl; oxo; hydroxy; aminocarbonyl; N—C$_{1-6}$alkyl-aminocarbonyl; N,N-di-C$_{1-6}$alkyl-aminocarbonyl; cyano; hydroxy-C$_{1-6}$alkyl; N—C$_{1-6}$alkoxy-C$_{1-6}$alkyl-aminocarbonyl; N-hydroxy-C$_{1-6}$alkyl-aminocarbonyl; N—C$_{1-6}$alkoxy-aminocarbonyl; or C$_{1-6}$alkyl which may be unsubstituted or substituted one or more times with halo or oxo;

or R$^{10}$ and R$^{11}$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

R$^a$, R$^b$, R$^c$ and R$^d$ each independent is: hydrogen; or C$_{1-6}$alkyl which may be unsubstituted or substituted one or more times with halo;

or R$^b$ and R$^c$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of R$^b$ and R$^c$ together with one of R$^7$ and R$^8$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of R$^b$ and R$^c$ together with one of R$^5$ and R$^6$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

each R$^e$ is independently: hydrogen; C$_{1-6}$alkyl; halo; C$_{1-6}$alkoxy; or cyano; wherein the C$_{1-6}$alkyl moieties may be unsubstituted or substituted one or more times with halo;

R$^f$ is: hydrogen; halo; or C$_{1-6}$alkyl which may be unsubstituted or substituted one or more times with halo;

R$^g$ is: hydrogen; C$_{1-6}$alkyl; C$_{3-6}$cycloalkyl; C$_{3-6}$cycloalkenyl; C$_{3-6}$cycloalkyl-C$_{1-6}$alkyl; halo; C$_{1-6}$alkyl-carbonyl; C$_{3-6}$cycloalkyl-carbonyl; C$_{3-6}$cycloalkyl-C$_{1-6}$alkyl-carbonyl; cyano-C$_{1-6}$alkyl-carbonyl; hydroxy-C$_{1-6}$alkyl-carbonyl; C$_{1-6}$alkoxy-C$_{1-6}$alkyl-carbonyl; carboxy; N-cyano-aminocarbonyl; N-cyano-N—C$_{1-6}$alkyl-aminocarbonyl; N—C$_{1-6}$alkyl-acetimidamidyl; N,N'-di-C$_{1-6}$alkyl-acetimidamidyl; N'-cyano-N—C$_{1-6}$alkyl-acetimidamidyl; N'-hydroxy-acetimidamidyl; N'—C$_{1-6}$alkoxy-acetimidamidyl; N'-hydroxy-N—C$_{1-6}$alkyl-acetimidamidyl; N'—C$_{1-6}$alkoxy-N—C$_{1-6}$alkyl-acetimidamidyl; 2-nitro-1-N—C$_{1-6}$alkylamino-vinyl; formyl; C$_{1-6}$alkyl-sulfonyl; C$_{3-6}$cycloalkyl-sulfonyl; C$_{3-6}$cycloalkyl-C$_{1-6}$alkyl-sulfonyl; C$_{1-6}$alkyl-sulfonyl-C$_{1-6}$alkyl; aminocarbonyl; N-hydroxy-aminocarbonyl; N—C$_{1-6}$alkoxy-aminocarbonyl; N—C$_{1-6}$alkyl-aminocarbonyl; aminocarbonyl-C$_{1-6}$alkyl; N—C$_{1-6}$alkyl-aminocarbonyl-C$_{1-6}$alkyl; N,N-di-C$_{1-6}$alkyl-aminocarbonyl-C$_{1-6}$alkyl; C$_{1-6}$alkoxy-carbonyl; N-hydroxy-N—C$_{1-6}$alkyl-aminocarbonyl; N—C$_{1-6}$alkoxy-N—C$_{1-6}$alkyl-aminocarbonyl; N,N-di-C$_{1-6}$alkyl-aminocarbonyl; aminosulfonyl; N—C$_{1-6}$alkyl-aminosulfonyl; N,N-di-C$_{1-6}$alkyl-aminosulfonyl; cyano; C$_{1-6}$alkoxy; C$_{1-6}$alkyl-sulfonylamino; N—C$_{1-6}$alkyl-sulfonylaminocarbonyl; N—(C$_{1-6}$alkyl-sulfonyl)-N—C$_{1-6}$alkyl-aminocarbonyl; N—(C$_{1-6}$alkyl-sulfonyl)-amino-C$_{1-6}$alkyl; amino; N—C$_{1-6}$alkyl-amino; N,N-di-C$_{1-6}$alkyl-amino; halo-C$_{1-6}$alkyl; heterocyclyl; heteroaryl; or hydroxyl; wherein the C$_{1-6}$alkyl moieties may be unsubstituted or substituted one or more times with halo; and wherein the heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$;

or R$^f$ and R$^g$ together with the atoms to which they are attached may form a four, five, six or seven membered saturated or partially saturated ring that may optionally include one or two heteroatoms selected from —O—, —NR$^a$— or —S—, and which may be optionally substituted one or more times with R$^i$;

R$^h$ is: hydrogen; C$_{1-6}$alkyl; C$_{3-6}$cycloalkyl; C$_{3-6}$cycloalkenyl; C$_{3-6}$cycloalkyl-C$_{1-6}$alkyl; C$_{1-6}$alkyl-carbonyl; C$_{3-6}$cycloalkyl-carbonyl; C$_{3-6}$cycloalkyl-C$_{1-6}$alkyl-carbonyl; cyano-C$_{1-6}$alkyl-carbonyl; hydroxy-C$_{1-6}$alkyl-carbonyl; C$_{1-6}$alkoxy-C$_{1-6}$alkyl-carbonyl; N-cyano-aminocarbonyl; N-cyano-N—C$_{1-6}$alkyl-aminocarbonyl; N—C$_{1-6}$alkyl-acetimidamidyl; N,N'-di-C$_{1-6}$alkyl-acetimidamidyl; N'-cyano-N—C$_{1-6}$alkyl-acetimidamidyl; N'-hydroxy-acetimidamidyl; N'—C$_{1-6}$alkoxy-acetimidamidyl; N'-hydroxy-N—C$_{1-6}$alkyl-acetimidamidyl; N'—C$_{1-6}$alkoxy-N—C$_{1-6}$alkyl-acetimidamidyl; 2-nitro-1-N—C$_{1-6}$alkylamino-vinyl; formyl; C$_{1-6}$alkyl-sulfonyl; C$_{3-6}$cycloalkyl-sulfonyl; C$_{3-6}$cycloalkyl-C$_{1-6}$alkyl-sulfonyl; C$_{1-6}$alkyl-sulfonyl-C$_{1-6}$alkyl; aminocarbonyl; N-hydroxy-aminocarbonyl; N—C$_{1-6}$alkoxy-aminocarbonyl; N—C$_{1-6}$alkyl-aminocarbonyl; N-hydroxy-N—C$_{1-6}$alkyl-aminocarbonyl; N—C$_{1-6}$alkoxy-N—C$_{1-6}$alkyl-aminocarbonyl; N,N-di-C$_{1-6}$alkyl-aminocarbonyl; aminosulfonyl; N—C$_{1-6}$alkyl-aminosulfonyl; N,N-di-C$_{1-6}$alkyl-aminosulfonyl; cyano; C$_{1-6}$alkyl-sulfonylamino; C$_{1-6}$alkyl-sulfonylamino-C$_{1-6}$alkyl; N—(C$_{1-6}$alkyl-sulfonyl)aminocarbonyl; N—(C$_{1-6}$alkyl-sulfonyl)-N—C$_{1-6}$alkyl-aminocarbonyl; N—(C$_{1-6}$alkyl-sulfonyl)-amino-C$_{1-6}$alkyl; aminocarbonyl-C$_{1-6}$alkyl; N—C$_{1-6}$alkyl-aminocarbonyl-C$_{1-6}$alkyl; N,N-di-C$_{1-6}$alkyl-aminocarbonyl-C$_{1-6}$alkyl; C$_{1-6}$alkoxy-carbonyl; halo-C$_{1-6}$alkyl; heterocyclyl; or heteroaryl; wherein the C$_{1-6}$alkyl moieties may be unsubstituted or substituted one or more times with halo; and wherein the heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$;

or R$^h$ and one of R$^{10}$ and R$^{11}$ together with the atoms to which they are attached may form a four, five, six or seven membered aromatic, partially saturated or unsaturated ring that may optionally include one or two additional heteroatom selected from —O—, —NR$^a$— or —S—, and which may be optionally substituted one or more times with R$^i$—;

or one of R$^f$ and R$^g$ and one of R$^{10}$ and R$^{11}$ together with the atoms to which they are attached may form a three, four, five, six or seven membered aromatic, partially saturated or unsaturated ring that may optionally include an additional heteroatom selected from —O—, —NR$^a$— or —S—, and which may be optionally substituted one or more times with R$^i$;

R$^i$ is: C$_{1-6}$alkyl; halo; oxo; hydroxy; acetyl; C$_{1-6}$alkyl-carbonyl; amino-carbonyl; hydroxy-C$_{1-6}$alkyl; cyano; heteroaryl; or C$_{1-6}$alkoxy; wherein the C$_{1-6}$alkyl moieties may be unsubstituted or substituted one or more times with halo; and R$^j$ and R$^k$ each independent is: hydrogen; or C$_{1-6}$alkyl which may be unsubstituted or substituted one or more times with halo.

In certain embodiments of formula I, when A is a heteroatom, then X is —CH—.

In certain embodiments of formula I, when Y is a heteroatom, then q is 1 or 2.

In certain embodiments of formula I, when Y and Z are heteroatom, then q is 2 and r is 2 or 3.

In certain embodiments of formula I, when Z is a heteroatom and A is —(CR$_j$R$_k$)$_t$—; —NR$^a$—(CR$_j$R$_k$)$_t$; —O—(CR$_j$R$_k$)$_t$; —S—(CR$_j$R$_k$)$_t$; or —SO$_2$—(CR$_j$R$_k$)$_t$; then t is from 2 to 4.

In certain embodiments of formula I, m is 0.
In certain embodiments of formula I, m is 1.
In certain embodiments of formula I, n is 0.
In certain embodiments of formula I, n is 1.
In certain embodiments of formula I, p is from 0 to 2.
In certain embodiments of formula I, p is 0 or 1.
In certain embodiments of formula I, p is 0.
In certain embodiments of formula I, p is 1.
In certain embodiments of formula I, p is 2.
In certain embodiments of formula I, p is 3.
In certain embodiments of formula I, q is 0.
In certain embodiments of formula I, q is 1.
In certain embodiments of formula I, q is 2.
In certain embodiments of formula I, r is 1.
In certain embodiments of formula I, r is 2.
In certain embodiments of formula I, r is 3.
In certain embodiments of formula I, t is from 0 to 3.
In certain embodiments of formula I, t is 0.
In certain embodiments of formula I, t is 1.
In certain embodiments of formula I, t is 2.
In certain embodiments of formula I, t is 3.

In certain embodiments of formula I, A is: a bond; —CH$_2$—; —C(O)—; —NR$^a$—; —O—; —S—; or —SO$_2$—.

In certain embodiments of formula I, A is: a bond; —(CR$_j$R$_k$)$_t$—; —C(O)—(CR$_j$R$_k$)$_t$—; —(CR$_j$R$_k$)$_t$—C(O)—; —(CR$_j$R$_k$)$_t$—NR$^a$—; —C(O)NR$^a$—(CR$_j$R$_k$)$_t$—; —(CR$_j$R$_k$)$_t$—NR$^a$C(O)—; —(CR$_j$R$_k$)$_t$—O—; —(CR$_j$R$_k$)$_t$—S—; or —(CR$_j$R$_k$)$_t$—SO$_2$—.

In certain embodiments of formula I, A is: a bond; —C(O)—(CR$_j$R$_k$)$_t$—; —(CR$_j$R$_k$)$_t$—C(O)—; —(CR$_j$R$_k$)$_t$—NR$^a$—; —C(O)NR$^a$—(CR$_j$R$_k$)$_t$—; (CR$_j$R$_k$)$_t$—NR$^a$C(O)—; or —(CR$_j$R$_k$)$_t$—O—.

In certain embodiments of formula I, A is: a bond; —NR$^a$—; —O—; or —S—.

In certain embodiments of formula I, A is: a bond; —NR$^a$—; or —O—.

In certain embodiments of formula I, A is a bond.
In certain embodiments of formula I, A is —CH$_2$—.
In certain embodiments of formula I, A is —C(O)—.
In certain embodiments of formula I, A is
In certain embodiments of formula I, A is —O—.
In certain embodiments of formula I, A is —S—.
In certain embodiments of formula I, A is —SO$_2$—.
In certain embodiments of formula I, A is —C(O)NR$^a$—(CH$_2$)$_t$.
In certain embodiments of formula I, A is —(CH$_2$)$_t$—NR$^a$C(O)—.
In certain embodiments of formula I, A is —(CR$_j$R$_k$)$_t$—.
In certain embodiments of formula I, A is —CR$_j$R$_k$—.
In certain embodiments of formula I, A is —C(O)—(CR$_j$R$_k$)$_t$—.
In certain embodiments of formula I, A is —(CR$_j$R$_k$)$_t$—C(O)—.
In certain embodiments of formula I, A is —NR$^a$—(CR$_j$R$_k$)$_t$—.
In certain embodiments of formula I, A is —(CR$_j$R$_k$)$_t$—NR$^a$—.
In certain embodiments of formula I, A is —C(O)NR$^a$—(CR$_j$R$_k$)$_t$—.
In certain embodiments of formula I, A is (CR$_j$R$_k$)$_t$—NR$^a$C(O)—.

In certain embodiments of formula I, A is —O—(CR$_j$R$_k$)$_t$—.
In certain embodiments of formula I, A is —(CR$_j$R$_k$)$_t$—O—.
In certain embodiments of formula I, A is —S—(CR$_j$R$_k$)$_t$—.
In certain embodiments of formula I, A is —(CR$_j$R$_k$)$_t$—S—.
In certain embodiments of formula I, A is —SO$_2$—(CR$_j$R$_k$)$_t$—.
In certain embodiments of formula I, A is —(CR$_j$R$_k$)$_t$—SO$_2$—.
In certain embodiments of formula I, A is —(CH$_2$)$_2$—O—.
In certain embodiments of formula I, A is —(CH$_2$)—O—.
In certain embodiments of formula I, A is —O—(CH$_2$)$_2$—.
In certain embodiments of formula I, A is —O—(CH$_2$)—.
In certain embodiments of formula I, A is —(CH$_2$)$_2$—C(O)—.
In certain embodiments of formula I, A is —(CH$_2$)—C(O)—.
In certain embodiments of formula I, A is —C(O)—(CH$_2$)$_2$—.
In certain embodiments of formula I, A is —C(O)—(CH$_2$)—.
In certain embodiments of formula I, A is —C(O)—NH—.
In certain embodiments of formula I, A is —CH$_2$—C(O)—NH—.
In certain embodiments of formula I, A is —NH—.
In certain embodiments of formula I, A is —(CH$_2$)$_2$—NH—.
In certain embodiments of formula I, A is —CH$_2$—NH—.
In certain embodiments of formula I, A is —NH—(CH$_2$)$_2$—.
In certain embodiments of formula I, A is —NH—CH$_2$—.
In certain embodiments of formula I, A is —NH—C(O)—.
In certain embodiments of formula I, t is from 0 to 3.
In certain embodiments of formula I, t is from 1 to 3.
In certain embodiments of formula I, t is from 0 to 2.
In certain embodiments of formula I, t is 0.
In certain embodiments of formula I, t is 1.
In certain embodiments of formula I, t is 2.
In certain embodiments of formula I, t is 3.
In certain embodiments of formula I, t is 4.

In certain embodiments of formula I, W is —CR$^b$R$^c$— or —O—.
In certain embodiments of formula I, W is —CR$^b$R$^c$—.
In certain embodiments of formula I, W is —O—.
In certain embodiments of formula I, W is —NR$^d$—.
In certain embodiments of formula I, W is —S—.
In certain embodiments of formula I, W is —SO$_2$—.
In certain embodiments of formula I, W is —CH$_2$—.

In certain embodiments of formula I, one or two of X$^1$, X$^2$, X$^3$ and X$^4$ is N and the others are CR$^e$.
In certain embodiments of formula I, three of X$^1$, X$^2$, X$^3$ and X$^4$ are CR$^e$ and the other is N.
In certain embodiments of formula I, X$^1$, X$^2$, X$^3$ and X$^4$ are CR$^e$.
In certain embodiments of formula I, X$^1$ is N and X$^2$, X$^3$ and X$^4$ are CR$^e$.
In certain embodiments of formula I, X$^2$ is N and X$^1$, X$^3$ and X$^4$ are CR$^e$.
In certain embodiments of formula I, X$^1$ and X$^4$ are N, and X$^2$ and X$^3$ are CR$^a$.
In certain embodiments of formula I, X$^2$ and X$^3$ are N, and X$^1$ and X$^4$ are CR$^e$.
In certain embodiments of formula I, X$^1$ and X$^2$ are N, and X$^3$ and X$^4$ are CR$^e$.

In certain embodiments of formula I, Y is —O—, —CR$^f$R$^g$— or —NR$^h$—.

In certain embodiments of formula I, Y is —CR$^f$R$^g$— or —NR$^h$—.

In certain embodiments of formula I, Y is —O—.
In certain embodiments of formula I, Y is —S—.
In certain embodiments of formula I, Y is —SO$_2$—.
In certain embodiments of formula I, Y is —CR$^f$R$^g$—.
In certain embodiments of formula I, Y is —NR$^h$—.
In certain embodiments of formula I, Z is CH.
In certain embodiments of formula I, Z is N.
In certain embodiments of formula I, each R$^1$ is independently: C$_{1-6}$alkyl; halo; C$_{1-6}$alkoxy; cyano; halo-C$_{1-6}$alkyl; or halo-C$_{1-6}$alkoxy.
In certain embodiments of formula I, R$^1$ is hydrogen.
In certain embodiments of formula I, R$^1$ is C$_{1-6}$alkyl.
In certain embodiments of formula I, R$^2$ is hydrogen.
In certain embodiments of formula I, R$^2$ is C$_{1-6}$alkyl.
In certain embodiments of formula I, R$^3$ is hydrogen.
In certain embodiments of formula I, R$^3$ is C$_{1-6}$alkyl.
In certain embodiments of formula I, R$^4$ is hydrogen.
In certain embodiments of formula I, R$^4$ is C$_{1-6}$alkyl.
In certain embodiments of formula I, R$^5$ is hydrogen.
In certain embodiments of formula I, R$^5$ is C$_{1-6}$alkyl.
In certain embodiments of formula I, R$^6$ is hydrogen.
In certain embodiments of formula I, R$^6$ is C$_{1-6}$alkyl.
In certain embodiments of formula I, R$^7$ is hydrogen.
In certain embodiments of formula I, R$^7$ is C$_{1-6}$alkyl.
In certain embodiments of formula I, R$^8$ is hydrogen.
In certain embodiments of formula I, R$^8$ is C$_{1-6}$alkyl.
In certain embodiments of formula I, R$^3$ and R$^4$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^3$ and R$^4$ together with the atoms to which they are attached form a three, four or five membered saturated ring.

In certain embodiments of formula I, R$^5$ and R$^6$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^5$ and R$^6$ together with the atoms to which they are attached form a three, four or five membered saturated ring.

In certain embodiments of formula I, R$^7$ and R$^8$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^7$ and R$^8$ together with the atoms to which they are attached form a three, four or five membered saturated ring.

In certain embodiments of formula I, one of R$^3$ and R$^4$ together with one of R$^5$ and R$^6$ and the atoms to which they are attached form a three, four, five, six or seven membered ring that may optionally include one or two heteroatoms selected from —O—, —NR$^a$— or —S—, and which may be optionally substituted one or more times with R$^i$.

In certain embodiments of formula I, one of R$^5$ and R$^6$ together with one of R$^7$ and R$^8$ and the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, each R$^9$ is independently: C$_{1-6}$alkyl; halo; or halo-C$_{1-6}$alkyl.
In certain embodiments of formula I, R$^9$ is C$_{1-6}$alkyl.
In certain embodiments of formula I, R$^9$ is halo.
In certain embodiments of formula I, R$^9$ is C$_{1-6}$alkoxy.
In certain embodiments of formula I, R$^9$ is cyano.
In certain embodiments of formula I, R$^9$ is halo-C$_{1-6}$alkyl.
In certain embodiments of formula I, each R$^9$ is independently: fluoro; chloro; or trifluoromethyl.
In certain embodiments of formula I, R$^{10}$ is: hydrogen; halo; or C$_{1-6}$alkyl which may be unsubstituted or substituted one or more times with halo or oxo.
In certain embodiments of formula I, R$^{10}$ is: hydrogen or C$_{1-6}$alkyl.
In certain embodiments of formula I, R$^{10}$ is hydrogen.
In certain embodiments of formula I, R$^{10}$ is C$_{1-6}$alkyl.
In certain embodiments of formula I, R$^{10}$ is methyl.
In certain embodiments of formula I, R$^{10}$ is halo.
In certain embodiments of formula I, R$^{10}$ is carboxy.
In certain embodiments of formula I, R$^{10}$ is C$_{1-6}$alkyl-carbonyl.
In certain embodiments of formula I, R$^{10}$ is C$_{1-6}$alkoxy-carbonyl. In certain embodiments of formula I, R$^{10}$ is oxo.
In certain embodiments of formula I, R$^{10}$ is hydroxy.
In certain embodiments of formula I, R$^{10}$ is aminocarbonyl.
In certain embodiments of formula I, R$^{10}$ is N—C$_{1-6}$alkyl-aminocarbonyl.
In certain embodiments of formula I, R$^{10}$ is N,N-di-C$_{1-6}$alkyl-aminocarbonyl.
In certain embodiments of formula I, R$^{10}$ is cyano
In certain embodiments of formula I, R$^{10}$ is hydroxy-C$_{1-6}$alkyl.
In certain embodiments of formula I, R$^{10}$ is N—C$_{1-6}$alkoxy-C$_{1-6}$alkyl-aminocarbonyl.
In certain embodiments of formula I, R$^{10}$ is N-hydroxy-C$_{1-6}$alkyl-aminocarbonyl.
In certain embodiments of formula I, R$^{10}$ is N—C$_{1-6}$alkoxy-aminocarbonyl.
In certain embodiments of formula I, R$^{11}$ is: hydrogen; halo; oxo; hydroxy; or C$_{1-6}$alkyl which may be unsubstituted or substituted one or more times with halo; or oxo.
In certain embodiments of formula I, R$^{11}$ is: hydrogen; halo; carboxy; C$_{1-6}$alkyl-carbonyl; C$_{1-6}$alkoxy-carbonyl; oxo; hydroxy; aminocarbonyl; N—C$_{1-6}$alkyl-aminocarbonyl; N,N-di-C$_{1-6}$alkyl-aminocarbonyl; or C$_{1-6}$alkyl which may be unsubstituted or substituted one or more times with halo or oxo.
In certain embodiments of formula I, R$^{11}$ is: hydrogen; halo; or C$_{1-6}$alkyl.
In certain embodiments of formula I, R$^{11}$ is: hydrogen; C$_{1-6}$alkyl; or halo.
In certain embodiments of formula I, R$^{11}$ is: hydrogen; or C$_{1-6}$alkyl.
In certain embodiments of formula I, R$^{11}$ is hydrogen.
In certain embodiments of formula I, R$^{11}$ is C$_{1-6}$alkyl
In certain embodiments of formula I, R$^{101}$ is methyl.
In certain embodiments of formula I, R$^{11}$ is halo.
In certain embodiments of formula I, R$^{11}$ is oxo.
In certain embodiments of formula I, R$^{11}$ is C$_{1-6}$alkyl-sulfonylamino
In certain embodiments of formula I, R$^{11}$ is C$_{1-6}$alkyl-sulfonylamino-C$_{1-6}$alkyl.
In certain embodiments of formula I, R$^{11}$ is cyano.

In certain embodiments of formula I, $R^{11}$ is hydroxy-$C_{1-6}$alkyl.

In certain embodiments of formula I, $R^{11}$ is N—$C_{1-6}$alkoxy-$C_{1-6}$alkyl-aminocarbonyl.

In certain embodiments of formula I, $R^{11}$ is N-hydroxy-$C_{1-6}$alkyl-aminocarbonyl.

In certain embodiments of formula I, $R^{11}$ is N—$C_{1-6}$alkoxy-aminocarbonyl.

In certain embodiments of formula I, $R^{12}$ is: hydrogen; or $C_{1-6}$alkyl.

In certain embodiments of formula I, $R^{12}$ is hydrogen.

In certain embodiments of formula I, $R^{12}$ is halo.

In certain embodiments of formula I, $R^{12}$ is carboxy.

In certain embodiments of formula I, $R^{12}$ is $C_{1-6}$alkyl-carbonyl.

In certain embodiments of formula I, $R^{12}$ is $C_{1-6}$alkoxy-carbonyl.

In certain embodiments of formula I, $R^{12}$ is oxo.

In certain embodiments of formula I, $R^{12}$ is hydroxy.

In certain embodiments of formula I, $R^{12}$ is aminocarbonyl.

In certain embodiments of formula I, $R^{12}$ is N—$C_{1-6}$alkyl-aminocarbonyl.

In certain embodiments of formula I, $R^{12}$ is N,N-di-$C_{1-6}$alkyl-aminocarbonyl.

In certain embodiments of formula I, $R^{12}$ is cyano.

In certain embodiments of formula I, $R^{12}$ is hydroxy-$C_{1-6}$alkyl.

In certain embodiments of formula I, $R^{12}$ is N—$C_{1-6}$alkoxy-$C_{1-6}$alkyl-aminocarbonyl.

In certain embodiments of formula I, $R^{12}$ is N-hydroxy-$C_{1-6}$alkyl-aminocarbonyl.

In certain embodiments of formula I, $R^{12}$ is N—$C_{1-6}$alkoxy-aminocarbonyl.

In certain embodiments of formula I, $R^{12}$ is $C_{1-6}$alkyl.

In certain embodiments of formula I, $R^{12}$ is methyl.

In certain embodiments of formula I, $R^{10}$ and $R^{11}$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, $R^{10}$ and $R^{11}$ together with the atoms to which they are attached form a four, five, six or seven membered ring;

In certain embodiments of formula I, $R^a$ is hydrogen.

In certain embodiments of formula I, $R^a$ is $C_{1-6}$alkyl.

In certain embodiments of formula I, $R^b$ is hydrogen.

In certain embodiments of formula I, $R^b$ is $C_{1-6}$alkyl.

In certain embodiments of formula I, $R^c$ is hydrogen.

In certain embodiments of formula I, $R^c$ is $C_{1-6}$alkyl.

In certain embodiments of formula I, $R^b$ and $R^c$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, one of $R^b$ and $R^c$ together with one of $R^7$ and $R^8$ and the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, one of $R^b$ and $R^c$ together with one of $R^5$ and $R^6$ and the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, $R^d$ is hydrogen.

In certain embodiments of formula I, $R^d$ is $C_{1-6}$alkyl.

In certain embodiments of formula I, each $R^e$ is independently: hydrogen; $C_{1-6}$alkyl; halo; or halo-$C_{1-6}$alkyl.

In certain embodiments of formula I, each $R^e$ is independently: hydrogen; $C_{1-6}$alkyl; or halo.

In certain embodiments of formula I, each $R^e$ is independently: hydrogen; or halo.

In certain embodiments of formula I, each $R^e$ is independently: hydrogen; or fluoro.

In certain embodiments of formula I, $R^e$ is hydrogen.

In certain embodiments of formula I, $R^e$ is $C_{1-6}$alkyl.

In certain embodiments of formula I, $R^e$ is halo.

In certain embodiments of formula I, $R^e$ is $C_{1-6}$alkoxy.

In certain embodiments of formula I, $R^e$ is cyano. In certain embodiments of formula I, $R^e$ is halo-$C_{1-6}$alkyl.

In certain embodiments of formula I, each $R^f$ is independently: hydrogen; or $C_{1-6}$alkyl.

In certain embodiments of formula I, $R^f$ is hydrogen.

In certain embodiments of formula I, $R^f$ is $C_{1-6}$alkyl.

In certain embodiments of formula I, $R^f$ is halo.

In certain embodiments of formula I, $R^g$ is: $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N—$C_{1-6}$alkyl-sulfonylaminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; amino; N—$C_{1-6}$alkyl-amino; N,N-di-$C_{1-6}$alkyl-amino; halo-$C_{1-6}$alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$.

In certain embodiments of formula I, $R^g$ is: hydrogen; $C_{1-6}$alkyl; $C_{3-6}$cycloalkyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; amino; N—$C_{1-6}$alkyl-amino; N,N-di-$C_{1-6}$alkyl-amino; halo-$C_{1-6}$alkyl; or hydroxyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^i$.

In certain embodiments of formula I, $R^g$ is hydrogen.

In certain embodiments of formula I, $R^g$ is $C_{1-6}$alkyl.

In certain embodiments of formula I, $R^g$ is $C_{3-6}$cycloalkyl which may be unsubstituted or substituted one or more times with $R^i$.

In certain embodiments of formula I, $R^g$ is $C_{3-6}$cycloalkyl-$C_{1-6}$alkyl which may be unsubstituted or substituted one or more times with $R^i$.

In certain embodiments of formula I, $R^g$ is halo.

In certain embodiments of formula I, $R^g$ is $C_{1-6}$alkyl-carbonyl.

In certain embodiments of formula I, $R^g$ is $C_{3-6}$cycloalkyl-carbonyl wherein the $C_{3-6}$cycloalkyl moiety may be unsubstituted or substituted one or more times with $R^i$.

In certain embodiments of formula I, $R^g$ is $C_{3-6}$cycloalkyl-$C_{1-6}$alkyl-carbonyl wherein the $C_{3-6}$cycloalkyl-$C_{1-6}$alkyl moiety may be unsubstituted or substituted one or more times with $R^i$.

In certain embodiments of formula I, $R^g$ is $C_{1-6}$alkyl-sulfonyl.

In certain embodiments of formula I, $R^g$ is $C_{3-6}$cycloalkyl-sulfonyl.

In certain embodiments of formula I, $R^g$ is $C_{3-6}$cycloalkyl-$C_{1-6}$alkyl-sulfonyl.

In certain embodiments of formula I, $R^g$ is aminocarbonyl.

In certain embodiments of formula I, $R^g$ is N—$C_{1-6}$alkyl-aminocarbonyl.

In certain embodiments of formula I, $R^g$ is N,N-di-$C_{1-6}$alkyl-aminocarbonyl.

In certain embodiments of formula I, $R^g$ is aminosulfonyl.

In certain embodiments of formula I, $R^g$ is N—$C_{1-6}$alkyl-aminosulfonyl.

In certain embodiments of formula I, $R^g$ is N,N-di-$C_{1-6}$alkyl-aminosulfonyl.

In certain embodiments of formula I, $R^g$ is cyano.

In certain embodiments of formula I, $R^g$ is $C_{1-6}$alkoxy.

In certain embodiments of formula I, $R^g$ is $C_{1-6}$alkyl-sulfonylamino

In certain embodiments of formula I, $R^g$ is amino

In certain embodiments of formula I, $R^g$ is N—$C_{1-6}$alkyl-amino

In certain embodiments of formula I, $R^g$ is N,N-di-$C_{1-6}$alkyl-amino

In certain embodiments of formula I, $R^g$ is halo-$C_{1-6}$alkyl.

In certain embodiments of formula I, $R^g$ is hydroxy.

In certain embodiments of formula I, $R^g$ is $C_{3-6}$cycloalkeny which may be unsubstituted or substituted one or more times with $R^i$.

In certain embodiments of formula I, $R^g$ is cyano-$C_{1-6}$alkyl-carbonyl.

In certain embodiments of formula I, $R^g$ is hydroxy-$C_{1-6}$alkyl-carbonyl.

In certain embodiments of formula I, $R^g$ is $C_{1-6}$alkoxy-$C_{1-6}$alkyl-carbonyl.

In certain embodiments of formula I, $R^g$ is carboxy.

In certain embodiments of formula I, $R^g$ is N-cyano-aminocarbonyl.

In certain embodiments of formula I, $R^g$ is N-cyano-N—$C_{1-6}$alkyl-aminocarbonyl.

In certain embodiments of formula I, $R^g$ is N—$C_{1-6}$alkyl-acetimidamidyl.

In certain embodiments of formula I, $R^g$ is N,N'-di-$C_{1-6}$alkyl-acetimidamidyl.

In certain embodiments of formula I, $R^g$ is N'-cyano-N—$C_{1-6}$alkyl-acetimidamidyl.

In certain embodiments of formula I, $R^g$ is N'-hydroxy-acetimidamidyl.

In certain embodiments of formula I, $R^g$ is N'—$C_{1-6}$alkoxy-acetimidamidyl.

In certain embodiments of formula I, $R^g$ is N'-hydroxy-N—$C_{1-6}$alkyl-acetimidamide; N'—$C_{1-6}$alkoxy-N—$C_{1-6}$alkyl-acetimidamidyl.

In certain embodiments of formula I, $R^g$ is 2-nitro-1-N—$C_{1-6}$alkylamino-vinyl.

In certain embodiments of formula I, $R^g$ is $C_{1-6}$alkyl-sulfonyl-$C_{1-6}$alkyl.

In certain embodiments of formula I, $R^g$ is N-hydroxy-aminocarbonyl.

In certain embodiments of formula I, $R^g$ is N—$C_{1-6}$alkoxy-aminocarbonyl.

In certain embodiments of formula I, $R^g$ is N-hydroxy-N—$C_{1-6}$alkyl-aminocarbonyl.

In certain embodiments of formula I, $R^g$ is N—$C_{1-6}$alkoxy-N—$C_{1-6}$alkyl-aminocarbonyl.

In certain embodiments of formula I, $R^g$ is N—$C_{1-6}$alkyl-sulfonylaminocarbonyl.

In certain embodiments of formula I, $R^g$ is N—($C_{1-6}$alkyl-sulfonyl)-N—$C_{1-6}$alkyl-aminocarbonyl.

In certain embodiments of formula I, $R^g$ is aminocarbonyl-$C_{1-6}$alkyl.

In certain embodiments of formula I, $R^g$ is N—$C_{1-6}$alkyl-aminocarbonyl-$C_{1-6}$alkyl In certain embodiments of formula I, $R^g$ is N,N-di-$C_{1-6}$alkyl-aminocarbonyl-$C_{1-6}$alkyl.

In certain embodiments of formula I, $R^g$ is $C_{1-6}$alkoxy-carbonyl.

In certain embodiments of formula I, $R^g$ is heterocyclyl which may be unsubstituted or substituted one or more times with $R^i$.

In embodiments of formula I wherein $R^g$ is heterocyclyl, such heterocyclyl may be oxetanyl, tetrahydrofuranyl, tetrahydropyranyl, azetidinyl, pyrrolidinyl, piperidinyl, azepinyl or piperazinyl, each of which may be unsubstituted or substituted one or more times with $R^i$.

In certain embodiments of formula I, $R^g$ is heteroaryl which may be unsubstituted or substituted one or more times with $R^i$.

In embodiments of formula I wherein $R^g$ is heteroaryl, such heteroaryl may be pyridinyl, pyrimidinyl, triazinyl, pyrrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^g$ is heteroaryl, such heteroaryl may be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^g$ is triazolyl.

In certain embodiments of formula I, $R^g$ is [1,2,4]triazol-4-yl.

In certain embodiments of formula I, $R^g$ is [1,2,4]triazol-3-yl.

In certain embodiments of formula I, $R^g$ is 4-methyl-[1,2,4]triazol-3-yl.

In certain embodiments of formula I, $R^g$ is [1,2,4]triazol-1-yl.

In certain embodiments of formula I, $R^g$ is [1,2,3]triazol-1-yl.

In certain embodiments of formula I, $R^g$ is [1,2,3]triazol-4-yl.

In certain embodiments of formula I, $R^g$ is 4-methyl-[1,2,4]triazol-3-yl.

In certain embodiments of formula I, $R^g$ is pyrazolyl.

In certain embodiments of formula I, $R^g$ is pyrazol-3-yl.

In certain embodiments of formula I, $R^g$ is pyrazol-1-yl.

In certain embodiments of formula I, $R^g$ is pyrazol-4-yl.

In certain embodiments of formula I, $R^g$ is imidazolyl.

In certain embodiments of formula I, $R^g$ is imidazol-1-yl.

In certain embodiments of formula I, $R^g$ is 1-methyl-imidazol-2-yl.

In certain embodiments of formula I, $R^g$ is isoxazolyl.

In certain embodiments of formula I, $R^g$ is 3-hydroxyisoxazol-5-yl.

In certain embodiments of formula I, $R^g$ is oxdiazolyl.

In certain embodiments of formula I, $R^g$ is [1,2,4]oxadiazol-5-yl.

In certain embodiments of formula I, $R^g$ is [1,2,4]oxadiazol-3-yl.

In certain embodiments of formula I, $R^g$ is [1,2,3]oxadiazol-2-yl.

In certain embodiments of formula I, $R^g$ is [1,2,3]oxadiazol-2-one-5-yl.

In certain embodiments of formula I, $R^g$ is tetrazolyl.

In certain embodiments of formula I, $R^g$ is tetrazol-5-yl.

In certain embodiments of formula I, $R^g$ is tetrazol-1-yl.

In certain embodiments of formula I, $R^g$ is tetrazol-2-yl.

In certain embodiments of formula I, $R^g$ is pyrazolyl.

In certain embodiments of formula I, $R^g$ is pyridazinyl.

In certain embodiments of formula I, $R^g$ is triazinyl.

In certain embodiments of formula I, $R^f$ and $R^g$ together with the atoms to which they are attached form a three, four, five, six or seven membered saturated or partially saturated ring.

In certain embodiments of formula I, $R^f$ and $R^g$ together with the atoms to which they are attached form a three membered ring.

In certain embodiments of formula I, $R^f$ and $R^g$ together with the atoms to which they are attached form a four membered ring.

In certain embodiments of formula I, $R^f$ and $R^g$ together with the atoms to which they are attached form a five membered ring.

In certain embodiments of formula I, $R^f$ and $R^g$ together with the atoms to which they are attached form a six membered ring.

In certain embodiments of formula I, $R^f$ and $R^g$ together with the atoms to which they are attached form a seven membered ring.

In certain embodiments of formula I, $R^h$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N—($C_{1-6}$alkyl-sulfonyl)aminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$.

In certain embodiments of formula I, $R^h$ is: hydrogen; $C_{1-6}$alkyl; $C_{3-6}$cycloalkyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; N,N-di-$C_{1-6}$alkyl-aminocarbonyl; aminosulfonyl; N—$C_{1-6}$alkyl-aminosulfonyl; or N,N-di-$C_{1-6}$alkyl-aminosulfonyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; or N,N-di-$C_{1-6}$alkyl-aminocarbonyl; aminosulfonyl; N—$C_{1-6}$alkyl-aminosulfonyl; or N,N-di-$C_{1-6}$alkyl-aminosulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; or $C_{3-6}$cycloalkyl-$C_{1-6}$alkyl-sulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; or $C_{3-6}$cycloalkyl-$C_{1-6}$alkyl-carbonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is hydrogen.

In certain embodiments of formula I, $R^h$ is $C_{1-6}$alkyl.

In certain embodiments of formula I, $R^h$ is $C_{3-6}$cycloalkyl which may be unsubstituted or substituted one or more times with $R^i$.

In certain embodiments of formula I, $R^h$ is $C_{3-6}$cycloalkyl-$C_{1-6}$alkyl.

In certain embodiments of formula I, $R^h$ is $C_{1-6}$alkyl-carbonyl.

In certain embodiments of formula I, $R^h$ is $C_{3-6}$cycloalkyl-carbonyl.

In certain embodiments of formula I, $R^h$ is $C_{3-6}$cycloalkyl-$C_{1-6}$alkyl-carbonyl.

In certain embodiments of formula I, $R^h$ is $C_{1-6}$alkyl-sulfonyl.

In certain embodiments of formula I, $R^h$ is $C_{3-6}$cycloalkyl-sulfonyl.

In certain embodiments of formula I, $R^h$ is $C_{3-6}$cycloalkyl-$C_{1-6}$alkyl-sulfonyl.

In certain embodiments of formula I, $R^h$ is aminocarbonyl.

In certain embodiments of formula I, $R^h$ is N—$C_{1-6}$alkyl-aminocarbonyl.

In certain embodiments of formula I, $R^h$ is N,N-di-$C_{1-6}$alkyl-aminocarbonyl.

In certain embodiments of formula I, $R^h$ is aminosulfonyl.

In certain embodiments of formula I, $R^h$ is N—$C_{1-6}$alkyl-aminosulfonyl.

In certain embodiments of formula I, $R^h$ is or N,N-di-$C_{1-6}$alkyl-aminosulfonyl.

In certain embodiments of formula I, $R^h$ is $C_{3-6}$cycloalkenyl.

In certain embodiments of formula I, $R^h$ is cyano-$C_{1-6}$alkyl-carbonyl.

In certain embodiments of formula I, $R^h$ is hydroxy-$C_{1-6}$alkyl-carbonyl.

In certain embodiments of formula I, $R^h$ is $C_{1-6}$alkoxy-$C_{1-6}$alkyl-carbonyl.

In certain embodiments of formula I, $R^h$ is N-cyano-aminocarbonyl.

In certain embodiments of formula I, $R^h$ is N-cyano-N—$C_{1-6}$alkyl-aminocarbonyl.

In certain embodiments of formula I, $R^h$ is N—$C_{1-6}$alkyl-acetimidamidyl.

In certain embodiments of formula I, $R^h$ is N,N'-di-$C_{1-6}$alkyl-acetimidamidyl.

In certain embodiments of formula I, $R^h$ is N'-cyano-N—$C_{1-6}$alkyl-acetimidamidyl.

In certain embodiments of formula I, $R^h$ is N'-hydroxy-acetimidamidyl.

In certain embodiments of formula I, $R^h$ is N'—$C_{1-6}$alkoxy-acetimidamidyl.

In certain embodiments of formula I, $R^h$ is N'-hydroxy-N—$C_{1-6}$alkyl-acetimidamidyl.

In certain embodiments of formula I, $R^h$ is N'—$C_{1-6}$alkoxy-N—$C_{1-6}$alkyl-acetimidamidyl.

In certain embodiments of formula I, $R^h$ is 2-nitro-1-N—$C_{1-6}$alkylamino-vinyl.

In certain embodiments of formula I, $R^h$ is $C_{1-6}$alkyl-sulfonyl-$C_{1-6}$alkyl.

In certain embodiments of formula I, $R^h$ is N-hydroxy-aminocarbonyl.

In certain embodiments of formula I, $R^h$ is N—$C_{1-6}$alkoxy-aminocarbonyl.

In certain embodiments of formula I, $R^h$ is N-hydroxy-N—$C_{1-6}$alkyl-aminocarbonyl.

In certain embodiments of formula I, $R^h$ is N—$C_{1-6}$alkoxy-N—$C_{1-6}$alkyl-aminocarbonyl.

In certain embodiments of formula I, $R^h$ is $C_{1-6}$alkyl-sulfonylamino-$C_{1-6}$alkyl.

In certain embodiments of formula I, $R^h$ is N—($C_{1-6}$alkyl-sulfonyl)aminocarbonyl.

In certain embodiments of formula I, $R^h$ is N—($C_{1-6}$alkyl-sulfonyl)-N—$C_{1-6}$alkyl-aminocarbonyl.

In certain embodiments of formula I, $R^h$ is aminocarbonyl-$C_{1-6}$alkyl.

In certain embodiments of formula I, $R^h$ is N—$C_{1-6}$alkyl-aminocarbonyl-$C_{1-6}$alkyl In certain embodiments of formula I, $R^h$ is N,N-di-$C_{1-6}$alkyl-aminocarbonyl-$C_{1-6}$alkyl.

In certain embodiments of formula I, $R^h$ is $C_{1-6}$alkoxy-carbonyl.

In certain embodiments of formula I, $R^h$ is heterocyclyl which may be unsubstituted or substituted one or more times with $R^i$.

In certain embodiments of formula I, $R^h$ is heteroaryl which may be unsubstituted or substituted one or more times with $R^i$.

In embodiments of formula I wherein $R^h$ is heteroaryl, such heteroaryl may be pyridinyl, pyrimidinyl, pyrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^h$ is heteroaryl, such heteroaryl may be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^h$ is acetyl.

In certain embodiments of formula I, $R^h$ is methanesulfonyl.

In certain embodiments of formula I, $R^h$ is cyclopropylcarbonyl.

In certain embodiments of formula I, $R^h$ and one of $R^{10}$ and $R^{11}$ together with the atoms to which they are attached form a four, five, six or seven membered aromatic, partially saturated or unsaturated ring.

In certain embodiments of formula I, $R^h$ and one of $R^{10}$ and $R^{11}$ together with the atoms to which they are attached form a four membered ring.

In certain embodiments of formula I, $R^h$ and one of $R^{10}$ and $R^{11}$ together with the atoms to which they are attached form a five membered ring.

In certain embodiments of formula I, $R^h$ and one of $R^{10}$ and $R^{11}$ together with the atoms to which they are attached form a six membered ring.

In certain embodiments of formula I, $R^h$ and one of $R^{10}$ and $R^{11}$ together with the atoms to which they are attached form a seven membered ring.

In certain embodiments of formula I, one of $R^f$ and $R^g$ and one of $R^{10}$ and $R^{11}$ together with the atoms to which they are attached form a four, five, six or seven membered aromatic, partially saturated or unsaturated ring.

In certain embodiments of formula I, one of $R^f$ and $R^g$ and one of $R^{10}$ and $R^{11}$ together with the atoms to which they are attached form a five or six membered aromatic ring.

In certain embodiments of formula I, one of $R^f$ and $R^g$ and one of $R^{10}$ and $R^{11}$ together with the atoms to which they are attached form a five membered aromatic ring.

In certain embodiments of formula I, one of $R^f$ and $R^g$ and one of $R^{10}$ and $R^{11}$ together with the atoms to which they are attached form a six membered aromatic ring.

In certain embodiments of formula I, one of $R^f$ and $R^g$ and one of $R^{10}$ and $R^{11}$ together with the atoms to which they are attached form a five or six membered saturated ring.

In certain embodiments of formula I, one of $R^f$ and $R^g$ and one of $R^{10}$ and $R^{11}$ together with the atoms to which they are attached form a five membered saturated ring.

In certain embodiments of formula I, one of $R^f$ and $R^g$ and one of $R^{10}$ and $R^{11}$ together with the atoms to which they are attached form a six membered saturated ring.

In certain embodiments of formula I, one of $R^f$ and $R^g$ and one of $R^{10}$ and $R^{11}$ together with the atoms to which they are attached form a four membered ring.

In certain embodiments of formula I, one of $R^f$ and $R^g$ and one of $R^{10}$ and $R^{11}$ together with the atoms to which they are attached form a five membered ring.

In certain embodiments of formula I, one of $R^f$ and $R^g$ and one of $R^{10}$ and $R^{11}$ together with the atoms to which they are attached form a six membered ring.

In certain embodiments of formula I, one of $R^f$ and $R^g$ and one of $R^{10}$ and $R^{11}$ together with the atoms to which they are attached form a seven membered ring.

In certain embodiments of formula I, $R^i$ is: $C_{1-6}$alkyl; halo; oxo; hydroxy; acetyl; or $C_{1-6}$alkoxy.

In certain embodiments of formula I, $R^i$ is $C_{1-6}$alkyl.

In certain embodiments of formula I, $R^i$ is halo.
In certain embodiments of formula I, $R^i$ is $C_{1-6}$alkoxy.
In certain embodiments of formula I, $R^i$ is halo-$C_{1-6}$alkyl.
In certain embodiments of formula I, $R^i$ is oxo.
In certain embodiments of formula I, $R^i$ is hydroxy.
In certain embodiments of formula I, $R^i$ is acetyl.
In certain embodiments of formula I, $R^i$ is $C_{1-6}$alkyl-carbonyl.
In certain embodiments of formula I, $R^i$ is amino-carbonyl.
In certain embodiments of formula I, $R^i$ is hydroxy-$C_{1-6}$alkyl.
In certain embodiments of formula I, $R^i$ is cyano.
In certain embodiments of formula I, $R^i$ is heteroaryl;
In certain embodiments of formula I, $R^j$ and $R^k$ each independent is: hydrogen; or methyl.
In certain embodiments of formula I, $R^j$ is hydrogen.
In certain embodiments of formula I, $R^k$ is hydrogen.
In certain embodiments of the invention, the group

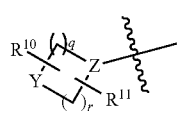

is:

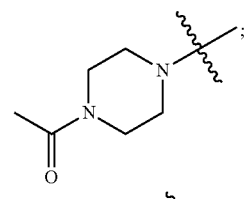

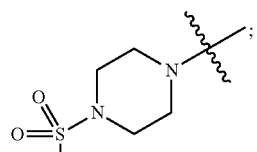

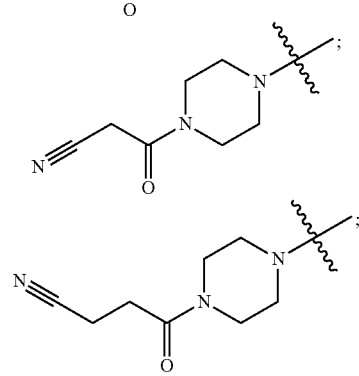

-continued

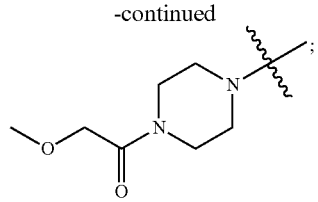

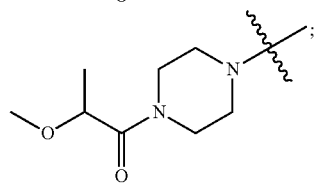

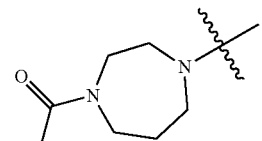

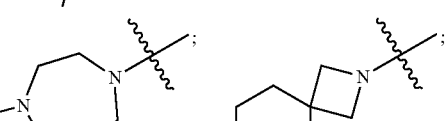

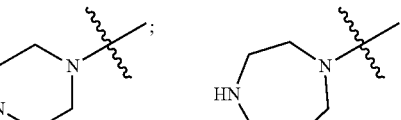

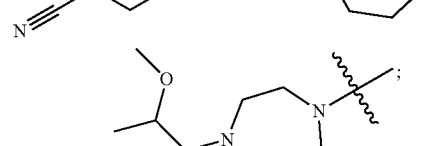

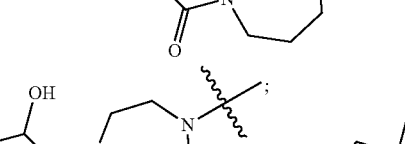

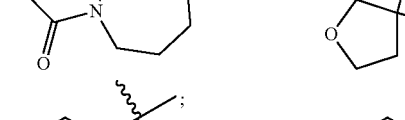

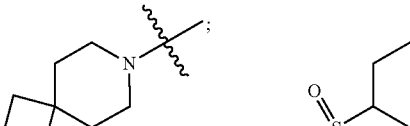

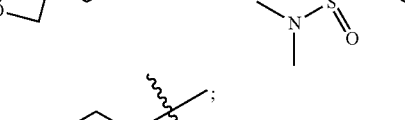

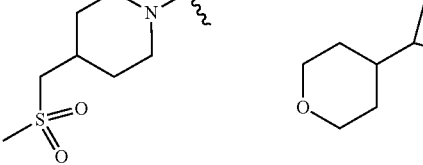

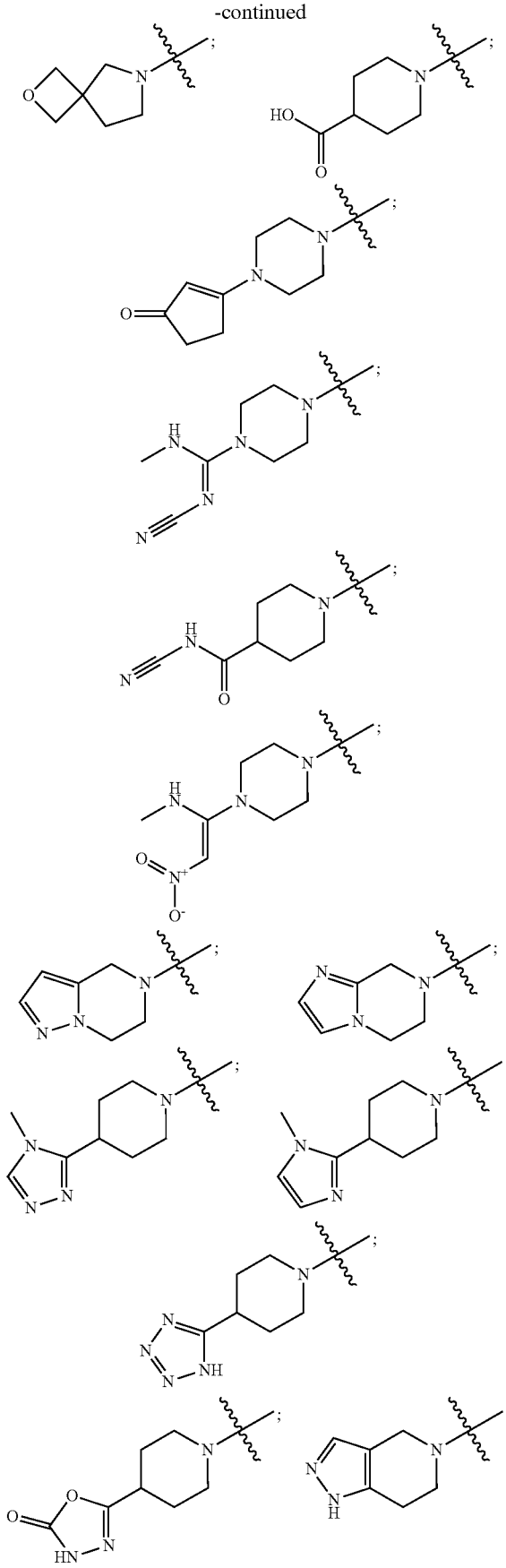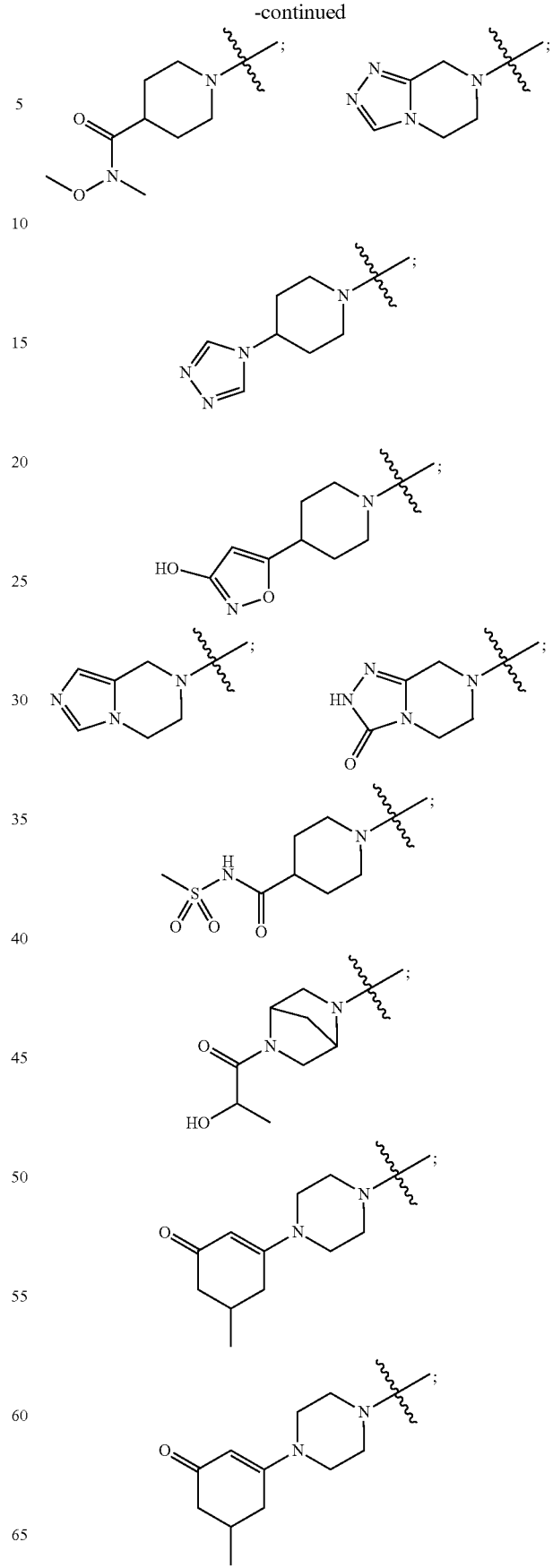

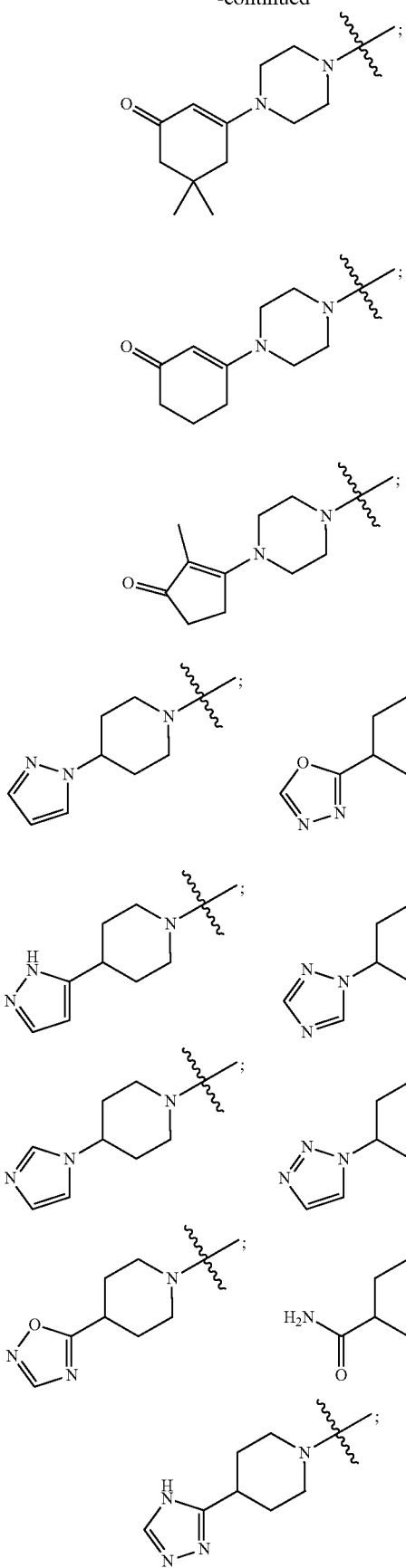
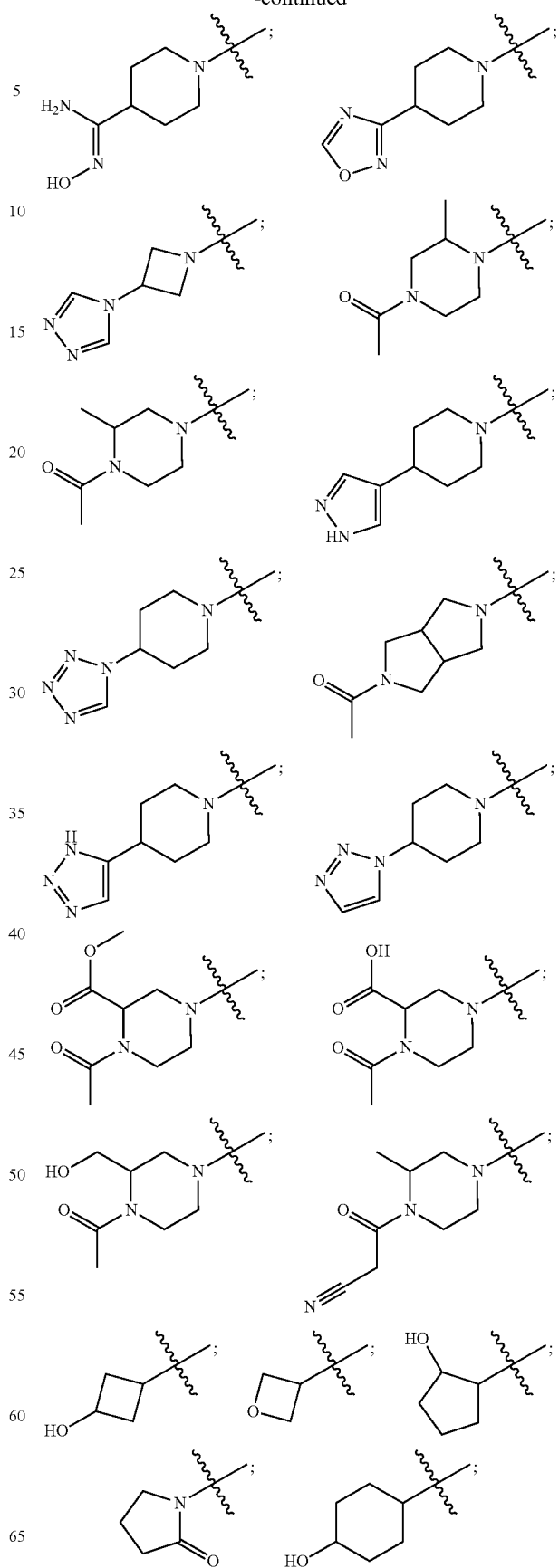

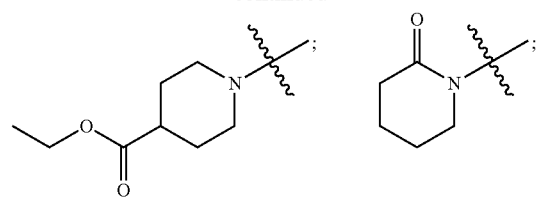
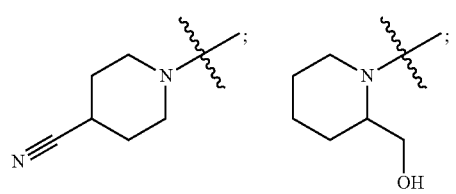
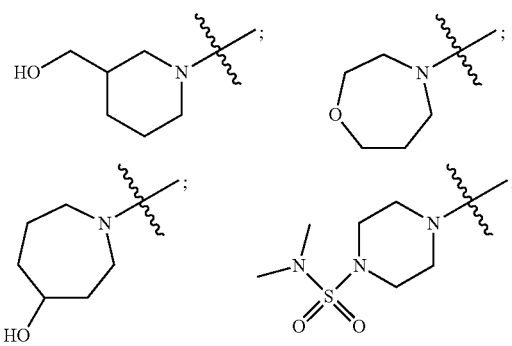
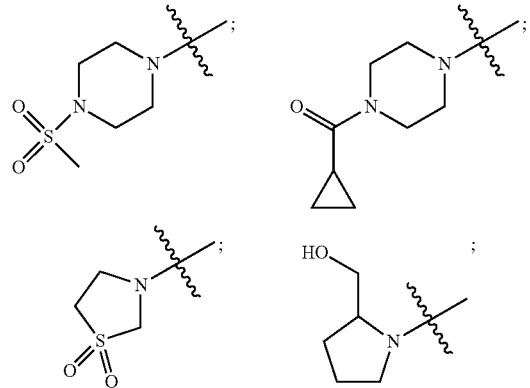
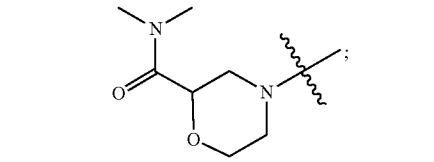
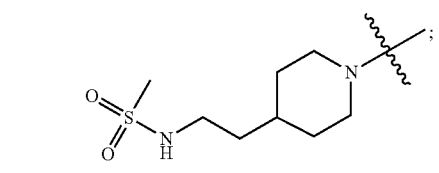
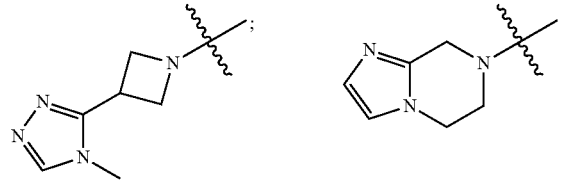
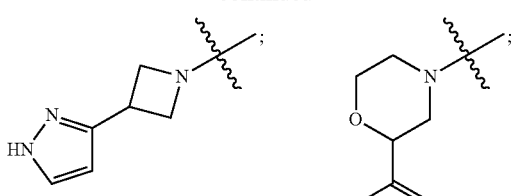
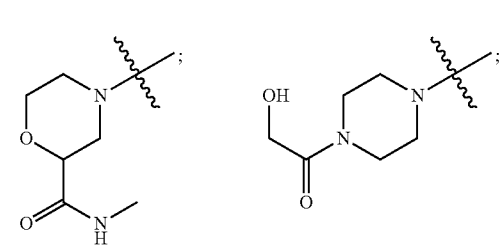
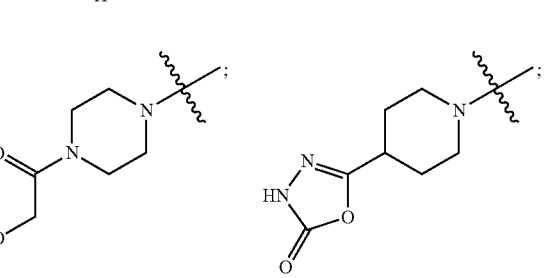
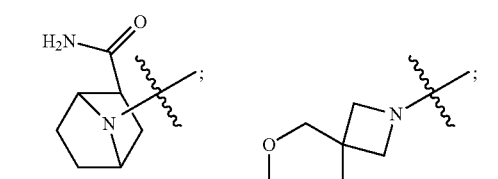
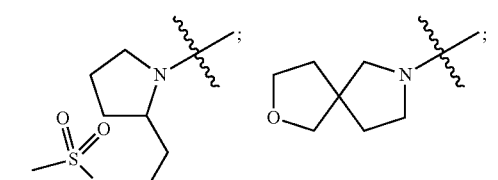
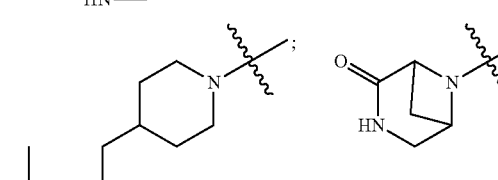
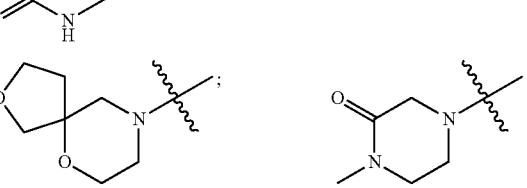
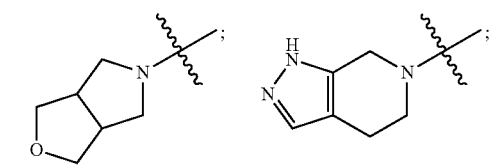

37
-continued
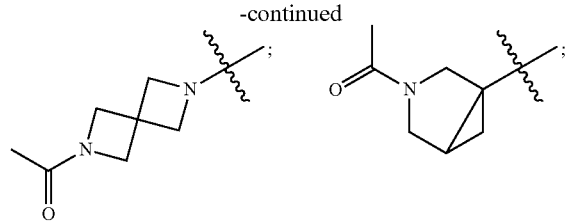
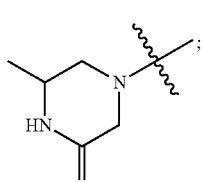
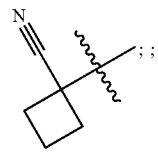
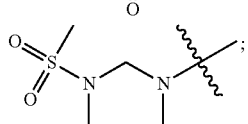
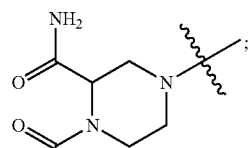
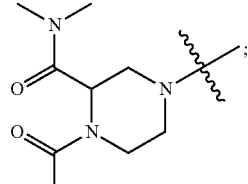
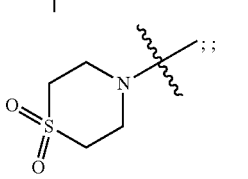
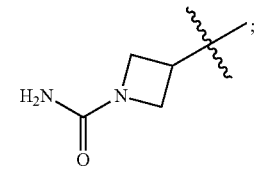
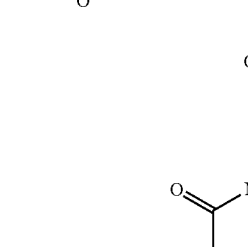
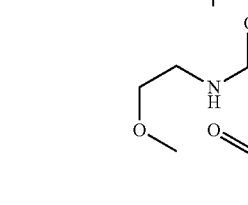
38
-continued
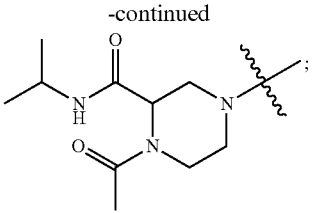
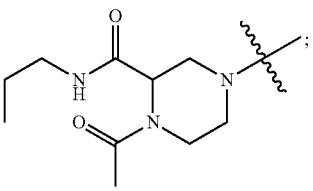
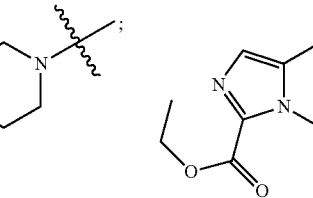
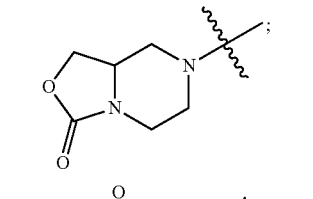
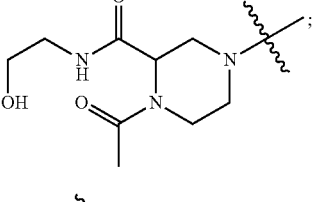
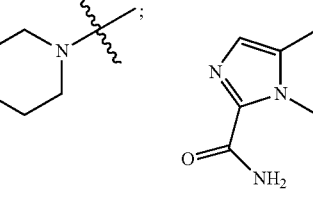
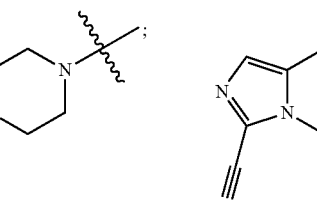
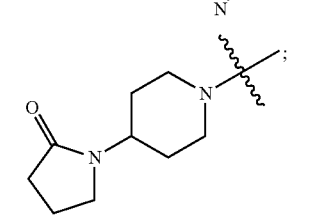

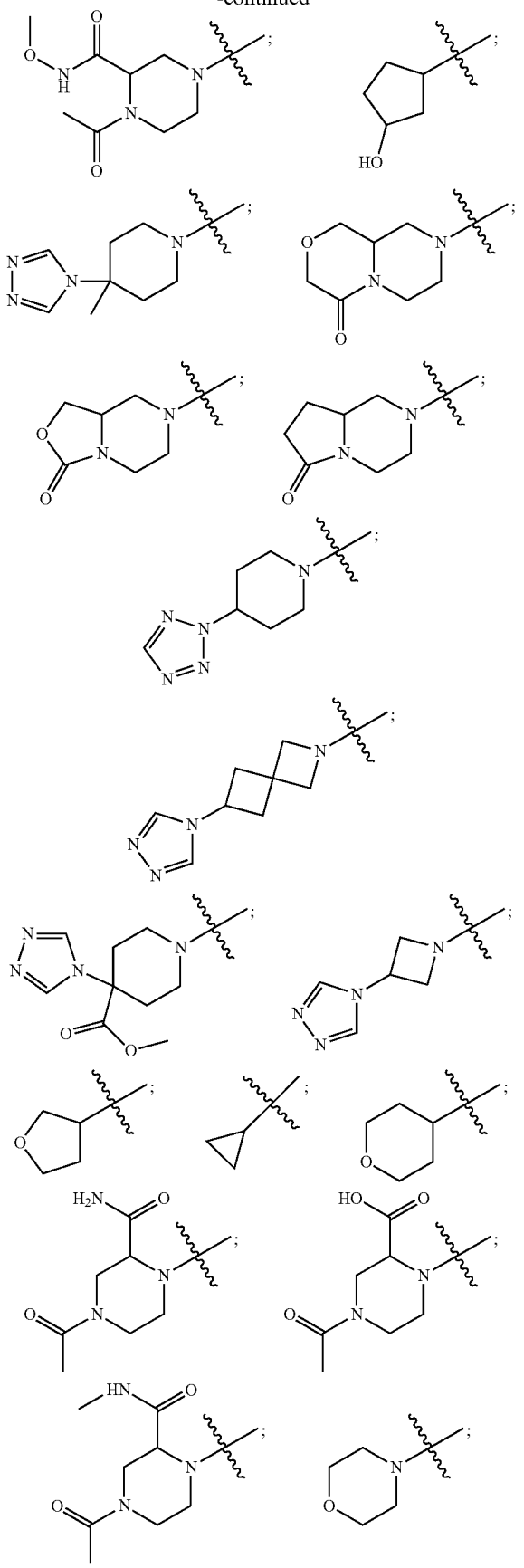
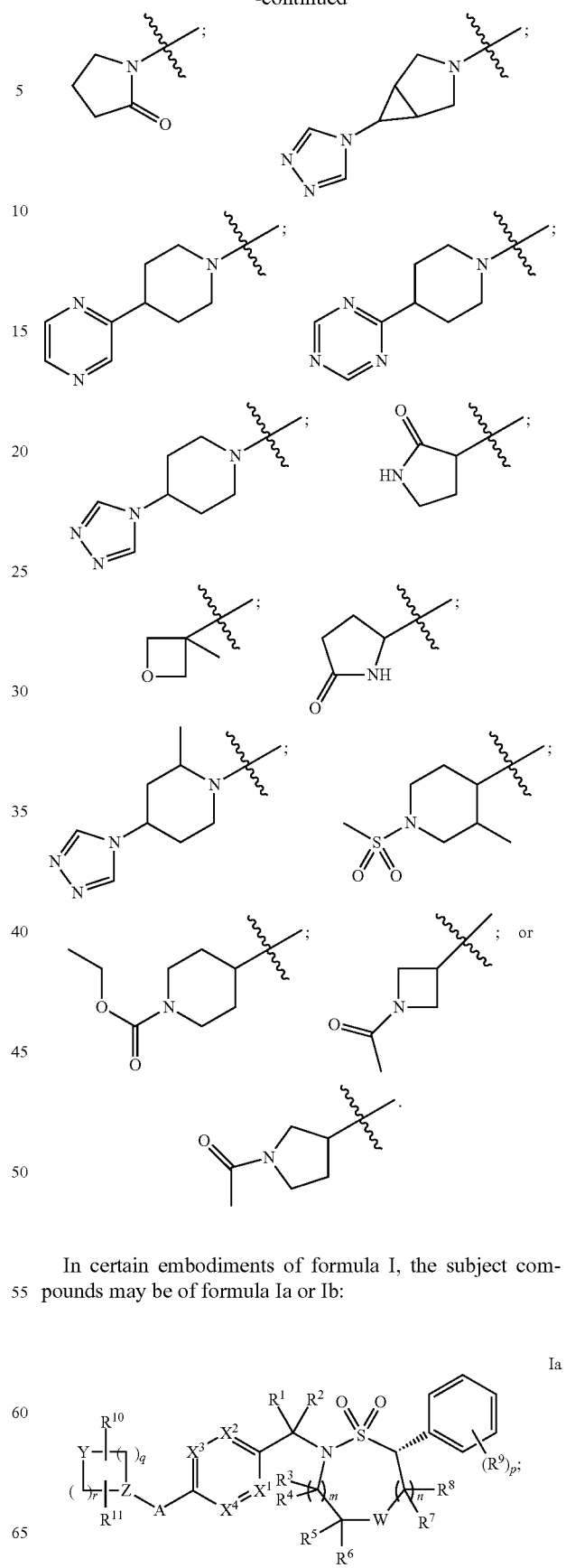
In certain embodiments of formula I, the subject compounds may be of formula Ia or Ib:
Ia -continued

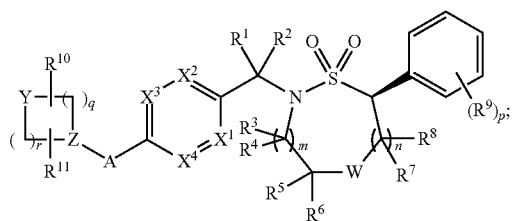
Ib wherein m, n, p, q, r, A, W, X¹, X², X³, X⁴, Y, Z, R¹, R², R³, R⁴, R⁵, R⁶, R⁷, R⁸, R⁹, R¹⁰ and R¹¹, and the group

are as defined herein.

In certain embodiments, the subject compounds are of formula Ia.

In certain embodiments, the subject compounds are of formula Ib.

In certain embodiments of formula I, the subject compounds may be of formula IIa or IIb

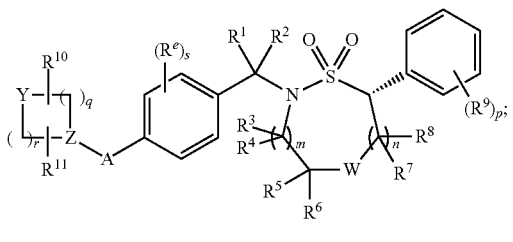
IIa

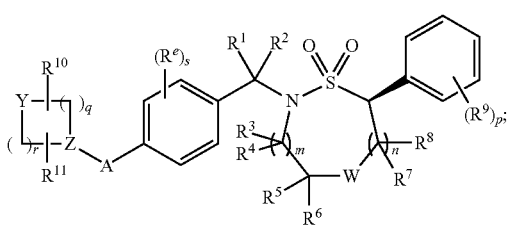
IIb wherein s is from 0 to 3,
and m, n, p, q, r, A, W, Y, Z, R¹, R², R³, R⁴, R⁵, R⁶, R⁷, R⁸, R⁹, R¹⁰, R¹¹ and $R^e$, and the group

are as defined herein.

In certain embodiments, the subject compounds are of formula IIa.

In certain embodiments, the subject compounds are of formula IIb.

In certain embodiments of formula IIa or IIb, $R^e$ is halo.
In certain embodiments of formula IIa or IIb, $R^e$ is fluoro.

In certain embodiments of formula IIa or IIb, s is 0 or 1.
In certain embodiments of formula IIa or IIb, s is 0.
In certain embodiments of formula IIa or IIb, s is 1.
In certain embodiments of formula IIa or IIb, s is 1 or 2.
In certain embodiments of formula IIa or IIb, s is 2.
In certain embodiments of formula IIa or IIb, s is 1, 2 or 3.
In certain embodiments of formula IIa or IIb, s is 2 or 3.
In certain embodiments of formula IIa or IIb, s is 3.

In certain embodiments of formula I, the subject compounds may be of formula IIIa or IIb:

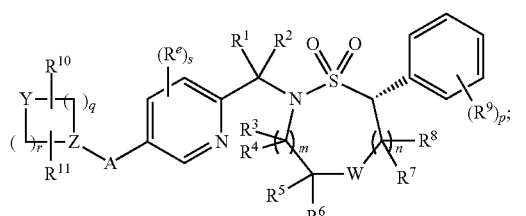
IIIa

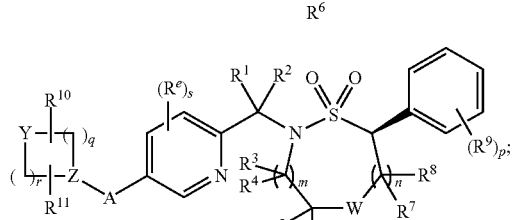
IIIb wherein m, n, p, q, r, s, A, W, Y, Z, R¹, R², R³, R⁴, R⁵, R⁶, R⁷, R⁸, R⁹, R¹⁰, R¹¹ and $R^e$, and the group

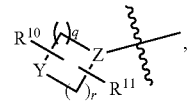

are as defined herein.

In certain embodiments, the subject compounds are of formula IIIa.

In certain embodiments, the subject compounds are of formula IIIb.

In certain embodiments of formula I, the subject compounds may be of formula IVa or IVb

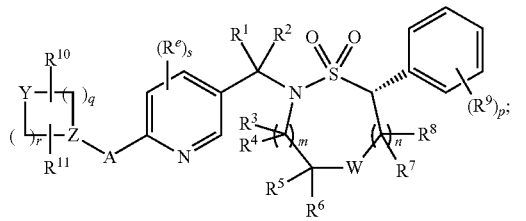
IVa

-continued

IVb

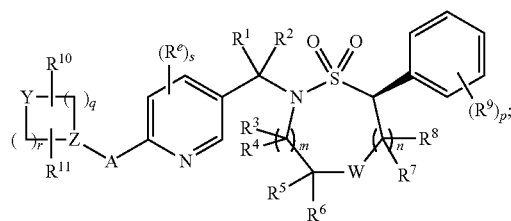

wherein m, n, p, q, r, s, A, W, Y, Z, R$^1$, R$^2$, R$^3$, R$^4$, R$^5$, R$^6$, R$^7$, R$^8$, R$^9$, R$^{10}$, R$^{11}$ and R$^e$, and the group

are as defined herein.

In certain embodiments, the subject compounds are of formula IVa.

In certain embodiments, the subject compounds are of formula IVb.

In certain embodiments of formula I, the subject compounds may be of formula Va or Vb:

Va

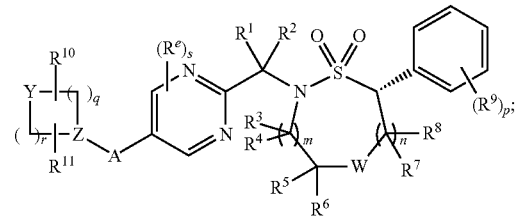

Vb

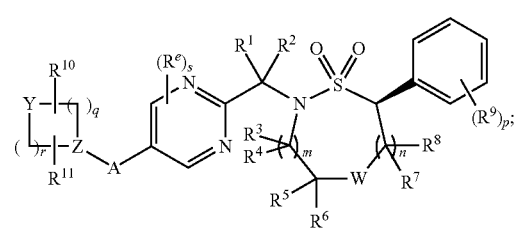

wherein m, n, p, q, r, s, A, W, Y, Z, R$^1$, R$^2$, R$^3$, R$^4$, R$^5$, R$^6$, R$^7$, R$^8$, R$^9$, R$^{10}$, R$^{11}$ and R$^e$, and the group

are as defined herein.

In certain embodiments, the subject compounds are of formula Va.

In certain embodiments, the subject compounds are of formula Vb.

In certain embodiments of formula I, the subject compounds may be of formula VIa or VIb:

VIa

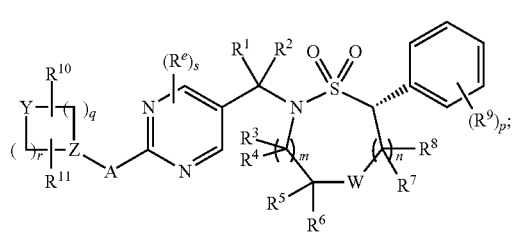

VIb

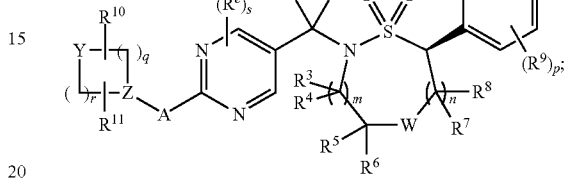

wherein m, n, p, q, r, s, A, W, Y, Z, R$^1$, R$^2$, R$^3$, R$^4$, R$^5$, R$^6$, R$^7$, R$^8$, R$^9$, R$^{10}$, R$^{11}$ and R$^e$, and the group

are as defined herein.

In certain embodiments, the subject compounds are of formula VIa.

In certain embodiments, the subject compounds are of formula VIb.

In certain embodiments of formula I, the subject compounds may be of formula VIIa or VIIb:

VIIa

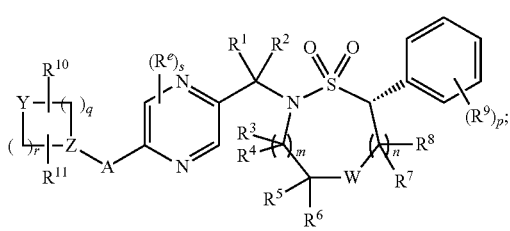

VIIb

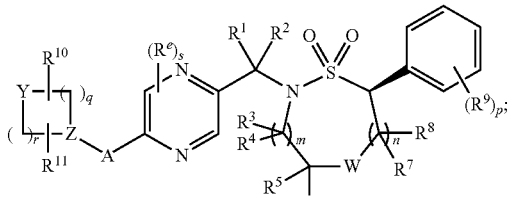

wherein m, n, p, q, r, s, A, W, Y, Z, R$^1$, R$^2$, R$^3$, R$^4$, R$^5$, R$^6$, R$^7$, R$^8$, R$^9$, R$^{10}$, R$^{11}$ and R$^e$, and the group

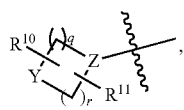

are as defined herein.

In certain embodiments, the subject compounds are of formula VIIa.

In certain embodiments, the subject compounds are of formula VIIb.

In certain embodiments of formula I, the subject compounds may be of formula VIIIa or VIIIb:

VIIIa

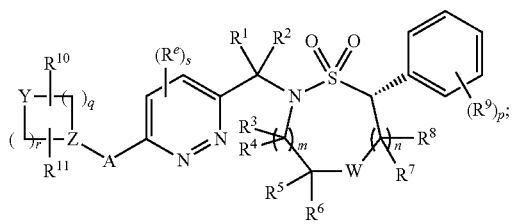

VIIIb

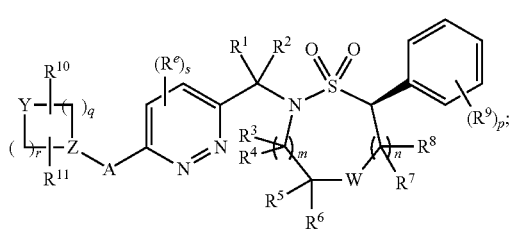

wherein m, n, p, q, r, s, A, W, Y, Z, $R^1$, $R^2$, $R^3$, $R^4$, $R^5$, $R^6$, $R^7$, $R^8$, $R^9$, $R^{10}$, $R^{11}$ and $R^e$, and the group

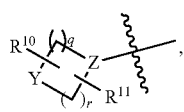

are as defined herein.

In certain embodiments, the subject compounds are of formula VIIIa.

In certain embodiments, the subject compounds are of formula VIIIb.

In certain embodiments of formula I, the subject compounds may be of formula IXa or IXb:

IXa

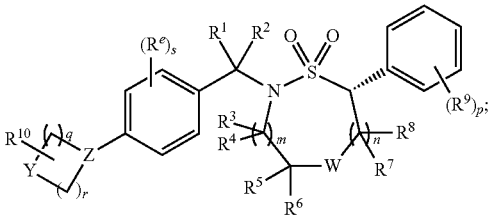

IXb

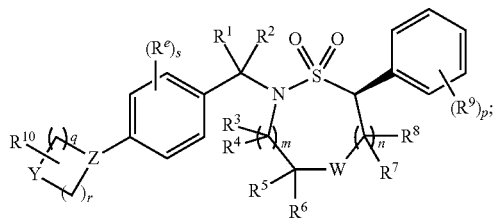

wherein m, n, p, q, r, s, W, Y, Z, $R^1$, $R^2$, $R^3$, $R^4$, $R^5$, $R^6$, $R^7$, $R^8$, $R^9$, $R^{10}$, $R^{11}$ and $R^e$, and the group

are as defined herein.

In certain embodiments, the subject compounds are of formula IXa.

In certain embodiments, the subject compounds are of formula IXb.

In certain embodiments of formula I, the subject compounds may be of formula Xa or Xb:

Xa

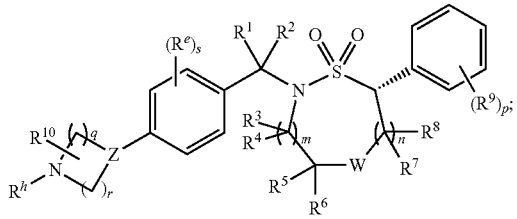

Xb

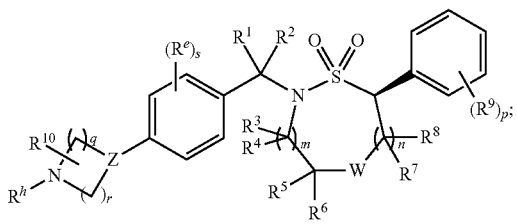

wherein m, n, p, q, r, s, W, Y, Z, $R^1$, $R^2$, $R^3$, $R^4$, $R^5$, $R^6$, $R^7$, $R^8$, $R^9$, $R^{10}$, $R^{11}$, $R^e$ and $R^h$ are as defined herein.

In certain embodiments, the subject compounds are of formula Xa.

In certain embodiments, the subject compounds are of formula Xb.

In certain embodiments of formula I, the subject compounds may be of formula XIa or XIb:

XIa

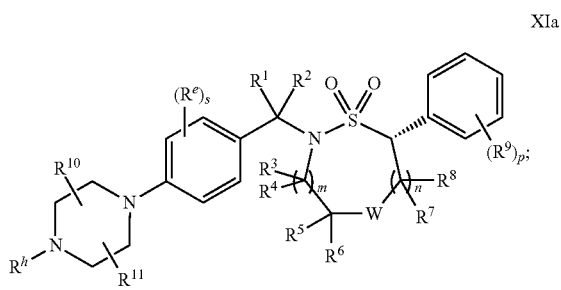

XIa

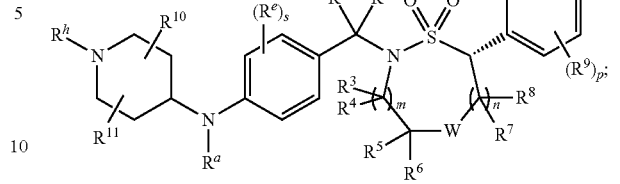
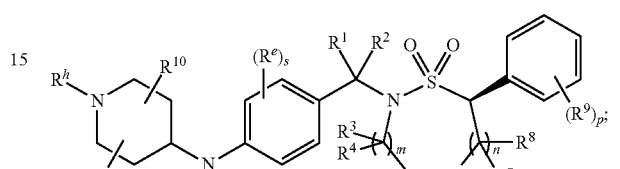

XIIIa

XIIIa wherein m, n, p, s, W, $R^1$, $R^2$, $R^3$, $R^4$, $R^5$, $R^6$, $R^7$, $R^8$, $R^9$, $R^{10}$, $R^{11}$, $R^a$, $R^e$ and $R^h$ are as defined herein.

In certain embodiments, the subject compounds are of formula XIIIa.

In certain embodiments, the subject compounds are of formula XIIIb.

In certain embodiments of formula I, the subject compounds may be of formula XIVa or XIVb:

wherein m, n, p, s, W, $R^1$, $R^2$, $R^3$, $R^4$, $R^5$, $R^6$, $R^7$, $R^8$, $R^9$, $R^{10}$, $R^{11}$, $R^e$ and $R^h$ are as defined herein.

In certain embodiments, the subject compounds are of formula XIa.

In certain embodiments, the subject compounds are of formula XIb.

In certain embodiments of formula I, the subject compounds may be of formula XIIa or XIIb:

XIIa

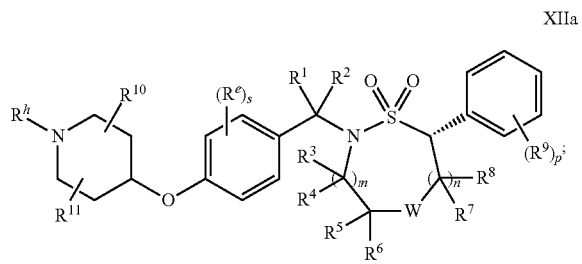

XIIa

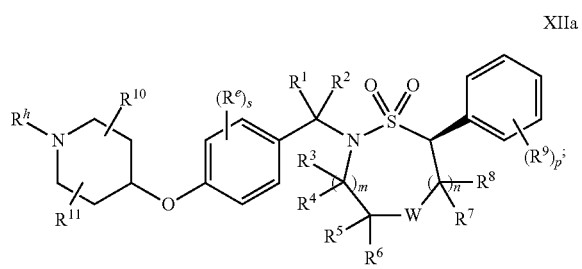

XIVa

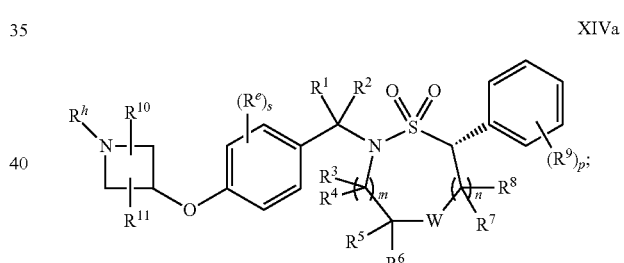

XIVb

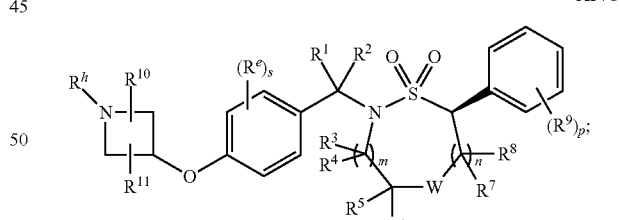

wherein m, n, p, s, W, $R^1$, $R^2$, $R^3$, $R^4$, $R^5$, $R^6$, $R^7$, $R^8$, $R^9$, $R^{10}$, $R^{11}$, $R^e$ and $R^h$ are as defined herein.

In certain embodiments, the subject compounds are of formula XIIa.

In certain embodiments, the subject compounds are of formula XIIb.

In certain embodiments of formula I, the subject compounds may be of formula XIIIa or XIIIb;

wherein m, n, p, s, W, $R^1$, $R^2$, $R^3$, $R^4$, $R^5$, $R^6$, $R^7$, $R^8$, $R^9$, $R^{10}$, $R^{11}$, $R^e$ and $R^h$ are as defined herein.

In certain embodiments, the subject compounds are of formula XIVa.

In certain embodiments, the subject compounds are of formula XIVb.

In certain embodiments of formula I, the subject compounds may be of formula XVa or XVb:

XVa

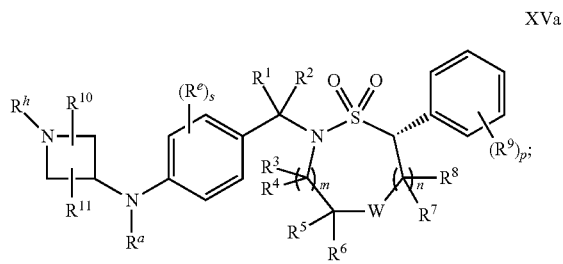

XVb

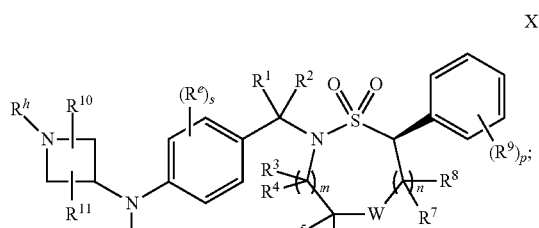

wherein m, n, p, s, W, $R^1$, $R^2$, $R^3$, $R^4$, $R^5$, $R^6$, $R^7$, $R^8$, $R^9$, $R^{10}$, $R^{11}$, $R^e$ and $R^h$ are as defined herein.

In certain embodiments, the subject compounds are of formula XVa.

In certain embodiments, the subject compounds are of formula XVb.

In certain embodiments of formula I, the subject compounds may be of formula XVIa or XVIb:

XVIa

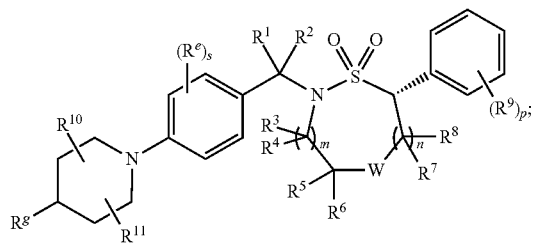

XVIa

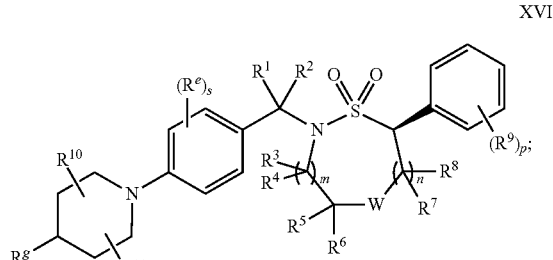

wherein m, n, p, s, W, $R^1$, $R^2$, $R^3$, $R^4$, $R^5$, $R^6$, $R^7$, $R^8$, $R^9$, $R^{10}$, $R^{11}$, $R^e$ and $R^g$ are as defined herein.

In certain embodiments, the subject compounds are of formula XVIa.

In certain embodiments, the subject compounds are of formula XVIb.

In certain embodiments of formula I, the subject compounds may be of formula XVIIa or XVIIb:

XVIIa

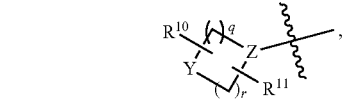

XVIIb

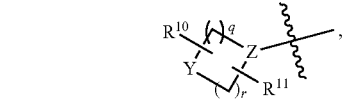

wherein p, q, r, s, A, Y, Z, $R^1$, $R^2$, $R^3$, $R^9$, $R^{10}$, $R^{11}$ and $R^e$, and the group

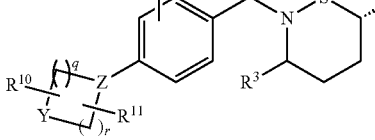

are as defined herein.

In certain embodiments, the subject compounds are of formula XVIIa.

In certain embodiments, the subject compounds are of formula XVIIb.

In certain embodiments of formula I, the subject compounds may be of formula XVIIIa or XVIIIb:

XVIIIa

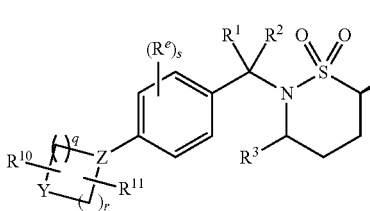

XVIIIb

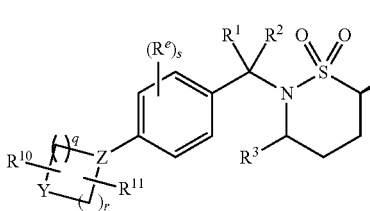

wherein p, q, r, s, Y, Z, $R^1$, $R^2$, $R^3$, $R^9$, $R^{10}$, $R^{11}$ and $R^e$, and the group

are as defined herein.

In certain embodiments, the subject compounds are of formula XVIIIa.

In certain embodiments, the subject compounds are of formula XVIIIb.

In certain embodiments of formula I, the subject compounds may be of formula XIXa or XIXb:

XIXa

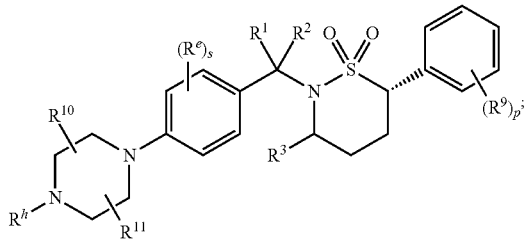

XIXb

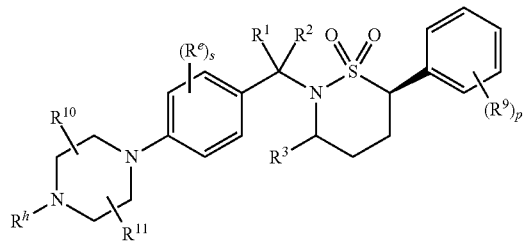

wherein m, n, p, s, $R^1$, $R^2$, $R^3$, $R^9$, $R^{10}$, $R^{11}$, $R^e$ and $R^h$ are as defined herein.

In certain embodiments, the subject compounds are of formula XIXa.

In certain embodiments, the subject compounds are of formula XIXb.

In certain embodiments of formula I, the subject compounds may be of formula XXa or XXb:

XXa

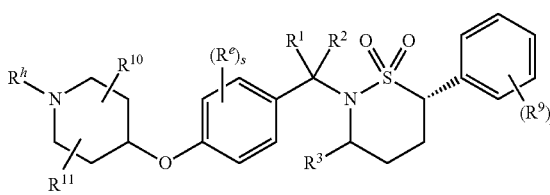

XXb

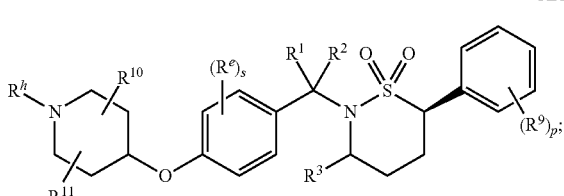

wherein m, n, p, s, $R^1$, $R^2$, $R^3$, $R^9$, $R^{10}$, $R^{11}$, $R^e$ and $R^h$ are as defined herein.

In certain embodiments, the subject compounds are of formula XXa.

In certain embodiments, the subject compounds are of formula XXb.

In certain embodiments of formula I, the subject compounds may be of formula XXIa or XXIb:

XXIa

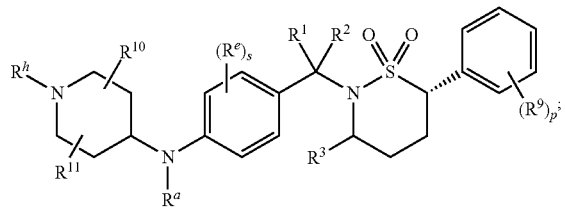

XXIb

wherein m, n, p, s, $R^1$, $R^2$, $R^3$, $R^9$, $R^{10}$, $R^{11}$, $R^a$, $R^e$ and $R^h$ are as defined herein.

In certain embodiments, the subject compounds are of formula XXIa.

In certain embodiments, the subject compounds are of formula XXIb.

In certain embodiments of formula I, the subject compounds may be of formula XXIIa or XXIIb:

XXIIa

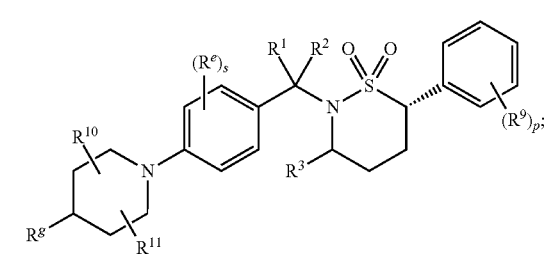

XXIIb

wherein m, n, p, s, $R^1$, $R^2$, $R^3$, $R^9$, $R^{10}$, $R^{11}$, $R^e$ and $R^g$ are as defined herein.

In certain embodiments, the subject compounds are of formula XXIIa.

In certain embodiments, the subject compounds are of formula XXIIb.

In certain embodiments, the subject compounds may be of one of formulas XXIIIa through XIIId:

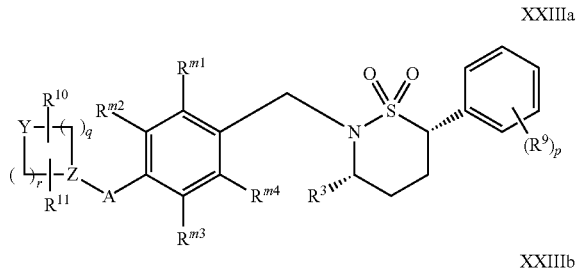

XXIIIa

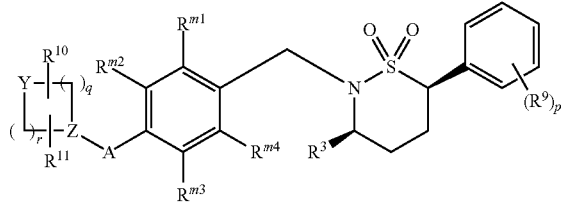

XXIIIb

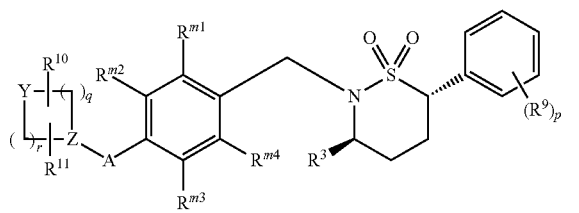

XXIIIc

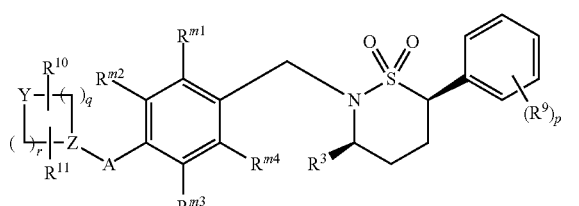

XXIIId

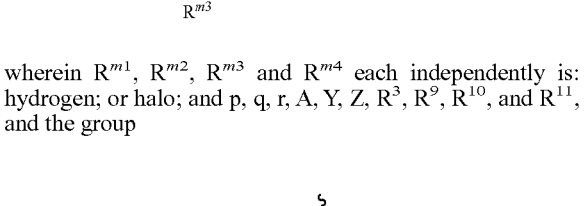

wherein $R^{m1}$, $R^{m2}$, $R^{m3}$ and $R^{m4}$ each independently is: hydrogen; or halo; and p, q, r, A, Y, Z, $R^3$, $R^9$, $R^{10}$, and $R^{11}$, and the group

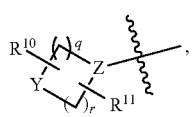

are as defined herein.

In certain embodiments, the subject compounds are of formula XXIIIa.

In certain embodiments, the subject compounds are of formula XXIIIb.

In certain embodiments, the subject compounds are of formula XXIIIc.

In certain embodiments, the subject compounds are of formula XXIIId.

In certain embodiments, $R^{m1}$, $R^{m2}$, $R^{m3}$ and $R^{m4}$ each independently is: hydrogen; or fluoro.

In certain embodiments, $R^{m1}$ is fluoro and $R^{m2}$, $R^{m3}$ and $R^{m4}$ are hydrogen.

In certain embodiments, $R^{m2}$ is fluoro and $R^{m1}$, $R^{m3}$ and $R^{m4}$ are hydrogen.

In certain embodiments, $R^{m3}$ is fluoro and $R^{m1}$, $R^{m2}$ and $R^{m4}$ are hydrogen.

In certain embodiments, $R^{m1}$ and $R^{m2}$ are fluoro and $R^{m3}$ and $R^{m4}$ are hydrogen.

In certain embodiments, $R^{m1}$ and $R^{m3}$ are fluoro and $R^{m2}$ and $R^{m4}$ are hydrogen.

In certain embodiments, $R^{m1}$ and $R^{m4}$ are fluoro and $R^{m2}$ and $R^{m3}$ are hydrogen.

In certain embodiments, $R^{m1}$, $R^{m2}$ and $R^{m4}$ are fluoro and $R^{m3}$ is hydrogen.

In certain embodiments, $R^{m1}$, $R^{m2}$, $R^{m3}$ and $R^{m4}$ are fluoro.

In certain embodiments, the subject compounds may be of one of formula XXIVa through XXIVd:

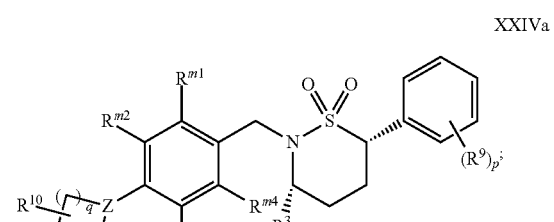

XXIVa

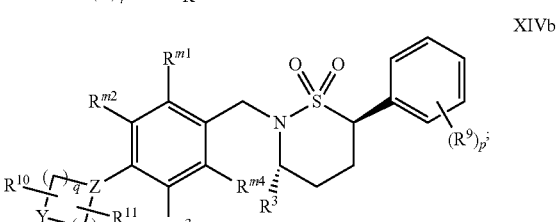

XIVb

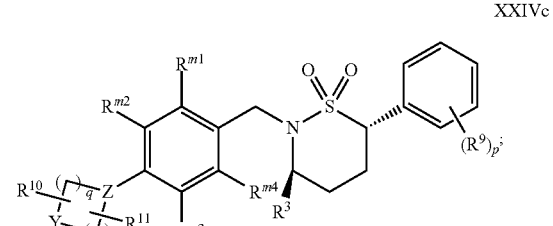

XXIVc

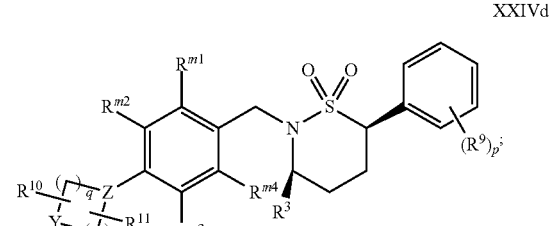

XXIVd wherein p, q, r, Y, Z, $R^3$, $R^9$, $R^{10}$, $R^{11}$, $R^{m1}$, $R^{m2}$, $R^{m3}$ and $R^{m4}$, and the group

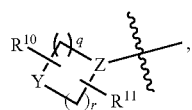

are as defined herein.

In certain embodiments, the subject compounds are of formula XXIXa.

In certain embodiments, the subject compounds are of formula XXIXb.

In certain embodiments, the subject compounds are of formula XXIXc.

In certain embodiments, the subject compounds are of formula XXIXd.

In certain embodiments of formula I, the subject compounds may be of one of formulas XXVa through XXVd:

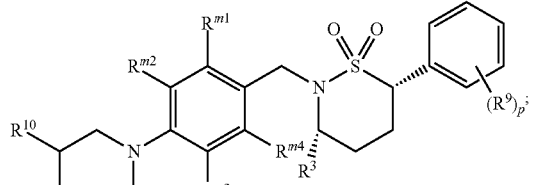

XXVa

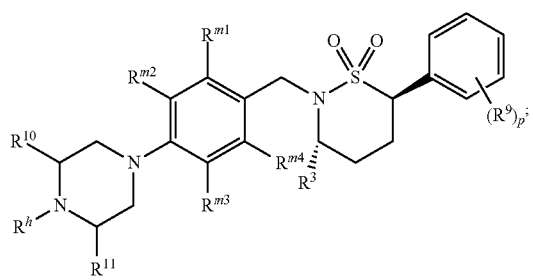

XXVb

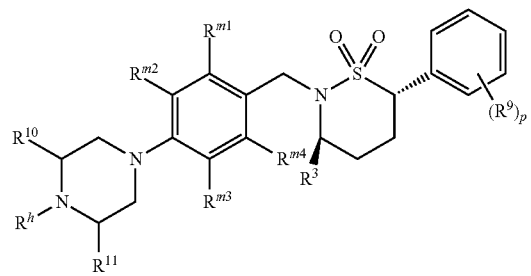

XXVc

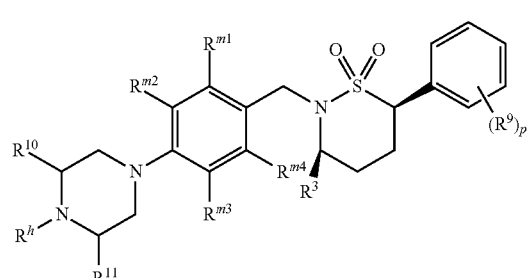

XXVd wherein p, $R^3$, $R^9$, $R^{10}$, $R^{11}$, $R^h$, $R^{m1}$, $R^{m2}$, $R^{m3}$, and $R^{m4}$ are as defined herein.

In certain embodiments, the subject compounds are of formula XXVa.

In certain embodiments, the subject compounds are of formula XXVb.

In certain embodiments, the subject compounds are of formula XXVc.

In certain embodiments, the subject compounds are of formula XXVd.

In certain embodiments of formula I, the subject compounds may be of one of formulas XXVIa through XXVId:

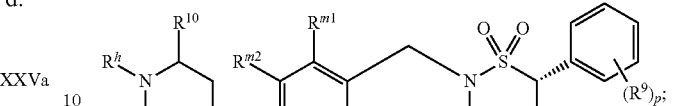

XXVIa

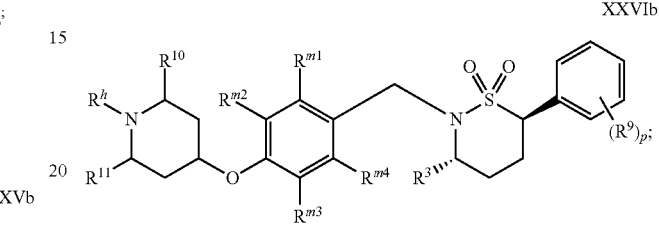

XXVIb

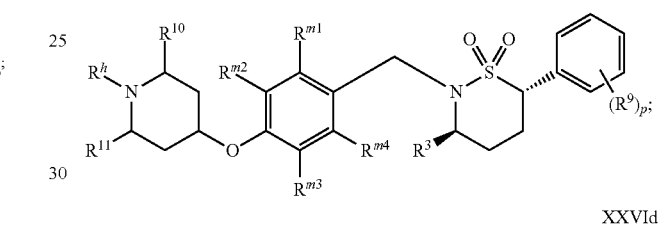

XXVIc

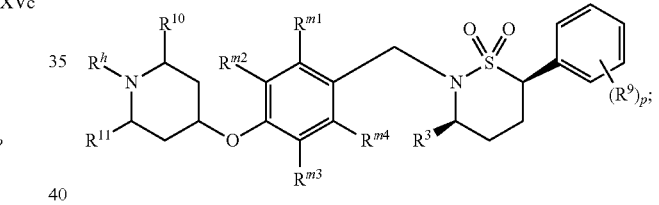

XXVId wherein p, $R^3$, $R^9$, $R^{10}$, $R^{11}$, $R^h$, $R^{m1}$, $R^{m2}$, $R^{m3}$ and $R^{m4}$ are as defined herein.

In certain embodiments, the subject compounds are of formula XXVIa.

In certain embodiments, the subject compounds are of formula XXVIb.

In certain embodiments, the subject compounds are of formula XXVIc.

In certain embodiments, the subject compounds are of formula XXVId.

In certain embodiments of formula I, the subject compounds may be of one of formulas XXVIIa through XXVIId;

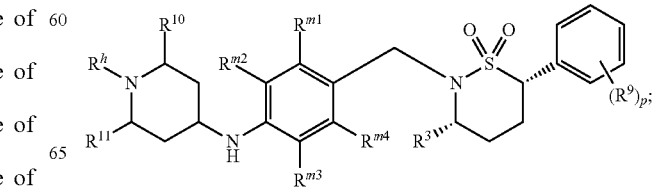

XXVIIa

-continued

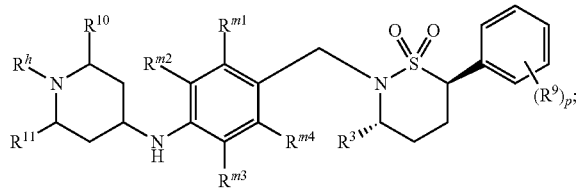
XXVIIb

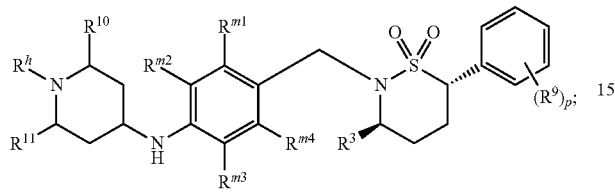
XXVIIc

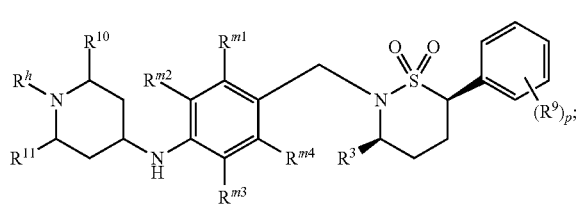
XXVIId wherein p, $R^3$, $R^9$, $R^{10}$, $R^{11}$, $R^h$, $R^{m1}$, $R^{m2}$, $R^{m3}$ and $R^{m4}$ are as defined herein.

In certain embodiments, the subject compounds are of formula XXVIIa.

In certain embodiments, the subject compounds are of formula XXVIIb.

In certain embodiments, the subject compounds are of formula XXVIIc.

In certain embodiments, the subject compounds are of formula XXVIId.

In certain embodiments of formula I, the subject compounds may be of one of formulas XXVIIIa through XXVIIId:

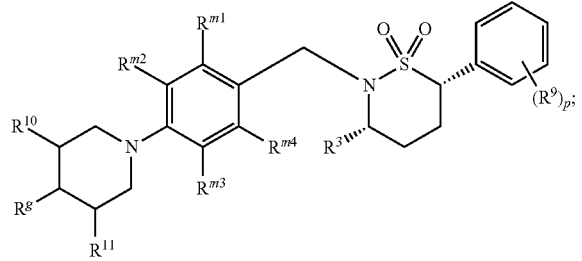
XVIIIa

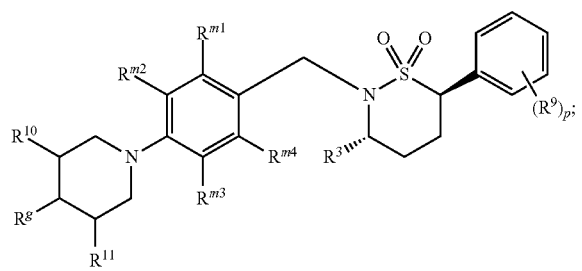
XXVIIIb

-continued

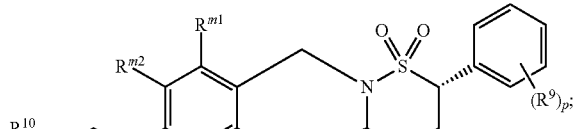
XXVIIIc

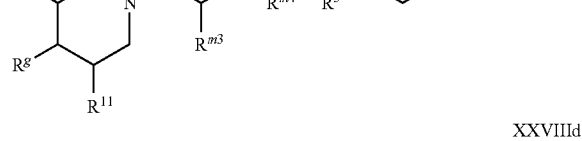
XXVIIId

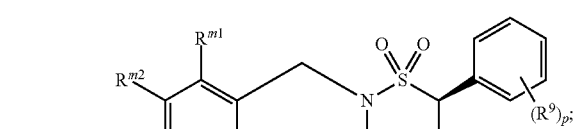

wherein p, $R^3$, $R^9$, $R^{10}$, $R^{11}$, $R^h$, $R^{m1}$, $R^{m2}$, $R^{m3}$ and $R^{m4}$ are as defined herein.

In certain embodiments, the subject compounds are of formula XXVIIIa.

In certain embodiments, the subject compounds are of formula XXVIIIb.

In certain embodiments, the subject compounds are of formula XXVIIIc.

In certain embodiments, the subject compounds are of formula XXVIIId.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis or osteoarthritis.

The disease may be asthma or COPD.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein LG is a leaving group such as halo, sulfonate, or the like, and m, n, p, q, A, $X^1$, $X^2$, $X^3$, $X^4$, $R^1$, $R^2$, $R^3$, $R^4$, $R^5$, $R^6$, $R^7$, $R^8$, $R^9$, $R^{10}$, $R^b$ and $R^c$ are as defined herein.

certain embodiments. Similarly, the chloro group of compound b may in certain embodiments be replaced by other halo or leaving group.

A cyclization reaction is carried out in step 2 to afford thiazinane compound d. The cyclization may be achieved in the presence of a strong base such as an alkyl lithium reagent, using polar aprotic solvent under anhydrous conditions.

In step 3, thiazinane compound c is reacted with aryalkyl halide compound e to yield aralkyl thiazinane f. The reaction of step 3 may be carried out in the presence of a strong base such as sodium hydride under anhydrous polar aprotic solvent conditions. The bromo groups of compound e may be replaced by other suitable leaving groups used in the art.

Thiazinane compound f may be treated with reagent g in step 4A to provide sultam compound h, which is a compound of formula I in accordance with the invention. In embodiments wherein A is oxygen such that reagent g is a cyclic

SCHEME A

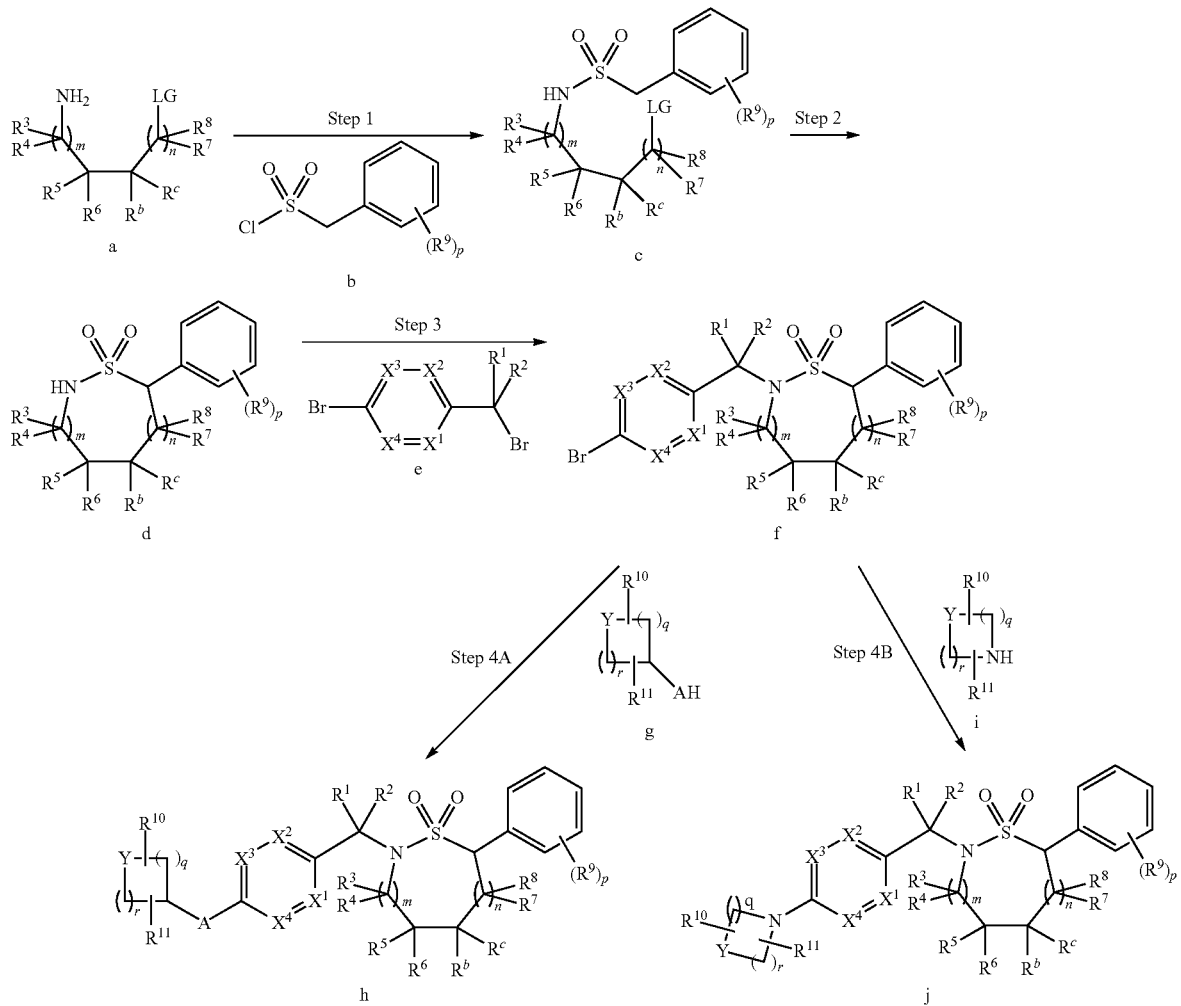

In step 1 of Scheme A, alkyl amine a is reacted with benzyl sulfonyl chloride b to form sulfonamide compound c. The reaction of step 1 may be carried out in a polar aprotic solvent such as THF or methylene chloride, and in the presence of a tertiary amine base or weak base such as potassium carbonate. The leaving group of compound a may be bromo in alcohol, the reaction of step 4A may utilize a copper catalyst with hydrophobic solvent, in the presence of cesium carbonate or like base.

Alternatively, step 4B may be carried out wherein Thiazinane compound f undergoes amination by reaction with cyclic amine i to afford sultam compound j, which is a compound of formula I in accordance with the invention. The reaction of step may utilize a suitable palladium catalyst under Buchwald reaction conditions.

Scheme B below shows another synthetic procedure usable to prepare specific compounds of formula I, wherein TBS is tri-(tert-butyl)-silyl, and m, n, p, q, A, $X^1$, $X^2$, $X^3$, $X^4$, Y, $R^1$, $R^2$, $R^3$, $R^4$, $R^5$, $R^6$, $R^9$ and $R^{10}$ are as defined herein.

m. In certain embodiments the tri-(tert-butyl)-slilyloxy group may be replaced with other leaving groups.

In step 2, sulfonamide compound m is reacted with iodochloromethane to provide an alkenylsulfonamide compound n. This reaction may be achieved in the presence of a strong base such as an alkyl lithium reagent, using polar aprotic solvent

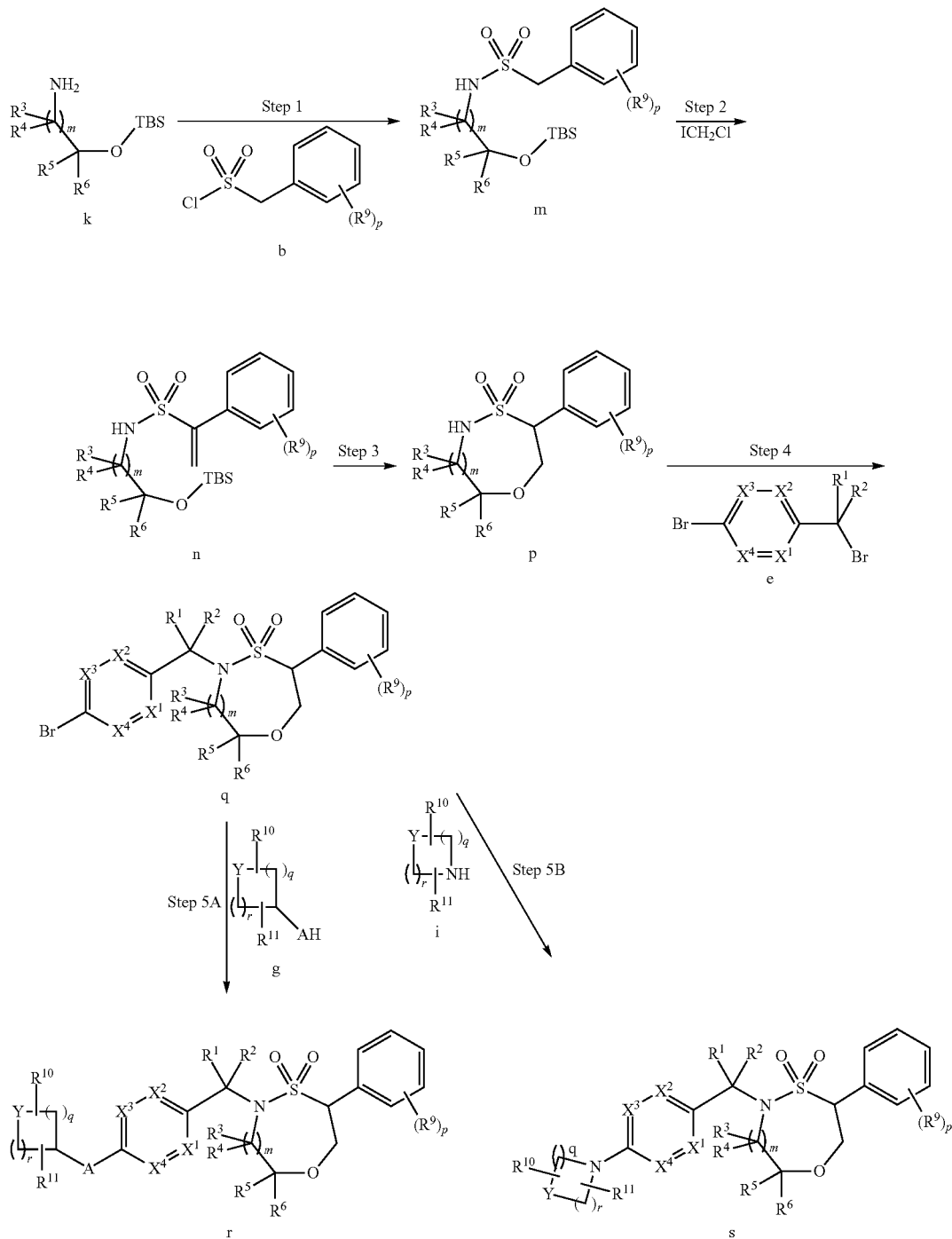

SCHEME B

In step 1 of Scheme B, tri-(tert-butyl)-slilyloxy amine k is reacted with benzyl sulfonyl chloride b, as described above with reference to Scheme A, to form sulfonamide compound such as THF under anhydrous conditions. In certain embodiments iodochloromethane may be replaced with other methylene reagents.

In step 3, a cyclization reaction is affected to provide oxathiazepane compound p. The cyclization may be carried out in the presence of an amine base under polar aprotic solvent conditions.

In step 4, oxathiazepane compound p is reacted with aryalkyl halide compound e to yield aralkyl oxathiazepane compound q, in the manner described above with reference to Scheme A.

Steps 5A or 5B may then be carried out by reaction of oxathiazepane compound q with reagents g and i respectively, in the manner described above with reference to Scheme A, to afford sultam compounds r and s respectively, which are compounds of formula I in accordance with the invention.

Many variations on the procedures of Scheme A and Scheme B are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally.

The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

List of Abbreviations
AcOH Acetic acid
AIBN 2,2′-Azobis(2-methylpropionitrile)
Atm. Atmosphere
$(BOC)_2O$ di-tert-Butyl dicarbonate
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1′-Bis(diphenylphosphino)ferrocene
$Et_2O$ Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N′,N′-tetramethyluronium hexafluorophosphate
HOBT 1-Hydroxybenzotriazole
HPLC High pressure liquid chromatography
RP HPLC Reverse phase high pressure liquid chromatography
i-PrOH Isopropanol/isopropyl alcohol
LCMS Liquid Chromatograph/Mass Spectroscopy
MeOH Methanol/Methyl alcohol
MW Microwaves
NBS N-Bromosuccinimide
NMP 1-Methyl-2-pyrrolidinone
PSI Pound per square inch
r.t. Room temperature
TBDMS tert-Butyldimethylsilyl
TFA Trifluoroacetic acid
THF Tetrahydrofuran
TLC Thin layer chromatography Preparations 1 and 2: (3R)-3-Aminobutan-1-ol and (3S)-3-Aminobutan-1-ol

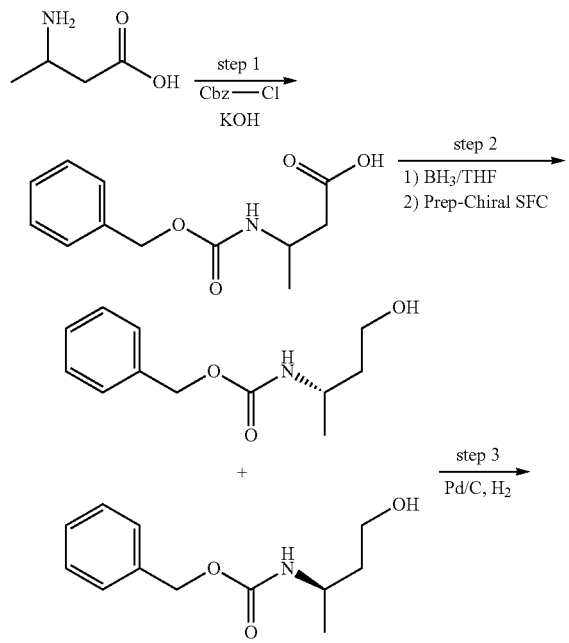

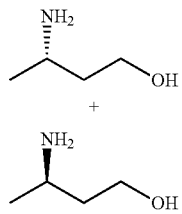

Step 1 3-[[(Benzyloxy)carbonyl]amino]butanoic acid

Into a 2000-mL 4-necked round-bottom flask was placed a solution of 3-aminobutanoic acid (100 g, 969.75 mmol, 1.00 equiv) in water (1000 mL), followed by the addition of potassium hydroxide (136 g, 2.42 mol, 2.50 equiv) in several batches. To this was added benzyl chloroformate (247 g, 1.45 mol, 1.50 equiv) dropwise with stirring at 0-5° C. The resulting solution was stirred at 25° C. for 5 h. The reaction progress was monitored by LCMS. The resulting solution was extracted with 3×250 mL of dichloromethane and the aqueous layers were combined. The pH value of the water phase was adjusted to 3 with hydrogen chloride (2 mol/L). The precipitates were collected by filtration and dried to afford 102 g (44%) of 3-[[(benzyloxy)carbonyl]amino]butanoic acid as a white solid.

Step 2: Benzyl N-[(2S)-4-hydroxybutan-2-yl]carbamate and Benzyl N-[(2R)-4-hydroxybutan-2-yl]carbamate Into a 2000-mL 3-necked round-bottom flask purged and maintained with an inert atmosphere of nitrogen was placed a solution of 3-[[(benzyloxy)carbonyl]amino]butanoic acid (102 g, 429.92 mmol, 1.00 equiv) in THF (300 mL), followed by the addition of $BH_3$/THF (1N) (645 mL, 1.50 equiv) dropwise with stirring at 0-5° C. The resulting solution was stirred at 40° C. for 2 h, quenched by the addition of 200 mL of methanol and concentrated under vacuum. The residue was purified on a silica gel column eluting with ethyl acetate: petroleum ether (1:2). The crude product (70 g) was purified by Prep-SFC with the following conditions (prep SFC): Column, Phenomenex Lux 5 u Cellulose-4, 2.12*25.5 um; mobile phase, $CO_2$ (85%), ethanol (15%); Detector, UV 254 nm. This resulted in 30 g (31.5%) of benzyl N-[(2R)-4-hydroxybutan-2-yl]carbamate as an off-white solid and 30 g (31.5%) of benzyl N-[(2S)-4-hydroxybutan-2-yl]carbamate as an off-white solid.

Step 3: (3R)-3-Aminobutan-1-ol and (3S)-3-Aminobutan-1-ol

Into a 1000-mL round-bottom flask was placed a solution of benzyl N-[(2S)-4-hydroxybutan-2-yl]carbamate (30 g, 134.4 mmol, 1.00 equiv) in methanol (500 mL) and palladium carbon (3 g, 0.10 equiv). The resulting solution was stirred at 25° C. for 12 h under an atmosphere of hydrogen. The solids were filtered out and the filtrate was concentrated under vacuum to afford 11.7 g (92%) of (3S)-3-aminobutan-1-ol as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]±; measured $[\alpha]_D^{20.2}$ +11.65° (C=1.22 g/100 mL in EtOH), lit. $[\alpha]_D^{20}$+16.3° (c=4.5 in EtOH) (J. Org. Chem. 1996, 61, 2293-2304.).

Using the above procedure, 12.0 g 12 g (94%) of (3R)-3-aminobutan-1-ol was isolated as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]±; measured $[\alpha]_D^{20.2}$ −11.1° (C=0.32 g/100 mL in EtOH), lit. $[\alpha]_D^{25}$ −25° (c=1.25 in EtOH) (*Tetrahedron: Asymmetry* 1999, 10, 2213-2224.).

Preparation 3: (R)—N-(4-Chlorobutan-2-yl)-1-phenylmethanesulfonamide

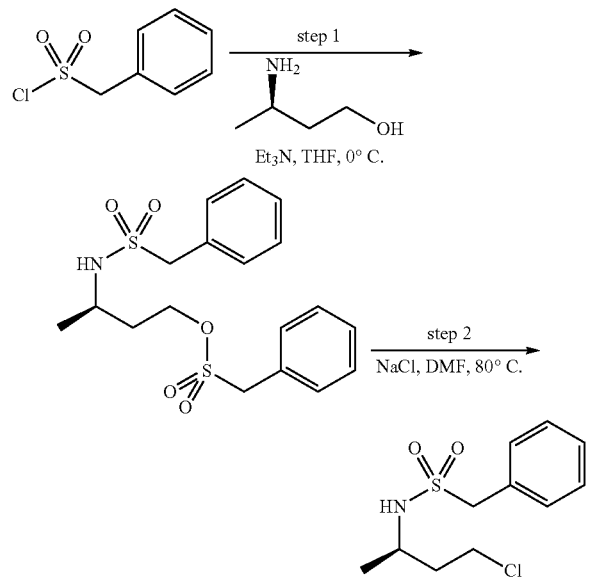

Step 1: (R)-3-(Phenylmethylsulfonamido)butyl phenylmethanesulfonate

To a solution of (3R)-3-aminobutan-1-ol (1.0 g, 11.2 mmol) and triethylamine (3.3 mL, 23.6 mmol) in tetrahydrofuran (37 mL) at 0° C. was slowly added phenylmethanesulfonyl chloride (4.49 g, 23.6 mmol) and the reaction was stirred at room temperature for 16 hours. MTBE (100 mL) was then added and the Et₃N.HCl salt was removed by filtration. The filtrate was then concentrated to give crude (R)-3-(phenylmethylsulfonamido)butyl phenylmethanesulfonate which was used without purification. LCMS (ESI), m/z, 398 [M+H]+.

Step 2: (R)—N-(4-Chlorobutan-2-yl)-1-phenylmethanesulfonamide

To the crude (R)-3-(phenylmethylsulfonamido)butyl phenylmethanesulfonate (23.6 mmol) was added sodium chloride (984 mg, 16.8 mmol) and dimethylformamide (37 mL) and the reaction was stirred at 80° C. for 16 hours. The reaction was then diluted with EtOAc, washed with water (×2) and brine, dried with MgSO₄, concentrated and purified by silica gel column chromatography (0-50% Acetone in Heptane, 216 nM) to give (R)—N-(4-chlorobutan-2-yl)-1-phenylmethanesulfonamide (1.71 g, 6.53 mmol, 58% yield over 2 steps). LCMS (ESI), m/z, 261 [M+H]+.

Additional compounds made using the above procedure are shown in Table 1.

TABLE 1

| | Structure | Name | LCMS (ESI), m/z, [M + H]+ |
|---|---|---|---|
| 4 | 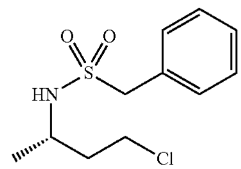 [SMILES: C[C@@H](CCCl)NS(=O)(=O)Cc1ccccc1] | (S)-N-(4-chlorobutan-2-yl)-1-phenylmethanesulfonamide | 261 |
| 5 | 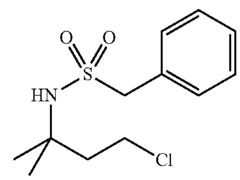 [SMILES: CC(C)(CCCl)NS(=O)(=O)Cc1ccccc1] | N-(4-chloro-2-methyl-butan-2-yl)-1-phenyl-methanesulfonamide | 275 |
| 6 | 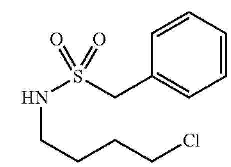 [SMILES: O=S(=O)(Cc1ccccc1)NCCCCCl] | N-(4-chlorobutyl)-1-phenylmethanesulfonamide | 261 |

Preparation 7: N-(2-bromoethyl)(phenyl)methanesulfonamide

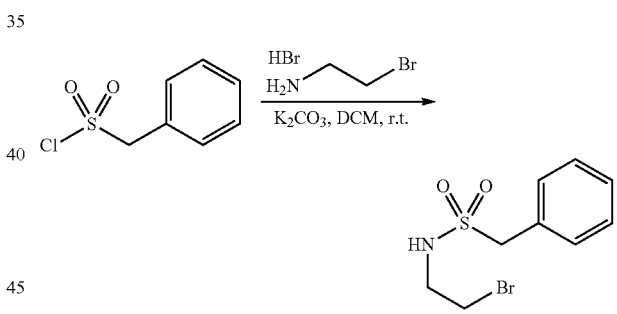

K₂CO₃ (8.7 g, 62 mmol) was added into a mixture of phenylmethanesulfonyl chloride (6 g, 31 mmol) and 2-bromoethanamine hydrobromide (6.4 g, 31 mmol) in DCM (100 mL) at 0° C. And the resulting mixture was stirred at r.t. for 4 hours and left standing overnight. Upon the completion of reaction, water (100 mL) was added in and DCM phase was separated. The aqueous phase was extracted with DCM. The combined organic phase was dried over Na₂SO₄, filtered and concentrated in vacuo to provide a crude which was separated with column chromatography (silica gel with 200-300 mesh, 0 to 50% of EtOAc in petroleum ether) to provide compound N-(2-bromoethyl)(phenyl)methanesulfonamide (7.0 g, 80%) as a pale yellow solid. ¹H NMR (300 MHz, CDCl₃) δ 7.40 (m, 5H), 4.58 (m, 1H), 4.29 (s, 2H), 3.34-3.29 (m, 4H). LCMS (ESI), 300, 302 [M+Na]+, Br pattern found.

Preparation 8
N-(2-bromoethyl)(4-fluorophenyl)methanesulfonamide

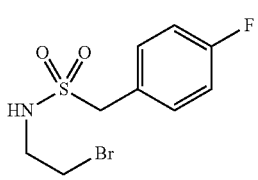

N-(2-bromoethyl)(4-fluorophenyl)methanesulfonamide was also made using the above procedure, replacing phenylmethanesulfonyl chloride with 4-fluoro-phenylmethanesulfonyl chloride. $^1$H NMR (300 MHz, CDCl$_3$) δ 7.43-7.38 (m, 2H), 7.13-7.07 (m, 2H), 4.62 (br s, 1H), 4.26 (s, 2H), 3.41-3.32 (m, 4H).

Preparation 9:
N-(3-bromopropyl)(phenyl)methanesulfonamide

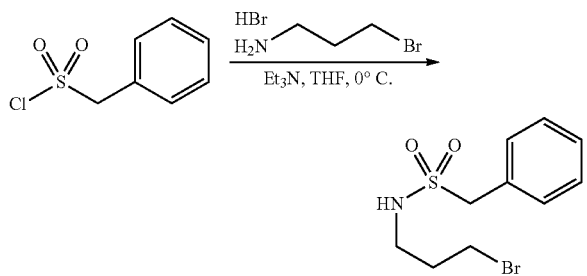

A solution of phenylmethanesulfonyl chloride (2.19 g, 10 mmol) was added into a suspension of 3-bromopropan-1-amine hydrobromide (2.19 g, 10 mmol) and Et$_3$N (2.02 g, 20 mmol) in THF (50 mL) at 0° C. The mixture was stirred at 0° C. for 5 min. TLC confirmed the completion of reaction. Solid was filtered out with suction, and the filtrate was concentrated to provide compound N-(3-bromopropyl)(phenyl)methanesulfonamide (2.7 g, quant.) as a pale yellow solid which was used in the next step without further purification. $^1$H NMR (300 MHz, CDCl$_3$) δ 7.40 (m, 5H), 4.48 (m, 1H), 4.27 (s, 2H), 3.41 (t, J=6.6 Hz, 2H), 3.16 (q, 2H), 2.01 (m, 2H). LCMS (ESI), m/z, 314 and 316 [M+Na]+, Br pattern found.

Preparation 10: N-(3-bromopropyl)(4-fluorophenyl)methanesulfonamide

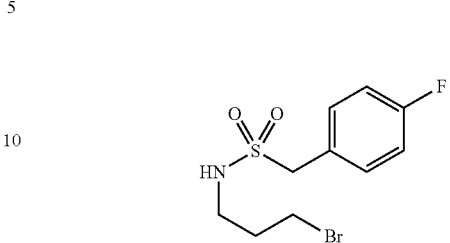

N-(3-bromopropyl)(4-fluorophenyl)methanesulfonamide was prepared using the above procedure. $^1$H NMR (300 MHz, CDCl$_3$) δ 7.42-7.37 (m, 2H), 7.13-7.07 (m, 2H), 4.26 (m, 1H), 4.24 (s, 2H), 3.46-3.42 (m, 2H), 3.20-3.16 (m, 2H), 2.05-2.00 (m, 2H).

Preparation 11: 6-Phenyl-1,2-thiazinane 1,1-dioxide

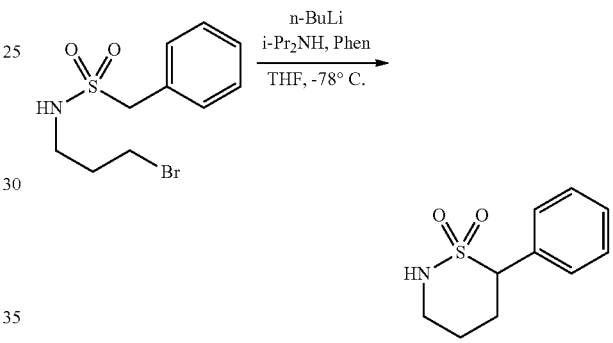

To a solution of N-(3-bromopropyl)-1-phenylmethanesulfonamide (2.3 g, 7.9 mmol), diisopropylamine (0.28 mL, 2.0 mmol) and 1,10-phenanthroline (3.6 mg, 0.02 mmol) in tetrahydrofuran (26 mL) at −78° C. was added n-BuLi (6.8 mL, 2.5 M in hexanes) dropwise and the reaction was stirred for 16 hours. Saturated NH$_4$Cl was then added and the reaction was diluted with EtOAc, washed with water and brine, dried with MgSO$_4$, concentrated and purified by silica gel column chromatography (0-50% EtOAc/heptane) to 6-Phenyl-1,2-thiazinane 1,1-dioxide (1.3 g, 80% yield). $^1$H NMR (300 MHz, DMSO-d$_6$) δ 7.40-7.35 (m, 5H), 6.98 (m, 1H), 4.12 (dd, 1H), 3.26-3.20 (m, 2H), 2.40-2.30 (m, 1H), 2.16-2.12 (m, 1H), 1.77-1.65 (m, 2H). LCMS (ESI), m/z, 234 [M+Na]+. (Reference: D. Askin, et al. Org. Lett. 2003, 4175.)

Additional compounds made using the above procedure are shown in Table 2.

TABLE 2

| | Structure | Name | LCMS (ESI), m/z, [M + H]+ |
|---|---|---|---|
| 12 | 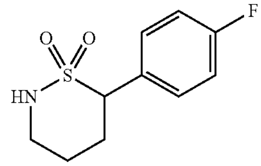 [SMILES: O=S1(=O)NCCCC1c1ccc(F)cc1] | 6-(4-fluorophenyl)-1,2-thiazinane 1,1-dioxide | 230 |

TABLE 2-continued

| | Structure | Name | LCMS (ESI), m/z, [M + H]+ |
|---|---|---|---|
| 13 | 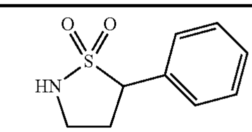 | 5-phenylisothiazolidine 1,1-dioxide | 198 |
| 14 | 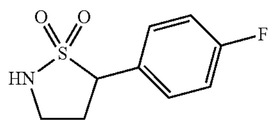 [SMILES: O=S1(=O)NCCC1c1ccc(F)cc1] | 5-(4-fluorophenyl)isothiazolidine 1,1-dioxide | 216 |
| 15 | 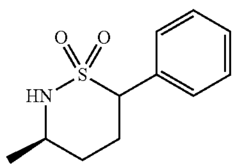 | (3R)-3-methyl-6-phenyl-1,2-thiazinane 1,1-dioxide | 226 |
| 16 | 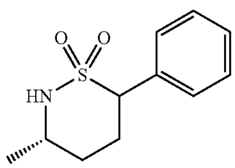 | (3S)-3-methyl-6-phenyl-1,2-thiazinane 1,1-dioxide | 226 |
| 17 | 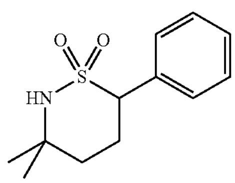 [SMILES: CC1(C)CCC(c2ccccc2)S(=O)(=O)N1] | 3,3-dimethyl-6-phenyl-1,2-thiazinane 1,1-dioxide | 240 |
| 18 | 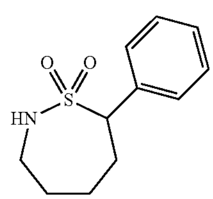 [SMILES: O=S1(=O)NCCCCC1c1ccccc1] | 7-phenyl-1,2-thiazepane 1,1-dioxide | 226 |

Preparation 19: 3-Phenyl-1,4,5-oxathiazepane 4,4-dioxide

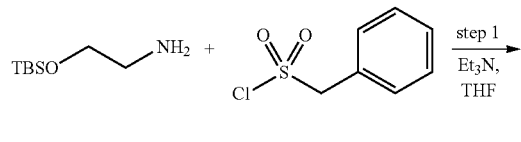

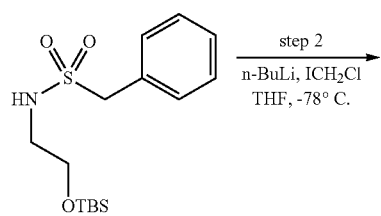

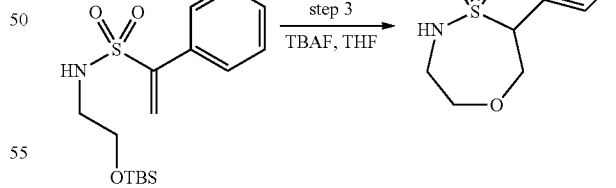

Step 1: N-(2-((Tert-butyldimethylsilyl)oxy)ethyl)-1-phenylmethanesulfonamide To a solution of 2-((tert-butyldimethylsilyl)oxy)ethanamine (11.7 g, 66.6 mmol) and triethylamine (11.2 mL, 79.9 mmol) in tetrahydrofuran (222 mL) at 0° C. was slowly added phenylmethanesulfonyl chloride (12.7 g, 66.6 mmol) portionwise and the reaction was stirred at room temperature for 16 hours. MTBE was then added and the Et₃N.HCl salt was removed by filtration. The filtrate was then concentrated and purified by silica gel column chromatography (0-30% Acetone in heptane, 216 nM) to N-(2-((tert-butyldimethylsilyl)oxy)ethyl)-1-phenylmethanesulfonamide (17.8 g, 81% yield). LCMS (ESI), m/z, 330. [M+H]+.

Step 2: N-(2-((Tert-butyldimethylsilyl)oxy)ethyl)-1-phenylethenesulfonamid

To a solution of N-[2-[tert-butyl(dimethyl)silyl]oxyethyl]-1-phenyl-methanesulfonamide (33 g, 100.2 mmol) in tetrahydrofuran (334 mL) at −78° C. was slowly added n-BuLi (2.5 M in hexanes) (100 mL, 250 mmol) via cannula and the reaction was stirred at −78° C. was 2 hours. Chloroiodomethane (8.3 mL, 110 mmol) was then slowly added and the reaction was stirred at −78° C. for one hour, then allowed to warm to room temperature and aged for 16 hours. The reaction was then quenched with saturated NH₄Cl and extracted with dichloromethane, dried with MgSO₄, concentrated and purified by silica gel column chromatography (0-60% EtOAc in heptane) to give N-[2-[tert-butyl(dimethyl)silyl]oxyethyl]-1-phenyl-ethenesulfonamide (24 g, 70% yield). LCMS (ESI), m/z, 342. [M+H]+.

Step 3: 3-Phenyl-1,4,5-oxathiazepane 4,4-dioxide

To a solution of N-(2-((Tert-butyldimethylsilyl)oxy)ethyl)-1-phenylethenesulfonamide (717 mg, 2.1 mmol) in tetrahydrofuran (7 mL) at 0° C. was added tetrabutylammonium fluoride (1.0 M in THF) (2.2 mL, 2.2 mmol) dropwise and the reaction was stirred at room temperature for 16 hours. Saturated NH₄Cl was then added and the product was extracted with dichloromethane (×2), dried with MgSO₄, concentrated and purified by silica gel column chromatography (0-100% EtOAc in heptane) to give 3-phenyl-1,4,5-oxathiazepane 4,4-dioxide (401 mg, 84% yield). (24 g, 70% yield). LCMS (ESI), m/z, 228. [M+H]+. (Reference: P. Hansen, et al. Org. Lett. 2008, 2951).

Additional compounds made using the above procedure are shown in Table 3.

TABLE 3

| | Structure | Name | LCMS (ESI), m/z, [M + H]+ |
|---|---|---|---|
| 20 | 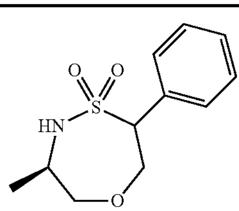 | (6R)-6-methyl-3-phenyl-1,4,5-oxathiazepane 4,4-dioxide | 242 |
| 21 | 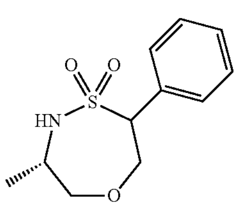 [SMILES: C[C@H]1COCC(c2ccccc2)S(=O)(=O)N1] | (6S)-6-methyl-3-phenyl-1,4,5-oxathiazepane 4,4-dioxide | 242 |
| 22 | | (7S)-7-methyl-3-phenyl-1,4,5-oxathiazepane 4,4-dioxide | 242 |
| 23 | | (7R)-7-methyl-3-phenyl-1,4,5-oxathiazepane 4,4-dioxide | 242 |

Examples 1 and 2

(R)-1-(4-(4-((1,1-Dioxido-6-phenyl-1,2-thiazinan-2-yl)methyl)-3-fluorophenyl)piperazin-1-yl)ethanone and (S)-1-(4-(4-((1,1-Dioxido-6-phenyl-1,2-thiazinan-2-yl)methyl)-3-fluorophenyl)piperazin-1-yl)ethanone

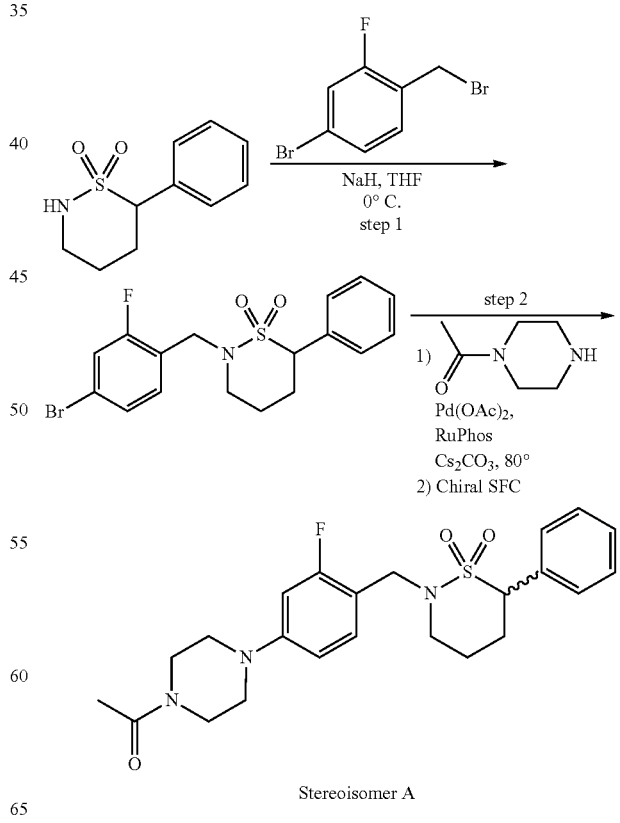

Stereoisomer A

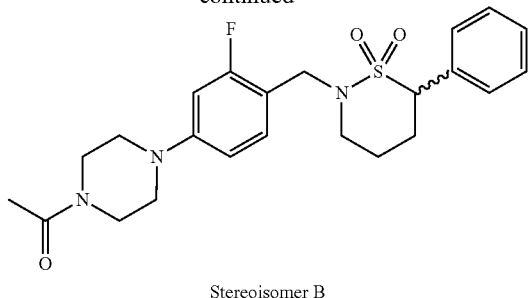

Stereoisomer B

Step 1: 2-(4-Bromo-2-fluorobenzyl)-6-phenyl-1,2-thiazinane 1,1-dioxide

To a solution of 6-phenyl-1,2-thiazinane 1,1-dioxide (300 mg, 1.42 mmol) and 4-bromo-1-(bromomethyl)-2-fluorobenzene (456 mg, 1.7 mmol) in N,N-dimethylacetamide (5 mL) at 0° C. was added sodium hydride (60% in mineral oil) (68 mg, 1.85 mmol) and the reaction was stirred at room temperature for 2 hours. Water was added and the reaction was diluted with EtOAc, washed with brine, dried with MgSO$_4$, filtered and purified by silica gel column chromatography (0-60% EtOAc/heptane) to give 2-(4-bromo-2-fluorobenzyl)-6-phenyl-1,2-thiazinane 1,1-dioxide (396 mg, 70% yield). LCMS (ESI), m/z, 398 [M+H]+.

Step 2: (R)-1-(4-(4-(((1,1-Dioxido-6-phenyl-1,2-thiazinan-2-yl)methyl)-3-fluorophenyl)piperazin-1-yl)ethanone and (S)-1-(4-(4-(((1,1-Dioxido-6-phenyl-1,2-thiazinan-2-yl)methyl)-3-fluorophenyl)piperazin-1-yl)ethanone 2-[(4-Bromo-2-fluoro-phenyl)methyl]-6-phenyl-thiazinane 1,1-dioxide (208 mg, 0.52 mmol), Pd(OAc)$_2$ (5.8 mg, 0.026 mmol), 2-dicyclohexylphosphine-2',6'-di-iso-propoxy-1,1'-biphenyl (24.8 mg, 0.052 mmol) and cesium carbonate (254 mg, 0.78 mmol) were weighed out in a vial and the vial was purged with nitrogen. 1,4-Dioxane (2.5 mL) and 1-piperazin-1-ylethanone (100 mg, 0.78 mmol) were then added and the reaction was stirred at 80° C. for 2 hours. The reaction was then filtered through diatomaceous earth, concentrated and purified by reverse-phase HPLC to give 1-(4-(4-(((1,1-dioxido-6-phenyl-1,2-thiazinan-2-yl)methyl)-3-fluorophenyl)piperazin-1-yl)ethanone (210 mg, 89% yield).

The racemic mixture (150 mg) was separated by chiral SFC to give 1-(4-(4-(((1,1-dioxido-6-phenyl-1,2-thiazinan-2-yl)methyl)-3-fluorophenyl)piperazin-1-yl)ethanone as isolated stereoisomers in separate fractions: (ISOMER A) as a first fraction (50 mg, 33% yield) and 1-(4-(4-[1,1-d]oxido-6-phenyl-1,2-thiazinan-2-yl)methyl)-3-fluorophenyl)piperazin-1-yl)ethanone (ISOMER B) as a second fraction (77 mg, 51% yield):

1-(4-(4-(((1,1-dioxido-6-phenyl-1,2-thiazinan-2-yl)methyl)-3-fluorophenyl)piperazin-1-yl)ethanone (Stereoisomer A): $^1$H NMR (400 MHz, DMSO) δ 7.49-7.31 (m, 5H), 7.26 (t, J=8.8 Hz, 1H), 6.86-6.73 (m, 2H), 4.49 (dd, J=12.6, 3.2 Hz, 1H), 4.35 (q, J=14.4 Hz, 2H), 3.63-3.51 (m, 4H), 3.46 (t, J=12.9 Hz, 1H), 3.28-3.19 (m, 2H), 3.19-3.04 (m, 3H), 2.48-2.35 (m, 1H), 2.22-2.07 (m, 1H), 2.04 (s, 3H), 2.01-1.87 (m, 1H), 1.72-1.49 (m, 1H). LCMS (ESI), m/z, 446.1 [M+H]+.

1-(4-(4-(((1,1-dioxido-6-phenyl-1,2-thiazinan-2-yl)methyl)-3-fluorophenyl)piperazin-1-yl)ethanone (Stereoisomer B): $^1$H NMR (400 MHz, DMSO) δ 7.49-7.31 (m, 5H), 7.26 (t, J=8.8 Hz, 1H), 6.86-6.73 (m, 2H), 4.49 (dd, J=12.6, 3.2 Hz, 1H), 4.35 (q, J=14.4 Hz, 2H), 3.63-3.51 (m, 4H), 3.46 (t, J=12.9 Hz, 1H), 3.28-3.19 (m, 2H), 3.19-3.04 (m, 3H), 2.48-2.35 (m, 1H), 2.22-2.07 (m, 1H), 2.04 (s, 3H), 2.01-1.87 (m, 1H), 1.72-1.49 (m, 1H). LCMS (ESI), m/z, 446.1 [M+H]+.

Examples 3 and 4

(S)-2-(2-Fluoro-4-((1-(methylsulfonyl)piperidin-4-yl)oxy)benzyl)-6-phenyl-1,2-thiazinane 1,1-dioxide and (R)-2-(2-Fluoro-4-((1-(methylsulfonyl)piperidin-4-yl)oxy)benzyl)-6-phenyl-1,2-thiazinane 1,1-dioxide

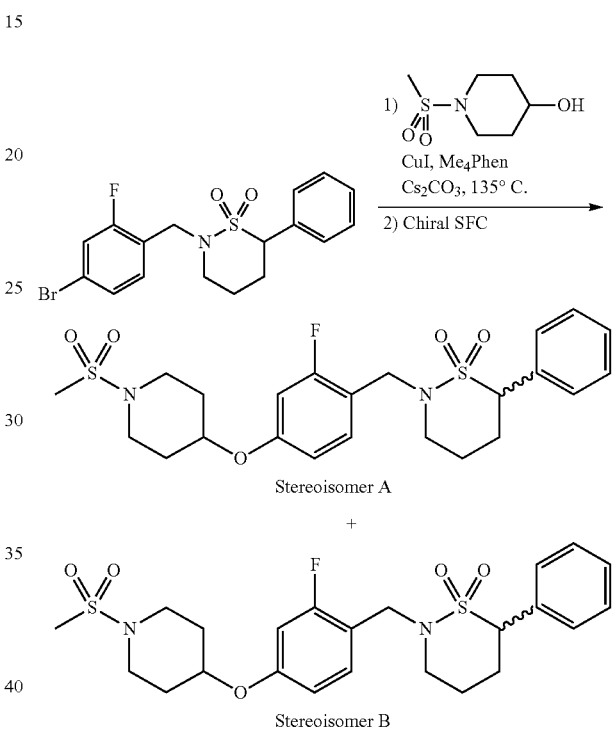

Stereoisomer A

+

Stereoisomer B 2-(4-bromo-2-fluorobenzyl)-6-phenyl-1,2-thiazinane 1,1-dioxide (100 mg, 0.25 mmol), 1-methylsulfonylpiperidin-4-ol (67.2 mg, 0.38 mmol), copper(I) iodide (9.5 mg, 0.05 mmol), 3,4,7,8-tetramethyl-1,10-phenanthroline (24 mg, 0.1 mmol) and cesium carbonate (123 mg, 0.38 mmol) were weighed out in a vial and the vial was purged with nitrogen. p-Xylene (1 mL) was then added and the reaction was stirred at 135° C. for 16 hours. The reaction was then filtered through diatomaceous earth, concentrated and purified by reverse-phase HPLC to give 2-(2-fluoro-4-((1-(methylsulfonyl)piperidin-4-yl)oxy)benzyl)-6-phenyl-1,2-thiazinane 1,1-dioxide (50.1 mg, 40% yield).

The racemic mixture (40 mg) was separated by chiral SFC to give 2-(2-fluoro-4-((1-(methylsulfonyl)piperidin-4-yl)oxy)benzyl)-6-phenyl-1,2-thiazinane 1,1-dioxide as isolated stereoisomers in separate fractions: ISOMER A as a first fraction (11.4 mg, 29% yield) and ISOMER B as a second fraction (11.6 mg, 29% yield).

1-(4-(4#1,1-dioxido-6-phenyl-1,2-thiazinan-2-yl)methyl)-3-fluorophenyl)piperazin-1-yl)ethanone (Stereoisomer A): $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.91 (s, 3H), 2.48-2.39 (m, 1H), 2.21-2.08 (m, 1H), 2.08-1.91 (m, 3H), 1.82-1.68 (m, 2H), 1.68-1.57 (m, 1H). LCMS (ESI), m/z, 497.1 [M+H]+.

1-(4-(4#1,1-dioxido-6-phenyl-1,2-thiazinan-2-yl)methyl)-3-fluorophenyl)piperazin-1-yl)ethanone (Stereoisomer B): $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.91 (s, 3H), 2.48-2.39 (m, 1H), 2.21-2.08 (m, 1H), 2.08-1.91 (m, 3H), 1.82-1.68 (m, 2H), 1.68-1.57 (m, 1H). LCMS (ESI), m/z, 497.1 [M+H]+.

Example 5

(3S)-2-[[2-Fluoro-4-[4-(1,2,4-triazol-4-yl)-1-piperidyl]phenyl]methyl]-3-methyl-6-phenyl-thiazinane 1,1-dioxide

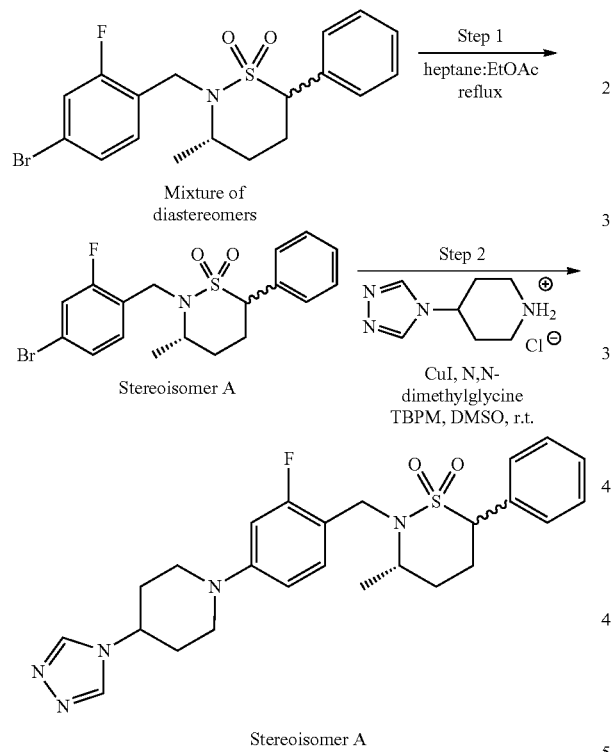

Step 1 (3S)-2-[(4-Bromo-2-fluoro-phenyl)methyl]-3-methyl-6-phenyl-thiazinane 1,1-dioxide (3S)-2-(4-bromo-2-fluorobenzyl)-3-methyl-6-phenyl-1,2-thiazinane 1,1-dioxide (40 g, 97 mmol, 15:85 mixture of cis/trans isomers, prepared as described in Step 1 of Example 1) was suspended in heptane (750 mL) and the suspension was heated to reflux. Ethyl acetate was slowly added until complete dissolution of the material occurred (250 mL). The solution was then subjected to a hot filtration, cooled to room temperature and store at 4° C. for 16 hours. Crystals were collected by filtration to give (3S)-2-[(4-bromo-2-fluoro-phenyl)methyl]-3-methyl-6-phenyl-thiazinane 1,1-dioxide Stereoisomer A (30 g, 73 mmol, 72% yield). $^1$H NMR (300 MHz, DMSO) δ 7.55-7.31 (m, 8H), 4.61-4.43 (m, 2H), 4.41-4.29 (m, 1H), 4.23-4.00 (m, 1H), 2.48-2.34 (m, 1H), 2.18-2.03 (m, 1H), 1.92-1.72 (m, 1H), 1.72-1.58 (m, 1H), 1.12-1.03 (d, J=6.8 Hz, 3H); LCMS [M+1]+=412.1.

Step 2 (3S)-2-[[2-Fluoro-4-[4-(1,2,4-triazol-4-yl)-1-piperidyl]phenyl]methyl]-3-methyl-6-phenyl-thiazinane 1,1-dioxide A vial was charged with (3S)-2-[(4-bromo-2-fluoro-phenyl)methyl]-3-methyl-6-phenyl-thiazinane 1,1-dioxide (250 mg, 0.61 mmol), 4-(1,2,4-triazol-4-yl)piperidine hydrochloride (172 mg, 0.91 mmol), cuprous iodide (35 mg, 0.18 mmol), N,N-dimethylglycine (38 mg, 0.36 mmol) and tetrabutylphosphonium malonate (1.3 g, 1.9 mmol) and the vial was purged with nitrogen for. Dimethyl sulfoxide (3 mL) was then added and the vial was purged with nitrogen for an additional 2 minutes. The reaction mixture was then sonicated for 5 minutes and stirred at 45° C. for 20 hours. The DMSO solution was then directly purified by preparative HPLC to give (3S)-2-[[2-fluoro-4-[4-(1,2,4-triazol-4-yl)-1-piperidyl]phenyl]methyl]-3-methyl-6-phenyl-thiazinane 1,1-dioxide Stereoisomer A (109 mg, 0.23 mmol, 37% yield) as a white solid. $^1$H NMR (400 MHz, DMSO) δ 8.66-8.62 (s, 2H), 7.49-7.43 (m, 2H), 7.43-7.29 (m, 4H), 6.87-6.82 (m, 1H), 6.80-6.73 (m, 1H), 4.49-4.24 (m, 4H), 4.15-4.04 (m, 1H), 3.90-3.80 (m, 2H), 2.89-2.77 (m, 2H), 2.47-2.35 (m, 1H), 2.15-2.04 (m, 3H), 2.04-1.89 (m, 2H), 1.88-1.74 (m, 1H), 1.70-1.60 (m, 1H), 1.14-1.05 (m, J=6.9 Hz, 3H); LCMS [M+1]$^+$=484.2.

Example 6

(3S)-2-[[2-fluoro-4-[4-(tetrazol-1-yl)-1-piperidyl]phenyl]methyl]-3-methyl-6-phenyl-thiazinane 1,1-dioxide

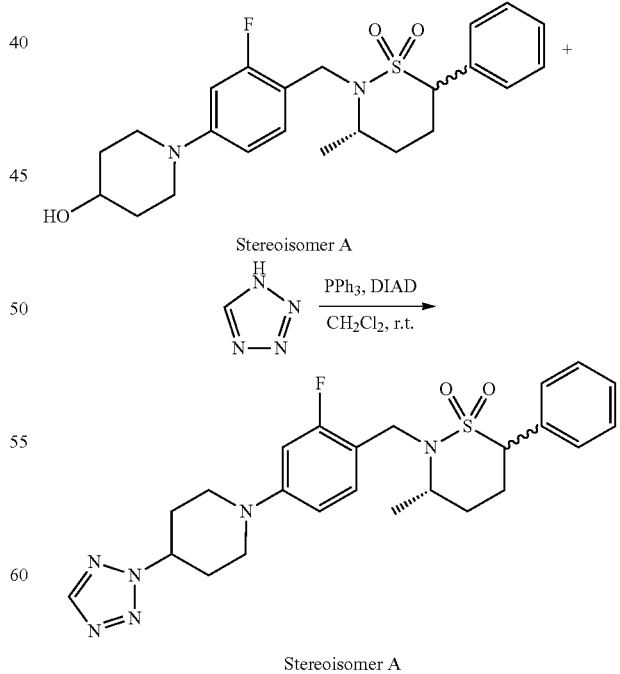

To a solution of 1-[3-fluoro-4-[[(3S)-3-methyl-1,1-dioxo-6-phenyl-thiazinan-2 yl]methyl]phenyl]piperidin-4-ol Stereoisomer A (200 mg, 0.46 mmol, prepared as described in Example 5), tetrazole (36 mg, 0.51 mmol) and triphenylphosphine (135 mg, 0.51 mmol) in dichloromethane (2.5 mL) was added diisopropyl azodicarboxylate (103 mg, 0.51 mmol) dropwise and the reaction was stirred at r.t. for 16 hours. The reaction was partitioned between water and dichloromethane and the organic layer was concentrated and purified by preparative HPLC to give (3S)-2-[[2-fluoro-4-[4-(tetrazol-1-yl)-1-piperidyl]phenyl]methyl]-3-methyl-6-phenyl-thiazinane 1,1-dioxide Stereoisomer A (57.4 mg, 0.12 mmol, 26% yield) as a white solid. $^1$H NMR (400 MHz, DMSO) δ 8.99-8.96 (s, 1H), 7.49-7.43 (m, 2H), 7.43-7.29 (m, 4H), 6.89-6.82 (m, 1H), 6.82-6.75 (m, 1H), 5.18-5.07 (m, 1H), 4.50-4.36 (m, 2H), 4.33-4.25 (m, 1H), 4.16-4.03 (m, 1H), 3.87-3.76 (m, 2H), 3.10-2.98 (m, 2H), 2.47-2.37 (m, 1H), 2.31-2.23 (m, 2H), 2.19-2.04 (m, 3H), 1.89-1.73 (m, 1H), 1.70-1.59 (m, 1H), 1.13-1.06 (d, J=6.8 Hz, 3H); LCMS [M+1]$^+$=485.2.

Example 7

(3S)-2-[[2-Fluoro-4-[4-(1,2,4-oxadiazol-3-yl)-1-piperidyl]phenyl]methyl]-3-methyl-6-phenyl-thiazinane 1,1-dioxide

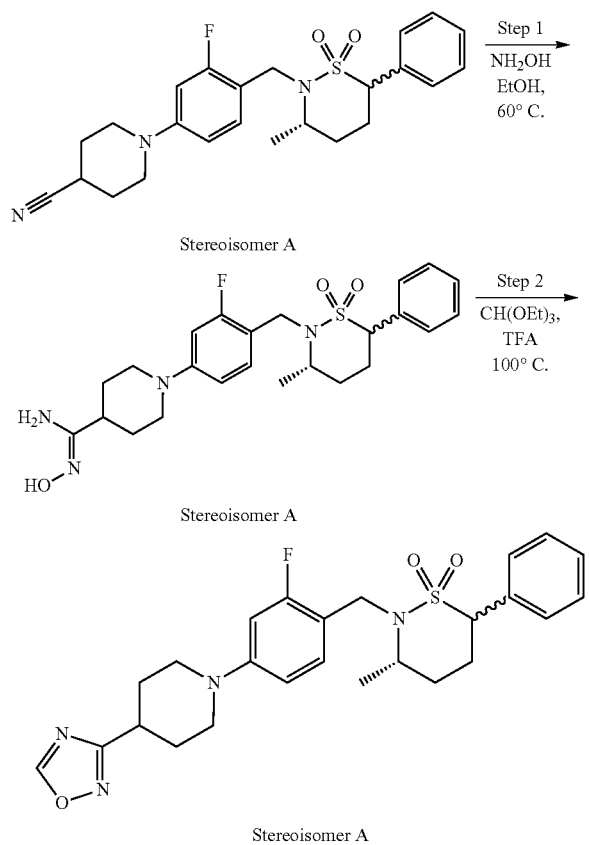

Step 1 1-[3-fluoro-4-[[(3S)-3-methyl-1,1-dioxo-6-phenyl-thiazinan-2-yl]methyl]phenyl]-N'-hydroxy-piperidine-4-carboxamidine To s solution of 1-[3-fluoro-4-[[(3S)-3-methyl-1,1-dioxo-6-phenyl-thiazinan-2-yl]methyl]phenyl]-piperidine-4-carbonitrile Stereoisomer A (1.37 g, 3.12 mmol, prepared as described in Example 5) in ethanol (15 mL) was added hydroxylamine (50 mass % in water, 0.29 mL, 9.4 mmol) and the reaction was stirred at 60° C. for 2 hours. The solution was concentrated and purified by preparative HPLC to give 1-[3-fluoro-4-[[(3S,6R)-3-methyl-1,1-dioxo-6-phenyl-thiazinan-2-yl]methyl]phenyl]-N'-hydroxy-piperidine-4-carboxamidine Stereoisomer A (1.1 g, 75% yield) as a white solid. $^1$H NMR (400 MHz, DMSO) δ 8.82-8.76 (s, 1H), 7.48-7.43 (m, 2H), 7.42-7.33 (m, 3H), 7.32-7.26 (m, 1H), 6.82-6.76 (m, 1H), 6.72-6.65 (m, 1H), 5.36-5.26 (s, 2H), 4.49-4.42 (m, 1H), 4.42-4.36 (m, 1H), 4.31-4.23 (m, 1H), 4.15-4.01 (m, 1H), 3.80-3.67 (m, 2H), 2.72-2.59 (m, 2H), 2.46-2.36 (m, 1H), 2.21-2.04 (m, 2H), 1.84-1.74 (m, 3H), 1.73-1.57 (m, 3H), 1.12-1.04 (d, J=6.8 Hz, 3H); LCMS [M+1]$^+$=475.2.

Step 2 (3S)-2-[[2-Fluoro-4-[4-(1,2,4-oxadiazol-3-yl)-1-piperidyl]phenyl]methyl]-3-methyl-6-phenyl-thiazinane 1,1-dioxide A solution of 1-[3-fluoro-4-[[(3S)-3-methyl-1,1-dioxo-6-phenyl-thiazinan-2-yl]methyl]phenyl]-N'-hydroxy-piperidine-4-carboxamidine Stereoisomer A (150 mg, 0.32 mmol) in triethyl orthoformate (2 mL) was heated to 100° C. for 1 hour. 2 drops of trifluoroacetic acid were then added and the reaction was stirred at 100° C. for 1 hour. The solution was then concentrated and purified by preparative HPLC to give (3S)-2-[[2-fluoro-4-[4-(1,2,4-oxadiazol-3-yl)-1-piperidyl]phenyl]methyl]-3-methyl-6-phenyl-thiazinane 1,1-dioxide Stereoisomer A (31.8 mg, 21% yield). $^1$H NMR (400 MHz, DMSO) δ 9.53-9.49 (s, 1H), 7.49-7.43 (m, 2H), 7.43-7.35 (m, 3H), 7.35-7.29 (m, 1H), 6.85-6.79 (m, 1H), 6.77-6.69 (m, 1H), 4.50-4.36 (m, 2H), 4.32-4.23 (m, 1H), 4.15-4.02 (m, 1H), 3.81-3.69 (m, 2H), 3.13-3.01 (m, 1H), 2.97-2.83 (m, 2H), 2.46-2.37 (m, 1H), 2.14-1.97 (m, 3H), 1.89-1.70 (m, 3H), 1.70-1.59 (m, 1H), 1.13-1.05 (d, J=6.8 Hz, 3H); LCMS [M+1]$^+$=485.2.

Example 8 4-(((3S)-3-methyl-1,1-dioxido-6-phenyl-1,2-thiazinan-2-yl)methyl)-N-(tetrahydro-2H-pyran-4-yl)benzamide

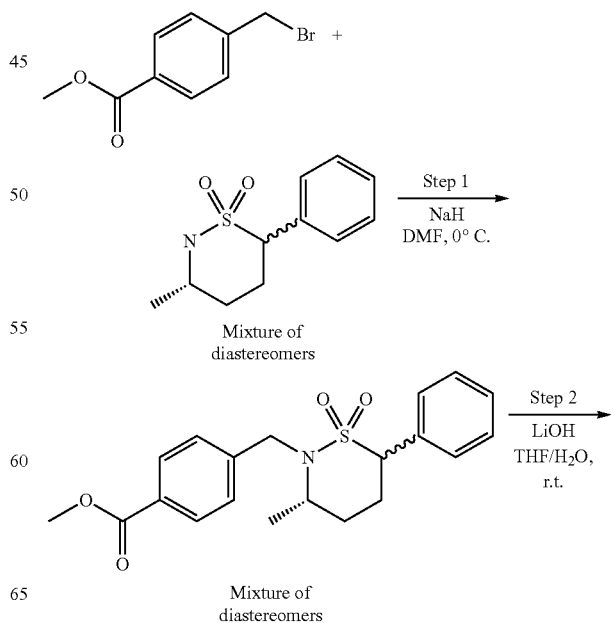

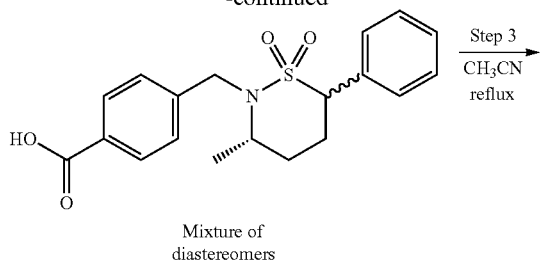

Mixture of diastereomers

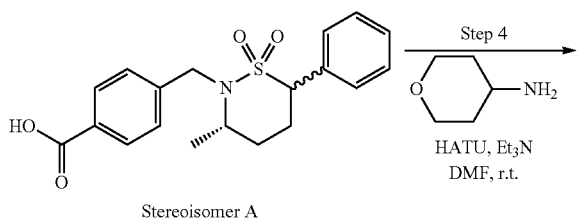

Stereoisomer A

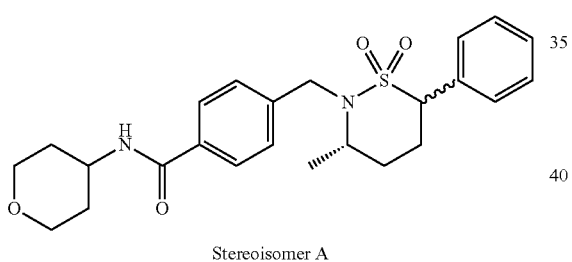

Stereoisomer A

Step 1 Methyl (S)-methyl 4-((3-methyl-1,1-dioxido-6-phenyl-1,2-thiazinan-2-yl)methyl)benzoate To a solution of (S)-3-methyl-6-phenyl-1,2-thiazinane 1,1-dioxide (20 g, 88.9 mmol) and methyl 4-(bromomethyl)benzoate (22.4 g, 97.6 mmol) in N,N-dimethylformamide (295 mL) at 0° C. was added sodium hydride (60% in mineral oil, 4.6 g, 115 mmol) in small portions and the reaction was stirred at room temperature for 3 hours. Water (500 mL) was then added and the precipitate was collected by filtration to give crude methyl (S)-methyl 4-((3-methyl-1,1-dioxido-6-phenyl-1,2-thiazinan-2-yl)methyl)benzoate.

Step 2 (S)-4-((3-Methyl-1,1-dioxido-6-phenyl-1,2-thiazinan-2-yl)methyl)benzoic acid To a solution of crude methyl (S)-methyl 4-((3-methyl-1,1-dioxido-6-phenyl-1,2-thiazinan-2-yl)methyl)benzoate in tetrahydrofuran (300 mL) and water (100 mL) was added lithium hydroxide (21.3 g, 890 mmol) and the reaction was stirred at room temperature for 16 hours. Sodium hydroxide (1N in water, 100 mL) and water (200 mL) were then added to the reaction and the solution was washed with ethyl acetate. The aqueous layer was then acidified to pH=1 with concentrated hydrochloric acid and the precipitate was collected by filtration and dried under vacuum to give 33 grams of crude (S)-4-((3-methyl-1,1-dioxido-6-phenyl-1,2-thiazinan-2-yl)methyl)benzoic acid (85:15 mixture of trans:cis isomers).

Step 3 4-[[(3S)-3-methyl-1,1-dioxo-6-phenyl-thiazinan-2-yl]methyl]benzoic acid The crude mixture of diastereomers was dissolved in boiling acetonitrile (500 mL), subjected to a hot filtration and then cooled to room temperature and stored at 4° C. for 16 hours. Crystals were collected by filtration to give 4-[[(3S)-3-methyl-1,1-dioxo-6-phenyl-thiazinan-2-yl]methyl]benzoic acid Stereoisomer A (6 g, 16.6 mmol, 19% yield). $^1$H NMR (400 MHz, DMSO) δ 12.99-12.69 (s, 1H), 7.98-7.87 (m, 2H), 7.55-7.43 (m, 4H), 7.43-7.33 (m, 3H), 4.67-4.55 (m, 1H), 4.50-4.36 (m, 2H), 4.20-4.05 (m, 1H), 2.47-2.37 (m, 2H), 2.19-2.06 (m, 1H), 1.91-1.76 (m, 1H), 1.72-1.61 (m, 1H), 1.11-1.01 (d, J=6.8 Hz, 3H); LCMS [M+1]$^+$=360.1.

Step 4 4-(((3S)-3-methyl-1,1-dioxido-6-phenyl-1,2-thiazinan-2-yl)methyl)-N-(tetrahydro-2H-pyran-4-yl)benzamide To a solution of 4-[[(3S)-3-methyl-1,1-dioxo-6-phenyl-thiazinan-2-yl]methyl]benzoic acid Stereoisomer A (75 mg, 0.21 mmol), tetrahydropyran-4-amine (64 mg, 0.63 mmol) and triethylamine (0.12 mL, 0.83 mmol) in N,N-dimethylformamide (1.5 mL) was added O-(7-azabenzotriazol-1-yl)-N,N,N',N'-tetramethyluronium hexafluorophosphate (121 mg, 0.31 mmol) and the reaction was stirred at room temperature for 2 hours. The reaction was then partitioned between dichloromethane and saturated sodium bicarbonate in water. The organic layer was separated, concentrated and purified by preparative HPLC to give 4-(((3S)-3-methyl-1,1-dioxido-6-phenyl-1,2-thiazinan-2-yl)methyl)-N-(tetrahydro-2H-pyran-4-yl)benzamide Stereoisomer A (66.4 mg, 0.15 mmol, 72% yield). $^1$H NMR (400 MHz, DMSO) δ 8.27-8.19 (d, J=7.7 Hz, 1H), 7.85-7.77 (m, 2H), 7.50-7.43 (m, 4H), 7.43-7.34 (m, 3H), 4.64-4.53 (m, 1H), 4.47-4.33 (m, 2H), 4.18-4.06 (m, 1H), 4.06-3.93 (m, 1H), 3.91-3.81 (m, 2H), 3.46-3.33 (m, 2H), 2.48-2.37 (m, 1H), 2.17-2.08 (m, 1H), 1.92-1.69 (m, 3H), 1.70-1.50 (m, 3H), 1.11-1.02 (d, J=6.9 Hz, 3H); LCMS [M+1]$^+$=443.2.

The above compounds of Examples 1-8, together with additional compounds made using the above procedures, are shown in Table 4 below, together with RORc IC$_{50}$ (micromolar) and proton NMR data for selected compounds. Structures shown in table 4 with a 'waved line" bond ( ~~~ ) associated with a chiral center represent compounds for which stereoisomers of the compound have been isolated or synthesized, but for which specific stereochemistry of the chiral center has not been definitely identified.

TABLE 4

| | Structure | Name | Proton NMR | IC$_{50}$ |
|---|---|---|---|---|
| 1 | Stereoisomer A | 1-(4-(4-((1,1-Dioxido-6-phenyl-1,2-thiazinan-2-yl)methyl)-30 fluorophenyl)piperazin-1-yl)ethanone | $^1$H NMR (400 MHz, DMSO) δ 7.49-7.31 (m, 5H), 7.26 (t, J = 8.8 Hz, 1H), 6.86-6.73 (m, 2H), 4.49 (dd, J = 12.6, 3.2 Hz, 1H), 4.35 (q, J = 14.4 Hz, 2H), 3.63-3.51 (m, 4H), 3.46 (t, J = 12.9 Hz, 1H), 3.28-3.19 (m, 2H), 3.19-3.04 (m, 3H), 2.48-2.35 (m, 1H), 2.22-2.07 (m, 1H), 2.04 (s, 3H), 2.01-1.87 (m, 1H), 1.72-1.49 (m, 1H) | 0.247 |
| 2 | Stereoisomer B | 1-(4-(4-((1,1-Dioxido-6-phenyl-1,2-thiazinan-2-yl)methyl)-3-fluorophenyl)piperazin-1-yl)ethanone | $^1$H NMR (400 MHz, DMSO) δ 7.49-7.31 (m, 5H), 7.26 (t, J = 8.8 Hz, 1H), 6.86-6.73 (m, 2H), 4.49 (dd, J = 12.6, 3.2 Hz, 1H), 4.35 (q, J = 14.4 Hz, 2H), 3.63-3.51 (m, 4H), 3.46 (t, J = 12.9 Hz, 1H), 3.28-3.19 (m, 2H), 3.19-3.04 (m, 3H), 2.48-2.35 (m, 1H), 2.22-2.07 (m, 1H), 2.04 (s, 3H), 2.01-1.87 (m, 1H), 1.72-1.49 (m, 1H). | 0.157 |
| 3 | Stereoisomer A | 2-(2-Fluoro-4-((1-(methylsulfonyl)piperidin-4-yl)oxy)benzyl)-6-phenyl-1,2-thiazinane 1,1- | $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.91 (s, 3H), 2.48-2.39 (m, 1H), 2.21-2.08 (m, 1H), 2.08-1.91 (m, 3H), 1.82-1.68 (m, 2H), 1.68-1.57 (m, 1H) | 0.086 |
| 4 | Stereoisomer B | 2-(2-Fluoro-4-((1-(methylsulfonyl)piperidin-4-yl)oxy)benzyl)-6-phenyl-1,2-thiazinane 1,1-dioxide | $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.91 (s, 3H), 2.48-2.39 (m, 1H), 2.21-2.08 (m, 1H), 2.08-1.91 (m, 3H), 1.82-1.68 (m, 2H), 1.68-1.57 (m, 1H) | 0.037 |
| 5 | Stereoisomer A | 1-{4-[4-(1,1-Dioxo-6-phenyl-[1,2]thiazinan-2-ylmethyl)-3-fluoro-phenyl]-piperazin-1-yl}-ethanone | $^1$H NMR (400 MHz, DMSO) δ 7.53-7.32 (m, 5H), 7.29-7.22 (m, 1H), 6.85-6.80 (m, 1H), 6.80-6.75 (m, 1H), 4.54-4.44 (m, 1H), 4.38 (d, J = 14.4 Hz, 1H), 4.32 (d, J = 14.3 Hz, 1H), 3.63-3.52 (m, 4H), 3.52-3.40 (m, 1H), 3.28-3.20 (m, 2H), 3.20-3.04 (m, 3H), 2.47-2.36 (m, 1H), 2.18-2.07 (m, 1H), 2.04 (s, 3H), 2.02-1.91 (m, 1H), 1.71-1.56 (m, 1H). | 0.247 |

TABLE 4-continued

| | Structure | Name | Proton NMR | IC$_{50}$ |
|---|---|---|---|---|
| 6 | Stereoisomer B | 1-{4-[4-(1,1-Dioxo-6-phenyl-[1,2]thiazinan-2-ylmethyl)-3-fluoro-phenyl]-piperazin-1-yl}-ethanone | $^1$H NMR (400 MHz, DMSO) δ 7.49-7.32 (m, 5H), 7.30-7.21 (m, 1H), 6.84-6.80 (m, 1H), 6.80-6.75 (m, 1H), 4.55-4.44 (m, 1H), 4.38 (d, J = 14.2 Hz, 1H), 4.32 (d, J = 14.4 Hz, 1H), 3.60-3.52 (m, 4H), 3.52-3.40 (m, 1H), 3.26-3.19 (m, 2H), 3.19-3.04 (m, 3H), 2.48-2.36 (m, 1H), 2.18-2.06 (m, 1H), 2.04 (s, 3H), 2.01-1.92 (m, 1H), 1.69-1.57 (m, 1H). | 0.157 |
| 7 | 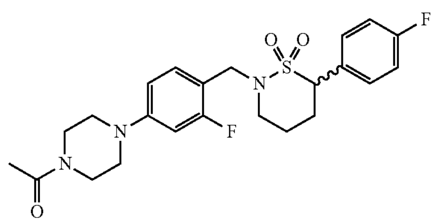 [SMILES: CC(=O)N1CCN(c2ccc(CN3CCCC(c4ccc(F)cc4)S3(=O)=O)c(F)c2)CC1] | 1-(4-{3-Fluoro-4-[6-(4-fluoro-phenyl)-1,1-dioxo-[1,2]thiazinan-2-ylmethyl]-phenyl}-piperazin-1-yl)-ethanone | $^1$H NMR (400 MHz, DMSO) δ 7.55-7.43 (m, 2H), 7.32-7.15 (m, 3H), 6.87-6.74 (m, 2H), 4.54 (dd, J = 12.6, 3.2 Hz, 1H), 4.34 (q, J = 14.4 Hz, 2H), 3.62-3.52 (m, 4H), 3.45 (t, J = 12.9 Hz, 1H), 3.27-3.19 (m, 2H), 3.19-3.04 (m, 3H), 2.48-2.29 (m, 1H), 2.19-2.08 (m, 1H), 2.04 (s, 3H), 2.02-1.85 (m, 1H), 1.70-1.52 (m, 1H). | 0.443 |
| 8 | 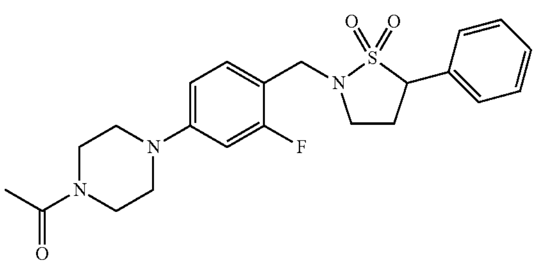 [SMILES: CC(=O)N1CCN(c2ccc(CN3CCC(c4ccccc4)S3(=O)=O)c(F)c2)CC1] | 1-{4-[4-(1,1-Dioxo-5-phenyl-isothiazolidin-2-ylmethyl)-3-fluoro-phenyl]-piperazin-1-yl}-ethanone | $^1$H NMR (400 MHz, DMSO) δ 7.52-7.35 (m, 5H), 7.26 (t, J = 8.6 Hz, 1H), 6.79 (d, J = 11.0 Hz, 2H), 4.65-4.52 (m, 1H), 4.20 (d, J = 14.5 Hz, 1H), 4.06 (d, J = 14.4 Hz, 1H), 3.64-3.50 (m, 4H), 3.29-3.08 (m, 6H), 2.63-2.52 (m, 1H), 2.49-2.42 (m, 1H), 2.04 (s, 3H). | 4.9 |
| 9 | 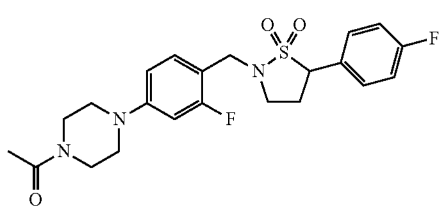 [SMILES: CC(=O)N1CCN(c2ccc(CN3CCC(c4ccc(F)cc4)S3(=O)=O)c(F)c2)CC1] | 1-(4-{3-Fluoro-4-[5-(4-fluoro-phenyl)-1,1-dioxo-isothiazolidin-2-ylmethyl]-phenyl}-piperazin-1-yl)-ethanone | $^1$H NMR (400 MHz, DMSO) δ 7.50 (dd, J = 8.7, 5.5 Hz, 2H), 7.26 (t, J = 8.8 Hz, 3H), 6.79 (d, J = 11.2 Hz, 2H), 4.62 (dd, J = 10.9, 7.9 Hz, 1H), 4.20 (d, J = 14.4 Hz, 1H), 4.06 (d, J = 14.4 Hz, 1H), 3.62-3.51 (m, 4H), 3.29-3.09 (m, 6H), 2.64-2.52 (m, 1H), 2.48-2.39 (m, 1H), 2.04 (s, 3H). | 7.6 |
| 10 | 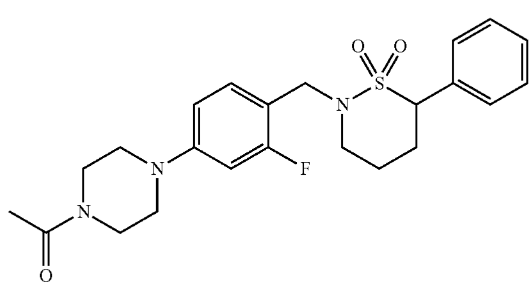 [SMILES: CC(=O)N1CCN(c2ccc(CN3CCCC(c4ccccc4)S3(=O)=O)c(F)c2)CC1] | 1-{4-[4-(1,1-Dioxo-6-phenyl-[1,2]thiazinan-2-ylmethyl)-3-fluoro-phenyl]-piperazin-1-yl}-ethanone | $^1$H NMR (400 MHz, DMSO) δ 7.49-7.31 (m, 5H), 7.26 (t, J = 8.8 Hz, 1H), 6.86-6.73 (m, 2H), 4.49 (dd, J = 12.6, 3.2 Hz, 1H), 4.35 (q, J = 14.4 Hz, 2H), 3.63-3.51 (m, 4H), 3.46 (t, J = 12.9 Hz, 1H), 3.28-3.19 (m, 2H), 3.19-3.04 (m, 3H), 2.48-2.35 (m, 1H), 2.22-2.07 (m, 1H), 2.04 (s, 3H), 2.01-1.87 (m, 1H), 1.72-1.49 (m, 1H). | 0.149 |

TABLE 4-continued

| | Structure | Name | Proton NMR | IC$_{50}$ |
|---|---|---|---|---|
| 11 | 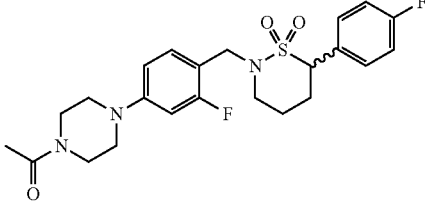  Stereoisomer A | 1-(4-{3-Fluoro-4-[6-(4-fluoro-phenyl)-1,1-dioxo-[1,2]thiazinan-2-ylmethyl]-phenyl}-piperazin-1-yl)-ethanone | $^{1}$H NMR (400 MHz, DMSO) δ 7.54-7.44 (m, 2H), 7.30-7.19 (m, 3H), 6.84-6.74 (m, 2H), 4.59-4.48 (m, 1H), 4.38 (d, J = 14.4 Hz, 1H), 4.31 (d, J = 14.4 Hz, 1H), 3.64-3.52 (m, 4H), 3.52-3.37 (m, 1H), 3.26-3.19 (m, 2H), 3.19-3.07 (m, 3H), 2.48-2.30 (m, 1H), 2.18-2.07 (m, 1H), 2.04 (s, 3H), 2.02-1.86 (m, 1H), 1.71-1.57 (m, 1H). | 0.125 |
| 12 | 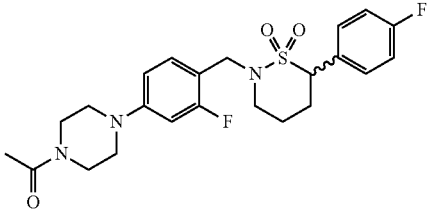 [SMILES: CC(=O)N1CCN(c2ccc(CN3CCCC(c4ccc(F)cc4)S3(=O)=O)c(F)c2)CC1]  Stereoisomer B | 1-(4-{3-Fluoro-4-[6-(4-fluoro-phenyl)-1,1-dioxo-[1,2]thiazinan-2-ylmethyl]-phenyl}-piperazin-1-yl)-ethanone | $^{1}$H NMR (400 MHz, DMSO) δ 7.54-7.43 (m, 2H), 7.32-7.17 (m, 3H), 6.85-6.73 (m, 2H), 4.59-4.48 (m, 1H), 4.38 (d, J = 14.4 Hz, 1H), 4.31 (d, J = 14.4 Hz, 1H), 3.61-3.52 (m, 4H), 3.52-3.38 (m, 1H), 3.25-3.19 (m, 2H), 3.19-3.02 (m, 3H), 2.48-2.30 (m, 1H), 2.17-2.07 (m, 1H), 2.04 (s, 3H), 2.02-1.87 (m, 1H), 1.69-1.57 (m, 1H). | 0.241 |
| 13 | 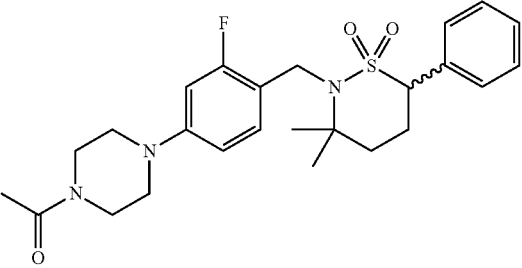 [SMILES: CC(=O)N1CCN(c2ccc(CN3C(C)(C)CCC(c4ccccc4)S3(=O)=O)c(F)c2)CC1]  Stereoisomer A | 1-{4-[4-(3,3-Dimethyl-1,1-dioxo-6-phenyl-[1,2]thiazinan-2-ylmethyl)-3-fluoro-phenyl]-piperazin-1-yl}-ethanone | $^{1}$H NMR (400 MHz, DMSO) δ 7.53-7.34 (m, 6H), 6.86-6.77 (m, 1H), 6.77-6.66 (m, 1H), 4.57-4.48 (m, 1H), 4.43 (d, J = 17.5 Hz, 1H), 4.19 (d, J = 17.5 Hz, 1H), 3.61-3.51 (m, 4H), 3.23-3.16 (m, 2H), 3.16-3.07 (m, 2H), 2.77-2.56 (m, 1H), 2.20-2.06 (m, 1H), 2.04 (s, 3H), 2.01-1.92 (m, 1H), 1.88-1.73 (m, 1H), 1.42 (s, 3H), 1.14 (s, 3H). | 0.142 |
| 14 | 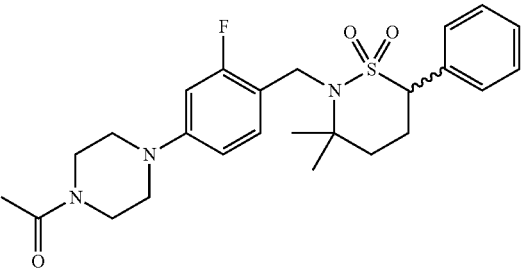 [SMILES: CC(=O)N1CCN(c2ccc(CN3C(C)(C)CCC(c4ccccc4)S3(=O)=O)c(F)c2)CC1]  Stereoisomer B | 1-{4-[4-(3,3-Dimethyl-1,1-dioxo-6-phenyl-[1,2]thiazinan-2-ylmethyl)-3-fluoro-phenyl]-piperazin-1-yl}-ethanone | $^{1}$H NMR (400 MHz, DMSO) δ 7.54-7.35 (m, 6H), 6.86-6.78 (m, 1H), 6.78-6.66 (m, 1H), 4.58-4.47 (m, 1H), 4.43 (d, J = 17.4 Hz, 1H), 4.19 (d, J = 17.5 Hz, 1H), 3.61-3.51 (m, 4H), 3.24-3.16 (m, 2H), 3.16-3.07 (m, 2H), 2.77-2.58 (m, 1H), 2.17-2.07 (m, 1H), 2.04 (s, 3H), 2.01-1.92 (m, 1H), 1.86-1.75 (m, 1H), 1.42 (s, 3H), 1.14 (s, 3H). | 1.9 |
| 15 | 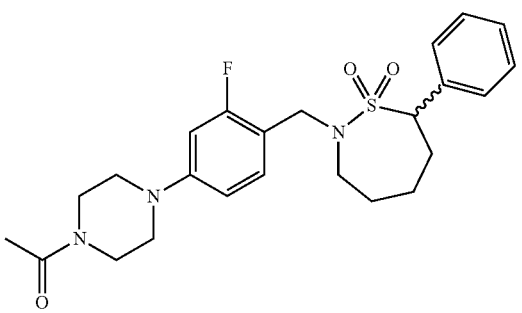 [SMILES: CC(=O)N1CCN(c2ccc(CN3CCCCC(c4ccccc4)S3(=O)=O)c(F)c2)CC1]  Stereoisomer A | 1-{4-[4-(1,1-Dioxo-7-phenyl-[1,2]thiazepan-2-ylmethyl)-3-fluoro-phenyl]-piperazin-1-yl}-ethanone | $^{1}$H NMR (400 MHz, DMSO) δ 7.43-7.29 (m, 5H), 7.29-7.21 (m, 1H), 6.86-6.75 (m, 2H), 4.58 (d, J = 15.2 Hz, 1H), 4.45-4.34 (m, 1H), 4.27 (d, J = 15.2 Hz, 1H), 3.59-3.52 (m, 4H), 3.53-3.40 (m, 1H), 3.26-3.18 (m, 2H), 3.18-3.09 (m, 2H), 3.02-2.84 (m, 1H), 2.22-2.07 (m, 1H), 2.07-1.94 (m, 6H), 1.86-1.67 (m, 1H), 1.67-1.47 (m, 1H). | 0.011 |

TABLE 4-continued

| | Structure | Name | Proton NMR | IC$_{50}$ |
|---|---|---|---|---|
| 16 | Stereoisomer B | 1-{4-[4-(1,1-Dioxo-7-phenyl-[1,2]thiazepan-2-ylmethyl)-3-fluoro-phenyl]-piperazin-1-yl}-ethanone | $^1$H NMR (400 MHz, DMSO) δ 7.44-7.29 (m, 5H), 7.29-7.21 (m, 1H), 6.88-6.72 (m, 2H), 4.58 (d, J = 15.2 Hz, 1H), 4.45-4.33 (m, 1H), 4.27 (d, J = 15.1 Hz, 1H), 3.59-3.52 (m, 4H), 3.52-3.42 (m, 1H), 3.25-3.18 (m, 2H), 3.18-3.10 (m, 2H), 3.01-2.83 (m, 1H), 2.23-2.07 (m, 1H), 2.07-1.95 (m, 6H), 1.86-1.69 (m, 1H), 1.68-1.46 (m, 1H). | 0.032 |
| 17 | Stereoisomer A | 1-{4-[3-Fluoro-4-((3S)-3-methyl-1,1-dioxo-6-phenyl-[1,2]thiazinan-2-ylmethyl)-phenyl]-piperazin-1-yl}-ethanone | $^1$H NMR (400 MHz, DMSO) δ 7.49-7.43 (m, 2H), 7.43-7.28 (m, 4H), 6.81 (d, J = 8.8 Hz, 1H), 6.74 (d, J = 13.9 Hz, 1H), 4.52-4.44 (m, 1H), 4.41 (d, J = 17.0 Hz, 1H), 4.28 (d, J = 17.1 Hz, 1H), 4.18-4.00 (m, 1H), 3.63-3.51 (m, 4H), 3.26-3.15 (m, 2H), 3.15-3.02 (m, 2H), 2.47-2.30 (m, 1H), 2.15-2.05 (m, 1H), 2.03 (s, 3H), 1.92-1.71 (m, 1H), 1.71-1.54 (m, 1H), 1.08 (d, J = 6.8 Hz, 3H). | 0.016 |
| 18 | Stereoisomer B | 1-{4-[3-Fluoro-4-((3S)-3-methyl-1,1-dioxo-6-phenyl-[1,2]thiazinan-2-ylmethyl)-phenyl]-piperazin-1-yl}-ethanone | $^1$H NMR (400 MHz, DMSO) δ 7.53-7.34 (m, 5H), 7.32-7.24 (m, 1H), 6.87-6.74 (m, 2H), 4.48-4.30 (m, 3H), 3.60-3.48 (m, 5H), 3.25-3.18 (m, 2H), 3.18-3.11 (m, 2H), 2.81-2.61 (m, 1H), 2.17-1.95 (m, 5H), 1.67-1.53 (m, 1H), 1.34 (d, J = 7.1 Hz, 3H). | 0.047 |
| 19 | Stereoisomer A | 1-{4-[3-Fluoro-4-((3R)-3-methyl-1,1-dioxo-6-phenyl-[1,2]thiazinan-2-ylmethyl)-phenyl]-piperazin-1-yl}-ethanone | $^1$H NMR (400 MHz, DMSO) δ 7.49-7.43 (m, 2H), 7.43-7.25 (m, 4H), 6.81 (d, J = 9.0 Hz, 1H), 6.74 (d, J = 13.8 Hz, 1H), 4.52-4.44 (m, 1H), 4.41 (d, J = 17.1 Hz, 1H), 4.28 (d, J = 16.6 Hz, 1H), 4.17-4.01 (m, 1H), 3.62-3.50 (m, 4H), 3.23-3.15 (m, 2H), 3.15-3.07 (m, 2H), 2.48-2.29 (m, 1H), 2.15-2.05 (m, 1H), 2.03 (s, 3H), 1.90-1.73 (m, 1H), 1.70-1.57 (m, 1H), 1.08 (d, J = 6.7 Hz, 3H). | 2.8 |

TABLE 4-continued

| | Structure | Name | Proton NMR | IC$_{50}$ |
|---|---|---|---|---|
| 20 | 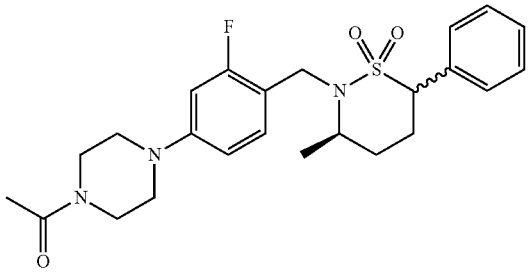 [SMILES: CC(=O)N1CCN(c2ccc(CN3[C@H](C)CCC(c4ccccc4)S3(=O)=O)c(F)c2)CC1]<br>Stereoisomer B | 1-{4-[3-Fluoro-4-((3R)-3-methyl-1,1-dioxo-6-phenyl-[1,2]thiazinan-2-ylmethyl)-phenyl]-piperazin-1-yl}-ethanone | $^1$H NMR (400 MHz, DMSO) δ 7.50-7.34 (m, 5H), 7.32-7.24 (m, 1H), 6.86-6.73 (m, 2H), 4.45-4.32 (m, 3H), 3.63-3.51 (m, 5H), 3.26-3.19 (m, 2H), 3.19-3.09 (m, 2H), 2.83-2.60 (m, 1H), 2.18-1.94 (m, 5H), 1.70-1.53 (m, 1H), 1.34 (d, J = 7.1 Hz, 3H). | 0.026 |
| 21 | 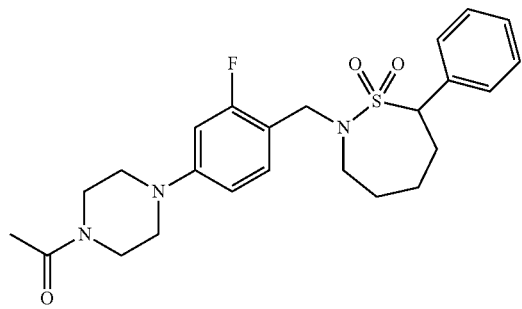 [SMILES: CC(=O)N1CCN(c2ccc(CN3CCCCC(c4ccccc4)S3(=O)=O)c(F)c2)CC1] | 1-{4-[4-(4,4-Dioxo-3-phenyl-[1,4,5]oxathiazepan-5-ylmethyl)-3-fluoro-phenyl]-piperazin-1-yl}-ethanone | $^1$H NMR (400 MHz, DMSO) δ 7.43-7.35 (m, 5H), 7.30-7.22 (m, 1H), 6.85-6.76 (m, 2H), 4.79-4.70 (m, 1H), 4.69-4.58 (d, J = 14.8 Hz, 1H), 4.27-4.07 (m, 3H), 4.05-3.97 (m, 1H), 3.90-3.79 (m, 1H), 3.77-3.64 (m, 1H), 3.60-3.51 (m, 4H), 3.26-3.19 (m, 2H), 3.19-3.11 (m, 2H), 3.05-2.94 (m, 1H), 2.04 (s, 3H). | 0.209 |
| 22 | 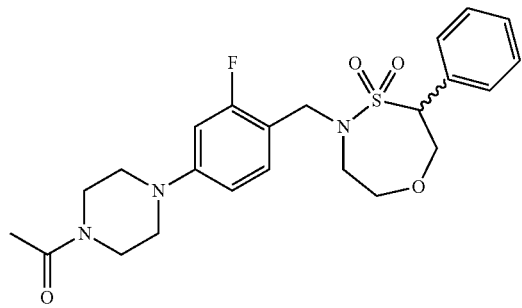 [SMILES: CC(=O)N1CCN(c2ccc(CN3CCOCC(c4ccccc4)S3(=O)=O)c(F)c2)CC1]<br>Stereoisomer A | 1-{4-[4-(4,4-Dioxo-3-phenyl-[1,4,5]oxathiazepan-5-ylmethyl)-3-fluoro-phenyl]-piperazin-1-yl}-ethanone | $^1$H NMR (400 MHz, DMSO) δ 7.43-7.35 (m, 5H), 7.30-7.22 (m, 1H), 6.85-6.76 (m, 2H), 4.79-4.70 (m, 1H), 4.69-4.58 (d, J = 14.8 Hz, 1H), 4.27-4.07 (m, 3H), 4.05-3.97 (m, 1H), 3.90-3.79 (m, 1H), 3.77-3.64 (m, 1H), 3.60-3.51 (m, 4H), 3.26-3.19 (m, 2H), 3.19-3.11 (m, 2H), 3.05-2.94 (m, 1H), 2.04-2.01 (s, 3H). | 0.751 |
| 23 | 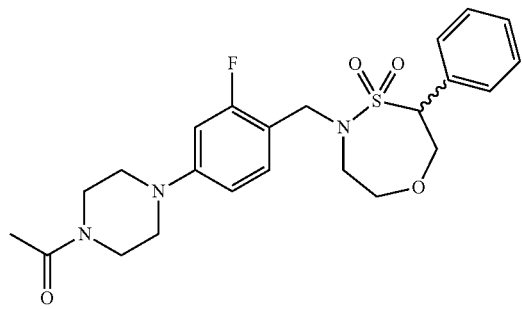 [SMILES: CC(=O)N1CCN(c2ccc(CN3CCOCC(c4ccccc4)S3(=O)=O)c(F)c2)CC1]<br>Stereoisomer B | 1-{4-[4-(4,4-Dioxo-3-phenyl-[1,4,5]oxathiazepan-5-ylmethyl)-3-fluoro-phenyl]-piperazin-1-yl}-ethanone | $^1$H NMR (400 MHz, DMSO) δ 7.46-7.34 (m, 5H), 7.33-7.18 (m, 1H), 6.88-6.74 (m, 2H), 4.79-4.72 (m, 1H), 4.68-4.57 (d, J = 14.8 Hz, 1H), 4.29-4.06 (m, 3H), 4.06-3.96 (m, 1H), 3.90-3.77 (m, 1H), 3.77-3.62 (m, 1H), 3.61-3.51 (m, 4H), 3.27-3.18 (m, 2H), 3.18-3.10 (m, 2H), 3.05-2.92 (m, 1H), 2.04-2.00 (s, 3H). | 0.045 |

TABLE 4-continued

| | Structure | Name | Proton NMR | IC$_{50}$ |
|---|---|---|---|---|
| 24 | 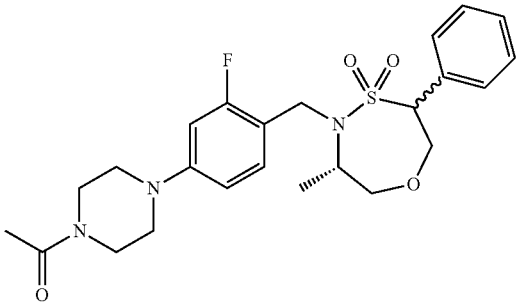 [SMILES: CC(=O)N1CCN(c2ccc(CN3[C@@H](C)COCC(c4ccccc4)S3(=O)=O)c(F)c2)CC1]<br>Stereoisomer A | 1-(4-(3-fluoro-4-(((6S)-6-methyl-4,4-dioxido-3-phenyl-1,4,5-oxathiazepan-5-yl)methyl)phenyl)piperazin-1-yl)ethanone | $^1$H NMR (400 MHz, DMSO) δ 7.48-7.28 (m, 6H), 6.89-6.73 (m, 2H), 4.61-4.50 (m, 2H), 4.34-4.26 (d, J = 14.7 Hz, 1H), 4.21-4.13 (m, 1H), 4.13-4.05 (m, 1H), 4.00-3.89 (m, 1H), 3.82-3.70 (m, 1H), 3.61-3.51 (m, 4H), 3.44-3.33 (m, 1H), 3.28-3.21 (m, 2H), 3.21-3.13 (m, 2H), 2.04 (s, 3H), 0.96-0.90 (d, J = 6.5 Hz, 3H). | 0.182 |
| 25 | 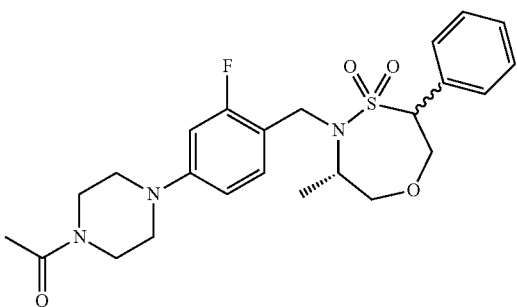 [SMILES: CC(=O)N1CCN(c2ccc(CN3[C@@H](C)COCC(c4ccccc4)S3(=O)=O)c(F)c2)CC1]<br>Stereoisomer B | 1-(4-(3-fluoro-4-(((6S)-6-methyl-4,4-dioxido-3-phenyl-1,4,5-oxathiazepan-5-yl)methyl)phenyl)piperazin-1-yl)ethanone | $^1$H NMR (400 MHz, DMSO) δ 7.45-7.35 (m, 5H), 7.34-7.28 (m, 1H), 6.82-6.76 (m, 1H), 6.76-6.67 (m, 1H), 4.89-4.81 (m, 1H), 4.51-4.42 (d, J = 17.0 Hz, 1H), 4.41-4.26 (m, 2H), 4.19-4.10 (d, J = 16.8 Hz, 1H), 4.01-3.92 (dd, J = 13.6, 3.2 Hz, 1H), 3.91-3.82 (m, 1H), 3.82-3.72 (m, 1H), 3.60-3.51 (m, 4H), 3.22-3.16 (m, 2H), 3.16-3.08 (m, 2H), 2.03 (s, 3H), 0.93-0.84 (d, J = 6.7 Hz, 3H). | 0.032 |
| 26 | 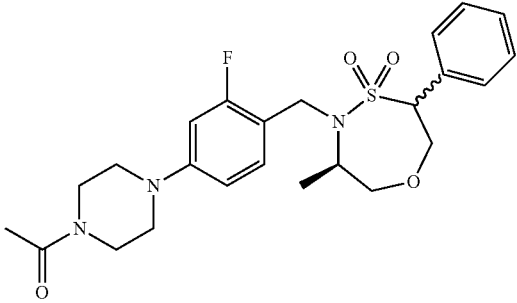 [SMILES: CC(=O)N1CCN(c2ccc(CN3[C@H](C)COCC(c4ccccc4)S3(=O)=O)c(F)c2)CC1]<br>Stereoisomer A | 1-(4-(3-fluoro-4-(((6R)-6-methyl-4,4-dioxido-3-phenyl-1,4,5-oxathiazepan-5-yl)methyl)phenyl)piperazin-1-yl)ethanone | $^1$H NMR (400 MHz, DMSO) δ 7.46-7.35 (m, 5H), 7.35-7.27 (m, 1H), 6.83-6.76 (m, 1H), 6.76-6.69 (dd, J = 14.0, 2.4 Hz, 1H), 4.87-4.81 (m, 1H), 4.50-4.42 (d, J = 17.0 Hz, 1H), 4.42-4.35 (m, 1H), 4.35-4.27 (m, 1H), 4.18-4.09 (d, J = 16.8 Hz, 1H), 4.00-3.92 (dd, J = 13.6, 3.2 Hz, 1H), 3.91-3.82 (m, 1H), 3.82-3.72 (m, 1H), 3.61-3.50 (m, 4H), 3.22-3.16 (m, 2H), 3.16-3.03 (m, 2H), 2.03 (s, 3H), 0.91-0.84 (d, J = 6.8 Hz, 3H). | 2. |
| 27 | 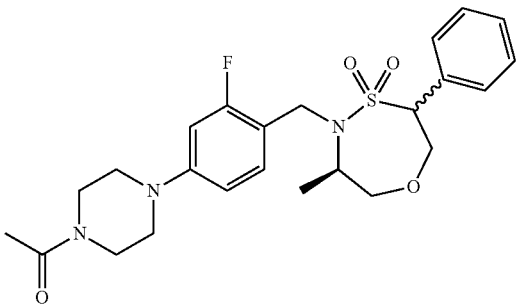 [SMILES: CC(=O)N1CCN(c2ccc(CN3[C@H](C)COCC(c4ccccc4)S3(=O)=O)c(F)c2)CC1]<br>Stereoisomer B | 1-(4-(3-fluoro-4-(((6R)-6-methyl-4,4-dioxido-3-phenyl-1,4,5-oxathiazepan-5-yl)methyl)phenyl)piperazin-1-yl)ethanone | $^1$H NMR (400 MHz, DMSO) δ 7.46-7.28 (m, 6H), 6.88-6.74 (m, 2H), 4.64-4.49 (m, 2H), 4.34-4.24 (d, J = 14.7 Hz, 1H), 4.22-4.13 (dd, J = 13.0, 6.5 Hz, 1H), 4.13-4.05 (m, 1H), 4.01-3.89 (m, 1H), 3.81-3.69 (m, 1H), 3.61-3.51 (m, 4H), 3.47-3.32 (m, 1H), 3.28-3.21 (m, 2H), 3.21-3.13 (m, 2H), 2.03 (s, 3H), 0.98-0.87 (d, J = 6.3 Hz, 3H). | 0.188 |

TABLE 4-continued

| | Structure | Name | Proton NMR | IC$_{50}$ |
|---|---|---|---|---|
| 28 | Stereoisomer A | 1-(4-(3-fluoro-4-(((7S)-7-methyl-4,4-dioxido-3-phenyl-1,4,5-oxathiazepan-5-yl)methyl)phenyl)piperazin-1-yl)ethanone | $^1$H NMR (400 MHz, DMSO) δ 7.48-7.34 (m, 5H), 7.29-7.22 (m, 1H), 6.86-6.74 (m, 2H), 4.80-4.71 (m, 1H), 4.69-4.58 (d, J = 15.1 Hz, 1H), 4.37-4.26 (d, J = 15.0 Hz, 1H), 4.22-3.97 (m, 3H), 3.61-3.51 (m, 4H), 3.39-3.30 (m, 1H), 3.25-3.20 (m, 2H), 3.20-3.09 (m, 2H), 2.81-2.69 (m, 1H), 2.02 (s, 2H), 1.22-1.11 (d, J = 6.1 Hz, 3H). | 0.104 |
| 29 | Stereoisomer B | 1-(4-(3-fluoro-4-(((7S)-7-methyl-4,4-dioxido-3-phenyl-1,4,5-oxathiazepan-5-yl)methyl)phenyl)piperazin-1-yl)ethanone | $^1$H NMR (400 MHz, DMSO) δ 7.45-7.36 (m, 6H), 7.28-7.22 (m, 1H), 6.84-6.73 (m, 2H), 4.78-4.67 (m, 1H), 4.68-4.57 (d, J = 14.8 Hz, 1H), 4.47-4.30 (m, 2H), 4.30-4.20 (d, J = 14.8 Hz, 1H), 3.90-3.78 (dd, J = 13.9, 3.6 Hz, 1H), 3.62-3.53 (m, 4H), 3.52-3.43 (m, 1H), 3.24-3.18 (m, 2H), 3.18-3.09 (m, 2H), 3.01-2.88 (m, 1H), 2.03 (s, 3H), 1.18-1.08 (d, J = 6.6 Hz, 3H). | 0.024 |
| 30 | Stereoisomer A | 1-(4-(3-fluoro-4-(((7R)-7-methyl-4,4-dioxido-3-phenyl-1,4,5-oxathiazepan-5-yl)methyl)phenyl)piperazin-1-yl)ethanone | $^1$H NMR (400 MHz, DMSO) δ 7.46-7.35 (m, 5H), 7.29-7.21 (m, 1H), 6.86-6.75 (m, 2H), 4.81-4.70 (m, 1H), 4.70-4.57 (d, J = 15.1 Hz, 1H), 4.36-4.25 (d, J = 14.8 Hz, 1H), 4.23-3.99 (m, 3H), 3.60-3.52 (m, 4H), 3.39-3.30 (m, 1H), 3.27-3.19 (m, 2H), 3.19-3.12 (m, 2H), 2.81-2.69 (m, 1H), 2.03 (s, 3H), 1.20-1.12 (d, J = 6.2 Hz, 3H). | 0.107 |
| 31 | Stereoisomer B | 1-(4-(3-fluoro-4-(((7R)-7-methyl-4,4-dioxido-3-phenyl-1,4,5-oxathiazepan-5-yl)methyl)phenyl)piperazin-1-yl)ethanone | $^1$H NMR (400 MHz, DMSO) δ 7.47-7.33 (m, 5H), 7.29-7.21 (m, 1H), 6.84-6.74 (m, 2H), 4.77-4.68 (m, 1H), 4.68-4.56 (d, J = 14.8 Hz, 1H), 4.46-4.31 (m, 2H), 4.31-4.20 (d, J = 14.7 Hz, 1H), 3.88-3.78 (m, 1H), 3.63-3.53 (m, 4H), 3.53-3.41 (m, 1H), 3.26-3.19 (m, 2H), 3.19-3.08 (m, 2H), 3.00-2.87 (m, 1H), 2.03 (s, 3H), 1.17-1.09 (d, J = 6.2 Hz, 3H). | 0.717 |

TABLE 4-continued

| | Structure | Name | Proton NMR | IC$_{50}$ |
|---|---|---|---|---|
| 32 | 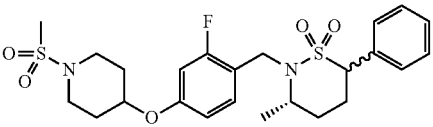 [SMILES: C[C@H]1CCC(c2ccccc2)S(=O)(=O)N1Cc1ccc(OC2CCN(S(C)(=O)=O)CC2)cc1F] Stereoisomer A | 2-(2-fluoro-4-((1-(methylsulfonyl)piperidin-4-yl)oxy)benzyl)-(3S)-3-methyl-6-phenyl-1,2-thiazinane 1,1-dioxide | $^1$H NMR (400 MHz, DMSO) δ 7.50-7.43 (m, 2H), 7.43-7.31 (m, 3H), 7.28-7.18 (m, 2H), 6.99-6.87 (m, 2H), 4.51-4.40 (d, J = 16.5 Hz, 1H), 4.40-4.30 (m, 1H), 4.27-4.15 (d, J = 16.5 Hz, 1H), 4.15-3.89 (m, 1H), 3.62-3.49 (m, 4H), 3.19-3.09 (m, 2H), 3.09-3.00 (m, 2H), 2.46-2.32 (m, 1H), 2.13-2.05 (m, 1H), 2.01 (s, 3H), 1.93-1.71 (m, 1H), 1.71-1.57 (m, 1H), 1.14-1.01 (d, J = 6.9 Hz, 3H). | 0.017 |
| 33 | 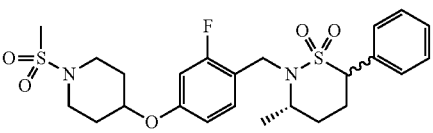 [SMILES: C[C@H]1CCC(c2ccccc2)S(=O)(=O)N1Cc1ccc(OC2CCN(S(C)(=O)=O)CC2)cc1F] Stereoisomer B | 2-(2-fluoro-4-((1-(methylsulfonyl)piperidin-4-yl)oxy)benzyl)-(3S)-3-methyl-6-phenyl-1,2-thiazinane 1,1-dioxide | | 0.013 |
| 34 | 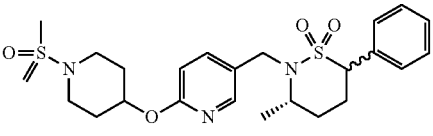 [SMILES: C=S(C)(=O)N1CCC(Oc2ccc(CN3[C@@H](C)CCC(c4ccccc4)S3(=O)=O)cn2)CC1] Stereoisomer A | 2-[6-(1-Methanesulfonyl-piperidin-4-yloxy)-pyridin-3-ylmethyl]-(3S)-3-methyl-6-phenyl-[1,2]thiazinane 1,1-dioxide | $^1$H NMR (400 MHz, DMSO) δ 8.17-8.10 (d, J = 2.3 Hz, 1H), 7.76-7.66 (m, 1H), 7.51-7.44 (m, 2H), 7.44-7.32 (m, 3H), 6.85-6.74 (d, J = 8.5 Hz, 1H), 5.24-4.98 (m, 1H), 4.56-4.36 (m, 2H), 4.36-4.18 (m, 1H), 4.17-3.94 (m, 1H), 3.46-3.31 (m, 2H), 3.20-3.05 (m, 2H), 2.96-2.85 (s, 3H), 2.46-2.26 (m, 1H), 2.18-1.96 (m, 3H), 1.95-1.57 (m, 4H), 1.23-1.02 (d, J = 6.8 Hz, 3H). | 0.686 |
| 35 | 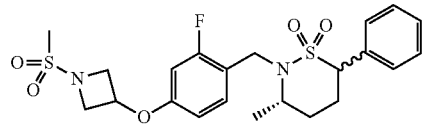 [SMILES: C[C@H]1CCC(c2ccccc2)S(=O)(=O)N1Cc1ccc(OC2CN(S(C)(=O)=O)C2)cc1F] Stereoisomer B | (3S,6S)-2-[6-(1-Methanesulfonyl-piperidin-4-yloxy)-pyridin-3-ylmethyl]-(3S)-3-methyl-6-phenyl-[1,2]thiazinane 1,1-dioxide | $^1$H NMR (400 MHz, DMSO) δ 8.17-8.12 (d, J = 2.4 Hz, 1H), 7.76-7.69 (m, 1H), 7.51-7.44 (m, 2H), 7.43-7.34 (m, 3H), 6.90-6.82 (d, J = 8.6 Hz, 1H), 5.21-5.07 (m, 1H), 4.45-4.27 (m, ,3H), 3.65-3.51 (m, 1H), 3.46-3.33 (m, 2H), 3.21-3.07 (m, 2H), 2.94-2.86 (s, 2H), 2.81-2.62 (d, J = 13.2 Hz, 1H), 2.20-1.99 (m, 4H), 1.92-1.70 (m, 2H), 1.70-1.55 (m, 1H), 1.42-1.28 (d, J = 6.9 Hz, 3H). | 1.1 |
| 36 | Stereoisomer A | 2-(2-fluoro-4-((1-(methylsulfonyl)azetidin-3-yl)oxy)benzyl)-(3S)-3-methyl-6-phenyl-1,2-thiazinane 1,1-dioxide | $^1$H NMR (400 MHz, DMSO) δ 7.50-7.32 (m, 6H), 6.81-6.70 (m, 2H), 5.10-4.97 (m, 1H), 4.55-4.40 (m, 2H), 4.37-4.23 (m, 3H), 4.18-4.02 (m, 1H), 3.98-3.85 (m, 2H), 3.10-3.00 (s, 3H), 2.48-2.30 (m, 1H), 2.16-2.04 (m, 1H), 1.89-1.72 (m, 1H), 1.73-1.60 (m, 1H), 1.13-1.05 (d, J = 6.8 Hz, 3H). | 0.071 |

TABLE 4-continued

| | Structure | Name | Proton NMR | IC$_{50}$ |
|---|---|---|---|---|
| 37 | 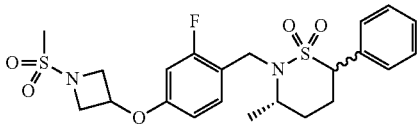 [SMILES: C[C@H]1CCC(c2ccccc2)S(=O)(=O)N1Cc1ccc(OC2CN(S(C)(=O)=O)C2)cc1F]<br>Stereoisomer B | 2-(2-fluoro-4-((1-(methylsulfonyl)azetidin-3-yl)oxy)benzyl)-(3S)-3-methyl-6-phenyl-1,2-thiazinane 1,1-dioxide | $^1$H NMR (400 MHz, DMSO) δ 7.50-7.43 (m, 2H), 7.43-7.33 (m, 4H), 6.86-6.72 (m, 2H), 5.14-4.99 (m, 1H), 4.48-4.36 (m, 3H), 4.36-4.26 (m, 2H), 3.97-3.85 (m, 2H), 3.66-3.49 (m, 1H), 3.12-3.02 (s, 3H), 2.81-2.63 (m, 1H), 2.23-1.98 (m, 2H), 1.70-1.58 (m, 1H), 1.44-1.28 (d, J = 7.0 Hz, 3H). | 0.194 |
| 38 | 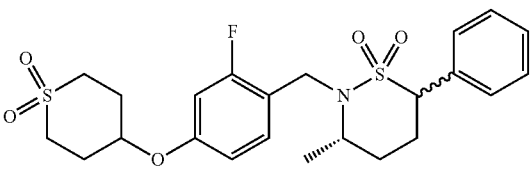 [SMILES: C[C@H]1CCC(c2ccccc2)S(=O)(=O)N1Cc1ccc(OC2CCS(=O)(=O)CC2)cc1F]<br>Stereoisomer A | 2-(4-((1,1-dioxidotetrahydro-2H-thiopyran-4-yl)oxy)-2-fluorobenzyl)-(3S)-3-methyl-6-phenyl-1,2-thiazinane 1,1-dioxide | | 0.135 |
| 39 | 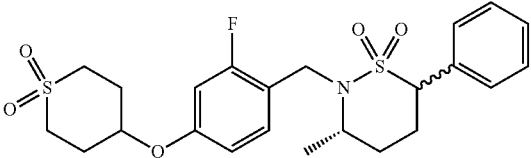 [SMILES: C[C@H]1CCC(c2ccccc2)S(=O)(=O)N1Cc1ccc(OC2CCS(=O)(=O)CC2)cc1F]<br>Stereoisomer B | 2-(4-((1,1-dioxidotetrahydro-2H-thiopyran-4-yl)oxy)-2-fluorobenzyl)-(3S)-3-methyl-6-phenyl-1,2-thiazinane 1,1-dioxide | $^1$H NMR (400 MHz, DMSO) δ 7.53-7.43 (m, 2H), 7.43-7.31 (m, 4H), 6.99-6.85 (m, 2H), 4.76-4.67 (m, 1H), 4.53-4.37 (m, 2H), 4.36-4.25 (m, 1H), 4.19-4.01 (m, 1H), 3.26-3.09 (m, 4H), 2.48-2.36 (m, 1H), 2.29-2.02 (m, 5H), 1.90-1.70 (m, 1H), 1.70-1.57 (m, 1H), 1.13-1.05 (d, J = 7.0 Hz, 3H). | 0.119 |
| 40 | 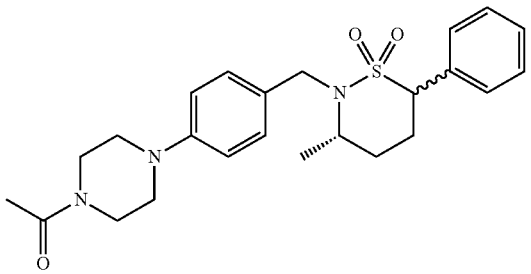 [SMILES: CC(=O)N1CCN(c2ccc(CN3[C@@H](C)CCC(c4ccccc4)S3(=O)=O)cc2)CC1]<br>Stereoisomer A | 1-(4-(4-(((3S)-3-methyl-1,1-dioxido-6-phenyl-1,2-thiazinan-2-yl)methyl)phenyl)piperazin-1-yl)ethanone | $^1$H NMR (400 MHz, DMSO) δ 7.49-7.43 (m, 2H), 7.43-7.32 (m, 3H), 7.29-7.18 (m, 2H), 6.97-6.88 (m, 2H), 4.49-4.40 (d, J = 16.5 Hz, 1H), 4.40-4.29 (m, 1H), 4.24-4.14 (d, J = 16.5 Hz, 1H), 4.13-3.98 (m, 1H), 3.64-3.48 (m, 4H), 3.17-3.10 (m, 2H), 3.10-3.01 (m, 2H), 2.47-2.30 (m, 1H), 2.15-2.05 (m, 1H), 2.03 (s, 3H), 1.89-1.70 (m, 1H), 1.70-1.52 (m, 1H), 1.17-1.03 (d, J = 6.9 Hz, 3H). | 0.081 |
| 41 | 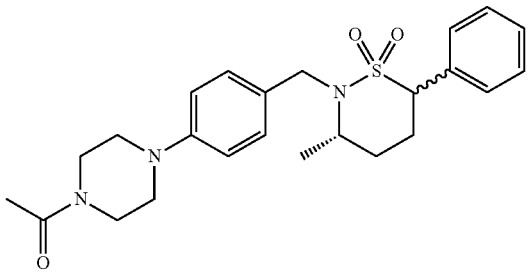 [SMILES: CC(=O)N1CCN(c2ccc(CN3[C@@H](C)CCC(c4ccccc4)S3(=O)=O)cc2)CC1]<br>Stereoisomer B | 1-(4-(4-(((3S)-3-methyl-1,1-dioxido-6-phenyl-1,2-thiazinan-2-yl)methyl)phenyl)piperazin-1-yl)ethanone | $^1$H NMR (400 MHz, DMSO) δ 7.50-7.43 (m, 2H), 7.41-7.36 (m, 3H), 7.28-7.20 (m, 2H), 7.00-6.95 (m, 2H), 4.39-4.24 (m, 3H), 3.61-3.55 (m, 4H), 3.21-3.14 (m, 2H), 3.12-3.08 (m, 2H), 2.78-2.63 (m, 1H), 2.12-1.95 (m, 6H), 1.64-1.53 (m, 1H), 1.37-1.27 (d, J = 7.1 Hz, 3H). | 0.126 |

TABLE 4-continued

| | Structure | Name | Proton NMR | IC$_{50}$ |
|---|---|---|---|---|
| 42 | Stereoisomer A | 1-(4-(5-(((3S)-3-methyl-1,1-dioxido-6-phenyl-1,2-thiazinan-2-yl)methyl)pyridin-2-yl)piperazin-1-yl)ethanone | $^1$H NMR (400 MHz, DMSO) δ 8.16-8.09 (d, J = 2.3 Hz, 1H), 7.61-7.53 (m, 1H), 7.52-7.43 (m, 2H), 7.43-7.33 (m, 3H), 6.95-6.83 (d, J = 8.8 Hz, 1H), 4.46-4.14 (m, 3H), 3.65-3.51 (m, 7H), 3.51-3.42 (m, 2H), 2.87-2.60 (m, 1H), 2.17-1.93 (s, 5H), 1.69-1.53 (m, 1H), 1.42-1.23 (d, J = 7.1 Hz, 3H). | 0.837 |
| 43 | Stereoisomer B | 1-(4-(5-(((3S)-3-methyl-1,1-dioxido-6-phenyl-1,2-thiazinan-2-yl)methyl)pyridin-2-yl)piperazin-1-yl)ethanone | $^1$H NMR (400 MHz, DMSO) δ 8.16-8.09 (d, J = 2.0 Hz, 1H), 7.59-7.51 (dd, J = 8.6, 2.5 Hz, 1H), 7.51-7.43 (m, 2H), 7.43-7.31 (m, 3H), 6.95-6.78 (d, J = 8.9 Hz, 1H), 4.51-4.30 (m, 1H), 4.30-4.13 (m, 1H), 4.15-3.92 (m, 1H), 3.63-3.48 (m, 6H), 3.48-3.38 (m, 2H), 2.47-2.26 (m, 1H), 2.16-2.05 (m, 1H), 2.02 (s, 3H), 1.92-1.70 (m, 1H), 1.70-1.56 (m, 1H), 1.19-1.07 (d, J = 6.8 Hz, 3H). | 1.5 |
| 44 | Stereoisomer A | (3S)-3-Methyl-2-(4-((1-(methylsulfonyl)piperidin-4-yl)oxy)benzyl)-6-phenyl-1,2-thiazinane 1,1-dioxide | $^1$H NMR (400 MHz, DMSO) δ 7.52-7.43 (m, 2H), 7.43-7.32 (m, 3H), 7.32-7.25 (m, 2H), 7.01-6.87 (m, 2H), 4.62-4.49 (m, 1H), 4.49-4.42 (m, 1H), 4.42-4.34 (dd, J = 12.8, 3.5 Hz, 1H), 4.27-4.18 (d, J = 16.6 Hz, 1H), 4.16-3.92 (m, 1H), 3.43-3.30 (m, 2H), 3.20-3.02 (m, 2H), 2.93-2.81 (s, 3H), 2.46-2.28 (m, 1H), 2.17-2.04 (m, 1H), 2.04-1.92 (m, 2H), 1.90-1.56 (m, 4H), 1.14-1.04 (d, J = 6.8 Hz, 3H). | 0.014 |
| 45 | Stereoisomer B | (3S)-3-Methyl-2-(4-((1-(methylsulfonyl)piperidin-4-yl)oxy)benzyl)-6-phenyl-1,2-thiazinane 1,1-dioxide | $^1$H NMR (400 MHz, DMSO) δ 7.50-7.44 (m, 2H), 7.44-7.33 (m, 3H), 7.33-7.26 (m, 2H), 7.06-6.94 (m, 2H), 4.63-4.49 (m, 1H), 4.45-4.26 (m, 1H), 4.26 (m, 1H), 3.61-3.45 (m, 1H), 3.44-3.31 (m, 2H), 3.20-3.05 (m, 2H), 2.95-2.85 (s, 3H), 2.83-2.63 (m, 1H), 2.17-1.93 (m, 4H), 1.85-1.66 (m, 2H), 1.66-1.52 (m, 1H), 1.38-1.29 (d, J = 7.0 Hz, 3H). | 0.022 |
| 46 | Stereoisomer A | 1-(4-(4-(((3R)-3-methyl-1,1-dioxido-6-phenyl-1,2-thiazinan-2-yl)methyl)phenyl)piperazin-1-yl)ethanone | $^1$H NMR (400 MHz, DMSO) δ 7.50-7.43 (m, 2H), 7.43-7.31 (m, 3H), 7.28-7.18 (m, 2H), 6.99-6.87 (m, 2H), 4.51-4.40 (d, J = 16.5 Hz, 1H), 4.40-4.30 (m, 1H), 4.27-4.15 (d, J = 16.5 Hz, 1H), 4.15-3.89 (m, 1H), 3.62-3.49 (m, 4H), 3.19-3.09 (m, 2H), 3.09-3.00 (m, 2H), 2.46-2.32 (m, 1H), 2.13-2.05 (m, 1H), 2.02 (s, 3H), 1.93-1.71 (m, 1H), 1.71-1.57 (m, 1H), 1.14-1.01 (d, J = 6.9 Hz, 3H). | |

TABLE 4-continued

| | Structure | Name | Proton NMR | IC$_{50}$ |
|---|---|---|---|---|
| 47 | Stereoisomer B | 1-(4-(4-(((3R)-3-methyl-1,1-dioxido-6-phenyl-1,2-thiazinan-2-yl)methyl)phenyl)piperazin-1-yl)ethanone | $^1$H NMR (400 MHz, DMSO) δ 7.52-7.43 (m, 2H), 7.43-7.32 (m, 3H), 7.29-7.19 (m, 2H), 7.02-6.91 (m, 2H), 4.44-4.21 (m, 3H), 3.63-3.54 (m, 4H), 3.54-3.46 (m, 1H), 3.23-3.13 (m, 2H), 3.12-3.05 (m, 2H), 2.82-2.63 (m, 1H), 2.13-1.95 (m, 5H), 1.66-1.54 (m, 1H), 1.37-1.28 (d, J = 7.1 Hz, 3H). | 0.299 |
| 48 | Stereoisomer A | 1-{4-[5-((3R)-3-Methyl-1,1-dioxo-6-phenyl-[1,2]thiazinan-2-ylmethyl)-pyridin-2-yl]-piperazin-1-yl}-ethanone | $^1$H NMR (400 MHz, DMSO) δ 8.16-8.08 (d, J = 2.3 Hz, 1H), 7.64-7.53 (m, 1H), 7.52-7.43 (m, 2H), 7.43-7.33 (m, 3H), 6.93-6.84 (d, J = 8.7 Hz, 1H), 4.46-4.16 (m, 3H), 3.63-3.50 (m, 7H), 3.50-3.43 (m, 2H), 2.81-2.60 (m, 1H), 2.15-1.98 (m, 5H), 1.70-1.48 (m, 1H), 1.41-1.27 (d, J = 7.0 Hz, 3H). | 1.5 |
| 49 | Stereoisomer B | 1-{4-[5-((3R)-3-Methyl-1,1-dioxo-6-phenyl-[1,2]thiazinan-2-ylmethyl)-pyridin-2-yl]-piperazin-1-yl}-ethanone | $^1$H NMR (400 MHz, DMSO) δ 8.16-8.10 (d, J = 2.3 Hz, 1H), 7.61-7.53 (m, 1H), 7.51-7.43 (m, 2H), 7.43-7.31 (m, 3H), 6.89-6.80 (d, J = 8.8 Hz, 1H), 4.50-4.34 (m, 2H), 4.30-4.14 (m, 1H), 4.12-3.95 (m, 1H), 3.58-3.48 (s, 6H), 3.48-3.39 (m, 2H), 2.46-2.27 (m, 1H), 2.15-2.06 (m, 1H), 2.03 (s, 3H), 1.91-1.71 (m, 1H), 1.70-1.51 (m, 1H), 1.17-1.08 (d, J = 6.6 Hz, 3H). | 5.5 |
| 50 | Stereoisomer A | 2-[6-(1-Methanesulfonyl-piperidin-4-yloxy)-pyridin-3-ylmethyl]-(3R)-3-methyl-6-phenyl-[1,2]thiazinane 1,1-dioxide | $^1$H NMR (400 MHz, DMSO) δ 8.18-8.13 (d, J = 2.4 Hz, 1H), 7.77-7.67 (m, 1H), 7.50-7.44 (m, 2H), 7.44-7.26 (m, 3H), 6.89-6.80 (d, J = 8.7 Hz, 1H), 5.23-5.10 (m, 1H), 4.48-4.27 (m, 3H), 3.65-3.50 (m, 1H), 3.49-3.32 (m, 2H), 3.22-3.06 (m, 2H), 2.96-2.84 (s, 2H), 2.83-2.61 (m, 1H), 2.17-1.96 (m, 4H), 1.90-1.68 (m, 2H), 1.68-1.57 (m, 1H), 1.42-1.31 (d, J = 7.1 Hz, 3H). | 0.168 |
| 51 | Stereoisomer B | 2-[6-(1-Methanesulfonyl-piperidin-4-yloxy)-pyridin-3-ylmethyl]-(3R)-3-methyl-6-phenyl-[1,2]thiazinane 1,1-dioxide | $^1$H NMR (400 MHz, DMSO) δ 8.18-8.10 (d, J = 2.0 Hz, 1H), 7.78-7.67 (m, 1H), 7.49-7.43 (m, 2H), 7.43-7.32 (m, 3H), 6.89-6.74 (d, J = 8.3 Hz, 1H), 5.21-5.03 (m, 1H), 4.53-4.36 (m, 2H), 4.36-4.20 (m, 1H), 4.19-3.94 (m, 1H), 3.44-3.33 (m, 2H), 3.20-3.06 (m, 2H), 2.89 (s, 2H), 2.47-2.29 (m, 1H), 2.20-1.97 (m, 3H), 1.94-1.58 (m, 4H), 1.17-1.06 (d, J = 6.8 Hz, 3H). | 1.4 |

TABLE 4-continued

| | Structure | Name | Proton NMR | IC$_{50}$ |
|---|---|---|---|---|
| 52 | 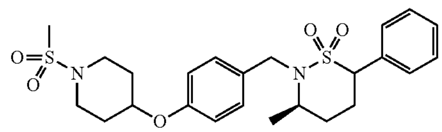 [SMILES: C[C@@H]1CCC(c2ccccc2)S(=O)(=O)N1Cc1ccc(OC2CCN(S(C)(=O)=O)CC2)cc1] | (3R)-3-Methyl-2-(4-((1-(methylsulfonyl)piperidin-4-yl)oxy)benzyl)-6-phenyl-1,2-thiazinane 1,1-dioxide | $^1$H NMR (400 MHz, DMSO) δ 7.52-7.43 (m, 2H), 7.43-7.34 (m, 3H), 7.34-7.24 (m, 2H), 7.06-6.94 (m, 2H), 4.65-4.47 (m, 1H), 4.46-4.24 (m, 3H), 3.66-3.44 (m, 1H), 3.44-3.31 (m, 2H), 3.22-3.05 (m, 2H), 2.94-2.84 (s, 3H), 2.80-2.62 (m, 1H), 2.15-1.90 (m, 4H), 1.83-1.65 (m, 2H), 1.65-1.51 (m, 1H), 1.42-1.27 (d, J = 7.1 Hz, 3H). | 0.020 |
| 53 | 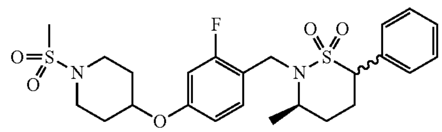 [SMILES: C[C@@H]1CCC(c2ccccc2)S(=O)(=O)N1Cc1ccc(OC2CCN(S(C)(=O)=O)CC2)cc1F] | 2-(2-fluoro-4-((1-(methylsulfonyl)piperidin-4-yl)oxy)benzyl)-(3R)-3-methyl-6-phenyl-1,2-thiazinane 1,1-dioxide | $^1$H NMR (400 MHz, DMSO) δ 7.51-7.43 (m, 2H), 7.43-7.30 (m, 4H), 6.96-6.89 (m, 1H), 6.89-6.83 (m, 1H), 4.71-4.52 (m, 1H), 4.50-4.32 (m, 3H), 3.68-3.46 (m, 1H), 3.44-3.31 (m, 2H), 3.22-3.04 (m, 2H), 2.95-2.86 (s, 2H), 2.83-2.60 (m, 1H), 2.24-1.92 (m, 4H), 1.92-1.67 (m, 2H), 1.67-1.57 (m, 1H), 1.44-1.28 (d, J = 6.9 Hz, 3H). | 0.006 |
| 54 | Stereoisomer A | 2-(2-fluoro-4-((1-(methylsulfonyl)piperidin-4-yl)oxy)benzyl)-6-phenyl-1,2-thiazinane 1,1-dioxide | | 0.037 |
| 55 | Stereoisomer B | 2-(2-fluoro-4-((1-(methylsulfonyl)piperidin-4-yl)oxy)benzyl)-6-phenyl-1,2-thiazinane 1,1-dioxide | $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.94-2.88 (s, 3H), 2.48-2.39 (m, 1H), 2.21-2.08 (m, 1H), 2.08-1.91 (m, 3H), 1.82-1.68 (m, 2H), 1.68-1.57 (m, 1H). | 0.086 |
| 56 | Stereoisomer A | 5-(2-fluoro-4-((1-(methylsulfonyl)piperidin-4-yl)oxy)benzyl)-3-phenyl-1,4,5-oxathiazepane 4,4-dioxide | $^1$H NMR (400 MHz, DMSO) δ 7.48-7.30 (m, 6H), 6.97-6.89 (m, 1H), 6.89-6.84 (m, 1H), 4.68-4.56 (m, 1H), 4.56-4.47 (m, 1H), 4.47-4.38 (m, 1H), 4.38-4.30 (m, 1H), 3.57-3.41 (m, 1H), 3.42-3.31 (m, 2H), 3.19-3.05 (m, 3H), 2.94-2.88 (s, 3H), 2.48-2.39 (m, 1H), 2.21-2.08 (m, 1H), 2.08-1.91 (m, 3H), 1.82-1.68 (m, 2H), 1.68-1.57 (m, 1H). | 0.094 |
| 57 | Stereoisomer B | 5-(2-fluoro-4-((1-(methylsulfonyl)piperidin-4-yl)oxy)benzyl)-3-phenyl-1,4,5-oxathiazepane 4,4-dioxide | | 0.014 |

TABLE 4-continued

| | Structure | Name | Proton NMR | IC$_{50}$ |
|---|---|---|---|---|
| 58 | Stereoisomer A | Cyclopropyl(4-(3-fluoro-4-(((3S)-3-methyl-1,1-dioxido-6-phenyl-1,2-thiazinan-2-yl)methyl)phenyl)piperazin-1-yl)methanone | $^1$H NMR (400 MHz, DMSO) δ 7.49-7.43 (m, 2H), 7.43-7.33 (m, 3H), 7.33-7.25 (m, 1H), 6.87-6.75 (m, 2H), 4.43-4.34 (m, 3H), 3.90-3.70 (s, 2H), 3.69-3.49 (m, 3H), 3.26-3.08 (s, 4H), 2.77-2.59 (d, J = 13.2 Hz, 1H), 2.17-1.93 (m, 3H), 1.67-1.57 (d, J = 37.7 Hz, 1H), 1.40-1.31 (d, J = 7.1 Hz, 3H), 0.81-0.68 (m, 4H). | 0.014 |
| 59 | Stereoisomer B | Cyclopropyl(4-(3-fluoro-4-(((3S)-3-methyl-1,1-dioxido-6-phenyl-1,2-thiazinan-2-yl)methyl)phenyl)piperazin-1-yl)methanone | $^1$H NMR (400 MHz, DMSO) δ 7.50-7.43 (m, 2H), 7.43-7.29 (m, 4H), 6.85-6.78 (m, 1H), 6.78-6.69 (m, 1H), 4.50-4.36 (m, 2H), 4.35-4.22 (m, 1H), 4.20-3.99 (m, 1H), 3.89-3.74 (m, 2H), 3.69-3.52 (m, 2H), 3.25-3.08 (d, J = 26.2 Hz, 4H), 2.46-2.38 (m, 1H), 2.18-1.94 (m, 2H), 1.89-1.72 (m, 1H), 1.72-1.59 (m, 1H), 1.16-1.04 (d, J = 6.8 Hz, 3H), 0.85-0.65 (m, 4H). | 0.015 |
| 60 | Stereoisomer A | Cyclopropyl(4-(4-(((3S)-3-methyl-1,1-dioxido-6-phenyl-1,2-thiazinan-2-yl)methyl)phenyl)piperazin-1-yl)methanone | $^1$H NMR (400 MHz, DMSO) δ 7.49-7.43 (m, 2H), 7.43-7.34 (m, 3H), 7.29-7.22 (m, 2H), 6.97-6.90 (m, 2H), 4.52-4.40 (d, J = 16.4 Hz, 1H), 4.40-4.31 (dd, J = 12.9, 3.5 Hz, 1H), 4.25-4.15 (d, J = 16.5 Hz, 1H), 4.11-4.00 (m, 1H), 3.89-3.72 (m, 2H), 3.70-3.52 (m, 3H), 3.21-3.04 (m, 5H), 2.46-2.39 (m, 2H), 2.17-1.95 (m, 2H), 1.88-1.73 (m, 1H), 1.70-1.56 (m, 1H), 1.15-1.05 (d, J = 6.9 Hz, 3H), 0.81-0.66 (m, 4H). | 0.015 |
| 61 | Stereoisomer B | Cyclopropyl(4-(4-(((3S)-3-methyl-1,1-dioxido-6-phenyl-1,2-thiazinan-2-yl)methyl)phenyl)piperazin-1-yl)methanone | $^1$H NMR (400 MHz, DMSO) δ 7.50-7.44 (m, 2H), 7.43-7.36 (m, 3H), 7.28-7.22 (m, 2H), 7.02-6.95 (m, 2H), 4.40-4.22 (m, 3H), 3.87-3.77 (m, 2H), 3.68-3.57 (m, 2H), 3.55-3.49 (m, 1H), 3.23-3.08 (m, 4H), 2.75-2.68 (m, 1H), 2.11-1.97 (m, 3H), 1.64-1.56 (m, 1H), 1.36-1.29 (d, J = 7.1 Hz, 3H), 0.79-0.68 (m, 4H). | 0.061 |
| 62 | 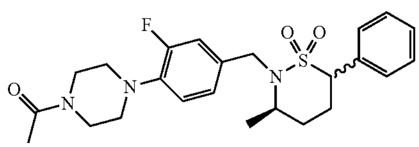 [SMILES: CC(=O)N1CCN(c2ccc(CN3[C@H](C)CCC(c4ccccc4)S3(=O)=O)cc2F)CC1] | 1-(4-(2-fluoro-4-(((3S)-3-methyl-1,1-dioxido-6-phenyl-1,2-thiazinan-2-yl)methyl)phenyl)piperazin-1-yl)ethanone | | 0.036 |
| 63 | Stereoisomer A | 1-(4-(3-fluoro-4-(((3S)-3-methyl-1,1-dioxido-5-phenylisothiazolidin-2-yl)methyl)phenyl)piperazin-1-yl)ethanone | | 0.57 |

TABLE 4-continued

| | Structure | Name | Proton NMR | IC$_{50}$ |
|---|---|---|---|---|
| 64 | 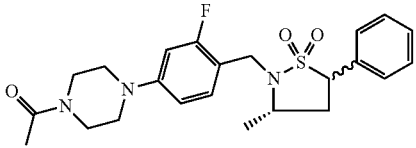 [SMILES: CC(=O)N1CCN(c2ccc(CN3[C@@H](C)CC(c4ccccc4)S3(=O)=O)c(F)c2)CC1] Stereoisomer B | 1-(4-(3-fluoro-4-(((3S)-3-methyl-1,1-dioxido-5-phenylisothiazolidin-2-yl)methyl)phenyl)piperazin-1-yl)ethanone | | 0.709 |
| 65 | 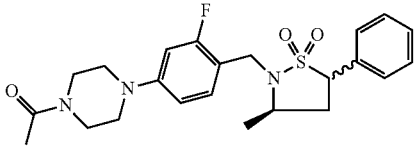 [SMILES: CC(=O)N1CCN(c2ccc(CN3[C@H](C)CC(c4ccccc4)S3(=O)=O)c(F)c2)CC1] Stereoisomer A | 1-(4-(3-fluoro-4-(((3R)-3-methyl-1,1-dioxido-5-phenylisothiazolidin-2-yl)methyl)phenyl)piperazin-1-yl)ethanone | | 2.3 |
| 66 | 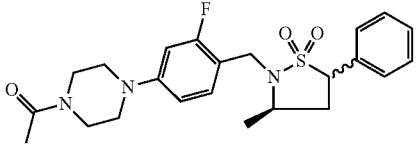 [SMILES: CC(=O)N1CCN(c2ccc(CN3[C@H](C)CC(c4ccccc4)S3(=O)=O)c(F)c2)CC1] Stereoisomer B | 1-(4-(3-fluoro-4-(((3S)-3-methyl-1,1-dioxido-5-phenylisothiazolidin-2-yl)methyl)phenyl)piperazin-1-yl)ethanone | | 0.31 |
| 67 | 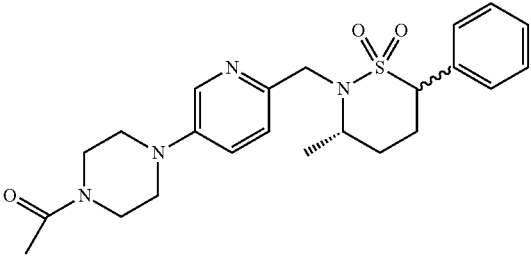 [SMILES: CC(=O)N1CCN(c2ccc(CN3[C@@H](C)CCC(c4ccccc4)S3(=O)=O)nc2)CC1] | 1-{4-[6-((3S)-3-Methyl-1,1-dioxo-6-phenyl-[1,2]thiazinan-2-ylmethyl)-pyridin-3-yl]-piperazin-1-yl}-ethanone | | 1.54 |
| 68 | 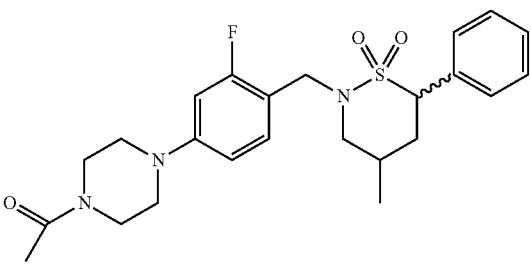 [SMILES: CC(=O)N1CCN(c2ccc(CN3CC(C)CC(c4ccccc4)S3(=O)=O)c(F)c2)CC1] Stereoisomer A | 1-{4-[3-Fluoro-4-(4-methyl-1,1-dioxo-6-phenyl-[1,2]thiazinan-2-ylmethyl)-phenyl]-piperazin-1-yl}-ethanone | | 0.403 |
| 69 | 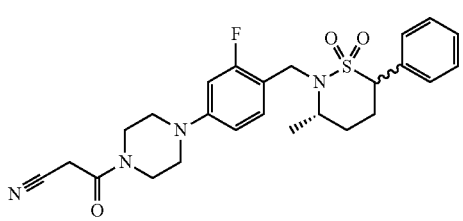 [SMILES: C[C@H]1CCC(c2ccccc2)S(=O)(=O)N1Cc1ccc(N2CCN(C(=O)CC#N)CC2)cc1F] Stereoisomer A | 3-{4-[3-Fluoro-4-((3S)-3-methyl-1,1-dioxo-6-phenyl-[1,2]thiazinan-2-ylmethyl)-phenyl]-piperazin-1-yl}-3-oxo-propionitrile | | 0.103 |

TABLE 4-continued

| | Structure | Name | Proton NMR | IC$_{50}$ |
|---|---|---|---|---|
| 71 | Stereoisomer B | 3-{4-[3-Fluoro-4-((3S)-3-methyl-1,1-dioxo-6-phenyl-[1,2]thiazinan-2-ylmethyl)-phenyl]-piperazin-1-yl}-3-oxo-propionitrile | | 0.041 |
| 72 | Stereoisomer A | 4-{4-[3-Fluoro-4-((3S)-3-methyl-1,1-dioxo-6-phenyl-[1,2]thiazinan-2-ylmethyl)-phenyl]-piperazin-1-yl}-4-oxo-butyronitrile | | 0.064 |
| 73 | Stereoisomer B | 4-{4-[3-Fluoro-4-((3S)-3-methyl-1,1-dioxo-6-phenyl-[1,2]thiazinan-2-ylmethyl)-phenyl]-piperazin-1-yl}-4-oxo-butyronitrile | | 0.466 |
| 74 | Stereoisomer A | 1-{4-[3-Fluoro-4-((3S)-3-methyl-1,1-dioxo-6-phenyl-[1,2]thiazinan-2-ylmethyl)-phenyl]-piperazin-1-yl}-2-methoxy-ethanone | | 0.029 |
| 75 | Stereoisomer B | 1-{4-[3-Fluoro-4-((3S)-3-methyl-1,1-dioxo-6-phenyl-[1,2]thiazinan-2-ylmethyl)-phenyl]-piperazin-1-yl}-2-methoxy-ethanone | | 0.167 |

TABLE 4-continued

| | Structure | Name | Proton NMR | IC$_{50}$ |
|---|---|---|---|---|
| 76 | Stereoisomer A | 1-{4-[3-Fluoro-4-((3S)-3-methyl-1,1-dioxo-6-phenyl-[1,2]thiazinan-2-ylmethyl)-phenyl]-piperazin-1-yl}-2-methoxy-propan-1-one | $^1$H NMR (400 MHz, DMSO) δ 7.50-7.43 (m, 2H), 7.43-7.28 (m, 4H), 6.85-6.78 (m, 1H), 6.78-6.69 (m, 1H), 4.49-4.43 (m, 1H), 4.43-4.37 (m, 1H), 4.33-4.20 (m, 2H), 4.16-4.03 (m, 1H), 3.73-3.55 (d, J = 30.5 Hz, 4H), 3.24-3.20 (s, 3H), 3.20-3.10 (m, 4H), 2.47-2.35 (m, 1H), 2.15-2.04 (m, 1H), 1.90-1.73 (m, 1H), 1.71-1.57 (m, 1H), 1.28-1.20 (d, J = 6.6 Hz, 3H), 1.13-1.04 (d, J = 6.9 Hz, 3H). | 0.031 |
| 77 | Stereoisomer B | 1-{4-[3-Fluoro-4-((3S)-3-methyl-1,1-dioxo-6-phenyl-[1,2]thiazinan-2-ylmethyl)-phenyl]-piperazin-1-yl}-2-methoxy-propan-1-one | $^1$H NMR (400 MHz, DMSO) δ 7.49-7.43 (m, 2H), 7.43-7.34 (m, 3H), 7.33-7.26 (m, 1H), 6.85-6.76 (m, 2H), 4.43-4.34 (m, 3H), 4.29-4.20 (m, 1H), 3.75-3.51 (m, 5H), 3.25-3.13 (m, 7H), 2.79-2.63 (m, 1H), 2.17-2.00 (m, 2H), 1.68-1.55 (m, 1H), 1.39-1.31 (d, J = 7.0 Hz, 3H), 1.28-1.20 (d, J = 6.5 Hz, 3H). | 0.138 |
| 78 | Stereoisomer A | 1-{4-[3-Fluoro-4-((3S)-3-methyl-1,1-dioxo-6-phenyl-[1,2]thiazinan-2-ylmethyl)-phenyl]-piperazin-1-yl}-2-hydroxy-propan-1-one | $^1$H NMR (400 MHz, DMSO) δ 7.50-7.43 (m, 2H), 7.43-7.29 (m, 4H), 6.86-6.78 (m, 1H), 6.78-6.69 (dd, J = 14.0, 2.4 Hz, 1H), 5.00-4.91 (d, J = 7.0 Hz, 1H), 4.57-4.35 (m, 3H), 4.35-4.23 (m, 1H), 4.16-4.00 (m, 1H), 3.78-3.46 (m, 4H), 3.21-3.03 (m, 5H), 2.46-2.28 (m, 1H), 2.18-2.00 (m, 1H), 1.90-1.71 (m, 1H), 1.71-1.57 (m, 1H), 1.29-1.15 (d, J = 6.6 Hz, 3H), 1.14-1.02 (d, J = 6.9 Hz, 3H). | 0.029 |
| 79 | Stereoisomer B | 1-{4-[3-Fluoro-4-((3S)-3-methyl-1,1-dioxo-6-phenyl-[1,2]thiazinan-2-ylmethyl)-phenyl]-piperazin-1-yl}-2-hydroxy-propan-1-one | $^1$H NMR (400 MHz, DMSO) δ 7.50-7.43 (m, 2H), 7.43-7.34 (m, 3H), 7.33-7.24 (m, 1H), 6.86-6.75 (m, 2H), 5.00-4.91 (d, J = 6.9 Hz, 1H), 4.51-4.42 (m, 1H), 4.42-4.33 (m, 3H), 3.78-3.47 (m, 5H), 3.25-3.14 (m, 4H), 2.78-2.62 (m, 1H), 2.19-1.96 (m, 2H), 1.69-1.56 (m, 1H), 1.40-1.30 (d, J = 7.1 Hz, 3H), 1.25-1.18 (d, J = 6.9 Hz, 2H). | 0.082 |
| 80 | Stereoisomer A | 1-{4-[3-Fluoro-4-((3S)-3-methyl-1,1-dioxo-6-phenyl-[1,2]thiazinan-2-ylmethyl)-phenyl]-[1,4]diazepan-1-yl}-ethanone | | 0.014 |

TABLE 4-continued

| | Structure | Name | Proton NMR | IC$_{50}$ |
|---|---|---|---|---|
| 81 | 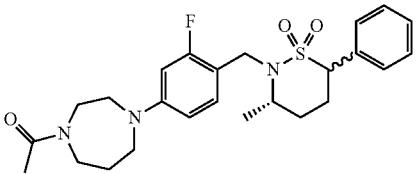 [SMILES: CC(=O)N1CCCN(c2ccc(CN3[C@@H](C)CCC(c4ccccc4)S3(=O)=O)c(F)c2)CC1] Stereoisomer B | 1-{4-[3-Fluoro-4-((3S)-3-methyl-1,1-dioxo-6-phenyl-[1,2]thiazinan-2-ylmethyl)-phenyl]-[1,4]diazepan-1-yl}-ethanone | | 0.118 |
| 82 | 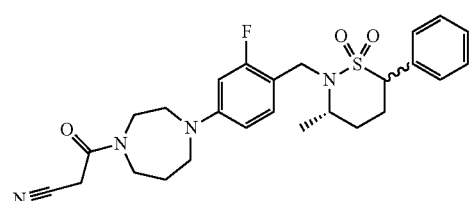 Stereoisomer A | 3-{4-[3-Fluoro-4-((3S)-3-methyl-1,1-dioxo-6-phenyl-[1,2]thiazinan-2-ylmethyl)-phenyl]-[1,4]diazepan-1-yl}-3-oxo-propionitrile | | 0.022 |
| 83 | 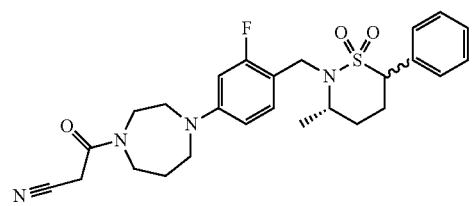 [SMILES: C[C@H]1CCC(c2ccccc2)S(=O)(=O)N1Cc1ccc(N2CCCN(C(=O)CC#N)CC2)cc1F] Stereoisomer B | 3-{4-[3-Fluoro-4-((3S)-3-methyl-1,1-dioxo-6-phenyl-[1,2]thiazinan-2-ylmethyl)-phenyl]-[1,4]diazepan-1-yl}-3-oxo-propionitrile | | 0.213 |
| 84 | 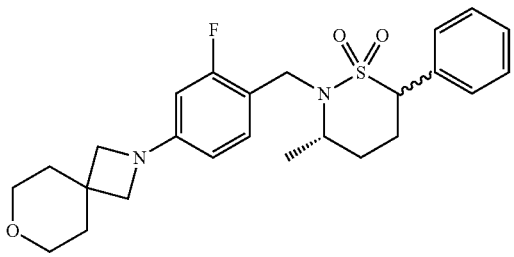 [SMILES: C[C@H]1CCC(c2ccccc2)S(=O)(=O)N1Cc1ccc(N2CC3(CCOCC3)C2)cc1F] Stereoisomer A | 2-[3-Fluoro-4-((3S)-3-methyl-1,1-dioxo-6-phenyl-[1,2]thiazinan-2-ylmethyl)-phenyl]-7-oxa-2-aza-spiro[3.5]nonane | | 0.023 |
| 85 | 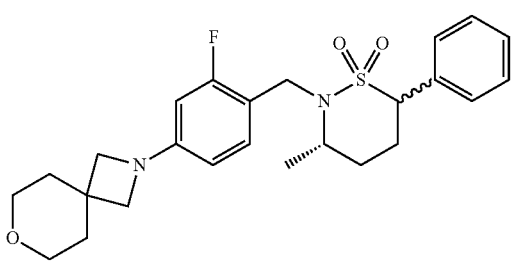 [SMILES: C[C@H]1CCC(c2ccccc2)S(=O)(=O)N1Cc1ccc(N2CC3(CCOCC3)C2)cc1F] Stereoisomer B | 2-[3-Fluoro-4-((3S)-3-methyl-1,1-dioxo-6-phenyl-[1,2]thiazinan-2-ylmethyl)-phenyl]-7-oxa-2-aza-spiro[3.5]nonane | | 0.089 |

TABLE 4-continued

| | Structure | Name | Proton NMR | IC$_{50}$ |
|---|---|---|---|---|
| 86 | Stereoisomer A | 1-[3-Fluoro-4-((3S)-3-methyl-1,1-dioxo-6-phenyl-[1,2]thiazinan-2-ylmethyl)-phenyl]-piperidine-4-carbonitrile | | 0.015 |
| 87 | Stereoisomer B | 1-[3-Fluoro-4-((3S)-3-methyl-1,1-dioxo-6-phenyl-[1,2]thiazinan-2-ylmethyl)-phenyl]-piperidine-4-carbonitrile | | 0.20 |
| 88 | Stereoisomer A | 1-[3-Fluoro-4-((3S)-3-methyl-1,1-dioxo-6-phenyl-[1,2]thiazinan-2-ylmethyl)-phenyl]-[1,4]diazepane | | 0.819 |
| 89 | Stereoisomer B | 1-[3-Fluoro-4-((3S)-3-methyl-1,1-dioxo-6-phenyl-[1,2]thiazinan-2-ylmethyl)-phenyl]-[1,4]diazepane | | 1.25 |
| 90 | Stereoisomer A | 1-{4-[3-Fluoro-4-((3S)-3-methyl-1,1-dioxo-6-phenyl-[1,2]thiazinan-2-ylmethyl)-phenyl]-[1,4]diazepan-1-yl}-2-methoxy-propan-1-one | | 0.076 |

TABLE 4-continued

| | Structure | Name | Proton NMR | IC$_{50}$ |
|---|---|---|---|---|
| 91 | Stereoisomer B | 1-{4-[3-Fluoro-4-((3S)-3-methyl-1,1-dioxo-6-phenyl-[1,2]thiazinan-2-ylmethyl)-phenyl]-[1,4]diazepan-1-yl}-2-hydroxy-propan-1-one | | 0.254 |
| 92 | Stereoisomer A | 1-{4-[3-Fluoro-4-((3S)-3-methyl-1,1-dioxo-6-phenyl-[1,2]thiazinan-2-ylmethyl)-phenyl]-[1,4]diazepan-1-yl}-2-methoxy-propan-1-one | | 0.154 |
| 93 | Stereoisomer B | 1-{4-[3-Fluoro-4-((3S)-3-methyl-1,1-dioxo-6-phenyl-[1,2]thiazinan-2-ylmethyl)-phenyl]-[1,4]diazepan-1-yl}-2-hydroxy-propan-1-one | | 0.049 |
| 94 | Stereoisomer A | 2-[3-Fluoro-4-((3S)-3-methyl-1,1-dioxo-6-phenyl-[1,2]thiazinan-2-ylmethyl)-phenyl]-6-oxa-2-aza-spiro[3.4]octane | | 0.054 |
| 95 | Stereoisomer B | 2-[3-Fluoro-4-((3S)-3-methyl-1,1-dioxo-6-phenyl-[1,2]thiazinan-2-ylmethyl)-phenyl]-6-oxa-2-aza-spiro[3.4]octane | | 0.093 |
| 96 | Stereoisomer A | (3S)-2-(2-Fluoro-4-piperazin-1-yl-benzyl)-3-methyl-6-phenyl-[1,2]thiazinane 1,1-dioxide | | 4.48 |

TABLE 4-continued

| | Structure | Name | Proton NMR | IC$_{50}$ |
|---|---|---|---|---|
| 97 | 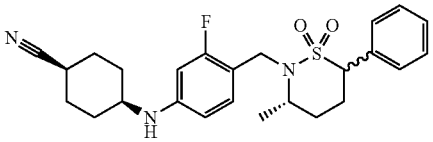 [SMILES: C[C@H]1CCC(c2ccccc2)S(=O)(=O)N1Cc1ccc(N[C@H]2CC[C@@H](C#N)CC2)cc1F] Stereoisomer A | 4-[3-Fluoro-4-((3S)-3-methyl-1,1-dioxo-6-phenyl-[1,2]thiazinan-2-ylmethyl)-phenylamino]-cyclohexanecarbonitrile | | 0.040 |
| 98 | 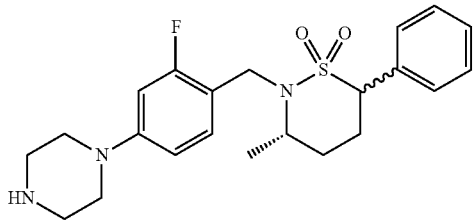 [SMILES: C[C@H]1CCC(c2ccccc2)S(=O)(=O)N1Cc1ccc(N2CCNCC2)cc1F] Stereoisomer B | (3S)-2-(3-Fluoro-4-piperazin-1-yl-benzyl)-3-methyl-6-phenyl-[1,2]thiazinane 1,1-dioxide | | 2.75 |
| 99 | 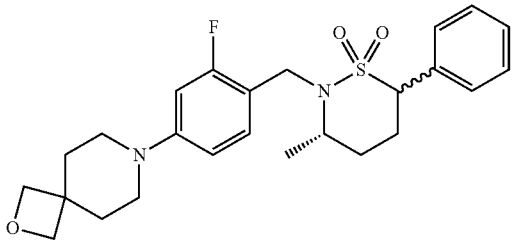 [SMILES: C[C@H]1CCC(c2ccccc2)S(=O)(=O)N1Cc1ccc(N2CCC3(CC2)COC3)cc1F] | 7-[3-Fluoro-4-((3S)-3-methyl-1,1-dioxo-6-phenyl-[1,2]thiazinan-2-ylmethyl)-phenyl]-2-oxa-7-aza-spiro[3.5]nonane | | 0.044 |
| 100 | 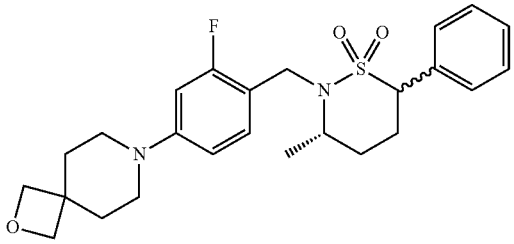 [SMILES: C[C@H]1CCC(c2ccccc2)S(=O)(=O)N1Cc1ccc(N2CCC3(CC2)COC3)cc1F] | 7-[3-Fluoro-4-((3S)-3-methyl-1,1-dioxo-6-phenyl-[1,2]thiazinan-2-ylmethyl)-phenyl]-2-oxa-7-aza-spiro[3.5]nonane | | 0.012 |
| 101 | 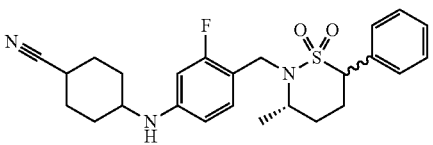 [SMILES: C[C@H]1CCC(c2ccccc2)S(=O)(=O)N1Cc1ccc(NC2CCC(C#N)CC2)cc1F] | 4-[3-Fluoro-4-((3S)-3-methyl-1,1-dioxo-6-phenyl-[1,2]thiazinan-2-ylmethyl)-phenylamino]-cyclohexanecarbonitrile | | 0.018 |
| 102 | 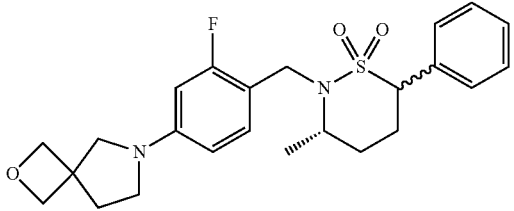 [SMILES: C[C@H]1CCC(c2ccccc2)S(=O)(=O)N1Cc1ccc(N2CCC3(COC3)C2)cc1F] Stereoisomer A | 6-[3-Fluoro-4-((3S)-3-methyl-1,1-dioxo-6-phenyl-[1,2]thiazinan-2-ylmethyl)-phenyl]-2-oxa-6-aza-spiro[3.4]octabne | | 0.025 |

TABLE 4-continued

| | Structure | Name | Proton NMR | IC$_{50}$ |
|---|---|---|---|---|
| 103 | 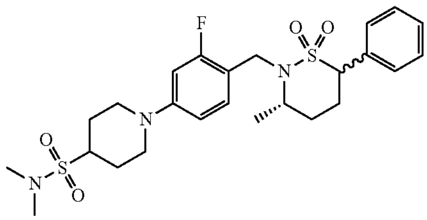 [SMILES: C[C@H]1CCC(c2ccccc2)S(=O)(=O)N1Cc1ccc(N2CCC(S(=O)(=O)N(C)C)CC2)cc1F] | 1-[3-Fluoro-4-((3S)-3-methyl-1,1-dioxo-6-phenyl-[1,2]thiazinan-2-ylmethyl)-phenyl]-piperidine-4-sulfonic acid dimethylamide | | 0.146 |
| 104 | Stereoisomer A | (3S)-2-[2-Fluoro-4-(4-methanesulfonyl-methyl-piperidin-1-yl)-benzyl]-3-methyl-6-phenyl-[1,2]thiazinane 1,1-dioxide | | 0.054 |
| 105 | Stereoisomer B | (3S)-2-[2-Fluoro-4-(4-methanesulfonyl-methyl-piperidin-1-yl)-benzyl]-3-methyl-6-phenyl-[1,2]thiazinane 1,1-dioxide | | 0.018 |
| 106 | Stereoisomer A | (3S)-2-{2-Fluoro-4-[3-(tetrahydro-pyran-4-yl)-azetidin-1-yl]-benzyl}-3-methyl-6-phenyl-[1,2]thiazinane 1,1-dioxide | | 0.020 |
| 107 | Stereoisomer B | 6-[3-Fluoro-4-((3S)-3-methyl-1,1-dioxo-6-phenyl-[1,2]thiazinan-2-ylmethyl)-phenyl]-2-oxa-6-aza-spiro[3.4]octane | | 0.020 |

TABLE 4-continued

| | Structure | Name | Proton NMR | IC$_{50}$ |
|---|---|---|---|---|
| 108 | Stereoisomer B | (3S)-2-{2-Fluoro-4-[3-(tetrahydro-pyran-4-yl)-azetidin-1-yl]-benzyl}-3-methyl-6-phenyl-[1,2]thiazinane 1,1-dioxide | | 0.033 |
| 109 | 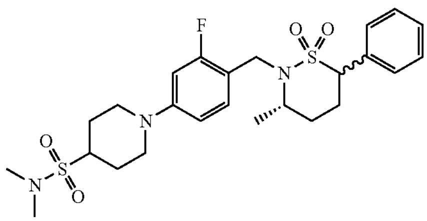 [SMILES: C[C@H]1CCC(c2ccccc2)S(=O)(=O)N1Cc1ccc(N2CCC(S(=O)(=O)N(C)C)CC2)cc1F] | 1-[3-Fluoro-4-((3S)-3-methyl-1,1-dioxo-6-phenyl-[1,2]thiazinan-2-ylmethyl)-phenyl]-piperidine-4-sulfonic acid dimethylamide | | 0.034 |
| 110 | Stereoisomer B | 4-[3-Fluoro-4-((3S)-3-methyl-1,1-dioxo-6-phenyl-91,2]thiazinan-2-ylmethyl)-phenylamino]-cyclohexanecarbo-nitrile | | 0.035 |
| 111 | Stereoisomer A | 4-[3-Fluoro-4-((3S)-3-methyl-1,1-dioxo-6-phenyl-[1,2]thiazinan-2-ylmethyl)-phenylamino]-cyclohexanecarbo-nitrile | | 0.049 |
| 112 | Stereoisomer B | 4-[3-Fluoro-4-((3S)-3-methyl-1,1-dioxo-6-phenyl-[1,2]thiazinan-2-ylmethyl)-phenylamino]-cyclohexanecarbo-nitrile | | 0.030 |
| 113 | Stereoisomer A | 2-(4-Acetyl-piperazin-1-yl)-5-((3S)-3-methyl-1,1-dioxo-6-phenyl-[1,2]thiazinan-2-ylmethyl)-benzonitrile | | 2.75 |

TABLE 4-continued

| | Structure | Name | Proton NMR | IC$_{50}$ |
|---|---|---|---|---|
| 114 | Stereoisomer B | 2-(4-Acetyl-piperazin-1-yl)-5-((3S)-3-methyl-1,1-dioxo-6-phenyl-[1,2]thiazinan-2-ylmethyl)-benzonitrile | | 0.201 |
| 115 | 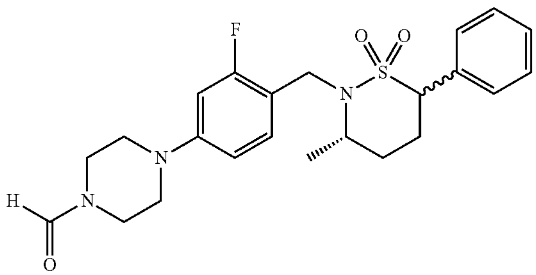 [SMILES: C[C@H]1CCC(c2ccccc2)S(=O)(=O)N1Cc1ccc(N2CCN(C=O)CC2)cc1F] | 4-[3-Fluoro-4-((3S)-3-methyl-1,1-dioxo-6-phenyl-[1,2]thiazinan-2-ylmethyl)-phenyl]-piperazine-1-carbaldehyde | | 0.073 |
| 116 | Stereoisomer A | 1-(4-{3-Fluoro-4-[(3S)-6-(2-fluoro-phenyl)-3-methyl-1,1-dioxo-[1,2]thiazinan-2-ylmethyl]-phenyl}-piperazin-1-yl)-ethanone | | 0.037 |
| 117 | Stereoisomer B | 1-(4-{3-Fluoro-4-[(3S)-6-(2-fluoro-phenyl)-3-methyl-1,1-dioxo-[1,2]thiazinan-2-ylmethyl]-phenyl}-piperazin-1-yl)-ethanone | | 0.003 |
| 118 | Stereoisomer B | 1-{4-[3-Fluoro-4-(4-methyl-1,1-dioxo-6-phenyl-[1,2]thiazinan-2-ylmethyl)-phenyl]-piperazin-1-yl}-ethanone | | 0.020 |

TABLE 4-continued

| | Structure | Name | Proton NMR | IC$_{50}$ |
|---|---|---|---|---|
| 119 | Stereoisomer C | 1-{4-[3-Fluoro-4-(4-methyl-1,1-dioxo-6-phenyl-[1,2]thiazinan-2-ylmethyl)-phenyl]-piperazin-1-yl}-ethanone | | 0.002 |
| 120 | 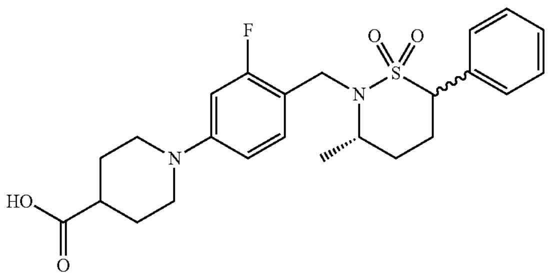 [SMILES: C[C@H]1CCC(c2ccccc2)S(=O)(=O)N1Cc1ccc(N2CCC(C(=O)O)CC2)cc1F] | 1-[3-Fluoro-4-((3S)-3-methyl-1,1-dioxo-6-phenyl-[1,2]thiazinan-2-ylmethyl)-phenyl]-piperidine-4-carboxylic acid | | 0.102 |
| 121 | Stereoisomer A | 1-(4-{3-Fluoro-4-[(3S)-6-(4-fluoro-phenyl)-3-methyl-1,1-dioxo-[1,2]thiazinan-2-ylmethyl]-phenyl}-piperazin-1-yl)-ethanone | | 0.014 |
| 122 | Stereoisomer B | 1-(4-{3-Fluoro-4-[(3S)-6-(4-fluoro-phenyl)-3-methyl-1,1-dioxo-[1,2]thiazinan-2-ylmethyl]-phenyl}-piperazin-1-yl)-ethanone | | 0.047 |
| 123 | 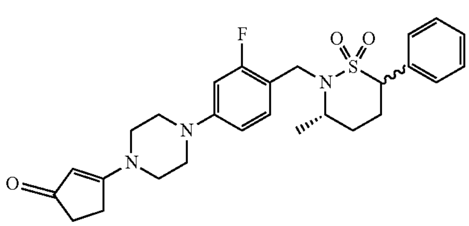 [SMILES: C[C@H]1CCC(c2ccccc2)S(=O)(=O)N1Cc1ccc(N2CCN(C3=CC(=O)CC3)CC2)cc1F] | 3-{4-[3-Fluoro-4-((3S)-3-methyl-1,1-dioxo-6-phenyl-[1,2]thiazinan-2-ylmethyl)-phenyl]-piperazin-1-yl}-cyclopent-2-enone | | 0.089 |
| 124 | 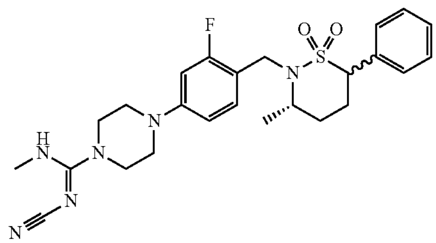 [SMILES: CN/C(=N\C#N)N1CCN(c2ccc(CN3[C@@H](C)CCC(c4ccccc4)S3(=O)=O)c(F)c2)CC1] | 1-(4-{3-Fluoro-4-[(3S)-6-phenyl-3-methyl-1,1-dioxo-[1,2]thiazinan-2-ylmethyl]-phenyl}-piperazin-1-yl)-(Z)-N'-cyano-N-methylacetimid-amide | | 0.010 |

TABLE 4-continued

| | Structure | Name | Proton NMR | IC$_{50}$ |
|---|---|---|---|---|
| 125 | 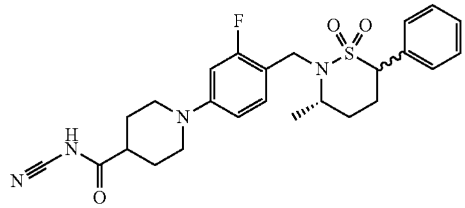 [SMILES: C[C@H]1CCC(c2ccccc2)S(=O)(=O)N1Cc1ccc(N2CCC(C(=O)NC#N)CC2)cc1F] | (3S)-6-phenyl-3-methyl-1,1-dioxo-[1,2]thiazinan-2-ylmethyl]-phenyl}-piperazin-1-yl)-N-cyanoacetamide | | 0.018 |
| 126 | 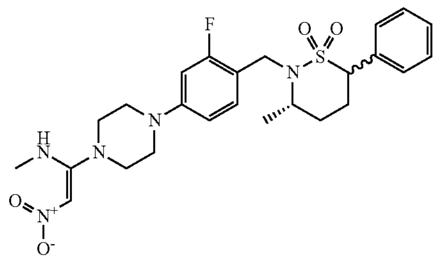 [SMILES: CN/C(=C\[N+](=O)[O-])N1CCN(c2ccc(CN3[C@@H](C)CCC(c4ccccc4)S3(=O)=O)c(F)c2)CC1] | ((E)-1-{4-[3-Fluoro-4-((3S)-3-methyl-1,1-dioxo-6-phenyl-[1,2]thiazinan-2-ylmethyl)-phenyl]-piperazin-1-yl}-2-nitro-vinyl)-methyl-amine | | 0.258 |
| 127 | Stereoisomer A | 1-(4-{3-Fluoro-4-[(3S)-6-(3-fluoro-phenyl)-3-methyl-1,1-dioxo-[1,2]thiazinan-2-ylmethyl]-phenyl}-piperazin-1-yl)-ethanone | $^1$H NMR (400 MHz, DMSO) δ 7.50-7.41 (m, 1H), 7.37-7.26 (m, 3H), 7.24-7.18 (m, 1H), 6.83-6.78 (m, 1H), 6.77-6.70 (m, 1H), 4.58-4.50 (dd, J = 12.6, 3.5 Hz, 1H), 4.45-4.38 (m, 1H), 4.31-4.24 (m, 1H), 4.16-4.02 (m, 1H), 3.62-3.51 (m, 4H), 3.22-3.16 (m, 2H), 3.15-3.08 (m, 2H), 2.47-2.29 (m, 1H), 2.16-2.07 (m, 1H), 2.06-2.01 (s, 2H), 1.89-1.71 (m, 1H), 1.70-1.58 (m, 1H), 1.13-1.04 (d, J = 6.9 Hz, 3H). | 0.058 |
| 128 | Stereoisomer B | 1-(4-{3-Fluoro-4-[(3S)-6-(3-fluoro-phenyl)-3-methyl-1,1-dioxo-[1,2]thiazinan-2-ylmethyl]-phenyl}-piperazin-1-yl)-ethanone | $^1$H NMR (400 MHz, DMSO) δ 7.50-7.41 (m, 1H), 7.35-7.17 (m, 4H), 6.85-6.75 (m, 2H), 4.52-4.43 (m, 1H), 4.40-4.35 (d, J = 2.3 Hz, 2H), 3.64-3.49 (m, 6H), 3.25-3.19 (m, 2H), 3.19-3.11 (m, 2H), 2.79-2.63 (m, 1H), 2.14-2.01 (m, 5H), 1.66-1.56 (m, 1H), 1.39-1.31 (d, J = 7.1 Hz, 3H). | 0.052 |
| 129 | Stereoisomer A | 1-{4-[2-Methyl-4-((3S)-3-methyl-1,1-dioxo-6-phenyl-[1,2]thiazinan-2-ylmethyl)-phenyl]-piperazin-1-yl}-ethanone | | 0.432 |

TABLE 4-continued

| | Structure | Name | Proton NMR | IC$_{50}$ |
|---|---|---|---|---|
| 130 | Stereoisomer B | 1-{4-[2-Methyl-4-((3S)-3-methyl-1,1-dioxo-6-phenyl-[1,2]thiazinan-2-ylmethyl)-phenyl]-piperazin-1-yl}-ethanone | | 0.072 |
| 131 | Stereoisomer A | 1-{4-[3-Methyl-4-((3S)-3-methyl-1,1-dioxo-6-phenyl-[1,2]thiazinan-2-ylmethyl)-phenyl]-piperazin-1-yl}-ethanone | | 0.501 |
| 132 | Stereoisomer B | 1-{4-[3-Methyl-4-((3S)-3-methyl-1,1-dioxo-6-phenyl-[1,2]thiazinan-2-ylmethyl)-phenyl]-piperazin-1-yl}-ethanone | | 3.93 |
| 133 | Stereoisomer A | 5-[3-Fluoro-4-((3S)-3-methyl-1,1-dioxo-6-phenyl-[1,2]thiazinan-2-ylmethyl)-phenyl]-4,5,6,7-tetrahydro-pyrazolo[1,5-a]pyrazine | | 0.244 |
| 134 | Stereoisomer B | 5-[3-Fluoro-4-((3S)-3-methyl-1,1-dioxo-6-phenyl-[1,2]thiazinan-2-ylmethyl)-phenyl]-4,5,6,7-tetrahydro-pyrazolo[1,5-a]pyrazine | | 0.33 |

TABLE 4-continued

| | Structure | Name | Proton NMR | IC$_{50}$ |
|---|---|---|---|---|
| 135 | Stereoisomer A | 7-[3-Fluoro-4-((3S)-3-methyl-1,1-dioxo-6-phenyl-[1,2]thiazinan-2-ylmethyl)-phenyl]-5,6,7,8-tetrahydro-imidazo[1,5-a]pyrazine | | 4.6 |
| 136 | Stereoisomer B | 7-[3-Fluoro-4-((3S)-3-methyl-1,1-dioxo-6-phenyl-[1,2]thiazinan-2-ylmethyl)-phenyl]-5,6,7,8-tetrahydro-imidazo[1,5-a]pyrazine | | 0.754 |
| 137 | Stereoisomer A | (3S)-2-{2-Fluoro-4-[4-(4-methyl-4H-[1,2,4]triazol-3-yl)-piperidin-1-yl]-benzyl}-3-methyl-6-phenyl-[1,2]thiazinane 1,1-dioxide | | 2.48 |
| 138 | Stereoisomer B | (3S)-2-{2-Fluoro-4-[4-(4-methyl-4H-[1,2,4]triazol-3-yl)-piperidin-1-yl]-benzyl}-3-methyl-6-phenyl-[1,2]thiazinane 1,1-dioxide | | 1.1 |
| 139 | Stereoisomer A | (3S)-2-{2-Fluoro-4-[4-(1-methyl-1H-imidazol-2-yl)-piperidin-1-yl]-benzyl}-3-methyl-6-phenyl-[1,2]thiazinane 1,1-dioxide | | 1.39 |

TABLE 4-continued

| | Structure | Name | Proton NMR | IC$_{50}$ |
|---|---|---|---|---|
| 140 | Stereoisomer B | (3S)-2-{2-Fluoro-4-[4-(1-methyl-1H-imidazol-2-yl)-piperidin-1-yl]-benzyl}-3-methyl-6-phenyl-[1,2]thiazinane 1,1-dioxide | | 0.41 |
| 141 | Stereoisomer A | (3S)-2-{2-Fluoro-4-[4-(1H-tetrazol-5-yl)-piperidin-1-yl]-benzyl}-3-methyl-6-phenyl-[1,2]thiazinane 1,1-dioxide | $^1$H NMR (400 MHz, DMSO) δ 7.49-7.43 (m, 2H), 7.43-7.35 (m, 3H), 7.35-7.29 (m, 1H), 6.87-6.80 (m, 1H), 6.78-6.70 (m, 1H), 4.50-4.43 (m, 1H), 4.43-4.36 (m, 1H), 4.32-4.24 (m, 1H), 4.18-4.02 (m, 1H), 3.82-3.70 (m, 2H), 3.22-3.16 (m, 1H), 2.96-2.85 (m, 2H), 2.47-2.36 (m, 1H), 2.17-1.99 (m, 3H), 1.91-1.72 (m, 3H), 1.71-1.59 (m, 1H), 1.15-1.05 (d, J = 6.9 Hz, 3H). | 0.057 |
| 142 | Stereoisomer B | (3S)-2-{2-Fluoro-4-[4-(1H-tetrazol-5-yl)-piperidin-1-yl]-benzyl}-3-methyl-6-phenyl-[1,2]thiazinane 1,1-dioxide | | 0.192 |
| 143 | Stereoisomer A | 5-{1-[3-Fluoro-4-((3S)-3-methyl-1,1-dioxo-6-phenyl-[1,2]thiazinan-2-ylmethyl)-phenyl]-piperidin-4-yl}-3H-[1,3,4]oxadiazol-2-one | | 0.044 |
| 144 | Stereoisomer B | 5-{1-[3-Fluoro-4-((3S)-3-methyl-1,1-dioxo-6-phenyl-[1,2]thiazinan-2-ylmethyl)-phenyl]-piperidin-4-yl}-3H-[1,3,4]oxadiazol-2-one | $^1$H NMR (400 MHz, DMSO) δ 12.34-11.83 (br s, 1H), 7.48-7.43 (m, 2H), 7.43-7.28 (m, 4H), 6.84-6.77 (m, 1H), 6.76-6.68 (m, 1H), 4.49-4.35 (m, 2H), 4.32-4.23 (m, 1H), 4.15-4.02 (m, 1H), 3.75-3.64 (m, 2H), 2.92-2.79 (m, 3H), 2.47-2.35 (m, 1H), 2.15-2.03 (m, 1H), 2.02-1.92 (m, 2H), 1.88-1.74 (m, 1H), 1.74-1.58 (m, 3H), 1.13-1.04 (d, J = 6.9 Hz, 3H). | 0.021 |

TABLE 4-continued

| | Structure | Name | Proton NMR | IC$_{50}$ |
|---|---|---|---|---|
| 145 | Stereoisomer A | 5-[3-Fluoro-4-((3S)-3-methyl-1,1-dioxo-6-phenyl-[1,2]thiazinan-2-ylmethyl)-phenyl]-4,5,6,7-tetrahydro-1H-pyrazolo[4,3-c]pyridine | | 0.242 |
| 146 | Stereoisomer A | 1-[3-Fluoro-4-((3S)-3-methyl-1,1-dioxo-6-phenyl-[1,2]thiazinan-2-ylmethyl)-phenyl]-piperidine-4-carboxylic acid methoxy-methyl-amide | | 0.142 |
| 147 | Stereoisomer B | 1-[3-Fluoro-4-((3S)-3-methyl-1,1-dioxo-6-phenyl-[1,2]thiazinan-2-ylmethyl)-phenyl]-piperidine-4-carboxylic acid methoxy-methyl-amide | | 1.78 |
| 148 | Stereoisomer A | 7-[3-Fluoro-4-((3S)-3-methyl-1,1-dioxo-6-phenyl-[1,2]thiazinan-2-ylmethyl)-phenyl]-5,6,7,8-tetrahydro-[1,2,4]triazolo[4,3-a]pyrazine | | 1.6 |
| 149 | Stereoisomer B | 7-[3-Fluoro-4-((3S)-3-methyl-1,1-dioxo-6-phenyl-[1,2]thiazinan-2-ylmethyl)-phenyl]-5,6,7,8-tetrahydro-[1,2,4]triazolo[4,3-a]pyrazine | | 1.46 |

| | Structure | Name | Proton NMR | IC₅₀ |
|---|---|---|---|---|
| 150 | Stereoisomer A | (3S)-2-[2-Fluoro-4-(4-[1,2,4]triazol-4-yl-piperidin-1-yl)-benzyl]-3-methyl-6-phenyl-[1,2]thiazinane 1,1-dioxide | ¹H NMR (400 MHz, DMSO) δ 8.67-8.61 (s, 2H), 7.49-7.43 (m, 2H), 7.43-7.28 (m, 4H), 6.88-6.81 (m, 1H), 6.81-6.72 (m, 1H), 4.49-4.23 (m, 4H), 4.15-4.01 (m, 1H), 3.92-3.79 (m, 2H), 2.89-2.76 (m, 2H), 2.46-2.37 (m, 1H), 2.15-2.04 (m, 3H), 2.04-1.88 (m, 2H), 1.88-1.73 (m, 1H), 1.71-1.59 (m, 1H), 1.14-1.04 (d, J = 6.8 Hz, 3H). | 0.029 |
| 151 | Stereoisomer B | (3S)-2-[2-Fluoro-4-(4-[1,2,4]triazol-4-yl-piperidin-1-yl)-benzyl]-3-methyl-6-phenyl-[1,2]thiazinane 1,1-dioxide | ¹H NMR (400 MHz, DMSO) δ 8.66-8.62 (s, 2H), 7.49-7.43 (m, 2H), 7.43-7.34 (m, 3H), 7.31-7.24 (m, 1H), 6.88-6.79 (m, 2H), 4.43-4.32 (m, 4H), 3.94-3.84 (m, 2H), 3.62-3.52 (m, 1H), 2.91-2.81 (m, 2H), 2.79-2.65 (m, 1H), 2.16-1.88 (m, 6H), 1.68-1.57 (m, 1H), 1.39-1.32 (d, J = 7.1 Hz, 3H). | 0.027 |
| 152 | Stereoisomer A | 5-{1-[3-Fluoro-4-((3S)-3-methyl-1,1-dioxo-6-phenyl-[1,2]thiazinan-2-ylmethyl)-phenyl]-piperidin-4-yl}-isoxazol-3-ol | ¹H NMR (400 MHz, DMSO) δ 11.33-10.90 (s, 1H), 7.49-7.43 (m, 2H), 7.43-7.34 (m, 3H), 7.34-7.28 (m, 1H), 6.84-6.78 (m, 1H), 6.76-6.68 (m, 1H), 5.83-5.78 (s, 1H), 4.49-4.34 (m, 2H), 4.32-4.23 (m, 1H), 4.15-4.02 (m, 1H), 3.80-3.68 (m, 2H), 2.93-2.76 (m, 3H), 2.47-2.35 (m, 1H), 2.15-2.05 (m, 1H), 2.04-1.92 (m, 2H), 1.88-1.74 (m, 1H), 1.73-1.58 (m, 3H), 1.13-1.05 (d, J = 6.8 Hz, 3H). | 0.029 |
| 153 | Stereoisomer B | 5-{1-[3-Fluoro-4-((3S)-3-methyl-1,1-dioxo-6-phenyl-[1,2]thiazinan-2-ylmethyl)-phenyl]-piperidin-4-yl}-isoxazol-3-ol | ¹H NMR (400 MHz, DMSO) δ 11.13-10.94 (br s, 1H), 7.49-7.43 (m, 2H), 7.43-7.33 (m, 3H), 7.29-7.23 (m, 1H), 6.85-6.74 (m, 2H), 5.83-5.78 (s, 1H), 4.42-4.32 (m, 3H), 3.84-3.72 (m, 2H), 3.62-3.50 (t, J = 6.5 Hz, 1H), 2.96-2.79 (m, 3H), 2.78-2.64 (m, 1H), 2.15-1.94 (m, 4H), 1.74-1.56 (m, 3H), 1.38-1.30 (d, J = 7.1 Hz, 3H), 11.31-10.73 (s, 1H). | 0.055 |
| 154 | Stereoisomer A | 7-[3-Fluoro-4-((3S)-3-methyl-1,1-dioxo-6-phenyl-[1,2]thiazinan-2-ylmethyl)-phenyl]-5,6,7,8-tetrahydro-imidazo[1,5-a]pyrazine | | 0.145 |

TABLE 4-continued

| | Structure | Name | Proton NMR | IC$_{50}$ |
|---|---|---|---|---|
| 155 | Stereoisomer B | 7-[3-Fluoro-4-((3S)-3-methyl-1,1-dioxo-6-phenyl-[1,2]thiazinan-2-ylmethyl)-phenyl]-5,6,7,8-tetrahydro-imidazo[1,5-a]pyrazine | | 0.175 |
| 156 | Stereoisomer B | 5-[3-Fluoro-4-((3S)-3-methyl-1,1-dioxo-6-phenyl-[1,2]thiazinan-2-ylmethyl)-phenyl]-4,5,6,7-tetrahydro-1H-pyrazolo[4,3-c]pyridine | | 0.272 |
| 157 | Stereoisomer A | 7-[3-Fluoro-4-((3S)-3-methyl-1,1-dioxo-6-phenyl-[1,2]thiazinan-2-ylmethyl)-phenyl]-5,6,7,8-tetrahydro-2H-[1,2,4]triazolo[4,3-a]pyrazin-3-one | | 1.7 |
| 158 | Stereoisomer B | 7-[3-Fluoro-4-((3S)-3-methyl-1,1-dioxo-6-phenyl-[1,2]thiazinan-2-ylmethyl)-phenyl]-5,6,7,8-tetrahydro-2H-[1,2,4]triazolo[4,3-a]pyrazin-3-one | | 3.93 |
| 159 | Stereoisomer A | 1-{4-[3-Methoxy-4-((3S)-3-methyl-1,1-dioxo-6-phenyl-[1,2]thiazinan-2-ylmethyl)-phenyl]-piperazin-1-yl}-ethanone | | 1.61 |

TABLE 4-continued

| | Structure | Name | Proton NMR | IC$_{50}$ |
|---|---|---|---|---|
| 160 | Stereoisomer B | 1-{4-[3-Methoxy-4-((3S)-3-methyl-1,1-dioxo-6-phenyl-[1,2]thiazinan-2-ylmethyl)-phenyl]-piperazin-1-yl}-ethanone | | 0.207 |
| 161 | Stereoisomer A | 1-{4-[2-Methoxy-4-((3S)-3-methyl-1,1-dioxo-6-phenyl-[1,2]thiazinan-2-ylmethyl)-phenyl]-piperazin-1-yl}-ethanone | | 3.08 |
| 162 | Stereoisomer B | 1-{4-[2-Methoxy-4-((3S)-3-methyl-1,1-dioxo-6-phenyl-[1,2]thiazinan-2-ylmethyl)-phenyl]-piperazin-1-yl}-ethanone | | 0.812 |
| 163 | Stereoisomer A | 1-{4-[2-Chloro-4-((3S)-3-methyl-1,1-dioxo-6-phenyl-[1,2]thiazinan-2-ylmethyl)-phenyl]-piperazin-1-yl}-ethanone | | 0.057 |
| 164 | Stereoisomer B | 1-{4-[2-Chloro-4-((3S)-3-methyl-1,1-dioxo-6-phenyl-[1,2]thiazinan-2-ylmethyl)-phenyl]-piperazin-1-yl}-ethanone | | 0.115 |

TABLE 4-continued

| | Structure | Name | Proton NMR | IC$_{50}$ |
|---|---|---|---|---|
| 165 | Stereoisomer not specified | N-{1-[3-Fluoro-4-((3S)-3-methyl-1,1-dioxo-6-phenyl-[1,2]thiazinan-2-ylmethyl)-phenyl]-piperidine-4-carbonyl}-methanesulfonamide | | 0.30 |
| 166 | Stereoisomer A | [3-Fluoro-4-((3S)-3-methyl-1,1-dioxo-6-phenyl-[1,2]thiazinan-2-ylmethyl)-phenyl]-(1-methanesulfonyl-piperidin-4-yl)-amine | $^1$H NMR (400 MHz, DMSO) δ 7.48-7.42 (m, 2H), 7.42-7.33 (m, 3H), 7.22-7.15 (m, 1H), 6.47-6.42 (m, 1H), 6.37-6.30 (m, 1H), 5.87-5.80 (d, J = 8.0 Hz, 1H), 4.45-4.37 (m, 1H), 4.37-4.29 (m, 1H), 4.26-4.18 (m, 1H), 4.12-4.00 (m, 1H), 3.56-3.45 (m, 2H), 3.41-3.32 (m, 1H), 2.95-2.84 (m, 5H), 2.46-2.34 (m, 1H), 2.13-2.03 (m, 1H), 2.03-1.91 (m, 2H), 1.88-1.71 (m, 1H), 1.69-1.58 (m, 1H), 1.48-1.33 (m, 2H), 1.13-1.05 (d, J = 6.8 Hz, 3H). | 0.025 |
| 167 | Stereoisomer B | [3-Fluoro-4-((3S)-3-methyl-1,1-dioxo-6-phenyl-[1,2]thiazinan-2-ylmethyl)-phenyl]-(1-methanesulfonyl-piperidin-4-yl)-amine | $^1$H NMR (400 MHz, DMSO) δ 7.49-7.42 (m, 2H), 7.42-7.33 (m, 3H), 7.18-7.09 (m, 1H), 6.49-6.43 (m, 1H), 6.43-6.36 (m, 1H), 5.99-5.93 (d, J = 7.9 Hz, 1H), 4.38-4.24 (m, 3H), 3.61-3.47 (m, 3H), 3.45-3.33 (m, 1H), 2.97-2.85 (m, 5H), 2.76-2.63 (m, 1H), 2.07-1.92 (m, 4H), 1.67-1.55 (m, 1H), 1.48-1.36 (m, 2H), 1.36-1.29 (d, J = 7.0 Hz, 3H). | 0.009 |
| 168 | Stereoisomer A | 1-{4-[4-(4,4-Dimethyl-1,1-dioxo-6-phenyl-[1,2]thiazinan-2-ylmethyl)-3-fluoro-phenyl]-piperazin-1-yl}-ethanone | $^1$H NMR (400 MHz, DMSO) δ 7.47-7.48 (m, 2 H), 7.39 (dd, 3 H), 7.26 (t, 1 H), 6.77-6.78 (m, 2 H), 4.52 (dd, 1 H), 4.39 (d, 1 H), 4.17 (d, 1 H), 3.52-3.57 (m, 4 H), 3.18-3.20 (m, 5 H), 2.77 (dd, 1 H), 2.42 (t, 1 H), 2.04 (s, 3 H), 1.81-1.84 (m, 1 H), 1.11 (s, 3 H), 0.93 (s, 3 H). | 1.0 |
| 169 | Stereoisomer A | 1-{4-[3-Fluoro-4-((4R)-4-methyl-1,1-dioxo-6-phenyl-[1,2]thiazinan-2-ylmethyl)-phenyl]-piperazin-1-yl}-ethanone | $^1$H NMR (400 MHz, DMSO) δ 7.48-7.49 (m, 2 H), 7.39 (dd, 3 H), 7.25 (t, 1 H), 6.77-6.79 (m, 2 H), 4.57 (dd, 1 H), 4.35 (d, 1 H), 4.17 (d, 1 H), 3.55 (d, 4 H), 3.43 (dd, 1 H), 3.21-3.24 (m, 2 H), 3.15 (t, 2 H), 2.94 (d, 1 H), 2.62-2.64 (m, 1 H), 2.03-1.95 (m, 5 H), 1.07 (d, 3 H). | 0.132 |

TABLE 4-continued

| | Structure | Name | Proton NMR | IC$_{50}$ |
|---|---|---|---|---|
| 170 | Stereoisomer B | 1-{4-[3-Fluoro-4-((4R)-4-methyl-1,1-dioxo-6-phenyl-[1,2]thiazinan-2-ylmethyl)-phenyl]-piperazin-1-yl}-ethanone | $^1$H NMR (400 MHz, DMSO) δ 7.48-7.49 (m, 2 H), 7.39 (dd, 3 H), 7.25 (t, 1 H), 6.77-6.79 (m, 2 H), 4.57 (dd, 1 H), 4.35 (d, 1 H), 4.17 (d, 1 H), 3.55 (d, 4 H), 3.43 (dd, 1 H), 3.21-3.24 (m, 2 H), 3.15 (t, 2 H), 2.94 (d, 1 H), 2.62-2.64 (m, 1 H), 2.03-1.95 (m, 5 H), 1.07 (d, 3 H). | 0.054 |
| 171 | Stereoisomer B | 1-{4-[4-(4,4-Dimethyl-1,1-dioxo-6-phenyl-[1,2]thiazinan-2-ylmethyl)-3-fluoro-phenyl]-piperazin-1-yl}-ethanone | | 0.20 |
| 172 | Stereoisomer A | 4-{(3S)-2-[4-(4-Acetyl-piperazin-1-yl)-2-fluoro-benzyl]-3-methyl-1,1-dioxo-[1,2]thiazinan-6-yl}-benzonitrile | | 1.02 |
| 173 | Stereoisomer B | 4-{(3S)-2-[4-(4-Acetyl-piperazin-1-yl)-2-fluoro-benzyl]-3-methyl-1,1-dioxo-[1,2]thiazinan-6-yl}-benzonitrile | | 2.06 |
| 174 | Stereoisomer A | 1-(4-{4-[(3S)-6-(4-Chloro-phenyl)-3-methyl-1,1-dioxo-[1,2]thiazinan-2-ylmethyl]-3-fluoro-phenyl}-piperazin-1-yl)-ethanone | | 0.077 |

TABLE 4-continued

| | Structure | Name | Proton NMR | IC$_{50}$ |
|---|---|---|---|---|
| 175 | Stereoisomer B | 1-(4-{4-[(3S)-6-(4-Chloro-phenyl)-3-methyl-1,1-dioxo-[1,2]thiazinan-2-ylmethyl]-3-fluoro-phenyl}-piperazin-1-yl)-ethanone | | 0.030 |
| 176 | Stereoisomer A | 1-(4-{3-Fluoro-4-[(3S)-6-(4-methoxy-phenyl)-3-methyl-1,1-dioxo-[1,2]thiazinan-2-ylmethyl]-phenyl}-piperazin-1-yl)-ethanone | | 0.133 |
| 177 | Stereoisomer B | 1-(4-{3-Fluoro-4-[(3S)-6-(4-methoxy-phenyl)-3-methyl-1,1-dioxo-[1,2]thiazinan-2-ylmethyl]-phenyl}-piperazin-1-yl)-ethanone | | 0.147 |
| 178 | Stereoisomer A | 1-[5'-((3S)-3-Methyl-1,1-dioxo-6-phenyl-[1,2]thiazinan-2-ylmethyl)-2,3,5,6-tetrahydro-[1,2']bipyrazinyl-4-yl]-ethanone | | 1.43 |
| 179 | Stereoisomer B | 1-[5'-((3S)-3-Methyl-1,1-dioxo-6-phenyl-[1,2]thiazinan-2-ylmethyl)-2,3,5,6-tetrahydro-[1,2']bipyrazinyl-4-yl]-ethanone | | 0.942 |

TABLE 4-continued

| | Structure | Name | Proton NMR | IC$_{50}$ |
|---|---|---|---|---|
| 180 | 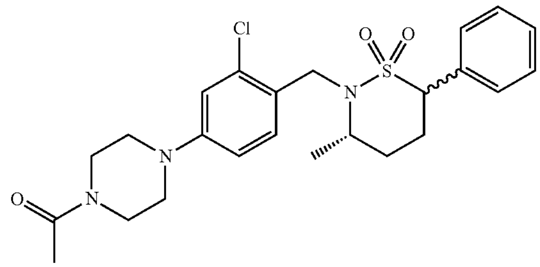 [SMILES: CC(=O)N1CCN(c2ccc(CN3[C@@H](C)CCC(c4ccccc4)S3(=O)=O)c(Cl)c2)CC1] | 1-{4-[3-Chloro-4-((3S)-3-methyl-1,1-dioxo-6-phenyl-[1,2]thiazinan-2-ylmethyl)-phenyl]-piperazin-1-yl}-ethanone | | 1.58 |
| 181 | Stereoisomer A | 1-{4-[3-Chloro-4-((3S)-3-methyl-1,1-dioxo-6-p-tolyl-[1,2]thiazinan-2-ylmethyl)-phenyl]-piperazin-1-yl}-ethanone | $^1$H NMR (400 MHz, DMSO) δ 7.36-7.29 (m, 3H), 7.22-7.17 (m, 2H), 6.84-6.78 (m, 1H), 6.77-6.70 (m, 1H), 4.45-4.34 (m, 2H), 4.31-4.22 (m, 1H), 4.15-4.00 (m, 1H), 3.60-3.51 (m, 4H), 3.23-3.15 (m, 2H), 3.15-3.07 (m, 2H), 2.48-2.34 (m, 1H), 2.34-2.28 (s, 3H), 2.11-2.00 (m, 4 H), 1.88-1.71 (m, 1H), 1.70-1.58 (m, 1H), 1.12-1.03 (d, J = 6.9 Hz, 3H). | 0.037 |
| 182 | Stereoisomer A | 1-{(1R,4R)-5-[3-Fluoro-4-((3S)-3-methyl-1,1-dioxo-6-phenyl-[1,2]thiazinan-2-ylmethyl)-phenyl]-2,5-diaza-bicyclo[2.2.1]hept-2-yl}-2-hydroxy-propan-1-one | | 0.041 |
| 183 | Stereoisomer B | 1-{(1R,4R)-5-[3-Fluoro-4-((3S)-3-methyl-1,1-dioxo-6-phenyl-[1,2]thiazinan-2-ylmethyl)-phenyl]-2,5-diaza-bicyclo[2.2.1]hept-2-yl}-2-hydroxy-propan-1-one | | 0.040 |
| 184 | Stereoisomer B | 1-{4-[3-Fluoro-4-((3S)-3-methyl-1,1-dioxo-6-p-tolyl-[1,2]thiazinan-2-ylmethyl)-phenyl]-piperazin-1-yl}-ethanone | | 0.098 |

TABLE 4-continued

| | Structure | Name | Proton NMR | IC$_{50}$ |
|---|---|---|---|---|
| 185 | 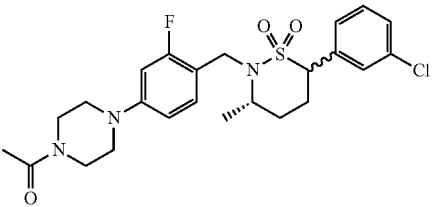 [SMILES: CC(=O)N1CCN(c2ccc(CN3[C@@H](C)CCC(c4cccc(Cl)c4)S3(=O)=O)c(F)c2)CC1] Stereoisomer A | 1-(4-{4-[(3S)-6-(3-Chloro-phenyl)-3-methyl-1,1-dioxo-[1,2]thiazinan-2-ylmethyl]-3-fluoro-phenyl}-piperazin-1-yl)-ethanone | $^1$H NMR (400 MHz, DMSO) δ 7.54-7.50 (m, 1H), 7.47-7.41 (m, 3H), 7.36-7.28 (m, 1H), 6.84-6.78 (m, 1H), 6.78-6.70 (m, 1H), 4.61-4.51 (m, 1H), 4.47-4.38 (m, 1H), 4.32-4.22 (m, 1H), 4.16-4.02 (m, 1H), 3.60-3.50 (m, 4H), 3.23-3.15 (m, 2H), 3.15-3.08 (m, 2H), 2.47-2.32 (m, 1H), 2.16-2.05 (m, 1H), 2.05-2.00 (s, 3H), 1.86-1.69 (m, 1H), 1.69-1.58 (m, 1H), 1.14-1.04 (d, J = 6.9 Hz, 3H). | 0.025 |
| 186 | 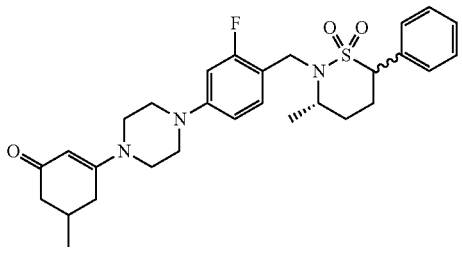 [SMILES: CC1CC(=O)C=C(N2CCN(c3ccc(CN4[C@@H](C)CCC(c5ccccc5)S4(=O)=O)c(F)c3)CC2)C1] | 3-{4-[3-Fluoro-4-((3S)-3-methyl-1,1-dioxo-6-phenyl-[1,2]thiazinan-2-ylmethyl)-phenyl]-piperazin-1-yl}-5-methyl-cyclohex-2-enone | | 0.179 |
| 187 | 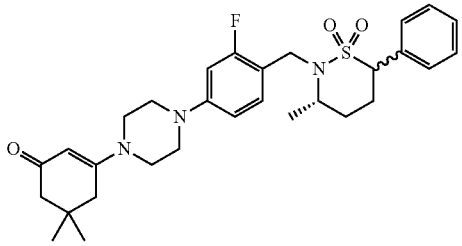 [SMILES: C[C@H]1CCC(c2ccccc2)S(=O)(=O)N1Cc1ccc(N2CCN(C3=CC(=O)CC(C)(C)C3)CC2)cc1F] | 3-{4-[3-Fluoro-4-((3S)-3-methyl-1,1-dioxo-6-phenyl-[1,2]thiazinan-2-ylmethyl)-phenyl]-piperazin-1-yl}-5,5-dimethyl-cyclohex-2-enone | | 0.647 |
| 188 | 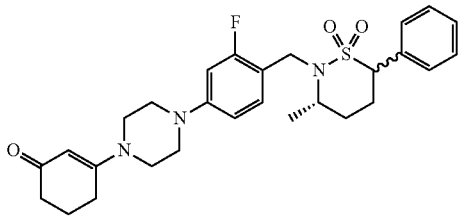 [SMILES: C[C@H]1CCC(c2ccccc2)S(=O)(=O)N1Cc1ccc(N2CCN(C3=CC(=O)CCC3)CC2)cc1F] | 3-{4-[3-Fluoro-4-((3S)-3-methyl-1,1-dioxo-6-phenyl-[1,2]thiazinan-2-ylmethyl)-phenyl]-piperazin-1-yl}-cyclohex-2-enone | | 0.108 |
| 189 | 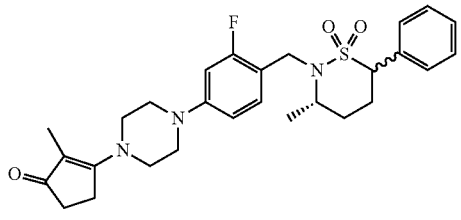 [SMILES: CC1=C(N2CCN(c3ccc(CN4[C@@H](C)CCC(c5ccccc5)S4(=O)=O)c(F)c3)CC2)CCC1=O] | 3-{4-[3-Fluoro-4-((3S)-3-methyl-1,1-dioxo-6-phenyl-[1,2]thiazinan-2-ylmethyl)-phenyl]-piperazin-1-yl}-2-methyl-cyclopent-2-enone | | 0.059 |
| 190 | 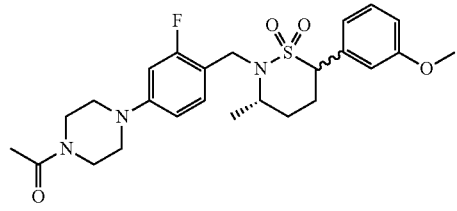 [SMILES: COc1cccc(C2CC[C@H](C)N(Cc3ccc(N4CCN(C(C)=O)CC4)cc3F)S2(=O)=O)c1] Stereoisomer A | 1-(4-{3-Fluoro-4-[(3S)-6-(3-methoxy-phenyl)-3-methyl-1,1-dioxo-[1,2]thiazinan-2-ylmethyl]-phenyl}-piperazin-1-yl)-ethanone | | 0.117 |

TABLE 4-continued

| | Structure | Name | Proton NMR | IC$_{50}$ |
|---|---|---|---|---|
| 191 | Stereoisomer B | 1-(4-{3-Fluoro-4-[(3S)-6-(3-methoxy-phenyl)-3-methyl-1,1-dioxo-[1,2]thiazinan-2-ylmethyl]-phenyl}-piperazin-1-yl)-ethanone | | 0.116 |
| 192 | Stereoisomer A | 1-{4-[3-Fluoro-4-((3S)-3-methyl-1,1-dioxo-6-m-tolyl-[1,2]thiazinan-2-ylmethyl)-phenyl]-piperazin-1-yl}-ethanone | $^1$H NMR (400 MHz, DMSO) δ 7.33-7.21 (m, 4H), 7.21-7.14 (m, 1H), 6.84-6.76 (m, 2H), 4.41-4.29 (m, 3H), 3.61-3.51 (m, 5H), 3.27-3.19 (m, 2H), 3.19-3.12 (m, 2H), 2.77-2.62 (m, 1H), 2.37-2.30 (s, 3H), 2.15-1.96 (m, 5H), 1.66-1.56 (m, 1H), 1.40-1.30 (d, J = 7.1 Hz, 3H). | 0.006 |
| 193 | Stereoisomer B | 1-{4-[3-Fluoro-4-((3S)-3-methyl-1,1-dioxo-6-m-tolyl-[1,2]thiazinan-2-ylmethyl)-phenyl]-piperazin-1-yl}-ethanone | $^1$H NMR (400 MHz, DMSO) δ 7.36-7.21 (m, 4H), 7.21-7.15 (m, 1H), 6.85-6.78 (m, 1H), 6.78-6.71 (m, 1H), 4.44-4.36 (m, 2H), 4.31-4.23 (m, 1H), 4.14-4.02 (m, 1H), 3.61-3.51 (m, 4H), 3.21-3.15 (m, 2H), 3.15-3.06 (m, 2H), 2.45-2.37 (m, 1H), 2.34-2.30 (s, 3H), 2.11-2.01 (m, 4H), 1.88-1.71 (m, 1H), 1.69-1.57 (m, 1H), 1.12-1.04 (d, J = 6.8 Hz, 3H). | 0.024 |
| 194 | Stereoisomer A | 1-{4-[4-((3S)-3-Ethyl-1,1-dioxo-6-phenyl-[1,2]thiazinan-2-ylmethyl)-3-fluoro-phenyl]-piperazin-1-yl}-ethanone | $^1$H NMR (400 MHz, DMSO) δ 7.38-7.40 (m, 6 H), 6.81 (dd, 1 H), 6.72 (dd, 1 H), 4.49 (dd, 1 H), 4.38 (d, 1 H), 4.23 (d, 1 H), 3.80 (d, 1 H), 3.54 (s, 4 H), 3.14 (dt, 4 H), 2.40 (d, 1 H), 2.08-2.10 (m, 1 H), 2.02 (s, 3 H), 1.73 (s, 2 H), 1.46 (q, 2 H), 0.70 (t, 3 H). | 0.018 |
| 195 | Stereoisomer B | 1-{4-[4-((3S)-3-Ethyl-1,1-dioxo-6-phenyl-[1,2]thiazinan-2-ylmethyl)-3-fluoro-phenyl]-piperazin-1-yl}-ethanone | $^1$H NMR (400 MHz, DMSO) δ 7.37-7.39 (m, 6 H), 6.77-6.80 (m, 2 H), 4.49 (d, 1 H), 4.36 (dd, 1 H), 4.28 (d, 1 H), 3.55 (s, 4 H), 3.15-3.20 (m, 5 H), 2.60-2.64 (m, 1 H), 2.04-2.05 (m, 6 H), 1.65 (d, 1 H), 1.51 (dt, 1 H), 0.68 (t, 3 H). | 0.073 |

TABLE 4-continued

| | Structure | Name | Proton NMR | IC$_{50}$ |
|---|---|---|---|---|
| 196 | Stereoisomer A | 1-{4-[4-(6,6-Dioxo-7-phenyl-6-thia-5-aza-spiro[2.5]oct-5-ylmethyl)-3-fluoro-phenyl]-piperazin-1-yl}-ethanone | $^1$H NMR (400 MHz, DMSO) δ 7.47 (dd, 2 H), 7.37-7.39 (m, 3 H), 7.21 (t, 1 H), 6.76-6.78 (m, 2 H), 4.60 (dd, 1 H), 4.45 (s, 2 H), 3.85 (d, 1 H), 3.54 (d, 4 H), 3.17 (dt, 4 H), 2.92 (t, 1 H), 2.38 (dd, 1 H), 2.03 (s, 3 H), 1.40 (d, 1 H), 0.67-0.75 (m, 2 H), 0.35-0.37 (m, 2 H). | 0.192 |
| 197 | Stereoisomer A | 1-{4-[3-Fluoro-4-((4S)-4-methyl-1,1-dioxo-6-phenyl-[1,2]thiazinan-2-ylmethyl)-phenyl]-piperazin-1-yl}-ethanone | $^1$H NMR (400 MHz, DMSO) δ 7.53-7.55 (m, 2 H), 7.43 (dd, 3 H), 7.30 (t, 1 H), 6.81-6.82 (m, 2 H), 4.62 (dd, 1 H), 4.40 (d, 1 H), 4.22 (d, 1 H), 3.60 (s, 4 H), 3.47 (dd, 1 H), 3.23 (dt, 4 H), 2.98 (d, 1 H), 2.66-2.68 (m, 1 H), 2.09-2.17 (m, 1 H), 2.08 (s, 3 H), 2.02 (d, 1 H), 1.12 (d, 3 H). | 0.356 |
| 198 | Stereoisomer B | 1-{4-[3-Fluoro-4-((4S)-4-methyl-1,1-dioxo-6-phenyl-[1,2]thiazinan-2-ylmethyl)-phenyl]-piperazin-1-yl}-ethanone | $^1$H NMR (400 MHz, DMSO) δ 7.41-7.42 (m, 5 H), 7.26 (t, 1 H), 6.79-6.81 (m, 2 H), 4.54 (dd, 1 H), 4.41 (d, 1 H), 4.32 (d, 1 H), 3.53-3.58 (m, 4 H), 3.17-3.20 (m, 5 H), 3.02 (d, 1 H), 2.04-2.3 (m, 6 H), 0.88 (d, 3 H). | 0.019 |
| 199 | Stereoisomer B | 1-{4-[4-(6,6-Dioxo-7-phenyl-6-thia-5-aza-spiro[2.5]oct-5-ylmethyl)-3-fluoro-phenyl]-piperazin-1-yl}-ethanone | $^1$H NMR (400 MHz, DMSO) δ 7.47 (dd, 2 H), 7.37-7.39 (m, 3 H), 7.21 (t, 1 H), 6.76-6.78 (m, 2 H), 4.60 (dd, 1 H), 4.45 (s, 2 H), 3.85 (d, 1 H), 3.54 (d, 4 H), 3.17 (dt, 4 H), 2.92 (t, 1 H), 2.38 (dd, 1 H), 2.03 (s, 3 H), 1.40 (d, 1 H), 0.67-0.75 (m, 2 H), 0.35-0.37 (m, 2 H). | 0.014 |
| 200 | Stereoisomer B | 1-(4-{4-[(3S)-6-(3-Chloro-phenyl)-3-methyl-1,1-dioxo-[1,2]thiazinan-2-ylmethyl]-3-fluoro-phenyl}-piperazin-1-yl)-ethanone | | 0.017 |

TABLE 4-continued

| | Structure | Name | Proton NMR | IC$_{50}$ |
|---|---|---|---|---|
| 201 | Stereoisomer A | 1-(4-{4-[(3S)-6-(2-Chloro-phenyl)-3-methyl-1,1-dioxo-[1,2]thiazinan-2-ylmethyl]-3-fluoro-phenyl}-piperazin-1-yl)-ethanone | | 0.183 |
| 202 | Stereoisomer A | 3-{(3S)-2-[4-(4-Acetyl-piperazin-1-yl)-2-fluoro-benzyl]-3-methyl-1,1-dioxo-[1,2]thiazinan-6-yl}-benzonitrile | | 0.738 |
| 203 | Stereoisomer B | 3-{(3S)-2-[4-(4-Acetyl-piperazin-1-yl)-2-fluoro-benzyl]-3-methyl-1,1-dioxo-[1,2]thiazinan-6-yl}-benzonitrile | | 0.206 |
| 204 | Stereoisomer B | 1-(4-{4-[(3S)-6-(2-Chloro-phenyl)-3-methyl-1,1-dioxo-[1,2]thiazinan-2-ylmethyl]-3-fluoro-phenyl}-piperazin-1-yl)-ethanone | | 0.052 |
| 205 | Stereoisomer A | 1-{4-[3-Fluoro-4-((3S)-3-methyl-1,1-dioxo-6-o-tolyl-[1,2]thiazinan-2-ylmethyl)-phenyl]-piperazin-1-yl}-ethanone | $^1$H NMR (400 MHz, DMSO) δ 7.47-7.42 (m, 1H), 7.35-7.28 (m, 1H), 7.26-7.20 (m, 3H), 6.84-6.78 (m, 1H), 6.77-6.70 (m, 1H), 4.64-4.51 (m, 1H), 4.38-4.30 (m, 2H), 4.18-4.02 (m, 1H), 3.60-3.51 (m, 4H), 3.22-3.16 (m, 2H), 3.16-3.06 (m, 2H), 2.48-2.44 (m, 1H), 2.44-2.39 (s, 3H), 2.07-1.97 (m, 4H), 1.97-1.83 (m, 1H), 1.70-1.58 (m, 1H), 1.15-1.04 (d, J = 7.0 Hz, 3H). | 0.307 |

TABLE 4-continued

| | Structure | Name | Proton NMR | IC$_{50}$ |
|---|---|---|---|---|
| 206 | Stereoisomer B | 1-{4-[3-Fluoro-4-((3S)-3-methyl-1,1-dioxo-6-o-tolyl-[1,2]thiazinan-2-ylmethyl)-phenyl]-piperazin-1-yl}-ethanone | $^1$H NMR (400 MHz, DMSO) δ 7.48-7.43 (m, 1H), 7.32-7.19 (m, 4H), 6.84-6.76 (m, 2H), 4.55-4.47 (m, 1H), 4.47-4.40 (m, 1H), 4.38-4.30 (m, 1H), 3.63-3.49 (m, 5H), 3.25-3.19 (m, 2H), 3.19-3.13 (m, 2H), 2.83-2.63 (m, 1H), 2.46-2.41 (s, 3H), 2.21-2.06 (m, 1H), 2.06-2.01 (s, 3H), 2.01-1.90 (m, 1H), 1.65-1.56 (m, 1H), 1.41-1.32 (d, J = 7.1 Hz, 3H). | 0.014 |
| 207 | Stereoisomer A | 2-{(3S)-2-[4-(4-Acetyl-piperazin-1-yl)-2-fluoro-benzyl]-3-methyl-1,1-dioxo-[1,2]thiazinan-6-yl}-benzonitrile | $^1$H NMR (400 MHz, DMSO) δ 7.93-7.89 (m, 1H), 7.84-7.71 (m, 2H), 7.63-7.57 (m, 1H), 7.36-7.28 (m, 1H), 6.84-6.78 (m, 1H), 6.78-6.71 (m, 1H), 4.66-4.56 (m, 1H), 4.47-4.37 (m, 1H), 4.37-4.28 (m, 1H), 4.21-4.06 (m, 1H), 3.61-3.51 (m, 4H), 3.23-3.16 (m, 2H), 3.16-3.09 (m, 2H), 2.64-2.54 (m, 1H), 2.24-2.13 (m, 1H), 2.05-2.02 (s, 3H), 2.01-1.89 (m, 1H), 1.75-1.62 (m, 1H), 1.16-1.07 (d, J = 6.8 Hz, 3H). | 1.81 |
| 208 | Stereoisomer B | 2-{(3S)-2-[4-(4-Acetyl-piperazin-1-yl)-2-fluoro-benzyl]-3-methyl-1,1-dioxo-[1,2]thiazinan-6-yl}-benzonitrile | $^1$H NMR (400 MHz, DMSO) δ 7.93-7.89 (m, 1H), 7.82-7.74 (m, 2H), 7.63-7.57 (m, 1H), 7.36-7.29 (m, 1H), 6.83-6.76 (m, 2H), 4.58-4.48 (m, 1H), 4.48-4.34 (m, 2H), 3.68-3.59 (m, 1H), 3.59-3.52 (m, 4H), 3.25-3.20 (m, 2H), 3.20-3.12 (m, 2H), 2.89-2.74 (m, 1H), 2.19-2.08 (m, 2H), 2.06-2.01 (s, 3H), 1.68-1.59 (m, 1H), 1.40-1.33 (d, J = 7.1 Hz, 3H). | 0.032 |
| 209 | 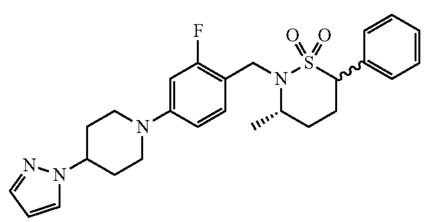 [SMILES: C[C@H]1CCC(c2ccccc2)S(=O)(=O)N1Cc1ccc(N2CCC(n3cccn3)CC2)cc1F] | (3S)-2-[2-Fluoro-4-(4-pyrazol-1-yl-piperidin-1-yl)-benzyl]-3-methyl-6-phenyl-[1,2]thiazinane 1,1-dioxide | | 0.121 |
| 210 | 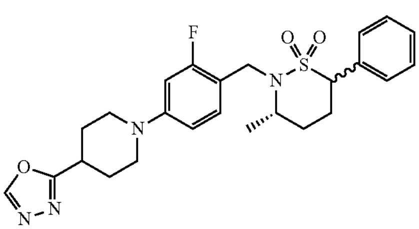 | (3S)-2-[2-Fluoro-4-(4-[1,3,4]oxadiazol-2-yl-piperidin-1-yl)-benzyl]-3-methyl-6-phenyl-[1,2]thiazinane 1,1-dioxide | $^1$H NMR (400 MHz, DMSO) δ 9.15-9.13 (s, 1H), 7.48-7.43 (m, 2H), 7.43-7.35 (m, 3H), 7.35-7.29 (m, 1H), 6.86-6.78 (m, 1H), 6.78-6.69 (m, 1H), 4.49-4.36 (m, 2H), 4.32-4.23 (m, 1H), 4.16-4.01 (m, 1H), 3.77-3.67 (m, 2H), 3.26-3.16 (m, 1H), 2.99-2.86 (m, 2H), 2.47-2.35 (m, 1H), 2.15-2.03 (m, 3H), 1.90-1.72 (m, 3H), 1.72-1.58 (m, 1H), 1.13-1.05 (d, J = 6.8 Hz, 3H). | 0.038 |

TABLE 4-continued

| | Structure | Name | Proton NMR | IC$_{50}$ |
|---|---|---|---|---|
| 211 | Stereoisomer A | (3S)-2-{2-Fluoro-4-[4-(2H-pyrazol-3-yl)-piperidin-1-yl]-benzyl}-3-methyl-6-phenyl-[1,2]thiazinane 1,1-dioxide | $^1$H NMR (400 MHz, DMSO) δ 12.67-12.30 (m, 1H), 7.67-7.50 (s, 1H), 7.48-7.44 (m, 2H), 7.42-7.34 (m, 3H), 7.34-7.28 (m, 1H), 6.88-6.76 (m, 1H), 6.76-6.67 (m, 1H), 6.15-6.01 (s, 1H), 4.50-4.36 (m, 2H), 4.31-4.23 (m, 1H), 4.15-4.01 (m, 1H), 3.83-3.70 (m, 2H), 2.87-2.73 (m, 3H), 2.46-2.36 (m, 1H), 2.16-2.04 (m, 1H), 2.01-1.90 (d, J = 12.9 Hz, 2H), 1.87-1.73 (m, 1H), 1.73-1.59 (m, 3H), 1.13-1.03 (d, J = 6.8 Hz, 3H). | 0.020 |
| 212 | Stereoisomer B | (3S)-2-{2-Fluoro-4-[4-(2H-pyrazol-3-yl)-piperidin-1-yl]-benzyl}-3-methyl-6-phenyl-[1,2]thiazinane 1,1-dioxide | | 0.016 |
| 213 | Stereoisomer A | (3S)-3-Methyl-6-phenyl-2-[4-(4-[1,2,4]triazol-4-yl-piperidin-1-yl)-benzyl]-[1,2]thiazinane 1,1-dioxide | $^1$H NMR (400 MHz, DMSO) δ 8.67-8.63 (s, 2H), 7.49-7.43 (m, 2H), 7.43-7.33 (m, 3H), 7.27-7.21 (m, 2H), 6.99-6.93 (m, 2H), 4.50-4.40 (m, 1H), 4.40-4.28 (m, 2H), 4.24-4.16 (m, 1H), 4.12-4.00 (m, 1H), 3.84-3.73 (m, 2H), 2.84-2.72 (m, 2H), 2.46-2.36 (m, 1H), 2.17-2.06 (m, 3H), 2.06-1.92 (m, 2H), 1.89-1.73 (m, 1H), 1.69-1.59 (m, 1H), 1.15-1.05 (d, J = 6.9 Hz, 3H). | 0.075 |
| 214 | Stereoisomer B | (3S)-3-Methyl-6-phenyl-2-[4-(4-[1,2,4]triazol-4-yl-piperidin-1-yl)-benzyl]-[1,2]thiazinane 1,1-dioxide | $^1$H NMR (400 MHz, DMSO) δ 8.68-8.62 (s, 2H), 7.50-7.43 (m, 2H), 7.43-7.34 (m, 3H), 7.28-7.21 (m, 2H), 7.04-6.97 (m, 2H), 4.39-4.25 (m, 4H), 3.89-3.77 (m, 2H), 3.60-3.47 (m, 1H), 2.87-2.76 (m, 2H), 2.76-2.64 (m, 1H), 2.18-1.92 (m, 7H), 1.66-1.55 (m, 1H), 1.37-1.30 (d, J = 7.0 Hz, 3H). | 0.239 |
| 215 | 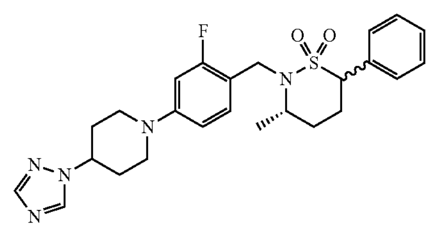 [SMILES: C[C@H]1CCC(c2ccccc2)S(=O)(=O)N1Cc1ccc(N2CCC(n3cncn3)CC2)cc1F] | (3S)-2-[2-Fluoro-4-(4-[1,2,4]triazol-1-yl-piperidin-1-yl)-benzyl]-3-methyl-6-phenyl-[1,2]thiazinane 1,1-dioxide | $^1$H NMR (400 MHz, DMSO) δ 8.63-8.55 (s, 1H), 7.99-7.93 (s, 1H), 7.49-7.43 (m, 2H), 7.43-7.28 (m, 4H), 6.87-6.81 (m, 1H), 6.80-6.72 (m, 1H), 4.57-4.34 (m, 3H), 4.32-4.23 (m, 1H), 4.16-4.01 (m, 1H), 3.90-3.78 (m, 2H), 2.98-2.85 (m, 2H), 2.47-2.36 (m, 1H), 2.16-1.92 (m, 5H), 1.88-1.74 (m, 1H), 1.70-1.60 (m, 1H), 1.14-1.06 (d, J = 6.8 Hz, 3H). | 0.030 |

| | Structure | Name | Proton NMR | IC$_{50}$ |
|---|---|---|---|---|
| 216 | 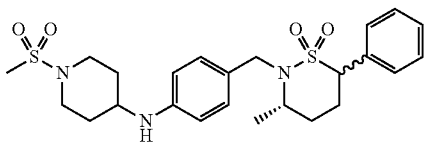 [SMILES: C[C@H]1CCC(c2ccccc2)S(=O)(=O)N1Cc1ccc(NC2CCN(S(C)(=O)=O)CC2)cc1] | (1-Methanesulfonyl-piperidin-4-yl)-[4-((3S)-3-methyl-1,1-dioxo-6-phenyl-[1,2]thiazinan-2-ylmethyl)-phenyl]-amine | $^1$H NMR (400 MHz, DMSO) δ 7.49-7.42 (m, 2H), 7.42-7.34 (m, 3H), 7.16-7.03 (m, 2H), 6.61-6.52 (m, 2H), 5.51-5.39 (d, J = 8.2 Hz, 1H), 4.42-4.35 (m, 1H), 4.35-4.28 (m, 1H), 4.15-4.08 (m, 1H), 4.08-3.98 (m, 1H), 3.56-3.45 (m, 2H), 2.95-2.84 (m, 5H), 2.46-2.34 (m, 1H), 2.13-2.04 (m, 1H), 2.02-1.93 (m, 2H), 1.86-1.69 (m, 1H), 1.68-1.58 (m, 1H), 1.49-1.34 (m, 3H), 1.13-1.06 (d, J = 6.9 Hz, 3H). | 0.009 |
| 217 | 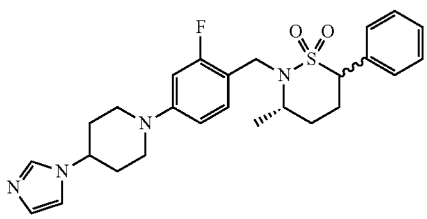 [SMILES: C[C@H]1CCC(c2ccccc2)S(=O)(=O)N1Cc1ccc(N2CCC(n3ccnc3)CC2)cc1F] | (3S)-2-[2-Fluoro-4-(4-imidazol-1-yl-piperidin-1-yl)-benzyl]-3-methyl-6-phenyl-[1,2]thiazinane 1,1-dioxide | $^1$H NMR (400 MHz, DMSO) δ 7.75-7.71 (m, 1H), 7.48-7.43 (m, 2H), 7.43-7.29 (m, 4H), 7.29-7.26 (m, 1H), 6.91-6.87 (m, 1H), 6.87-6.81 (m, 1H), 6.79-6.72 (m, 1H), 4.50-4.37 (m, 2H), 4.33-4.19 (m, 2H), 4.16-4.02 (m, 1H), 3.91-3.79 (m, 2H), 2.90-2.76 (m, 2H), 2.46-2.36 (m, 1H), 2.13-1.73 (m, 6H), 1.71-1.59 (m, 1H), 1.13-1.03 (d, J = 6.7 Hz, 3H). | 0.011 |
| 218 | Stereoisomer A | (3S)-2-[2-Fluoro-4-(4-[1,2,3]triazol-1-yl-piperidin-1-yl)-benzyl]-3-methyl-6-phenyl-[1,2]thiazinane 1,1-dioxide | $^1$H NMR (400 MHz, DMSO) δ 8.25-8.22 (s, 1H), 7.75-7.72 (d, J = 1.0 Hz, 1H), 7.49-7.43 (m, 2H), 7.43-7.29 (m, 4H), 6.88-6.82 (m, 1H), 6.81-6.74 (m, 1H), 4.81-4.67 (m, 1H), 4.51-4.37 (m, 2H), 4.34-4.24 (m, 1H), 4.17-4.02 (m, 1H), 3.91-3.79 (m, 2H), 3.03-2.87 (m, 2H), 2.47-2.34 (m, 1H), 2.20-1.98 (m, 5H), 1.88-1.73 (m, 1H), 1.70-1.60 (m, 1H), 1.15-1.06 (d, J = 6.9 Hz, 3H). | 0.011 |
| 219 | Stereoisomer A | (3S)-2-[2-Fluoro-4-(4-[1,2,4]oxadiazol-5-yl-piperidin-1-yl)-benzyl]-3-methyl-6-phenyl-[1,2]thiazinane 1,1-dioxide | $^1$H NMR (400 MHz, DMSO) δ 8.93-8.88 (s, 1H), 7.49-7.43 (m, 2H), 7.42-7.35 (m, 3H), 7.35-7.28 (m, 1H), 6.86-6.79 (m, 1H), 6.78-6.70 (m, 1H), 4.49-4.36 (m, 2H), 4.32-4.23 (m, 1H), 4.16-4.02 (m, 1H), 3.77-3.67 (m, 2H), 3.35-3.30 (m, 1H), 2.98-2.87 (m, 2H), 2.47-2.37 (m, 1H), 2.16-2.05 (m, 3H), 1.91-1.73 (m, 3H), 1.70-1.58 (m, 1H), 1.12-1.04 (d, J = 6.8 Hz, 3H). | 0.042 |
| 220 | Stereoisomer B | (3S)-2-[2-Fluoro-4-(4-[1,2,4]oxadiazol-5-yl-piperidin-1-yl)-benzyl]-3-methyl-6-phenyl-[1,2]thiazinane 1,1-dioxide | $^1$H NMR (400 MHz, DMSO) δ 8.93-8.89 (s, 1H), 7.49-7.43 (m, 2H), 7.43-7.34 (m, 3H), 7.31-7.23 (m, 1H), 6.86-6.76 (m, 2H), 4.41-4.34 (m, 3H), 3.82-3.72 (m, 2H), 3.61-3.51 (m, 1H), 3.37-3.31 (m, 1H), 3.01-2.90 (m, 2H), 2.79-2.64 (m, 1H), 2.18-1.99 (m, 4H), 1.90-1.76 (m, 2H), 1.67-1.56 (m, 1H), 1.38-1.32 (d, J = 7.1 Hz, 3H). | 0.043 |

TABLE 4-continued

| | Structure | Name | Proton NMR | IC$_{50}$ |
|---|---|---|---|---|
| 221 | Stereoisomer A | 1-[3-Fluoro-4-((3S)-3-methyl-1,1-dioxo-6-phenyl-[1,2]thiazinan-2-ylmethyl)-phenyl]-piperidine-4-carboxylic acid amide | $^1$H NMR (400 MHz, DMSO) δ 7.48-7.43 (m, 2H), 7.43-7.33 (m, 3H), 7.33-7.27 (m, 1H), 7.27-7.24 (m, 1H), 6.81-6.76 (m, 1H), 6.76-6.73 (s, 1H), 6.71-6.65 (m, 1H), 4.49-4.42 (m, 1H), 4.42-4.35 (m, 1H), 4.31-4.22 (m, 1H), 4.15-4.03 (m, 1H), 3.78-3.66 (m, 2H), 2.73-2.62 (m, 2H), 2.46-2.36 (m, 1H), 2.29-2.20 (m, 1H), 2.13-2.03 (m, 1H), 1.86-1.71 (m, 3H), 1.68-1.53 (m, 3H), 1.13-1.04 (d, J = 6.9 Hz, 3H). | 0.085 |
| 222 | Stereoisomer B | 1-[3-Fluoro-4-((3S)-3-methyl-1,1-dioxo-6-phenyl-[1,2]thiazinan-2-ylmethyl)-phenyl]-piperidine-4-carboxylic acid amide | $^1$H NMR (400 MHz, DMSO) δ 7.49-7.43 (m, 2H), 7.43-7.35 (m, 3H), 7.30-7.21 (m, 2H), 6.82-6.71 (m, 3H), 4.42-4.31 (m, 3H), 3.82-3.71 (m, 2H), 3.63-3.49 (m, 1H), 2.80-2.63 (m, 3H), 2.37-2.19 (m, 1H), 2.15-1.97 (m, 2H), 1.82-1.70 (m, 2H), 1.67-1.53 (m, 3H), 1.38-1.31 (d, J = 7.1 Hz, 3H). | 0.034 |
| 223 | Stereoisomer A | 1-(4-{3-Fluoro-4-[(3S)-6-(2-methoxy-phenyl)-3-methyl-1,1-dioxo-[1,2]thiazinan-2-ylmethyl]-phenyl}-piperazin-1-yl)-ethanone | | 0.135 |
| 224 | Stereoisomer B | 1-(4-{3-Fluoro-4-[6-(2-methoxy-phenyl)-(3S)-methyl-1,1-dioxo-[1,2]thiazinan-2-ylmethyl]-phenyl}-piperazin-1-yl)-ethanone | | 0.062 |
| 225 | Stereoisomer A | 2-{2-Fluoro-4-[4-(4H-[1,2,4]triazol-3-yl)-piperidin-1-yl]-benzyl}-(3S)-methyl-6-phenyl-[1,2]thiazinane 1,1-dioxide | | 0.15 |

TABLE 4-continued

| | Structure | Name | Proton NMR | IC$_{50}$ |
|---|---|---|---|---|
| 226 | Stereoisomer B | 2-{2-Fluoro-4-[4-(4H-[1,2,4]triazol-3-yl)-piperidin-1-yl]-benzyl}-(3S)-methyl-6-phenyl-[1,2]thiazinane 1,1-dioxide | | 0.281 |
| 227 | 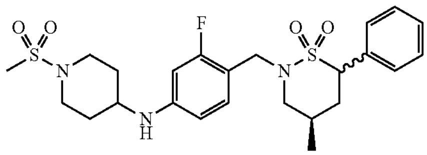 [SMILES: C[C@@H]1CC(c2ccccc2)S(=O)(=O)N(Cc2ccc(NC3CCN(S(C)(=O)=O)CC3)cc2F)C1] | [3-Fluoro-4-((4R)-methyl-1,1-dioxo-6-phenyl-[1,2]thiazinan-2-ylmethyl)-phenyl]-(1-methanesulfonyl-piperidin-4-yl)-amine | $^1$H NMR (400 MHz, DMSO) δ 7.40-7.42 (m, 5 H), 7.10 (t, 1 H), 6.42-6.43 (m, 2 H), 5.99 (d, 1 H), 4.51 (dd, 1 H), 4.29 (q, 2 H), 3.52 (d, 2 H), 3.34-3.44 (m, 1 H), 3.13 (t, 1 H), 3.00 (d, 1 H), 2.92 (d, 2 H), 2.87 (s, 3 H), 2.21 (d, 2 H), 2.07 (d, 1 H), 1.98 (d, 2 H), 1.39-1.42 (m, 2 H), 0.88 (d, 3 H). | 0.003 |
| 228 | Stereoisomer A | (3S)-Ethyl-2-[2-fluoro-4-(4-[1,2,4]triazol-4-yl-piperidin-1-yl)-benzyl]-6-phenyl-[1,2]thiazinane 1,1-dioxide | $^1$H NMR (400 MHz, DMSO) δ 8.64 (s, 2 H); 7.40-7.42 (m. 6 H); 6.80-6.81 (m, 2 H); 4.50 (dd, J = 12.7 3.6 Hz, 1 H); 4.35-4.38 (m, 2 H); 4.24 (d, J = 16.9 Hz, 1 H); 3.85 (d, J = 14.0 Hz, 3 H); 2.83 (t, J = 12.3 Hz, 2 H); 2.40 (t, J = 13.0 Hz, 1 H); 2.11 (d, J = 13.2 Hz, 3 H); 1.95-1.97 (m, 2 H); 1.74 (d, J = 7.8 Hz, 2 H); 1.47 (t, J = 7.3 Hz, 2 H); 0.72 (t, J = 7.3 Hz, 3 H). | 0.021 |
| 229 | Stereoisomer B | (3S)-Ethyl-2-[2-fluoro-4-(4-[1,2,4]triazol-4-yl-piperidin-1-yl)-benzyl]-6-phenyl-[1,2]thiazinane 1,1-dioxide | | 0.168 |
| 230 | 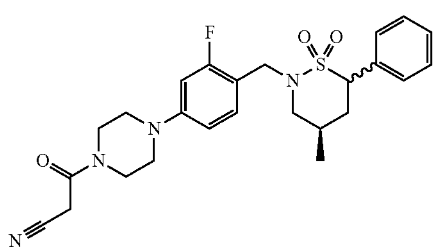 [SMILES: C[C@@H]1CC(c2ccccc2)S(=O)(=O)N(Cc2ccc(N3CCN(C(=O)CC#N)CC3)cc2F)C1] | 3-{4-[3-Fluoro-4-((4R)-methyl-1,1-dioxo-6-phenyl-[1,2]thiazinan-2-ylmethyl)-phenyl]-piperazin-1-yl}-3-oxo-propionitrile | | 0.093 |
| 231 | 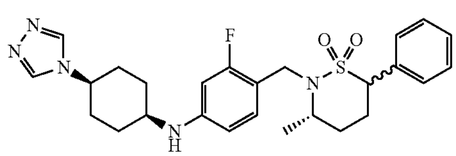 [SMILES: C[C@H]1CCC(c2ccccc2)S(=O)(=O)N1Cc1ccc(N[C@H]2CC[C@@H](n3cnnc3)CC2)cc1F] | [3-Fluoro-4-((3S)-methyl-1,1-dioxo-6-phenyl-[1,2]thiazinan-2-ylmethyl)-phenyl]-(4-[1,2,4]triazol-4-yl-cyclohexyl)-amine | | 0.073 |

TABLE 4-continued

| | Structure | Name | Proton NMR | IC$_{50}$ |
|---|---|---|---|---|
| 232 | 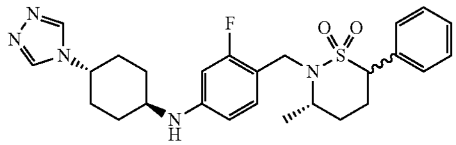 [SMILES: C[C@H]1CCC(c2ccccc2)S(=O)(=O)N1Cc1ccc(N[C@H]2CC[C@H](n3cnnc3)CC2)cc1F] | [3-Fluoro-4-((3S)-methyl-1,1-dioxo-6-phenyl-[1,2]thiazinan-2-ylmethyl)-phenyl]-(4-[1,2,4]triazol-4-yl-cyclohexyl)-amine | | 0.275 |
| 233 | 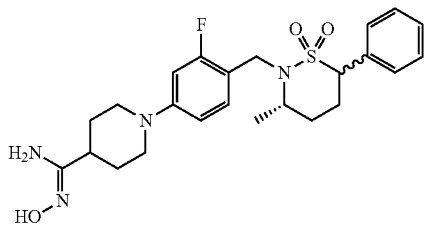 [SMILES: C[C@H]1CCC(c2ccccc2)S(=O)(=O)N1Cc1ccc(N2CCC(/C(N)=N/O)CC2)cc1F] | 1-[3-Fluoro-4-((3S)-methyl-1,1-dioxo-6-phenyl-[1,2]thiazinan-2-ylmethyl)-phenyl]-N-hydroxy-piperidine-4-carboxamidine | | 0.039 |
| 234 | 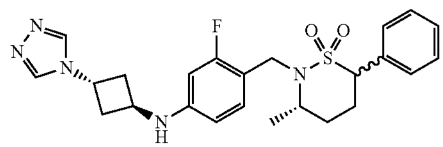 [SMILES: C[C@H]1CCC(c2ccccc2)S(=O)(=O)N1Cc1ccc(N[C@H]2C[C@H](n3cnnc3)C2)cc1F] | [3-Fluoro-4-((3S)-methyl-1,1-dioxo-6-phenyl-[1,2]thiazinan-2-ylmethyl)-phenyl]-(3-[1,2,4]triazol-4-yl-cyclobutyl)-amine | | 0.132 |
| 235 | Stereoisome A | 2-[2-Fluoro-4-(4-[1,2,4]oxadiazol-3-yl-piperidin-1-yl)-benzyl]-(3S)-methyl-6-phenyl-[1,2]thiazinane 1,1-dioxide | $^1$H NMR (400 MHz, DMSO) δ 9.53-9.49 (s, 1H), 7.49-7.43 (m, 2H), 7.43-7.35 (m, 3H), 7.35-7.29 (m, 1H), 6.85-6.79 (m, 1H), 6.77-6.69 (m, 1H), 4.50-4.36 (m, 2H), 4.32-4.23 (m, 1H), 4.15-4.02 (m, 1H), 3.81-3.69 (m, 2H), 3.13-3.01 (m, 1H), 2.97-2.83 (m, 2H), 2.46-2.37 (m, 1H), 2.14-1.97 (m, 3H), 1.89-1.70 (m, 3H), 1.70-1.59 (m, 1H), 1.13-1.05 (d, J = 6.8 Hz, 3H). | 0.040 |
| 236 | 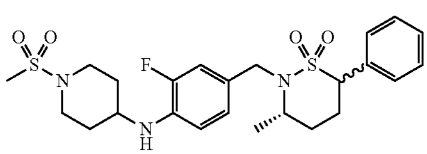 [SMILES: C[C@H]1CCC(c2ccccc2)S(=O)(=O)N1Cc1ccc(NC2CCN(S(C)(=O)=O)CC2)c(F)c1] | [2-Fluoro-4-((3S)-methyl-1,1-dioxo-6-phenyl-[1,2]thiazinan-2-ylmethyl)-phenyl]-(1-methanesulfonyl-piperidin-4-yl)-amine | $^1$H NMR (400 MHz, DMSO) δ 7.39-7.41 (m, 5 H), 6.98-7.00 (m, 2 H), 6.75 (t, 1 H), 5.15 (d, 1 H), 4.35-4.37 (m, 2 H), 4.15 (d, 1 H), 4.02-4.04 (m, 1 H), 3.54 (d, 2 H), 3.38-3.45 (m, 1 H), 2.86-3.95 (m, 4 H), 2.48-2.49 (m, 1H), 2.07-2.09 (m, 1 H), 1.94-1.97 (m, 2 H), 1.75-1.83 (m, 1 H), 1.63 (d, 1 H), 1.48-1.53 (m, 2 H), 1.09 (d, 3 H). | 0.006 |
| 237 | 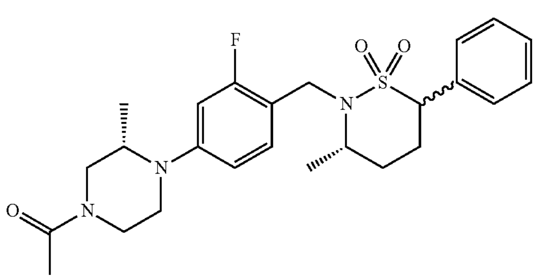 [SMILES: CC(=O)N1CCN(c2ccc(CN3[C@@H](C)CCC(c4ccccc4)S3(=O)=O)c(F)c2)[C@@H](C)C1] | 1-{4-[3-Fluoro-4-((3S)-methyl-1,1-dioxo-6-phenyl-[1,2]thiazinan-2-ylmethyl)-phenyl]-3-methyl-piperazin-1-yl}-ethanone | $^1$H NMR (400 MHz, DMSO) δ 7.38-7.40 (m, 6 H), 6.76 (s, 1 H), 6.66 (d, 1 H), 4.43-4.45 (m, 2 H), 4.27 (d, 1 H), 4.06-4.11 (m, 2 H), 3.76 (dd, 1 H), 3.37-3.42 (m, 3 H), 3.01 (t, 1 H), 2.86 (t, 1 H), 2.49-2.50 (m, 1 H), 2.04-2.15 (m, 3 H), 1.81 (q, 1 H), 1.65 (d, 1 H), 1.08 (d, 3 H), 0.91 (dd, 3 H). | 0.006 |

TABLE 4-continued

| | Structure | Name | Proton NMR | IC$_{50}$ |
|---|---|---|---|---|
| 238 | 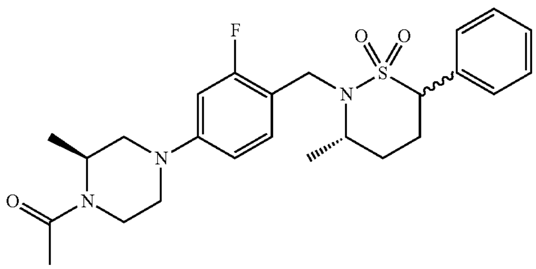 [SMILES: CC(=O)N1CCN(c2ccc(CN3[C@@H](C)CCC(c4ccccc4)S3(=O)=O)c(F)c2)C[C@@H]1C] | 1-{4-[3-Fluoro-4-((3S)-methyl-1,1-dioxo-6-phenyl-[1,2]thiazinan-2-ylmethyl)-phenyl]-2-methyl-piperazin-1-yl}-ethanone | $^1$H NMR (400 MHz, DMSO) δ 7.35-7.47 (m, 6 H); 6.61-6.76 (m, 2 H); 4.08-4.65 (m, 5 H); 3.32-3.74 (m, 3 H); 2.56-3.04 (br m, 2 H); 2.38-2.69 (m, 2 H); 2.01-2.16 (m, 4 H); 1.75-1.80 (m, 1 H); 1.62-1.66 (m, 1 H); 1.08-1.3 (m, 6 H). | 0.008 |
| 239 | Stereoisomer A | [4-((3S)-Ethyl-1,1-dioxo-6-phenyl-[1,2]thiazinan-2-ylmethyl)-3-fluoro-phenyl]-(1-methanesulfonyl-piperidin-4-yl)-amine | $^1$H NMR (400 MHz, DMSO) δ 7.40-7.42 (m, 5 H); 7.22 (t, J = 8.8 Hz, 1 H); 6.45 (dd, J = 8.6, 2.2 Hz, 1 H); 6.34 (dd, J = 13.5, 2.2 Hz, 1 H); 5.86 (d, J = 8.1 Hz, 1 H); 4.45 (dd, J = 12.7, 3.6 Hz, 1 H); 4.32 (d, J = 16.7 Hz, 1 H); 4.18 (d, J = 16.6 Hz, 1 H); 3.76-3.82 (m, 1 H); 3.51 (d, J = 11.8 Hz, 2 H); 2.87-3.95 (m, 5 H); 2.36-2.44 (m, 1 H); 2.10 (dd, J = 13.9, 3.9 Hz, 1 H); 1.97 (d, J = 12.8 Hz, 2 H); 1.68-1.77 (m, 2 H); 1.42-1.46 (m, 4 H); 0.71 (t, J = 7.3 Hz, 3 H). | 0.003 |
| 240 | Stereoisomer B | [4-((3S)-Ethyl-1,1-dioxo-6-phenyl-[1,2]thiazinan-2-ylmethyl)-3-fluoro-phenyl]-(1-methanesulfonyl-piperidin-4-yl)-amine | $^1$H NMR (400 MHz, DMSO) δ 7.35-7.37 (m, 5 H); 7.08 (t, J = 8.6 Hz, 1 H); 6.37-6.38 (m, 2 H); 5.93 (d, J = 8.1 Hz, 1 H); 4.37 (d, J = 14.3 Hz, 1 H); 4.29 (dd, J = 12.5, 3.0 Hz, 1 H); 4.19 (d, J = 14.3 Hz, 1 H); 3.48 (d, J = 11.9 Hz, 2 H); 3.34 (m, 1 H); 3.17 (m, 1 H); 2.83 (m, 5 H); 2.59-2.63 (m, 1 H); 1.94-2.00 (m, 5 H); 1.61 (d, J = 14.1 Hz, 1 H); 1.39-1.43 (m, 3 H); 0.64 (t, J = 7.3 Hz, 3 H). | 0.004 |
| 241 | 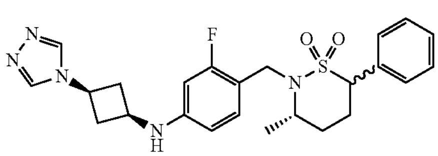 [SMILES: C[C@H]1CCC(c2ccccc2)S(=O)(=O)N1Cc1ccc(N[C@H]2C[C@@H](n3cnnc3)C2)cc1F] | [3-Fluoro-4-((3S)-methyl-1,1-dioxo-6-phenyl-[1,2]thiazinan-2-ylmethyl)-phenyl]-(3-[1,2,4]triazol-4-yl-cyclobutyl)-amine | | 0.085 |
| 242 | Stereoisomer A | 2-{2-Fluoro-4-[4-(1H-pyrazol-4-yl)-piperidin-1-yl]-benzyl}-(3S)-methyl-6-phenyl-[1,2]thiazinane 1,1-dioxide | $^1$H NMR (400 MHz, DMSO) δ 12.62-12.43 (br s, 1H), 7.55-7.34 (m, 7H), 7.33-7.26 (t, J = 9.0 Hz, 1 H), 6.85-6.78 (m, 1H), 6.74-6.66 (m, 1 H), 4.50-4.36 (m, 2H), 4.32-4.23 (m, 1H), 4.15-4.01 (m, 1H), 3.82-3.69 (m, 2H), 2.83-2.72 (m, 2H), 2.70-2.58 (m, 1H), 2.46-2.35 (m, 1H), 2.15-2.04 (m, 1H), 1.99-1.88 (m, 2H), 1.88-1.72 (m, 1H), 1.70-1.51 (m, 3H), 1.12-1.05 (d, J = 6.9 Hz, 3H). | 0.004 |

TABLE 4-continued

| | Structure | Name | Proton NMR | IC$_{50}$ |
|---|---|---|---|---|
| 243 | 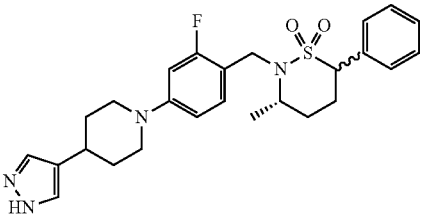 [SMILES: C[C@H]1CCC(c2ccccc2)S(=O)(=O)N1Cc1ccc(N2CCC(c3cn[nH]c3)CC2)cc1F] Stereoisomer B | 2-{2-Fluoro-4-[4-(1H-pyrazol-4-yl)-piperidin-1-yl]-benzyl}-(3S)-methyl-6-phenyl-[1,2]thiazinane 1,1-dioxide | $^1$H NMR (400 MHz, DMSO) δ 12.61-12.47 (br s, 1H), 7.59-7.33 (m, 7H), 7.30-7.22 (m, 1H), 6.85-6.79 (m, 1H), 6.79-6.73 (m, 1H), 4.42-4.33 (m, 3H), 3.84-3.74 (m, 2H), 3.61-3.50 (m, 1H), 2.87-2.76 (m, 2H), 2.75-2.60 (m, 2H), 2.16-1.99 (m, 2H), 1.99-1.89 (m, 2H), 1.67-1.51 (m, 3H), 1.37-1.32 (d, J = 7.1 Hz, 3H). | 0.003 |
| 244 | 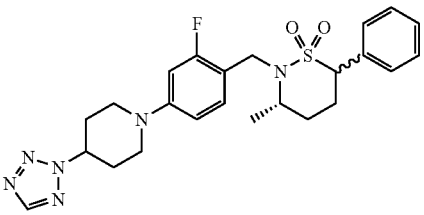 [SMILES: C[C@H]1CCC(c2ccccc2)S(=O)(=O)N1Cc1ccc(N2CCC(n3ncnn3)CC2)cc1F] Stereoisomer A | 2-[2-Fluoro-4-(4-tetrazol-1-yl)-piperidin-1-yl)-benzyl]-(3S)-methyl-6-phenyl-[1,2]thiazinane 1,1-dioxide | $^1$H NMR (400 MHz, DMSO) δ 8.99-8.96 (s, 1H), 7.49-7.43 (m, 2H), 7.43-7.29 (m, 4H), 6.89-6.82 (m, 1H), 6.82-6.75 (m, 1H), 5.18-5.07 (m, 1H), 4.50-4.36 (m, 2H), 4.33-4.25 (m, 1H), 4.16-4.03 (m, 1H), 3.87-3.76 (m, 2H), 3.10-2.98 (m, 2H), 2.47-2.37 (m, 1H), 2.31-2.23 (m, 2H), 2.19-2.04 (m, 3H), 1.89-1.73 (m, 1H), 1.70-1.59 (m, 1H), 1.13-1.06 (d, J = 6.8 Hz, 3H). | 0.024 |
| 245 | 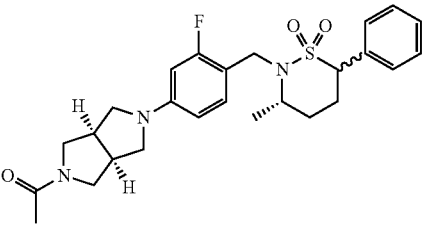 [SMILES: CC(=O)N1C[C@@H]2CN(c3ccc(CN4[C@@H](C)CCC(c5ccccc5)S4(=O)=O)c(F)c3)C[C@@H]2C1] | 1-{(3aR,6aS)-5-[3-Fluoro-4-((3S)-methyl-1,1-dioxo-6-phenyl-[1,2]thiazinan-2-ylmethyl)-phenyl]-hexahydro-pyrrolo[3,4-c]pyrrol-2-yl}-ethanone | | 0.189 |
| 246 | 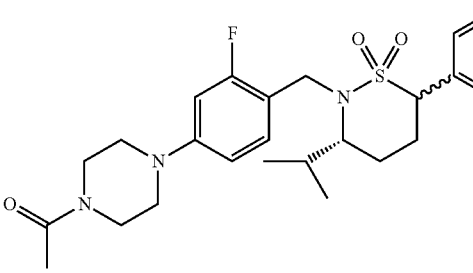 Stereoisomer A | 1-{4-[3-Fluoro-4-((3R)-isopropyl-1,1-dioxo-6-phenyl-[1,2]thiazinan-2-ylmethyl)-phenyl]-piperazin-1-yl}-ethanone | $^1$H NMR (400 MHz, DMSO) δ 7.41-7.43 (m, 6 H); 6.82 (dd, J = 8.8, 2.4 Hz, 1 H); 6.72 (dd, J = 14.0, 2.4 Hz, 1 H); 4.52 (dd, J = 12.7, 3.7 Hz, 1 H); 4.39 (d, J = 16.9 Hz, 1 H); 4.23 (d, J = 16.9 Hz, 1 H); 3.55 (m, 5 H); 3.19 (t, J = 5.0 Hz, 2 H); 3.12 (t, J = 5.1 Hz, 2 H); 2.34-2.38 (m, 1 H); 2.12 (dd, J = 13.8, 4.0 Hz, 1 H); 2.03 (s, 3 H); 1.87 (d, J = 14.0 Hz, 1 H); 1.73-1.77 (m, 2 H); 0.90 (d, J = 6.5 Hz, 3 H); 0.62 (d, J = 6.3 Hz, 3 H). | 0.030 |
| 247 | 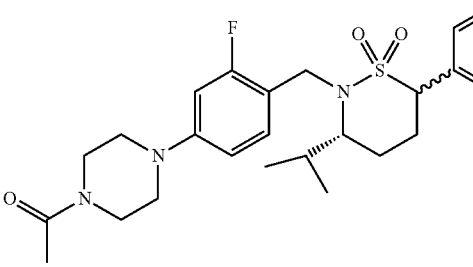 Stereoisomer B | 1-{4-[3-Fluoro-4-((3R)-isopropyl-1,1-dioxo-6-phenyl-[1,2]thiazinan-2-ylmethyl)-phenyl]-piperazin-1-yl}-ethanone | $^1$H NMR (400 MHz, DMSO) δ 7.36-7.38 (m, 6 HN); 6.78-6.80 (m, 2 H); 4.55 (d, J = 14.3 Hz, 1 H); 4.34 (dd, J = 12.5, 3.1 Hz, 1 H); 4.24 (d, J = 14.3 Hz, 1 H); 3.56 (s, 4 H); 3.23 (t, J = 4.9 Hz, 2 H); 3.16 (t, J = 5.1 Hz, 2 H); 2.81 (dd, J = 11.1, 4.6 Hz, 1 H); 2.56-2.60 (m, 1 H); 2.42-2.45 (m, 1 H); 2.04 (m, 6 H); 0.78 (d, J = 6.6 Hz, 3 H); 0.68 (d, J = 6.4 Hz, 3 H). | 0.029 |

TABLE 4-continued

| | Structure | Name | Proton NMR | IC$_{50}$ |
|---|---|---|---|---|
| 248 | Stereoisomer A | 1-(4-(4-((2,2-dioxido-3-phenylhexahydro-cyclopenta[c][1,2]thiazin-1(3H)-yl)methyl)-3-fluorophenyl)piper-azin-1-yl)ethanone | $^1$H NMR (400 MHz, DMSO) δ 7.39-7.40 (m, 5 H); 7.29 (t, J = 8.8 Hz, 1 H); 6.77-6.79 (m, 2 H); 4.39 (t, J = 15.0 Hz, 3 H); 3.52-3.58 (m, 5 H); 3.22 (t, J = 5.0 Hz, 2 H); 3.15 (t, J = 5.1 Hz, 2 H); 2.48-2.49 (m, 1 H); 2.35-2.43 (m, 1 H); 2.25-2.29 (m, 1 H); 2.03 (s, 3 H); 1.97 (d, J = 13.8 Hz, 1 H); 1.82 (br s, 1 H); 1.68-1.71 (m, 2 H); 1.42-1.55 (m, 1 H); 1.39 (t, J = 11.3 Hz, 1 H). | 0.007 |
| 249 | Stereoisomer A | 5-(2-fluoro-4-((1-(methylsulfonyl)piperidin-4-yl)amino)benzyl)-7-phenyl-6-thia-5-azaspiro[2.5]octane 6,6-dioxide | $^1$H NMR (400 MHz, DMSO) δ 7.47 (dd, J = 7.4, 1.9 Hz, 2 H); 7.35-7.43 (m, 3 H); 7.06 (t, J = 8.7 Hz, 1 H); 6.35-6.45 (m, 2 H); 5.97 (d, J = 8.1 Hz, 1 H); 4.57 (dd, J = 12.7, 3.3 Hz, 1 H); 4.39 (s, 2 H); 3.82 (d, J = 14.4 Hz, 1 H); 3.51 (d, J = 11.9 Hz, 2 H); 3.35-3.45 (m, 1 H); 2.85-2.95 (m, 6 H); 2.37 (dd, J = 14.5, 2.6 Hz, 1 H); 1.97 (d, J = 12.8 Hz, 2 H); 1.35-1.45 (m, 3 H); 0.65-0.75 (m, 2 H); 0.35-0.45 (m, 2 H). | 0.037 |
| 250 | Stereoisomer B | 1-(4-(4-((2,2-dioxido-3-phenylhexahydro-cyclopenta[c][1,2]thiazin-1(3H)-yl)methyl)-3-fluorophenyl)piper-azin-1-yl)ethanone | $^1$H NMR (400 MHz, DMSO) δ 7.39-7.40 (m, 5 H); 7.29 (t, J = 8.8 Hz, 1 H); 6.77-6.79 (m, 2 H); 4.39 (t, J = 15.0 Hz, 3 H); 3.52-3.58 (m, 5 H); 3.22 (t, J = 5.0 Hz, 2 H); 3.15 (t, J = 5.1 Hz, 2 H); 2.48-2.49 (m, 1 H); 2.35-2.43 (m, 1 H); 2.25-2.29 (m, 1 H); 2.03 (s, 3 H); 1.97 (d, J = 13.8 Hz, 1 H); 1.82 (br s, 1 H); 1.68-1.71 (m, 2 H); 1.42-1.55 (m, 1 H); 1.39 (t, J = 11.3 Hz, 1 H). | 0.011 |
| 251 | Stereoisomer C | 1-(4-(4-((2,2-dioxido-3-phenylhexahydro-cyclopenta[c][1,2]thiazin-1(3H)-yl)methyl)-3-fluorophenyl)piper-azin-1-yl)ethanone | $^1$H NMR (400 MHz, DMSO) δ 7.51-7.52 (m, 2 H); 7.38-7.40 (m, 4 H); 6.75-6.76 (m, 2 H); 4.67 (dd, J = 12.6, 3.6 Hz, 1 H); 4.36 (d, J = 16.9 Hz, 1 H); 4.21 (d, J = 16.8 Hz, 1 H); 3.75 (t, J = 4.4 Hz, 1 H); 3.55 (s, 4 H); 3.16 (dt, J = 28.0, 5.0 Hz, 4 H); 2.75 (td, J = 13.5, 4.8 Hz, 1 H); 2.28 (br s, 1 H); 2.15 (d, J = 14.4 Hz, 1 H); 2.03 (s, 3 H); 1.97 (t, J = 9.5 Hz, 1 H); 1.82 (d, J = 10.5 Hz, 1 H); 1.65-1.72 (m, 2 H); 1.44-1.61 (br m, 2 H). | 0.219 |

TABLE 4-continued

| | Structure | Name | Proton NMR | IC$_{50}$ |
|---|---|---|---|---|
| 252 | Stereoisomer D | 1-(4-(4-((2,2-dioxido-3-phenylhexahydro-cyclopenta[c][1,2]thiazin-1(3H)-yl)methyl)-3-fluorophenyl)piper-azin-1-yl)ethanone | $^1$H NMR (400 MHz, DMSO) δ 7.51-7.52 (m, 2 H); 7.38-7.40 (m, 4 H); 6.75-6.76 (m, 2 H); 4.67 (dd, J = 12.6, 3.6 Hz, 1 H); 4.36 (d, J = 16.9 Hz, 1 H); 4.21 (d, J = 16.8 Hz, 1 H); 3.75 (t, J = 4.4 Hz, 1 H); 3.55 (s, 4 H); 3.16 (dt, J = 28.0, 5.0 Hz, 4 H); 2.75 (td, J = 13.5, 4.8 Hz, 1 H); 2.28 (br s, 1 H); 2.15 (d, J = 14.4 Hz, 1 H); 2.03 (s, 3 H); 1.97 (t, J = 9.5 Hz, 1 H); 1.82 (d, J = 10.5 Hz, 1 H); 1.65-1.72 (m, 2 H); 1.44-1.61 (br m, 2 H). | 0.068 |
| 253 | Stereoisomer B | 5-(2-fluoro-4-((1-(methylsulfonyl)piperidin-4-yl)amino)benzyl)-7-phenyl-6-thia-5-azaspiro[2.5]octane 6,6-dioxide | $^1$H NMR (400 MHz, DMSO) δ 7.47 (dd, J = 7.4, 1.9 Hz, 2 H); 7.35-7.43 (m, 3 H); 7.06 (t, J = 8.7 Hz, 1 H); 6.35-6.45 (m, 2 H); 5.97 (d, J = 8.1 Hz, 1 H); 4.57 (dd, J = 12.7, 3.3 Hz, 1 H); 4.39 (s,l 2 H); 3.82 (d, J = 14.4 Hz, 1 H); 3.51 (d, J = 11.9 Hz, 2 H); 3.35-3.45 (m, 1 H);. 2.85-2.95 (m, 6 H); 2.37 (dd, J = 14.5, 2.6 Hz, 1 H); 1.97 (d, J = 12.8 Hz, 2 H); 1.35-1.45 (m, 3 H); 0.65-0.75 (m, 2 H); 0.35-0.45 (m, 2 H). | 0.007 |
| 254 | Stereoisomer A | 2-{2-Fluoro-4-[4-(3H-[1,2,3]triazol-4-yl)-piperidin-1-yl]-benzyl}-(3S)-methyl-6-phenyl-[1,2]thiazinane 1,1-dioxide | | 0.009 |
| 255 | Stereoisomer B | 2-{2-Fluoro-4-[4-(3H-[1,2,3]triazol-4-yl)-piperidin-1-yl]-benzyl}-(3S)-methyl-6-phenyl-[1,2]thiazinane 1,1-dioxide | $^1$H NMR (400 MHz, DMSO) δ 7.72-7.61 (s, 1H), 7.49-7.43 (m, 2H), 7.43-7.34 (m, 3H), 7.34-7.28 (m, 1H), 6.87-6.78 (m, 1H), 6.77-6.67 (m, 1H), 4.50-4.36 (m, 2H), 4.32-4.22 (m, 1H), 4.15-4.03 (m, 1H), 3.81-3.70 (m, 2H), 2.96-2.78 (m, 3H), 2.47-2.35 (m, 1H), 2.16-2.04 (m, 1H), 2.04-1.94 (m, 2H), 1.88-1.60 (m, 4H), 1.13-1.05 (d, J = 6.8 Hz, 3H). | 0.012 |
| 256 | Stereoisomer B | 2-[2-Fluoro-4-(4-[1,2,3]triazol-1-yl-piperidin-1-yl)-benzyl]-(3S)-methyl-6-phenyl-[1,2]thiazinane 1,1-dioxide | $^1$H NMR (400 MHz, DMSO) δ 8.25-8.22 (s, 1H), 7.75-7.72 (d, J = 1.1 Hz, 1H), 7.49-7.43 (m, 2H), 7.43-7.34 (m, 3H), 7.32-7.25 (m, 1H), 6.89-6.80 (m, 2H), 4.82-4.70 (m, 1H), 4.43-4.35 (m, 3H), 3.95-3.85 (m, 2H), 3.65-3.51 (m, 1H), 3.02-2.92 (m, 2H), 2.79-2.64 (m, 1H), 2.22-1.98 (m, 6H), 1.69-1.57 (m, 1H), 1.40-1.31 (d, J = 7.0 Hz, 3H). | 0.004 |

TABLE 4-continued

| | Structure | Name | Proton NMR | IC$_{50}$ |
|---|---|---|---|---|
| 257 | Stereoisomer A | 5-[2-Fluoro-4-(4-[1,2,4]triazol-4-yl-piperidin-1-yl)-benzyl]-7-phenyl-6-thia-5-aza-spiro[2.5]octane 6,6-dioxde | $^1$H NMR (400 MHz, DMSO) δ 8.64 (s, 2 H); 7.48 (dd, J = 7.4, 1.9 Hz, 2 H); 7.38-7.40 (m, 3 H); 7.21 (t, J = 8.8 Hz, 1 H); 6.80-6.81 (m, 2 H); 4.61 (dd, J = 12.7, 3.4 Hz, 1 H); 4.46 (s, 2 H); 4.37 (tt, J = 11.8, 4.1 Hz, 1 H); 3.85-3.89 (m, 3 H); 2.80-2.95 (m, 3 H); 2.40 (dd, J = 14.5, 2.7 Hz, 1 H); 2.06-2.11 (m, 2 H); 1.93-1.96 (m, 2 H); 1.40-1.43 (m, 1 H); 0.70-0.75 (m, 2 H); 0.34-0.39 (m, 2 H). | 0.054 |
| 258 | Stereoisomer A | 1-(4-(4-((7,7-dioxido-8-phenyl-2-oxa-7-thia-6-azaspiro[3.5]nonan-6-yl)methyl)-3-fluorophenyl)piperazin-1-yl)ethanone | | 1.04 |
| 259 | Stereoisomer B | 5-[2-Fluoro-4-(4-[1,2,4]triazol-4-yl-piperidin-1-yl)-benzyl]-7-phenyl-6-thia-5-aza-spiro[2.5]octane 6,6-dioxide | $^1$H NMR (400 MHz, DMSO) δ 8.64 (s, 2 H); 7.48 (dd, J = 7.4, 1.9 Hz, 2 H); 7.38-7.40 (m, 3 H); 7.21 (t, J = 8.8 Hz, 1 H); 6.80-6.81 (m, 2 H); 4.61 (dd, J = 12.7, 3.4 Hz, 1 H); 4.46 (s, 2 H); 4.37 (tt, J = 11.8, 4.1 Hz, 1 H); 3.85-3.89 (m, 3 H); 2.80-2.95 (m, 3 H); 2.40 (dd, J = 14.5, 2.7 Hz, 1 H); 2.06-2.11 (m, 2 H); 1.93-1.96 (m, 2 H); 1.40-1.43 (m, 1 H); 0.70-0.75 (m, 2 H); 0.34-0.39 (m, 2 H). | 0.057 |
| 260 | 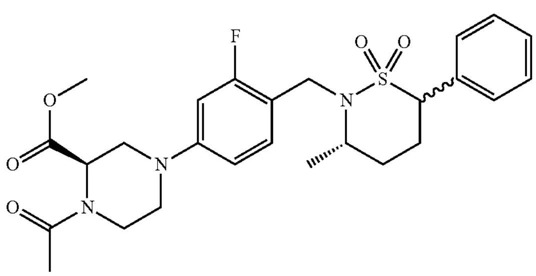 [SMILES: COC(=O)[C@H]1CN(c2ccc(CN3[C@@H](C)CCC(c4ccccc4)S3(=O)=O)c(F)c2)CCN1C(C)=O] | 1-Acetyl-4-[3-fluoro-4-((3S)-methyl-1,1-dioxo-6-phenyl-[1,2]thiazinan-2-ylmethyl)-phenyl]-piperazine-2-carboxylic acid methyl ester | $^1$H NMR (400 MHz, DMSO) δ 7.36-7.38 (m, 6 H); 6.75-6.78 (m, 1 H); 6.66-6.69 (m, 1 H); 5.02 (d, J = 76.0 Hz, 1 H); 4.42-4.44 (m, 2 H); 4.26 (d, J = 16.7 Hz, 1 H); 4.06-4.12 (m, 2 H); 3.83 (d, J = 13.3 Hz, 1 H); 3.65 (m, 4 H); 3.36-3.37 (m, 1 H); 2.92-2.94 (m, 1 H); 2.75-2.78 (m, 1 H); 2.59-2.63 (m, 1 H); 2.42 (m, 1 H); 2.09 (s, 3 H); 1.79 (d, J = 13.4 Hz, 1 H); 1.63 (d, J = 14.1 Hz, 1 H); 1.08 (d, J = 6.9 Hz, 3 H). | 0.031 |
| 261 | 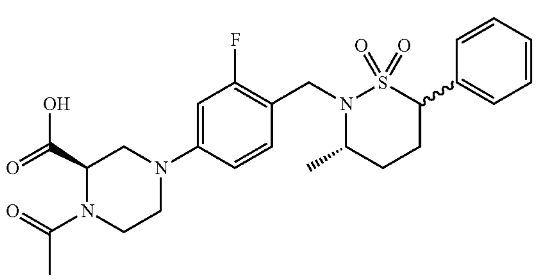 [SMILES: CC(=O)N1CCN(c2ccc(CN3[C@@H](C)CCC(c4ccccc4)S3(=O)=O)c(F)c2)C[C@@H]1C(=O)O] | 1-Acetyl-4-[3-fluoro-4-((3S)-methyl-1,1-dioxo-6-phenyl-[1,2]thiazinan-2-ylmethyl)-phenyl]-piperazine-2-carboxylic acid | | 0.379 |

| | Structure | Name | Proton NMR | IC$_{50}$ |
|---|---|---|---|---|
| 262 | 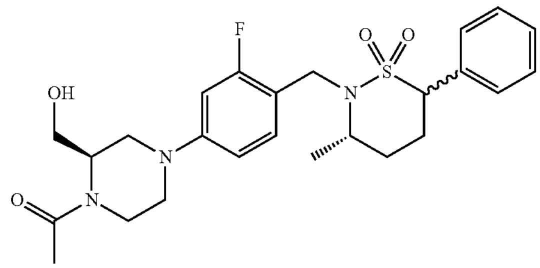 [SMILES: CC(=O)N1CCN(c2ccc(CN3[C@@H](C)CCC(c4ccccc4)S3(=O)=O)c(F)c2)C[C@@H]1CO] | 1-{4-[3-Fluoro-4-((3S)-methyl-1,1-dioxo-6-phenyl-[1,2]thiazinan-2-ylmethyl)-phenyl]-2-hydroxymethyl-piperazin-1-yl}-ethanone | | 0.082 |
| 263 | 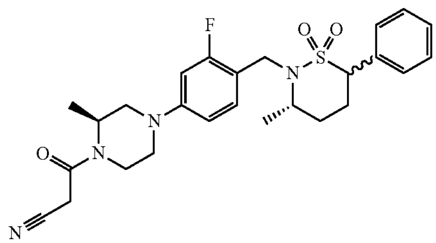 [SMILES: C[C@H]1CN(c2ccc(CN3[C@@H](C)CCC(c4ccccc4)S3(=O)=O)c(F)c2)CCN1C(=O)CC#N] | 3-{4-[3-Fluoro-4-((3S)-methyl-1,1-dioxo-6-phenyl-[1,2]thiazinan-2-ylmethyl)-phenyl]-2-methyl-piperazin-1-yl}-3-oxo-propionitrile | | 0.015 |
| 264 | 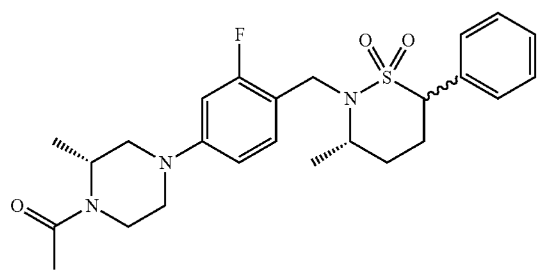 [SMILES: CC(=O)N1CCN(c2ccc(CN3[C@@H](C)CCC(c4ccccc4)S3(=O)=O)c(F)c2)C[C@H]1C] | 1-{4-[3-Fluoro-4-((3S)-methyl-1,1-dioxo-6-phenyl-[1,2]thiazinan-2-ylmethyl)-phenyl]-2-methyl-piperazin-1-yl}-ethanone | $^1$H NMR (400 MHz, DMSO) δ 7.35-7.47 (m, 6 H); 6.61-6.76 (m, 2 H); 4.08-4.65 (m, 5 H); 3.32-3.74 (m, 3 H); 2.56-3.04 (br m, 2 H); 2.38-2.69 (m, 2 H); 2.01-2.16 (m, 4 H); 1.75-1.80 (m, 1 H); 1.62-1.66 (m, 1 H); 1.08-1.3 (m, 6 H). | 0.018 |
| 265 | 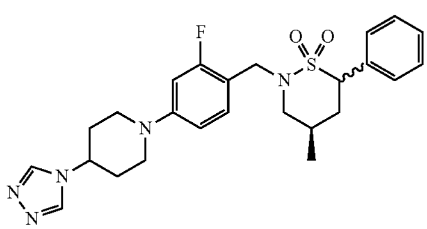 [SMILES: C[C@@H]1CC(c2ccccc2)S(=O)(=O)N(Cc2ccc(N3CCC(n4cnnc4)CC3)cc2F)C1] | 2-[2-Fluoro-4-(4-[1,2,4]triazol-4-yl-piperidin-1-yl)-benzyl]-(4R)-methyl-6-phenyl-[1,2]thiazinane 1,1-dioxide | $^1$H NMR (400 MHz, DMSO) δ 8.65 (s, 2 H); 7.35-7.45 (m, 5 H); 7.25 (t, J = 8.7 Hz, 1 H); 6.38-6.85 (m, 2 H); 4.54-4.56 (m, 1 H); 4.30-4.45 (m, 3 H); 3.90 (d, J = 12.9 Hz, 2 H); 3.18 (t, J = 12.5 Hz, 1 H); 3.03 (d, J = 14.0 Hz, 1 H); 2.86 (t, J = 12.4 Hz, 2 H); 2.13-2.25 (m, 4 H); 1.90-2.00 (m, 2 H); 1.36-1.47 (m, 1 H); 0.89 (d, J = 6.1 Hz, 3 H). | 0.066 |
| 266 | Stereoisomer B | 1-(4-(4-((7,7-dioxido-8-phenyl-2-oxa-7-thia-6-azaspiro[3.5]nonan-6-yl)methyl)-3-fluorophenyl)piperazin-1-yl)ethanone | | 4.33 |

TABLE 4-continued

| | Structure | Name | Proton NMR | IC$_{50}$ |
|---|---|---|---|---|
| 267 | 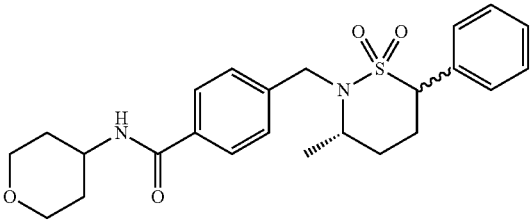 [SMILES: C[C@H]1CCC(c2ccccc2)S(=O)(=O)N1Cc1ccc(C(=O)NC2CCOCC2)cc1] Stereoisomer A | 4-((3S)-Methyl-1,1-dioxo-6-phenyl-[1,2]thiazinan-2-ylmethyl)-N-(tetrahydro-pyran-4-yl)-benzamide | | 2.81 |
| 268 | 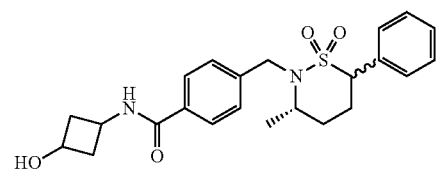 [SMILES: C[C@H]1CCC(c2ccccc2)S(=O)(=O)N1Cc1ccc(C(=O)NC2CC(O)C2)cc1] | N-(3-Hydroxy-cyclobutyl)-4-((3S)-methyl-1,1-dioxo-6-phenyl-[1,2]thiazinan-2-ylmethyl)-benzamide | | 3.25 |
| 269 | 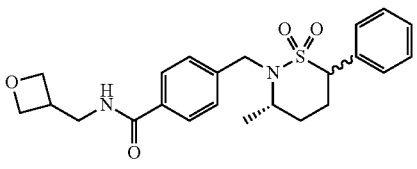 [SMILES: C[C@H]1CCC(c2ccccc2)S(=O)(=O)N1Cc1ccc(C(=O)NCC2COC2)cc1] | 4-((3S)-Methyl-1,1-dioxo-6-phenyl-[1,2]thiazinan-2-ylmethyl)-N-oxetan-3-ylmethyl-benzamide | | 1.67 |
| 270 | 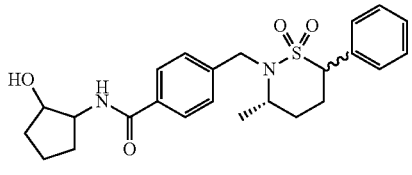 [SMILES: C[C@H]1CCC(c2ccccc2)S(=O)(=O)N1Cc1ccc(C(=O)NC2CCCC2O)cc1] | N-(2-Hydroxy-cyclopentyl)-4-((3S)-methyl-1,1-dioxo-6-phenyl-[1,2]thiazinan-2-ylmethyl)-benzamide | | 2.44 |
| 271 | 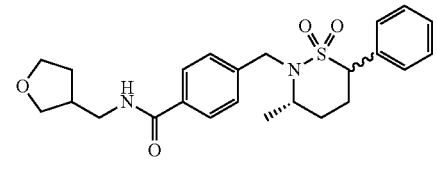 [SMILES: C[C@H]1CCC(c2ccccc2)S(=O)(=O)N1Cc1ccc(C(=O)NCC2CCOC2)cc1] | 4-((3S)-Methyl-1,1-dioxo-6-phenyl-[1,2]thiazinan-2-ylmethyl)-N-(tetrahydro-furan-3-ylmethyl)-benzamide | | 1.69 |
| 272 | 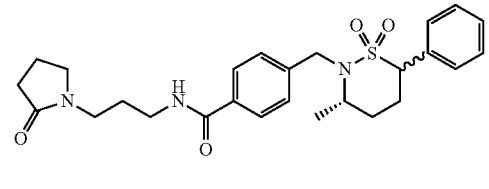 [SMILES: C[C@H]1CCC(c2ccccc2)S(=O)(=O)N1Cc1ccc(C(=O)NCCCN2CCCC2=O)cc1] | 4-((3S)-Methyl-1,1-dioxo-6-phenyl-[1,2]thiazinan-2-ylmethyl)-N-[3-(2-oxo-pyrrolidin-1-yl)-propyl]-benzamide | | 2.89 |
| 273 | 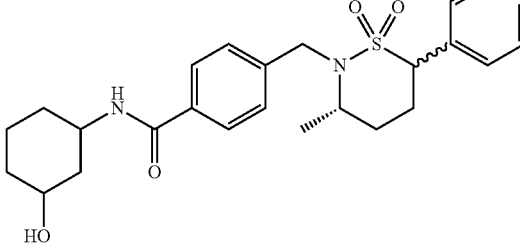 | N-(3-Hydroxy-cyclohexyl)-4-((3S)-methyl-1,1-dioxo-6-phenyl-[1,2]thiazinan-2-ylmethyl)-benzamide | | 5.47 |

TABLE 4-continued

| | Structure | Name | Proton NMR | IC$_{50}$ |
|---|---|---|---|---|
| 274 | 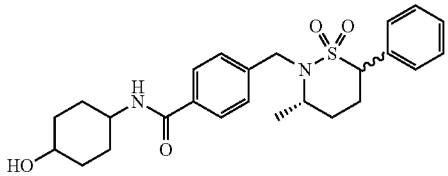 [SMILES: C[C@H]1CCC(c2ccccc2)S(=O)(=O)N1Cc1ccc(C(=O)NC2CCC(O)CC2)cc1] | N-(4-Hydroxy-cyclohexyl)-4-((3S)-methyl-1,1-dioxo-6-phenyl-[1,2]thiazinan-2-ylmethyl)-benzamide | | 4.41 |
| 275 | 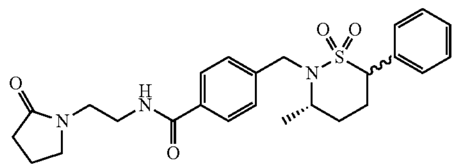 [SMILES: C[C@H]1CCC(c2ccccc2)S(=O)(=O)N1Cc1ccc(C(=O)NCCN2CCCC2=O)cc1] | 4-((3S)-Methyl-1,1-dioxo-6-phenyl-[1,2]thiazinan-2-ylmethyl)-N-[2-(2-oxo-pyrrolidin-1-yl)-ethyl]-benzamide | | 6.05 |
| 276 | 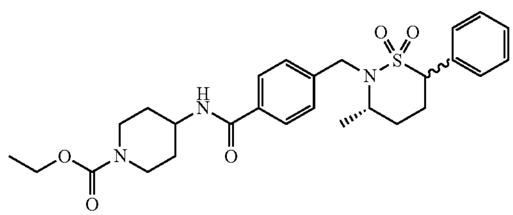 [SMILES: CCOC(=O)N1CCC(NC(=O)c2ccc(CN3[C@@H](C)CCC(c4ccccc4)S3(=O)=O)cc2)CC1] | 4-[4-((3S)-Methyl-1,1-dioxo-6-phenyl-[1,2]thiazinan-2-ylmethyl)-benzoylamino]-piperidine-1-carboxylic acid ethyl ester | | 4.44 |
| 277 | 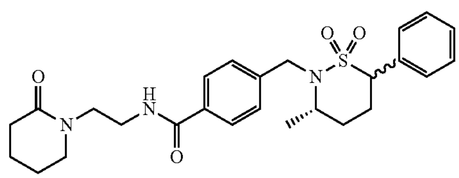 [SMILES: C[C@H]1CCC(c2ccccc2)S(=O)(=O)N1Cc1ccc(C(=O)NCCN2CCCCC2=O)cc1] | 4-((3S)-Methyl-1,1-dioxo-6-phenyl-[1,2]thiazinan-2-ylmethyl)-N-[2-(2-oxo-piperidin-1-yl)-ethyl]-benzamide | | 5.11 |
| 278 | 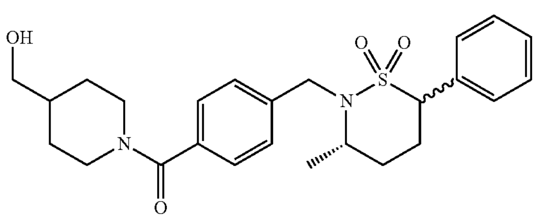 [SMILES: C[C@H]1CCC(c2ccccc2)S(=O)(=O)N1Cc1ccc(C(=O)N2CCC(CO)CC2)cc1] | (4-Hydroxymethyl-piperidin-1-yl)-[4-((3S)-methyl-1,1-dioxo-6-phenyl-[1,2]thiazinan-2-ylmethyl)-phenyl]-methanone | | 1.1 |
| 279 | 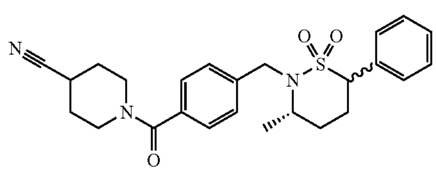 [SMILES: C[C@H]1CCC(c2ccccc2)S(=O)(=O)N1Cc1ccc(C(=O)N2CCC(C#N)CC2)cc1] | 1-[4-((3S)-Methyl-1,1-dioxo-6-phenyl-[1,2]thiazinan-2-ylmethyl)-benzoyl]-piperidine-4-carbonitrile | | 4.28 |
| 280 | 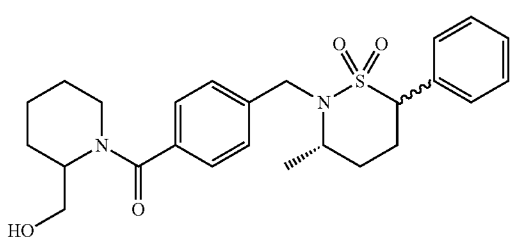 [SMILES: C[C@H]1CCC(c2ccccc2)S(=O)(=O)N1Cc1ccc(C(=O)N2CCCCC2CO)cc1] | (2-Hydroxymethyl-piperidin-1-yl)-[4-((3S)-methyl-1,1-dioxo-6-phenyl-[1,2]thiazinan-2-ylmethyl)-phenyl]-methanone | | 2.65 |

TABLE 4-continued

| | Structure | Name | Proton NMR | IC$_{50}$ |
|---|---|---|---|---|
| 281 | 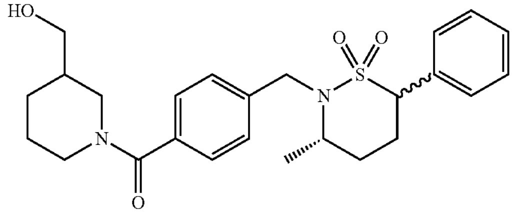 [SMILES: C[C@H]1CCC(c2ccccc2)S(=O)(=O)N1Cc1ccc(C(=O)N2CCCC(CO)C2)cc1] | (3-Hydroxymethyl-piperidin-1-yl)-[4-((3S)-methyl-1,1-dioxo-6-phenyl-[1,2]thiazinan-2-ylmethyl)-phenyl]-methanone | | 2.04 |
| 282 | 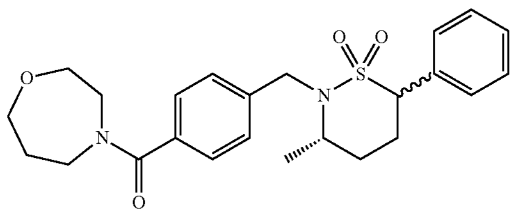 [SMILES: C[C@H]1CCC(c2ccccc2)S(=O)(=O)N1Cc1ccc(C(=O)N2CCCOCC2)cc1] | [4-((3S)-Methyl-1,1-dioxo-6-phenyl-[1,2]thiazinan-2-ylmethyl)-phenyl]-[1,4]oxazepan-4-yl-methanone | | 5.06 |
| 283 | 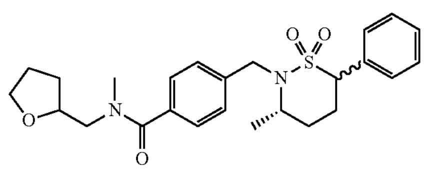 [SMILES: C[C@H]1CCC(c2ccccc2)S(=O)(=O)N1Cc1ccc(C(=O)N(C)CC2CCCO2)cc1] | N-Methyl-4-((3S)-methyl-1,1-dioxo-6-phenyl-[1,2]thiazinan-2-ylmethyl)-N-(tetrahydro-furan-2-ylmethyl)-benzamide | | 1.31 |
| 284 | 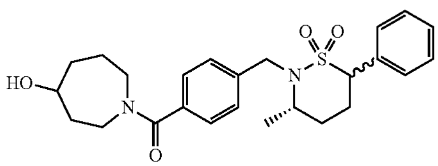 [SMILES: C[C@H]1CCC(c2ccccc2)S(=O)(=O)N1Cc1ccc(C(=O)N2CCCC(O)CC2)cc1] | (4-Hydroxy-azepan-1-yl)-[4-((3S)-methyl-1,1-dioxo-6-phenyl-[1,2]thiazinan-2-ylmethyl)-phenyl]-methanone | | 1.43 |
| 285 | 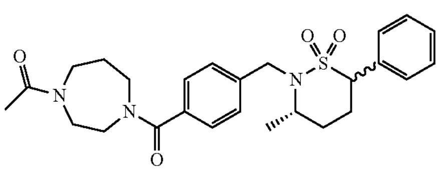 [SMILES: CC(=O)N1CCCN(C(=O)c2ccc(CN3[C@@H](C)CCC(c4ccccc4)S3(=O)=O)cc2)CC1] | 1-{4-[4-((3S)-Methyl-1,1-dioxo-6-phenyl-[1,2]thiazinan-2-ylmethyl)-benzoyl]-[1,4]diazepan-1-yl}-ethanone | | 4.0 |
| 286 | 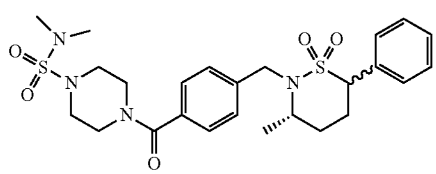 [SMILES: C[C@H]1CCC(c2ccccc2)S(=O)(=O)N1Cc1ccc(C(=O)N2CCN(S(=O)(=O)N(C)C)CC2)cc1] | 4-[4-((3S)-Methyl-1,1-dioxo-6-phenyl-[1,2]thiazinan-2-ylmethyl)-benzoyl]-piperazine-1-sulfonic acid dimethylamide | | 7.42 |
| 287 | 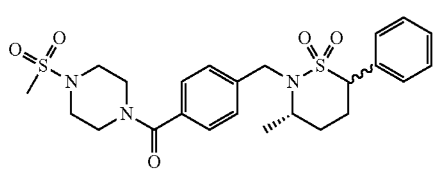 [SMILES: C[C@H]1CCC(c2ccccc2)S(=O)(=O)N1Cc1ccc(C(=O)N2CCN(S(C)(=O)=O)CC2)cc1] | (4-Methanesulfonyl-piperazin-1-yl)-[4-((3S)-methyl-1,1-dioxo-6-phenyl-[1,2]thiazinan-2-ylmethyl)-phenyl]-methanone | | 0.203 |
| 288 | 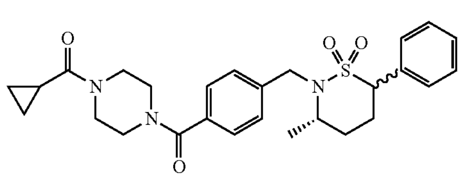 [SMILES: C[C@H]1CCC(c2ccccc2)S(=O)(=O)N1Cc1ccc(C(=O)N2CCN(C(=O)C3CC3)CC2)cc1] | (4-Cyclopropane carbonyl-piperazin-1-yl)-[4-((3S)-methyl-1,1-dioxo-6-phenyl-[1,2]thiazinan-2-ylmethyl)-phenyl]-methanone | | 2.67 |

TABLE 4-continued

| | Structure | Name | Proton NMR | IC$_{50}$ |
|---|---|---|---|---|
| 289 | 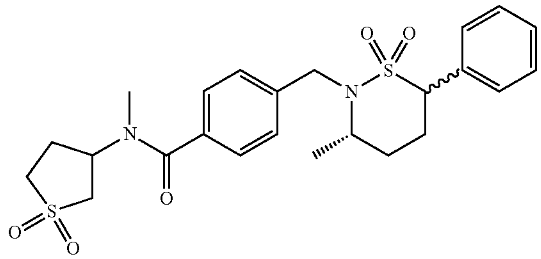 [SMILES: C[C@H]1CCC(c2ccccc2)S(=O)(=O)N1Cc1ccc(C(=O)N(C)C2CCS(=O)(=O)C2)cc1] | N-(1,1-Dioxo-tetrahydro-thiophen-3-yl)-N-methyl-4-((3S)-methyl-1,1-dioxo-6-phenyl-[1,2]thiazinan-2-ylmethyl)-benzamide | | 1.74 |
| 290 | 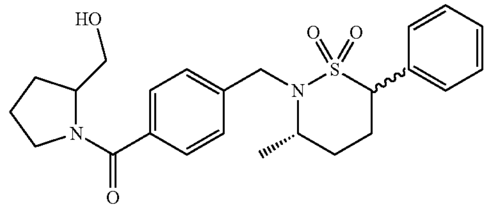 [SMILES: C[C@H]1CCC(c2ccccc2)S(=O)(=O)N1Cc1ccc(C(=O)N2CCCC2CO)cc1] | (2-Hydroxymethyl-pyrrolidin-1-yl)-[4-((3S)-methyl-1,1-dioxo-6-phenyl-[1,2]thiazinan-2-ylmethyl)-phenyl]-methanone | | 1.5 |
| 291 | 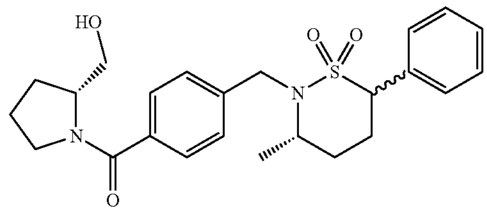 [SMILES: C[C@H]1CCC(c2ccccc2)S(=O)(=O)N1Cc1ccc(C(=O)N2CCC[C@@H]2CO)cc1] | (2-Hydroxymethyl-pyrrolidin-1-yl)-[4-((3S)-methyl-1,1-dioxo-6-phenyl-[1,2]thiazinan-2-ylmethyl)-phenyl]-methanone | | 0.911 |
| 292 | 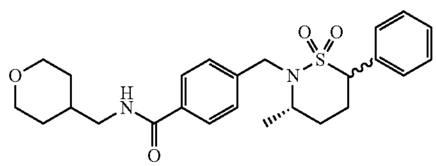 [SMILES: C[C@H]1CCC(c2ccccc2)S(=O)(=O)N1Cc1ccc(C(=O)NCC2CCOCC2)cc1] | 4-((3S)-Methyl-1,1-dioxo-6-phenyl-[1,2]thiazinan-2-ylmethyl)-N-(tetrahydro-pyran-4-ylmethyl)-benzamide | | 0.66 |
| 293 | 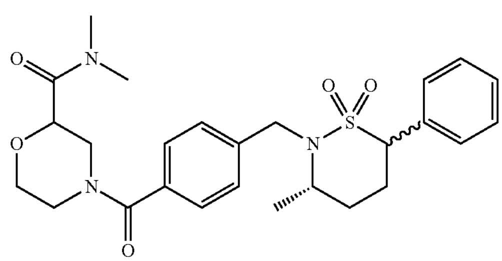 [SMILES: C[C@H]1CCC(c2ccccc2)S(=O)(=O)N1Cc1ccc(C(=O)N2CCOC(C(=O)N(C)C)C2)cc1] | 4-[4-((3S)-Methyl-1,1-dioxo-6-phenyl-[1,2]thiazinan-2-ylmethyl)-benzoyl]-morpholine-2-carboxylic acid dimethylamide | | 8.31 |
| 294 | 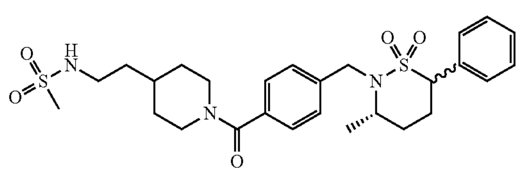 [SMILES: C[C@H]1CCC(c2ccccc2)S(=O)(=O)N1Cc1ccc(C(=O)N2CCC(CCNS(C)(=O)=O)CC2)cc1] | N-(2-{1-[4-((3S)-Methyl-1,1-dioxo-6-phenyl-[1,2]thiazinan-2-ylmethyl)-benzoyl]-piperidin-4-yl}-ethyl)-methanesulfonamide | | 1.77 |
| 295 | 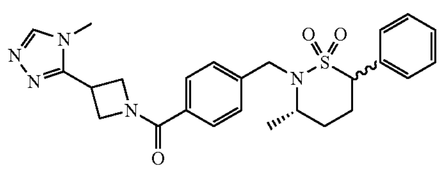 [SMILES: C[C@H]1CCC(c2ccccc2)S(=O)(=O)N1Cc1ccc(C(=O)N2CC(c3nncn3C)C2)cc1] | [4-((3S)-Methyl-1,1-dioxo-6-phenyl-[1,2]thiazinan-2-ylmethyl)-phenyl]-[3-(4-methyl-4H-[1,2,4]triazol-3-yl)-azetidin-1-yl]-methanone | | 5.35 |

TABLE 4-continued

| | Structure | Name | Proton NMR | IC$_{50}$ |
|---|---|---|---|---|
| 296 | 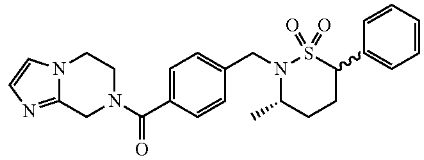 [SMILES: C[C@H]1CCC(c2ccccc2)S(=O)(=O)N1Cc1ccc(C(=O)N2CCn3ccnc3C2)cc1] | (5,6-Dihydro-8H-imidazo[1,2-a]pyrazin-7-yl)-[4-((3S)-methyl-1,1-dioxo-6-phenyl-[1,2]thiazinan-2-ylmethyl)-phenyl]-methanone | | 1.29 |
| 297 | 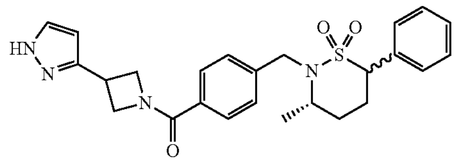 [SMILES: C[C@H]1CCC(c2ccccc2)S(=O)(=O)N1Cc1ccc(C(=O)N2CC(c3cc[nH]n3)C2)cc1] | [4-((3S)-Methyl-1,1-dioxo-6-phenyl-[1,2]thiazinan-2-ylmethyl)-phenyl]-[3-(1H-pyrazol-3-yl)-azetidin-1-yl]-methanone | | 2.69 |
| 298 | 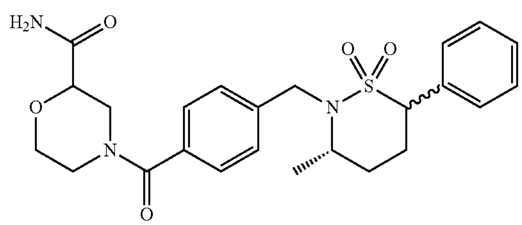 [SMILES: C[C@H]1CCC(c2ccccc2)S(=O)(=O)N1Cc1ccc(C(=O)N2CCOC(C(N)=O)C2)cc1] | 4-[4-((3S)-Methyl-1,1-dioxo-6-phenyl-[1,2]thiazinan-2-ylmethyl)-benzoyl]-morpholine-2-carboxylic acid amide | | 4.72 |
| 299 | 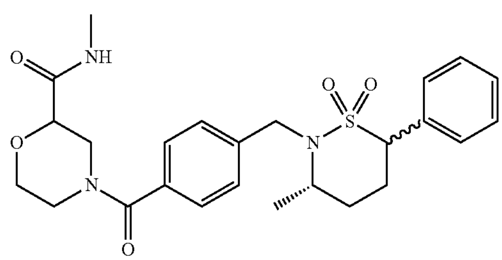 [SMILES: CNC(=O)C1CN(C(=O)c2ccc(CN3[C@@H](C)CCC(c4ccccc4)S3(=O)=O)cc2)CCO1] | 4-[4-((3S)-Methyl-1,1-dioxo-6-phenyl-[1,2]thiazinan-2-ylmethyl)-benzoyl]-morpholine-2-carboxylic acid methylamide | | 4.93 |
| 300 | Stereoisomer A | 1-{4-[4-(3,3-Dioxo-4-phenyl-3-thia-2-aza-bicyclo[4.1.1]oct-2-ylmethyl)-3-fluoro-phenyl]-piperazin-1-yl}-ethanone | $^1$H NMR (400 MHz, DMSO) δ 7.55-7.49 (m, 2H), 7.43-7.31 (m, 3H), 7.24-7.15 (m, 1H), 6.83-6.72 (m, 2H), 4.77-4.70 (dd, J = 12.0, 4.6 Hz, 1H), 4.70-4.63 (d, J = 14.7 Hz, 1H), 4.09-4.01 (d, J = 14.8 Hz, 1H), 3.65-3.58 (m, 1H), 3.58-3.51 (m, 4H), 3.23-3.16 (m, 2H), 3.17-3.10 (m, 2H), 2.76-2.58 (m, 3H), 2.38-2.05 (m, 4H), 2.06-2.00 (s, 3H). | 0.044 |
| 301 | Stereoisomer B | 1-{4-[4-(3,3-Dioxo-4-pheny-3-thia-2-aza-bicyclo[4.1.1]oct-2-ylmethyl)-3-fluoro-phenyl]-piperazin-1-yl}-ethanone | $^1$H NMR (400 MHz, DMSO) δ 7.55-7.49 (m, 2H), 7.43-7.31 (m, 3H), 7.24-7.15 (m, 1H), 6.83-6.72 (m, 2H), 4.77-4.70 (dd, J = 12.0, 4.6 Hz, 1H), 4.70-4.63 (d, J = 14.7 Hz, 1H), 4.09-4.01 (d, J = 14.8 Hz, 1H), 3.65-3.58 (m, 1H), 3.58-3.51 (m, 4H), 3.23-3.16 (m, 2H), 3.17-3.10 (m, 2H), 2.76-2.58 (m, 3H), 2.38-2.05 (m, 4H), 2.06-2.00 (s, 3H). | 0.308 |

TABLE 4-continued

| | Structure | Name | Proton NMR | IC$_{50}$ |
|---|---|---|---|---|
| 302 | Stereoisomer A | 3-{4-[4-(1,1-Dioxo-7-phenyl-[1,2]thiazepan-2-ylmethyl)-3-fluoro-phenyl]-piperazin-1-yl}-3-oxo-propionitrile | $^1$H NMR (400 MHz, DMSO) δ 7.25-7.43 (m, 6 H); 6.79-6.81 (m, 2 H); 4.58 (d, J = 15.2 Hz, 1 H); 4.39 (dd, J = 11.6, 2.7 Hz, 1 H); 4.27 (d, J = 15.2 Hz, 1 H); 4.09 (s, 2 H); 3.58 (t, J = 5.0 Hz, 2 H); 3.48 (t, J = 5.8 Hz, 3 H); 3.15-3.25 (m, 4 H); 2.88-2.97 (m, 1 H); 1.95-2.15 (m, 4 H); 1.72-1.82 (m, 1 H); 1.52-1.62 (m, 1 H). | 0.024 |
| 303 | Stereoisomer B | 3-{4-[4-(1,1-Dioxo-7-phenyl-[1,2]thiazepan-2-ylmethyl)-3-fluoro-phenyl]-piperazin-1-yl}-3-oxo-propionitrile | $^1$H NMR (400 MHz, DMSO) δ 7.25-7.43 (m, 6 H); 6.79-6.81 (m, 2 H); 4.58 (d, J = 15.2 Hz, 1 H); 4.39 (dd, J = 11.6, 2.7 Hz, 1 H); 4.27 (d, J = 15.2 Hz, 1 H); 4.09 (s, 2 H); 3.58 (t, J = 5.0 Hz, 2 H); 3.48 (t, J = 5.8 Hz, 3 H); 3.15-3.25 (m, 4 H); 2.88-2.97 (m, 1 H); 1.95-2.15 (m, 4 H); 1.72-1.82 (m, 1 H); 1.52-1.62 (m, 1 H). | 0.086 |
| 304 | Stereoisomer A | 1-{4-[4-(1,1-Dioxo-7-phenyl-[1,2]thiazepan-2-ylmethyl)-3-fluoro-phenyl]-piperazin-1-yl}-2-hydroxy-propan-1-one | $^1$H NMR (400 MHz, DMSO) δ 7.23-7.42 (m, 6 H); 6.75-6.85 (m, 2 H); 4.97 (d, J = 6.9 Hz, 1 H); 4.58 (d, J = 15.2 Hz, 1 H); 4.35-4.50 (m, 2 H); 4.28 (d, J = 15.2 Hz, 1 H); 3.43-3.70 (m, 5 H); 3.20 (br s, 4 H); 2.88-2.98 (m, 1 H); 1.95-2.20 (m, 4 H); 1.72-1.82 (m, 1 H); 1.56-1.62 (m, 1 H); 1.20 (d, J = 6.5 Hz, 3 H). | 0.038 |
| 305 | Stereoisomer B | 1-{4-[4-(1,1-Dioxo-7-phenyl-[1,2]thiazepan-2-ylmethyl)-3-fluoro-phenyl]-piperazin-1-yl}-2-hydroxy-propan-1-one | $^1$H NMR (400 MHz, DMSO) δ 7.23-7.42 (m, 6 H); 6.75-6.85 (m, 2 H); 4.97 (d, J = 6.9 Hz, 1 H); 4.58 (d, J = 15.2 Hz, 1 H); 4.35-4.50 (m, 2 H); 4.28 (d, J = 15.2 Hz, 1 H); 3.43-3.70 (m, 5 H); 3.20 (br s, 4 H); 2.88-2.98 (m, 1 H); 1.95-2.20 (m, 4 H); 1.72-1.82 (m, 1 H); 1.56-1.62 (m, 1 H); 1.20 (d, J = 6.5 Hz, 3 H). | 0.165 |
| 306 | Stereoisomer A | 1-{4-[4-(1,1-Dioxo-7-phenyl-[1,2]thiazepan-2-ylmethyl)-phenyl]-piperazin-1-yl}-ethanone | $^1$H NMR (400 MHz, DMSO) δ 7.30-7.45 (m, 5 H); 7.24 (d, J = 8.4 Hz, 2 H); 6.96 (d, J = 8.5 Hz, 2 H); 4.64 (d, J = 14.9 Hz, 1 H); 4.37 (dd, J = 11.6, 2.6 Hz, 1 H); 4.08 (d, J = 14.9 Hz, 1 H); 3.57 (br s, 4 H); 3.37-3.47 (m, 1 H); 3.12 (dt, J = 26.4, 5.0 Hz, 4 H); 2.85-2.93 (m, 1 H); 1.95-2.20 (m, 7 H); 1.70-1.80 (m, 1 H); 1.55-1.67 (m, 1 H). | 0.087 |
| 307 | Stereoisomer B | 1-{4-[4-(1,1-Dioxo-7-phenyl-[1,2]thiazepan-2-ylmethyl)-phenyl]-piperazin-1-yl}-ethanone | $^1$H NMR (400 MHz, DMSO) δ 7.30-7.45 (m, 5 H); 7.24 (d, J = 8.4 Hz, 2 H); 6.96 (d, J = 8.5 Hz, 2 H); 4.64 (d, J = 14.9 Hz, 1 H); 4.37 (dd, J = 11.6, 2.6 Hz, 1 H); 4.08 (d, J = 14.9 Hz, 1 H); 3.57 (br s, 4 H); 3.37-3.47 (m, 1 H); 3.12 (dt, J = 26.4, 5.0 Hz, 4 H); 2.85-2.93 (m, 1 H); 1.95-2.20 (m, 7 H); 1.70-1.80 (m, 1 H); 1.55-1.67 (m, 1 H). | 0.227 |

TABLE 4-continued

| | Structure | Name | Proton NMR | IC$_{50}$ |
|---|---|---|---|---|
| 308 | Stereoisomer A | 1-{4-[4-(1,1-Dioxo-7-phenyl-[1,2]thiazepan-2-ylmethyl)-3-fluoro-phenyl]-piperazin-1-yl}-2-hydroxy-ethanone | $^1$H NMR (400 MHz, DMSO) δ 7.22-7.40 (m, 6 H); 6.75-6.83 (m, 2 H); 4.55-4.65 (m, 2 H); 4.39 (dd, J = 11.6, 2.6 Hz, 1 H); 4.27 (d, J = 15.2 Hz, 1 H); 4.13 (d, J = 5.6 Hz, 2 H); 3.59 (br s, 2 H); 3.43-3.53 (m, 3 H); 3.20 (br s, 4 H); 2.87-2.98 (m, 1 H); 1.95-2.20 (m, 4 H); 1.70-1.83 (m, 1 H); 1.50-1.63 (m, 1 H). | 0.029 |
| 309 | Stereoisomer A | 1-{4-[4-(1,1-Dioxo-7-phenyl-[1,2]thiazepan-2-ylmethyl)-phenyl]-piperazin-1-yl}-2-hydroxy-propan-1-one | | 0.106 |
| 310 | Stereoisomer A | 3-{4-[4-(1,1-Dioxo-7-phenyl-[1,2]thiazepan-2-ylmethyl)-phenyl]-piperazin-1-yl}-3-oxo-propionitrile | $^1$H NMR (400 MHz, DMSO) δ 7.30-7.45 (m, 5 H); 7.24 (d, J = 8.4 Hz, 2 H); 6.96 (d, J = 8.5 Hz, 2 H); 4.64 (d, J = 14.9 Hz, 1 H); 4.36 (dd, J = 11.6, 2.6 Hz, 1 H); 4.06-4.12 (m, 3 H); 3.60 (t, J = 5.0 Hz, 2 H); 3.49 (t, J = 4.9 Hz, 2 H); 3.37-3.45 (m, 1 H); 3.15 (dt, J = 21.4, 5.0 Hz, 4 H); 2.85-2.93 (m, 1 H); 1.95-2.20 (m, 4 H); 1.70-1.80 (m, 1 H); 1.55-1.67 (m, 1 H). | 0.045 |
| 311 | Stereoisomer B | 1-{4-[4-(1,1-Dioxo-7-phenyl-[1,2]thiazepan-2-ylmethyl)-phenyl]-piperazin-1-yl}-2-hydroxy-propan-1-one | | 0.898 |
| 312 | Stereoisomer B | 3-{4-[4-(1,1-Dioxo-7-phenyl-[1,2]thiazepan-2-ylmethyl)-phenyl]-piperazin-1-yl}-3-oxo-propionitrile | $^1$H NMR (400 MHz, DMSO) δ 7.30-7.45 (m, 5 H); 7.24 (d, J = 8.4 Hz, 2 H); 6.96 (d, J = 8.5 Hz, 2 H); 4.64 (d, J = 14.9 Hz, 1 H); 4.36 (dd, J = 11.6, 2.6 Hz, 1 H); 4.06-4.12 (m, 3 H); 3.60 (t, J = 5.0 Hz, 2 H); 3.49 (t, J = 4.9 Hz, 2 H); 3.37-3.45 (m, 1 H); 3.15 (dt, J = 21.4, 5.0 Hz, 4 H); 2.85-2.93 (m, 1 H); 1.95-2.20 (m, 4 H); 1.70-1.80 (m, 1 H); 1.55-1.67 (m, 1 H). | 0.926 |
| 313 | Stereoisomer B | 1-{4-[4-(1,1-Dioxo-7-phenyl-[1,2]thiazepan-2-ylmethyl)-3-fluoro-phenyl]-piperazin-1-yl}-2-hydroxy-ethanone | $^1$H NMR (400 MHz, DMSO) δ 7.22-7.40 (m, 6 H); 6.75-6.83 (m, 2 H); 4.55-4.65 (m, 2 H); 4.39 (dd, J = 11.6, 2.6 Hz, 1 H); 4.27 (d, J = 15.2 Hz, 1 H); 4.13 (d, J = 5.6 Hz, 2 H); 3.59 (br s, 2 H); 3.43-3.53 (m, 3 H); 3.20 (br s, 4 H); 2.87-2.98 (m, 1 H); 1.95-2.20 (m, 4 H); 1.70-1.83 (m, 1 H); 1.50-1.63 (m, 1 H). | 0.592 |

TABLE 4-continued

| | Structure | Name | Proton NMR | IC$_{50}$ |
|---|---|---|---|---|
| 314 | 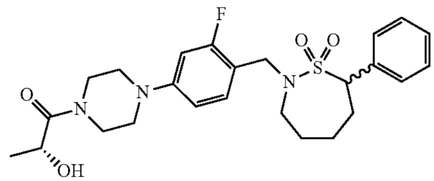 [SMILES: C[C@@H](O)C(=O)N1CCN(c2ccc(CN3CCCCC(c4ccccc4)S3(=O)=O)c(F)c2)CC1] | 1-{4-[4-(1,1-Dioxo-7-phenyl-[1,2]thiazepan-2-ylmethyl)-3-fluoro-phenyl]-piperazin-1-yl}-2-hydroxy-propan-1-one | | 0.237 |
| 315 | Stereoisomer A | 1-{4-[4-(1,1-Dioxo-7-phenyl-[1,2]thiazepan-2-ylmethyl)-phenyl]-piperazin-1-yl}-2-hydroxy-propan-1-one | | 0.321 |
| 316 | Stereoisomer A | 1-{4-[4-(1,1-Dioxo-7-phenyl-[1,2]thiazepan-2-ylmethyl)-phenyl]-piperazin-1-yl}-2-hydroxy-ethanone | | 0.173 |
| 317 | Stereoisomer B | 1-{4-[4-(1,1-Dioxo-7-phenyl-[1,2]thiazepan-2-ylmethyl)-phenyl]-piperazin-1-yl}-2-hydroxy-propan-1-one | | 3.4 |
| 318 | Stereoisomer B | 1-{4-[4-(1,1-Dioxo-7-phenyl-[1,2]thiazepan-2-ylmethyl)-phenyl]-piperazin-1-yl}-2-hydroxy-ethanone | | 1.97 |
| 319 | Stereoisomer A | 1-{4-[3-Fluoro-4-((3R)-methyl-1,1-dioxo-7-phenyl-[1,2]thiazepan-2-ylmethyl)-phenyl]-piperazin-1-yl}-ethanone | $^1$H NMR (400 MHz, DMSO) δ 7.34-7.36 (m, 6 H); 6.75-6.76 (m, 2 H); 4.56-4.59 (m, 2 H); 4.25-4.28 (m, 1 H); 4.16 (d, J = 17.1 Hz, 1 H); 3.54 (s, 4 H); 3.14 (dt, J = 27.8, 5.0 Hz, 4 H); 2.25-2.28 (m, 1 H); 2.02 (s, 3 H); 1.85-1.90 (m, 4 H); 1.58-1.70 (m, 1 H); 0.96 (d, J = 6.7 Hz, 3 H). | 0.008 |
| 320 | Stereoisomer A | 1-{4-[3-Fluoro-4-((3S)-methyl-1,1-dioxo-7-phenyl-[1,2]thiazepan-2-ylmethyl)-phenyl]-piperazin-1-yl}-ethanone | $^1$H NMR (400 MHz, DMSO) δ 7.34-7.36 (m, 6 H); 6.75-6.76 (m, 2 H); 4.56-4.59 (m, 2 H); 4.25-4.28 (m, 1 H); 4.16 (d, J = 17.1 Hz, 1 H); 3.54 (s, 4 H); 3.14 (dt, J = 27.8, 5.0 Hz, 4 H); 2.25-2.28 (m, 1 H); 2.02 (s, 3 H); 1.85-1.90 (m, 4 H); 1.58-1.70 (m, 1 H); 0.96 (d, J = 6.7 Hz, 3 H). | 1.92 |

TABLE 4-continued

| | Structure | Name | Proton NMR | IC$_{50}$ |
|---|---|---|---|---|
| 321 | Stereoisomer B | 1-{4-[3-Fluoro-4-((3R)-methyl-1,1-dioxo-7-phenyl-[1,2]thiazepan-2-ylmethyl)-phenyl]-piperazin-1-yl}-ethanone | $^1$H NMR (400 MHz, DMSO) δ 7.37-7.38 (m, 6 H); 6.84-6.87 (m, 2 H); 4.46 (s, 2 H); 4.06 (dd, J = 10.6, 5.8 Hz, 1 H); 3.59 (d, J = 5.2 Hz, 4 H); 3.22-3.25 (m, 4 H); 2.06 (s, 3 H); 1.92-2.03 (m, 3 H); 1.26-1.29 (m, 4 H); 1.10 (d, J = 6.4 Hz, 3 H). | 0.016 |
| 322 | Stereoisomer B | 1-{4-[3-Fluoro-4-((3S)-methyl-1,1-dioxo-7-phenyl-[1,2]thiazepan-2-ylmethyl)-phenyl]-piperazin-1-yl}-ethanone | $^1$H NMR (400 MHz, DMSO) δ 7.37-7.38 (m, 6 H); 6.84-6.87 (m, 2 H); 4.46 (s, 2 H); 4.06 (dd, J = 10.6, 5.8 Hz, 1 H); 3.59 (d, J = 5.2 Hz, 4 H); 3.22-3.25 (m, 4 H); 2.06 (s, 3 H); 1.92-2.03 (m, 3 H); 1.26-1.29 (m, 4 H); 1.10 (d, J = 6.4 Hz, 3 H). | 0.026 |
| 323 | Stereoisomer A | 2-[2-Fluoro-4-(4-[1,2,4]triazol-4-yl-piperidin-1-yl)-benzyl]-7-phenyl-[1,2]thiazepane 1,1-dioxide | $^1$H NMR (400 MHz, DMSO) δ 8.64 (s, 2 H); 7.30-7.42 (m, 5 H); 7.25 (t, J = 8.9 Hz, 1 H); 6.77-6.87 (m, 2 H); 4.58 (d, J = 15.2 Hz, 1 H); 4.32-4.43 (m, 2 H); 4.27 (d, J = 15.1 Hz, 1 H); 3.89 (d, J = 12.9 Hz, 2 H); 3.44-3.55 (m, 1 H); 2.81-2.99 (m, 3 H); 1.90-2.20 (m, 8 H); 1.72-1.83 (m, 1 H); 1.56-1.65 (m, 1 H). | 0.002 |
| 324 | Stereoisomer A | [4-(1,1,-Dioxo-7-phenyl-[1,2]thiazepan-2-ylmethyl)-phenyl]-(1-methanesulfonyl-piperidin-4-yl)-amine | $^1$H NMR (400 MHz, DMSO) δ 7.37-7.39 (m, 5 H); 7.11 (d, J = 8.3 Hz, 2 H); 6.62 (d, J = 8.3 Hz, 2 H); 5.60 (d, J = 8.2 Hz, 1 H); 4.59 (d, J = 14.6 Hz, 1 H); 4.35 (dd, J = 11.6, 2.6 Hz, 1 H); 4.03 (d, J = 14.6 Hz, 1 H); 3.54 (d, J = 11.8 Hz, 2 H); 3.39-3.42 (m, 2 H); 2.85-2.95 (m, 6 H); 2.00-2.08 (m, 6 H); 1.69-1.74 (m, 2 H); 1.44 (q, J = 11.3 Hz, 2 H). | 0.003 |
| 325 | Stereoisomer B | 2-[2-Fluoro-4-(4-[1,2,4]triazol-4-yl-piperidin-1-yl)-benzyl]-7-phenyl-[1,2]thiazepane 1,1-dioxide | $^1$H NMR (400 MHz, DMSO) δ 8.64 (s, 2 H); 7.30-7.42 (m, 5 H); 7.25 (t, J = 8.9 Hz, 1 H); 6.77-6.87 (m, 2 H); 4.58 (d, J = 15.2 Hz, 1 H); 4.32-4.43 (m, 2 H); 4.27 (d, J = 15.1 Hz, 1 H); 3.89 (d, J = 12.9 Hz, 2 H); 3.44-3.55 (m, 1 H); 2.81-2.99 (m, 3 H); 1.90-2.20 (m, 8 H); 1.72-1.83 (m, 1 H); 1.56-1.65 (m, 1 H). | 0.010 |
| 326 | Stereoisomer B | [4-(1,1-Dioxo-7-phenyl-[1,2]thiazepan-2-ylmethyl)-phenyl]-(1-methanesulfonyl-piperidin-4-yl)-amine | $^1$H NMR (400 MHz, DMSO) δ 7.36-7.38 (m, 5 H); 7.09 (d, J = 8.3 Hz, 2 H); 6.60 (d, J = 8.3 Hz, 2 H); 5.58 (d, J = 8.2 Hz, 1 H); 4.57 (d, J = 14.6 Hz, 1 H); 4.01 (d, J = 11.6, 2.6 Hz, 1 H); 4.01 (d, J = 14.6 Hz, 1 H); 3.52 (d, J = 11.8 Hz, 2 H); 3.37-3.40 (m, 2 H); 2.85-2.95 (m, 6 H); 1.99-2.07 (m, 6 H); 1.72-1.75 (m, 1 H); 1.61 (t, J = 11.4 Hz, 1 H); 1.39-1.44 (m, 2 H). | 0.004 |

TABLE 4-continued

| | Structure | Name | Proton NMR | IC$_{50}$ |
|---|---|---|---|---|
| 327 | Stereoisomer A | 1-{4-[3-Fluoro-4-(3-methyl-1,1-dioxo-7-phenyl-[1,2]thiazepan-2-ylmethyl)-phenyl]-piperazin-1-yl}-ethanone | $^1$H NMR (400 MHz, DMSO) δ 7.34-7.36 (m, 6 H); 6.75-6.76 (m, 2 H); 4.56-4.59 (m, 2 H); 4.25-4.28 (m, 1 H); 4.16 (d, J = 17.1 Hz, 1 H); 3.54 (s, 4 H); 3.14 (dt, J = 27.8, 5.0 Hz, 4 H); 2.25-2.28 (m, 1 H); 2.02 (s, 3 H); 1.85-1.90 (m, 4 H); 1.58-1.70 (m, 1 H); 0.96 (d, J = 6.7 Hz, 3 H). | 0.003 |
| 328 | Stereoisomer B | 1-{4-[3-Fluoro-4-(3-methyl-1,1-dioxo-7-phenyl-[1,2]thiazepan-2-ylmethyl)-phenyl]-piperazin-1-yl}-ethanone | $^1$H NMR (400 MHz, DMSO) δ 7.34-7.36 (m, 6 H); 6.75-6.76 (m, 2 H); 4.56-4.59 (m, 2 H); 4.25-4.28 (m, 1 H); 4.16 (d, J = 17.1 Hz, 1 H); 3.54 (s, 4 H); 3.14 (dt, J = 27.8, 5.0 Hz, 4 H); 2.25-2.28 (m, 1 H); 2.02 (s, 3 H); 1.85-1.90 (m, 4 H); 1.58-1.70 (m, 1 H); 0.96 (d, J = 6.7 Hz, 3 H). | 1.09 |
| 329 | Stereoisomer C | 1-{4-[3-Fluoro-4-(3-methyl-1,1-dioxo-7-phenyl-[1,2]thiazepan-2-ylmethyl)-phenyl]-piperazin-1-yl}-ethanone | $^1$H NMR (400 MHz, DMSO) δ 7.37-7.38 (m, 6 H); 6.84-6.87 (m, 2 H); 4.46 (s, 2 H); 4.06 (dd, J = 10.6, 5.8 Hz, 1 H); 3.59 (d, J = 5.2 Hz, 4 H); 3.22-3.25 (m, 4 H); 2.06 (s, 3 H); 1.92-2.03 (m, 3 H); 1.26-1.29 (m, 4 H); 1.10 (d, J = 6.4 Hz, 3 H). | 0.024 |
| 330 | Stereoisomer D | 1-{4-[3-Fluoro-4-(3-methyl-1,1-dioxo-7-phenyl-[1,2]thiazepan-2-ylmethyl)-phenyl]-piperazin-1-yl}-ethanone | $^1$H NMR (400 MHz, DMSO) δ 7.37-7.38 (m, 6 H); 6.84-6.87 (m, 2 H); 4.46 (s, 2 H); 4.06 (dd, J = 10.6, 5.8 Hz, 1 H); 3.59 (d, J = 5.2 Hz, 4 H); 3.22-3.25 (m, 4 H); 2.06 (s, 3 H); 1.92-2.03 (m, 3 H); 1.26-1.29 (m, 4 H); 1.10 (d, J = 6.4 Hz, 3 H). | 0.037 |
| 331 | Stereoisomer A | 1-{4-[3-Fluoro-4-(5-methyl-1,1-dioxo-7-phenyl-[1,2]thiazepan-2-ylmethyl)-phenyl]-piperazin-1-yl}-ethanone | $^1$H NMR (400 MHz, CDCl$_3$) δ 7.38-7.39 (m, 6 H); 6.69 (dd, J = 8.6, 2.5 Hz, 1 H); 6.56 (dd, J = 13.0, 2.4 Hz, 1 H); 4.46 (dd, J = 28.2, 14.9 Hz, 2 H); 4.30 (dd, J = 8.8, 5.0 Hz, 1 H); 3.76 (t, J = 5.1 Hz, 2 H); 3.62 (t, J = 5.1 Hz, 2 H); 3.40-3.41 (m, 1 H); 3.19 (dt, J = 13.9, 5.1 Hz, 4 H); 3.02 (ddd, J = 14.0, 7.4, 4.5 Hz, 1 H); 2.41-2.43 (m, 2 H); 2.14 (s, 3 H); 1.97-1.99 (m, 2 H); 1.79-1.82 (m, 1 H); 1.05 (d, J = 7.0 Hz, 3 H). | 0.022 |
| 332 | Stereoisomer B | 1-{4-[3-Fluoro-4-(5-methyl-1,1-dioxo-7-phenyl-[1,2]thiazepan-2-ylmethyl)-phenyl]-piperazin-1-yl}-ethanone | $^1$H NMR (400 MHz, CDCl$_3$) δ 7.34-7.36 (m, 6 H); 6.66 (dd, J = 8.6, 2.5 Hz, 1 H); 6.54 (dd, J = 13.1, 2.4 Hz, 1 H); 4.47-4.48 (m, 2 H); 4.03 (dd, J = 12.2, 2.8 Hz, 1 H); 3.73 (t, J = 5.1 Hz, 2 H); 3.56-3.58 (m, 3 H); 3.16 (dt, J = 13.6, 5.1 Hz, 4 H); 2.99-3.00 (m, 1 H); 2.21 (ddd, J = 15.0, 12.3, 9.7 Hz, 1 H); 2.11 (s, 3 H); 1.90-1.92 (m, 2 H); 1.69-1.73 (m, 2 H); 1.04 (d, J = 6.6 Hz, 3 H). | 0.071 |

TABLE 4-continued

| | Structure | Name | Proton NMR | IC$_{50}$ |
|---|---|---|---|---|
| 222 | Stereoisomer C | 1-{4-[3-Fluoro-4-(5-methyl-1,1-dioxo-7-phenyl-[1,2]thiazepan-2-ylmethyl)-phenyl]-piperazin-1-yl}-ethanone | $^1$H NMR (400 MHz, CDCl$_3$) δ 7.37-7.39 (m, 6 H); 6.70 (dd, J = 8.6, 2.5 Hz, 1 H); 6.58 (dd, J = 13.1, 2.4 Hz, 1 H); 4.51 (dd, J = 36.4, 14.9 Hz, 2 H); 4.06 (dd, J = 12.2, 2.8 Hz, 1 H); 3.77 (t, J = 5.1 Hz, 2 H); 3.59-3.62 (m, 3 H); 3.19 (dt, J = 13.6, 5.1 Hz, 4 H); 3.02-3.03 (m, 1 H); 2.24-2.25 (m, 1 H); 2.14 (s, 3 H); 1.94-1.96 (m, 2 H); 1.73-1.77 (m, 2 H); 1.07 (d, J = 6.6 Hz, 3 H). | 0.002 |
| 333 | Stereoisomer D | 1-{4-[3-Fluoro-4-(5-methyl-1,1-dioxo-7-phenyl-[1,2]thiazepan-2-ylmethyl)-phenyl]-piperazin-1-yl}-ethanone | $^1$H NMR (400 MHz, CDCl$_3$) 7.38-7.39 (6 H, m), 6.69 (1 H, dd, J = 8.58, 2.46 Hz), 6.56 (1 H, dd, J = 13.04, 2.44 Hz), 4.46 (2 H, dd, J = 28.11, 14.87 Hz), 4.30 (1 H, dd, J = 8.81, 4.98 Hz), 3.76 (2 H, t, J = 5.14 Hz), 3.61 (2 H, t, J = 5.06 Hz), 3.40-3.41 (1 H, m), 3.19 (4 H, dt, J = 13.90, 5.14 Hz), 3.02 (1 H, ddd, J = 14.01, 7.45, 4.51 Hz), 2.41-2.43 (2 H, m), 2.14 (3 H, s), 1.97-1.99 (2 H, m), 1.78-1.81 (1 H, m), 1.05 (3 H, d, J = 7.02 Hz). | 0.032 |
| 334 | Stereoisomer A | 1-{4-[3-Fluoro-4-(4-methyl-1,1-dioxo-7-phenyl-[1,2]thiazepan-2-ylmethyl)-phenyl]-piperazin-1-yl}-ethanone | $^1$H NMR (400 MHz, DMSO) δ 7.36-7.38 (m, 5 H); 7.24 (t, J = 8.8 Hz, 1 H); 6.78-6.80 (m, 2 H); 4.63 (d, J = 15.0 Hz, 1 H); 4.45 (dd, J = 11.1, 2.6 Hz, 1 H); 4.22 (d, J = 15.0 Hz, 1 H); 3.52-3.57 (m, 4 H); 3.16-3.20 (m, 5 H); 2.91 (dd, J = 15.6, 6.3 Hz, 1 H); 2.27-2.34 (m, 2 H); 2.03 (s, 3 H); 1.82-1.86 (m, 3 H); 0.86 (d, J = 6.8 Hz, 3 H). | 0.005 |
| 335 | Stereoisomer A | 1-{4-[4-(1,1-Dioxo-7-phenyl-[1,2]thiazepan-2-ylmethyl)-3-fluoro-phenyl]-3-methyl-piperazin-1-yl}-ethanone | $^1$H NMR (400 MHz, DMSO) δ 7.35-7.37 (m, 5 H); 7.24 (t, J = 8.8 Hz, 1 H); 6.70-6.73 (m, 2 H); 4.56 (d, J = 15.1 Hz, 1 H); 4.37 (dd, J = 11.6, 2.7 Hz, 1 H); 4.20-4.22 (m, 2 H); 4.03-4.09 (m, 1 H); 3.76 (dd, J = 63.5, 13.4 Hz, 1 H); 3.25-3.44 (m, 3 H); 2.91-2.94 (m, 3 H); 2.03-2.05 (m, 7 H); 1.74-1.80 (m, 1 H); 1.57 (t, J = 11.5 Hz, 1 H); 0.92 (dd, J = 28.4, 6.5 Hz, 3 H). | 0.008 |
| 336 | Stereoisomer A | 7-Phenyl-2-[4-(4-[1,2,4]triazol-4-yl-piperidin-1-yl)-benzyl]-[1,2]thiazepane 1,1-dioxide | $^1$H NMR (400 MHz, DMSO) δ 8.65 (s, 2 H); 7.36-7.37 (m, 5 H); 7.23 (d, J = 8.5 Hz, 2 H); 7.00 (d, J = 8.6 Hz, 2 H); 4.65 (d, J = 14.9 Hz, 1 H); 4.35-4.37 (m, 2 H); 4.08 (d, J = 14.9 Hz, 1 H); 3.82 (d, J = 12.6 Hz, 2 H); 3.41-3.43 (m, 1 H); 2.83-2.86 (m, 3 H); 2.00-2.05 (m, 8 H); 1.74-1.78 (m, 1 H); 1.63 (t, J = 11.1 Hz, 1 H). | 0.028 |

TABLE 4-continued

| | Structure | Name | Proton NMR | IC$_{50}$ |
|---|---|---|---|---|
| 337 | Stereoisomer A | 5-{1-[4-(1,1-Dioxo-7-phenyl-[1,2]thiazepan-2-ylmethyl)-phenyl]-piperidin-4-yl}-3H-[1,3,4]oxadiazol-2-one | | 0.024 |
| 338 | Stereoisomer B | 1-{4-[3-Fluoro-4-(4-methyl-1,1-dioxo-7-phenyl-[1,2]thiazepan-2-ylmethyl)-phenyl]-piperazin-1-yl}-ethanone | $^1$H NMR (400 MHz, DMSO) δ 7.35-7.36 (m, 5 H); 7.25 (t, J = 8.8 Hz, 1 H); 6.79-6.81 (m, 2 H); 4.54 (d, J = 15.4 Hz, 1 H); 4.36-4.38 (m, 2 H); 3.55 (d, J = 5.3 Hz, 4 H); 3.17-3.20 (m, 5 H); 2.60 (dd, J = 13.9, 9.6 Hz, 1 H); 2.09-2.14 (m, 3 H); 2.03 (s, 3 H); 1.79 (dd, J = 14.5, 6.8 Hz, 1 H); 1.43-1.47 (m, 1 H); 0.91 (d, J = 6.8 Hz, 3 H). | 0.012 |
| 339 | Stereoisomer C | 1-{4-[3-Fluoro-4-(4-methyl-1,1-dioxo-7-phenyl-[1,2]thiazepan-2-ylmethyl)-phenyl]-piperazin-1-yl}-ethanone | $^1$H NMR (400 MHz, DMSO) δ 7.35-7.36 (m, 5 H); 7.25 (t, J = 8.8 Hz, 1 H); 6.79-6.81 (m, 2 H); 4.54 (d, J = 15.4 Hz, 1 H); 4.36-4.38 (m, 2 H); 3.55 (m, J = 5.3 Hz, 4 H); 3.10-3.30 (m, 5 H); 2.60 (dd, J = 13.9, 9.6 Hz, 1 H); 1.95-2.25 (m, 6 H); 1.79 (dd, J = 14.5, 6.7 Hz, 1 H); 1.47 (t, J = 12.6 Hz, 1 H); 0.91 (d, J = 6.8 Hz, 3 H). | 0.015 |
| 340 | Stereoisomer D | 1-{4-[3-Fluoro-4-(4-methyl-1,1-dioxo-7-phenyl-[1,2]thiazepan-2-ylmethyl)-phenyl]-piperazin-1-yl}-ethanone | $^1$H NMR (400 MHz, DMSO) δ 7.37-7.39 (m, 5 H); 7.26 (t, J = 8.8 Hz, 1 H); 6.80-6.82 (m, 2 H); 4.65 (d, J = 15.0 Hz, 1 H); 4.47 (dd, J = 11.1, 2.6 Hz, 1 H); 4.24 (d, J = 15.0 Hz, 1 H); 3.57 (m, 4 H); 3.17-3.22 (m, 5 H); 2.93 (dd, J = 15.6, 6.3 Hz, 1 H); 2.29-2.36 (m, 2 H); 2.05 (s, 3 H); 1.83-1.87 (m, 3 H); 0.88 (d, J = 6.8 Hz, 3 H). | 0.054 |
| 341 | Stereoisomer B | 1-{4-[4-(1,1-Dioxo-7-phenyl-[1,2]thiazepan-2-ylmethyl)-3-fluoro-phenyl]-3-methyl-piperazin-1-yl}-ethanone | $^1$H NMR (400 MHz, DMSO) δ 7.35-7.37 (m, 5 H); 7.25 (t, J = 8.8 Hz, 1 H); 6.72-6.74 (m, 2 H); 4.56 (d, J = 15.1 Hz, 1 H); 4.37 (dd, J = 11.6, 2.7 Hz, 1 H); 4.21-4.23 (m, 2 H); 4.06 (s, 1 H); 3.76 (dd, J = 63.5, 13.4 Hz, 1 H); 3.25-3.44 (m, 3 H); 2.91-2.94 (m, 3 H); 2.03-2.05 (m, 7 H); 1.72-1.78 (m, 1 H); 1.56-1.62 (m, 1 H); 0.92 (dd, J = 28.1, 6.5 Hz, 3 H). | 0.026 |
| 342 | Stereoisomer B | 7-Phenyl-2-[4-(4-[1,2,4]triazol-4-yl-piperidin-1-yl)-benzyl]-[1,2]thiazepane 1,1-dioxide | $^1$H NMR (400 MHz, DMSO) δ 8.65 (s, 2 H); 7.36-7.37 (m, 5 H); 7.23 (d, J = 8.5 Hz, 2 H); 7.00 (d, J = 8.6 Hz, 2 H); 4.65 (d, J = 14.9 Hz, 1 H); 4.35-4.36 (m, 2 H); 4.08 (d, J = 14.9 Hz, 1 H); 3.82 (d, J = 12.6 Hz, 2 H); 3.41-3.43 (m, 1 H); 2.84-2.86 (m, 3 H); 1.99-2.04 (m, 8 H); 1.74-1.78 (m, 1 H); 1.63 (t, J = 11.2 Hz, 1 H). | 0.075 |

TABLE 4-continued

| | Structure | Name | Proton NMR | IC$_{50}$ |
|---|---|---|---|---|
| 343 | Stereoisomer B | 5-{1-[4-(1,1-Dioxo-7-phenyl-[1,2]thiazepan-2-ylmethyl)-phenyl]-piperidin-4-yl}-3H-[1,3,4]oxadiazol-2-one | | 0.449 |
| 344 | Stereoisomer A | 1-{4-[4-(1,1-Dioxo-7-phenyl-[1,2]thiazepan-2-ylmethyl)-2-fluoro-phenyl]-piperazin-1-yl}-ethanone | $^1$H NMR (400 MHz, DMSO) δ 7.38-7.40 (m, 5 H); 7.15-7.17 (m, 2 H); 7.05 (t, J = 8.6 Hz, 1 H); 4.70 (d, J = 15.4 Hz, 1 H); 4.41-4.44 (m, 1 H); 4.14 (d, J = 15.4 Hz, 1 H); 3.59 (s, 4 H); 3.45-3.47 (m, 1 H); 2.97-3.00 (m, 5 H); 2.05 (m, 7 H); 1.75-1.80 (m, 1 H); 1.61-1.66 (m, 1 H). | 0.032 |
| 345 | Stereoisomer A | [4-(1,1-Dioxo-7-phenyl-[1,2]thiazepan-2-ylmethyl)-3-fluoro-phenyl]-(1-methanesulfonyl-piperidin-4-yl)-amine | $^1$H NMR (400 MHz, DMSO) δ 7.36-7.37 (m, 5 H); 7.12 (t, J = 8.7 Hz, 1 H); 6.43-6.44 (m, 2 H); 5.99 (d, J = 8.1 Hz, 1 H); 4.51 (d, J = 14.9 Hz, 1 H); 4.36 (dd, J = 11.6, 2.7 Hz, 1 H); 4.23 (d, J = 14.9 Hz, 1 H); 3.43-3.48 (m, 4 H); 2.92-2.96 (m, 3 H); 2.88 (s, 3 H); 2.09-2.13 (m, 1 H); 1.99 (t, J = 7.5 Hz, 6 H); 1.77 (t, J = 11.8 Hz, 1 H); 1.58 (t, J = 11.6 Hz, 1 H); 1.40-1.44 (m, 2 H). | 0.008 |
| 346 | Stereoisomer B | 1-{4-[4 (1,1-Dioxo-7-phenyl-[1,2]thiazepan-2-ylmethyl)-2-fluoro-phenyl]-piperazin-1-yl}-ethanone | $^1$H NMR (400 MHz, DMSO) δ 7.35-7.37 (m, 5 H); 7.13-7.15 (m, 2 H); 7.04 (t, J = 8.6 Hz, 1 H); 4.68 (d, J = 15.4 Hz, 1 H); 4.39-4.42 (m, 1 H); 4.12 (d, J = 15.4 Hz, 1 H); 3.57 (d, J = 5.3 Hz, 4 H); 3.43-3.45 (m, 1 H); 2.95-2.98 (m, 5 H); 2.00-2.20 (m, 7 H); 1.73-1.78 (m, 1 H); 1.62 (t, J = 11.1 Hz, 1 H). | 0.050 |
| 347 | Stereoisomer B | [4-(1,1-Dioxo-7-phenyl-[1,2]thiazepan-2-ylmethyl)-3-fluoro-phenyl]-(1-methanesulfonyl-piperidin-4-yl)-amine | $^1$H NMR (400 MHz, DMSO) δ 7.34-7.35 (m, 5 H); 7.09 (t, J = 8.7 Hz, 1 H); 6.39-6.40 (m, 2 H); 5.95 (d, J = 8.1 Hz, 1 H); 4.47 (d, J = 14.9 Hz, 1 H); 4.32 (dd, J = 11.6, 2.7 Hz, 1 H); 4.19 (d, J = 14.9 Hz, 1 H); 3.40-3.45 (m, 4 H); 2.87-2.91 (m, 3 H); 2.85 (s, 3 H); 2.06-2.10 (m, 1 H); 1.96 (t, J = 7.4 Hz, 5 H); 1.71-1.77 (m, 1 H); 1.55 (t, J = 11.4 Hz, 1 H); 1.34-1.38 (m, 2 H). | 0.005 |
| 348 | 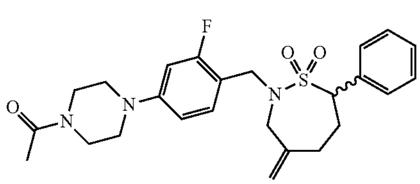 [SMILES: C=C1CCC(c2ccccc2)S(=O)(=O)N(Cc2ccc(N3CCN(C(C)=O)CC3)cc2F)C1] | 1-{4-[3-Fluoro-4-(4-methylene-1,1-dioxo-7-phenyl-[1,2]thiazepan-2-ylmethyl)-phenyl]-piperazin-1-yl}-ethanone | | 0.049 |

TABLE 4-continued

| | Structure | Name | Proton NMR | IC$_{50}$ |
|---|---|---|---|---|
| 349 | 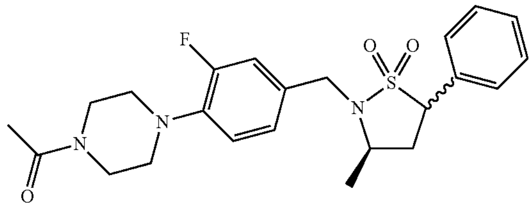 [SMILES: CC(=O)N1CCN(c2ccc(CN3[C@H](C)CC(c4ccccc4)S3(=O)=O)cc2F)CC1] | 1-{4-[3-Fluoro-4-((3R)-methyl-1,1-dioxo-5-phenyl-isothiazolidin-2-ylmethyl)-phenyl]-piperazin-1-yl}-ethanone | | 0.31 |
| 350 | Stereoisomer A | 1-{4-[4-(3,3-Dimethyl-1,1-dioxo-5-phenyl-isothiazolidin-2-ylmethyl)-3-fluoro-phenyl]-piperazin-1-yl}-ethanone | | 1.62 |
| 351 | Stereoisomer A | 1-{4-[4-(2,2-Dioxo-3-phenyl-2-thia-1-aza-spiro[4.4]non-1-ylmethyl)-3-fluoro-phenyl]-piperazin-1-yl}-ethanone | | 0.155 |
| 352 | Stereoisomer B | 1-{4-[4-(2,2-Dioxo-3-phenyl-2-thia-1-aza-spiro[4.4]non-1-ylmethyl)-3-fluoro-phenyl]-piperazin-1-yl}-ethanone | | 2.18 |
| 353 | Stereoisomer B | 1-{4-[4-(3,3-Dimethyl-1,1-dioxo-5-phenyl-isothiazolidin-2-ylmethyl)-3-fluoro-phenyl]-piperazin-1-yl}-ethanone | | 0.615 |
| 354 | 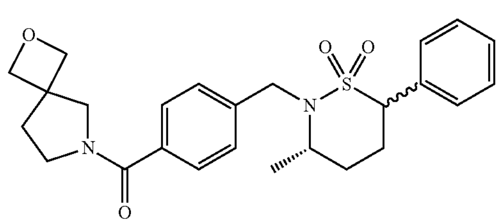 [SMILES: C[C@H]1CCC(c2ccccc2)S(=O)(=O)N1Cc1ccc(C(=O)N2CCC3(COC3)C2)cc1] | [4-((3S)-Methyl-1,1-dioxo-6-phenyl-[1,2]thiazinan-2-ylmethyl)-phenyl]-(2-oxa-6-aza-spiro[3.4]oct-6-yl)-methanone | | 3.01 |

TABLE 4-continued

| | Structure | Name | Proton NMR | IC$_{50}$ |
|---|---|---|---|---|
| 355 | 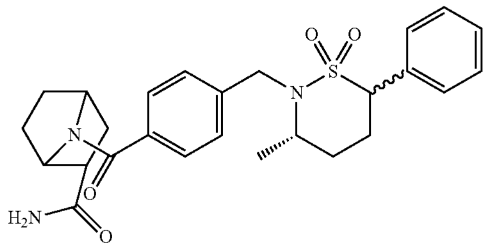 [SMILES: C[C@H]1CCC(c2ccccc2)S(=O)(=O)N1Cc1ccc(C(=O)N2C3CCC2C(C(N)=O)C3)cc1] | 7-[4-((3S)-Methyl-1,1-dioxo-6-phenyl-[1,2]thiazinan-2-ylmethyl)-benzoyl]-7-azabicyclo[2.2.1]heptane-2-carboxylic acid amide | | 0.51 |
| 356 | 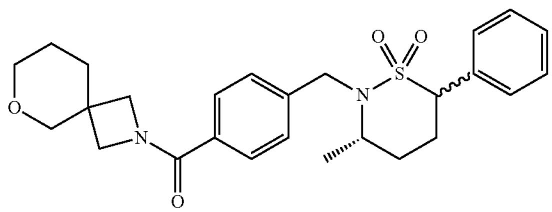 [SMILES: C[C@H]1CCC(c2ccccc2)S(=O)(=O)N1Cc1ccc(C(=O)N2CC3(CCCOC3)C2)cc1] | [4-((3S)-Methyl-1,1-dioxo-6-phenyl-[1,2]thiazinan-2-ylmethyl)-phenyl]-(6-oxa-2-azaspiro[3.5]non-2-yl)-methanone | | 3.17 |
| 357 | 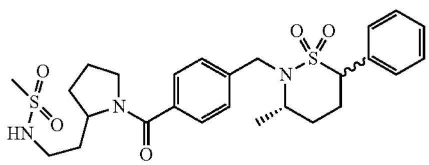 [SMILES: C[C@H]1CCC(c2ccccc2)S(=O)(=O)N1Cc1ccc(C(=O)N2CCCC2CCNS(C)(=O)=O)cc1] | N-(2-{1-[4-((3S)-Methyl-1,1-dioxo-6-phenyl-[1,2]thiazinan-2-ylmethyl)-benzoyl]-pyrrolidin-2-yl}-ethyl)-methanesulfonamide | | 0.108 |
| 358 | 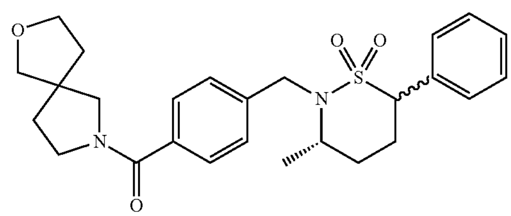 [SMILES: C[C@H]1CCC(c2ccccc2)S(=O)(=O)N1Cc1ccc(C(=O)N2CCC3(CCOC3)C2)cc1] | [4-((3S)-Methyl-1,1-dioxo-6-phenyl-[1,2]thiazinan-2-ylmethyl)-phenyl]-(2-oxa-7-azaspiro[4.4]non-7-yl)-methanone | | 1.22 |
| 359 | 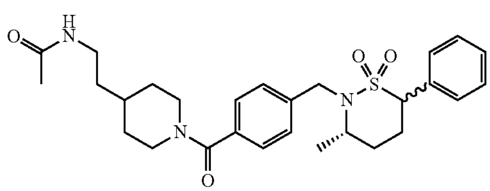 [SMILES: CC(=O)NCCC1CCN(C(=O)c2ccc(CN3[C@@H](C)CCC(c4ccccc4)S3(=O)=O)cc2)CC1] | N-(2-{1-[4-((3S)-Methyl-1,1-dioxo-6-phenyl-[1,2]thiazinan-2-ylmethyl)-benzoyl]-piperidin-4-yl}-ethyl)-acetamide | | 2.03 |
| 360 | 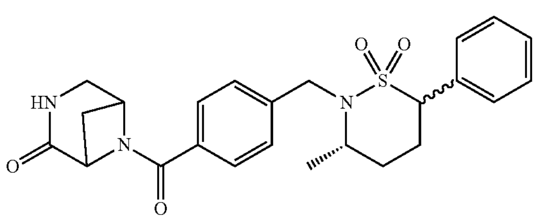 [SMILES: C[C@H]1CCC(c2ccccc2)S(=O)(=O)N1Cc1ccc(C(=O)N2C3CNC(=O)C2C3)cc1] | 6-[4-((3S)-Methyl-1,1-dioxo-6-phenyl-[1,2]thiazinan-2-ylmethyl)-benzoyl]-3,6-diazabicyclo[3.1.1]heptan-2-one | | 3.45 |
| 361 | 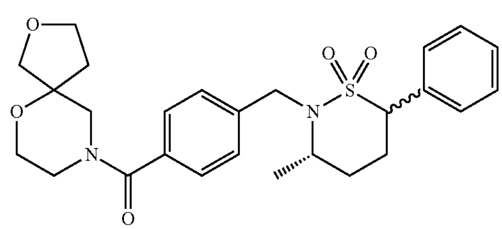 [SMILES: C[C@H]1CCC(c2ccccc2)S(=O)(=O)N1Cc1ccc(C(=O)N2CCOC3(CCOC3)C2)cc1] | (2,6-Dioxa-9-azaspiro[4.5]dec-9-yl)-[4-((3S)-methyl-1,1-dioxo-6-phenyl-[1,2]thiaznan-2-ylmethyl)-phenyl]-methanone | | 0.641 |

TABLE 4-continued

| | Structure | Name | Proton NMR | IC$_{50}$ |
|---|---|---|---|---|
| 362 | 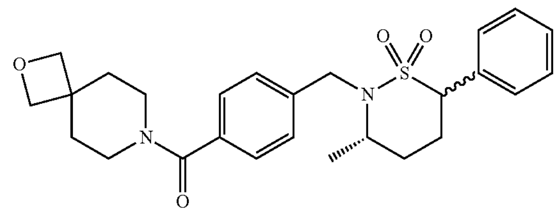 [SMILES: C[C@H]1CCC(c2ccccc2)S(=O)(=O)N1Cc1ccc(C(=O)N2CCC3(CC2)COC3)cc1] | [4-((3S)-Methyl-1,1-dioxo-6-phenyl-[1,2]thiazinan-2-ylmethyl)-phenyl]-(2-oxa-7-aza-spiro[3.5]non-7-yl)-methanone | | 0.903 |
| 363 | 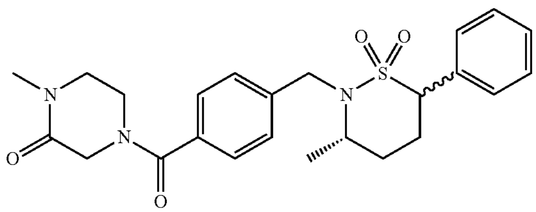 [SMILES: C[C@H]1CCC(c2ccccc2)S(=O)(=O)N1Cc1ccc(C(=O)N2CCN(C)C(=O)C2)cc1] | 1-Methyl-4-[4-((3S)-methyl-1,1-dioxo-6-phenyl-[1,2]thiazinan-2-ylmethyl)-benzoyl]-piperazin-2-one | | 2.43 |
| 364 | 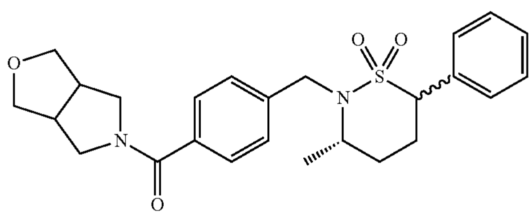 [SMILES: C[C@H]1CCC(c2ccccc2)S(=O)(=O)N1Cc1ccc(C(=O)N2CC3COCC3C2)cc1] | [4-((3S)-Methyl-1,1-dioxo-6-phenyl-[1,2]thiazinan-2-ylmethyl)-phenyl]-(tetrahydro-furo[3,4-c]pyrrol-5-yl)-methanone | | 2.92 |
| 365 | 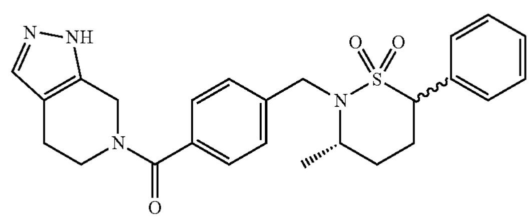 [SMILES: C[C@H]1CCC(c2ccccc2)S(=O)(=O)N1Cc1ccc(C(=O)N2CCc3cn[nH]c3C2)cc1] | [4-((3S)-Methyl-1,1-dioxo-6-phenyl-[1,2]thiazinan-2-ylmethyl)-phenyl]-(1,4,5,7-tetrahydro-pyrazolo[3,4-c]pyridin-6-yl)-methanone | | 1.35 |
| 366 | 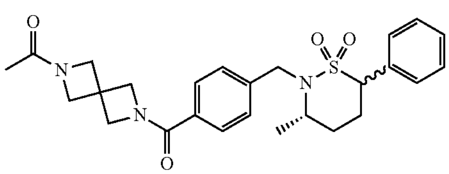 [SMILES: CC(=O)N1CC2(C1)CN(C(=O)c1ccc(CN3[C@@H](C)CCC(c4ccccc4)S3(=O)=O)cc1)C2] | 1-{6-[4-((3S)-Methyl-1,1-dioxo-6-phenyl-[1,2]thiazinan-2-ylmethyl)-benzoyl]-2,6-diaza-spiro[3.3]hept-2-yl}-ethanone | | 5.28 |
| 367 | 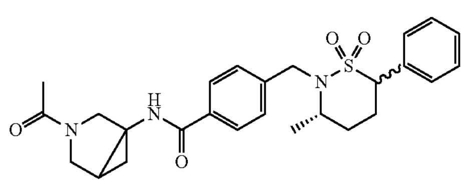 [SMILES: CC(=O)N1CC2CC2(NC(=O)c2ccc(CN3[C@@H](C)CCC(c4ccccc4)S3(=O)=O)cc2)C1] | N-(3-Acetyl-3-aza-bicyclo[3.1.0]hex-1-yl)-4-((3S)-methyl-1,1-dioxo-6-phenyl-[1,2]thiazinan-2-ylmethyl)-benzamide | | 2.27 |
| 368 | 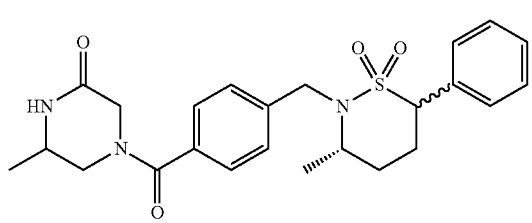 [SMILES: CC1CN(C(=O)c2ccc(CN3[C@@H](C)CCC(c4ccccc4)S3(=O)=O)cc2)CC(=O)N1] | 6-Methyl-4-[4-((3S)-methyl-1,1-dioxo-6-phenyl-[1,2]thiazinan-2-ylmethyl)-benzoyl]-piperazin-2-one | | 2.36 |

TABLE 4-continued

| | Structure | Name | Proton NMR | IC$_{50}$ |
|---|---|---|---|---|
| 369 | 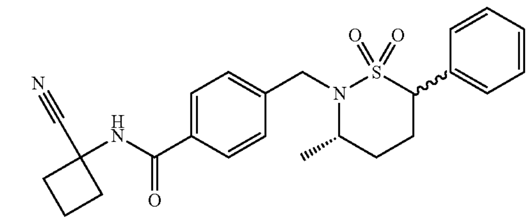 [SMILES: C[C@H]1CCC(c2ccccc2)S(=O)(=O)N1Cc1ccc(C(=O)NC2(C#N)CCC2)cc1] | N-(1-Cyano-cyclobutyl)-4-((3S)-methyl-1,1-dioxo-6-phenyl-[1,2]thiazinan-2-ylmethyl)-benzamide | | 3.48 |
| 370 | 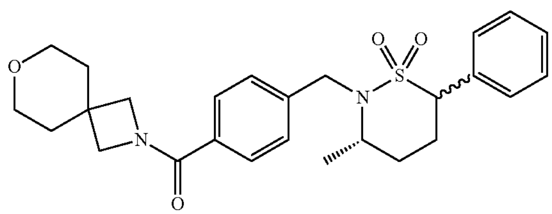 [SMILES: C[C@H]1CCC(c2ccccc2)S(=O)(=O)N1Cc1ccc(C(=O)N2CC3(CCOCC3)C2)cc1] | [4-((3S)-Methyl-1,1-dioxo-6-phenyl-[1,2]thiazinan-2-ylmethyl)-phenyl]-(7-oxa-2-aza-spiro[3.5]non-2-yl)-methanone | | 1.06 |
| 371 | 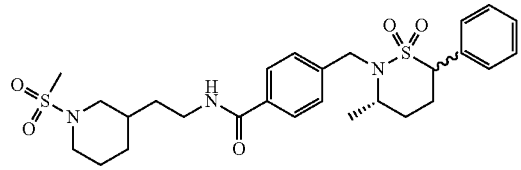 [SMILES: C[C@H]1CCC(c2ccccc2)S(=O)(=O)N1Cc1ccc(C(=O)NCCC2CCCN(S(C)(=O)=O)C2)cc1] | N-[2-(1-Methanesulfonyl-piperidin-3-yl)-ethyl]-4-((3S)-methyl-1,1-dioxo-6-phenyl-[1,2]thiazinan-2-ylmethyl)-benzamide | | 3.63 |
| 372 | 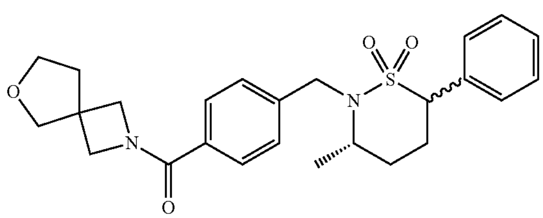 [SMILES: C[C@H]1CCC(c2ccccc2)S(=O)(=O)N1Cc1ccc(C(=O)N2CC3(CCOC3)C2)cc1] | [4-((3S)-Methyl-1,1-dioxo-6-phenyl-[1,2]thiazinan-2-ylmethyl)-phenyl]-(6-oxa-2-aza-spiro[3.4]oct-2-yl)-methanone | | 3.04 |
| 373 | 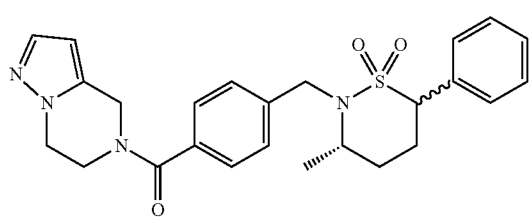 [SMILES: C[C@H]1CCC(c2ccccc2)S(=O)(=O)N1Cc1ccc(C(=O)N2CCn3nccc3C2)cc1] | (6,7-Dihydro-4H-pyrazolo[1,5-a]pyrazin-5-yl)-[4-((3S)-methyl-1,1-dioxo-6-phenyl-[1,2]thiazinan-2-ylmethyl)-phenyl]-methanone | | 4.36 |
| 374 | 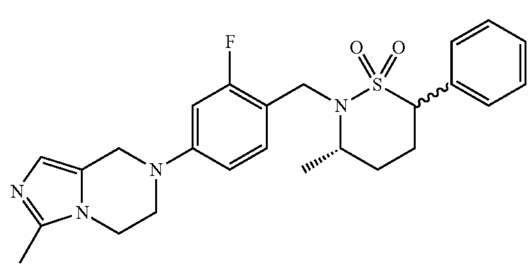 [SMILES: Cc1ncc2n1CCN(c1ccc(CN3[C@@H](C)CCC(c4ccccc4)S3(=O)=O)c(F)c1)C2] | 7-[3-Fluoro-4-((3S)-methyl-1,1-dioxo-6-phenyl-[1,2]thiazinan-2-ylmethyl)-phenyl]-3-methyl-5,6,7,8-tetrahydro-imidazo[1,5-a]pyrazine | | 0.166 |

TABLE 4-continued

| | Structure | Name | Proton NMR | IC$_{50}$ |
|---|---|---|---|---|
| 375 | 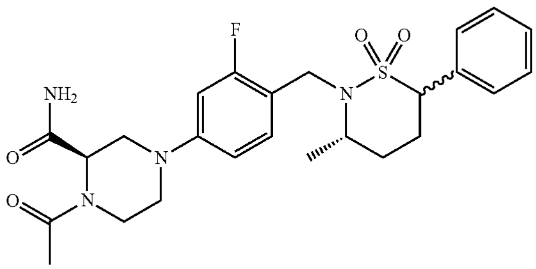 [SMILES: CC(=O)N1CCN(c2ccc(CN3[C@@H](C)CCC(c4ccccc4)S3(=O)=O)c(F)c2)C[C@@H]1C(N)=O] | (R)-1-Acetyl-4-[3-fluoro-4-((3S)-methyl-1,1-dioxo-6-phenyl-[1,2]thiazinan-2-ylmethyl)-phenyl]-piperazine-2-carboxylic acid amide | | 0.156 |
| 376 | 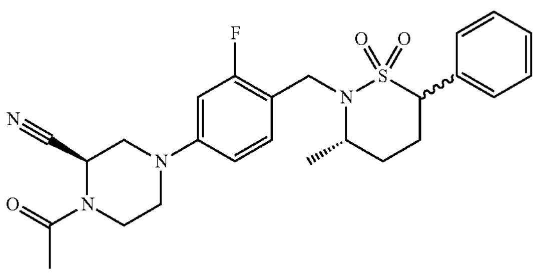 [SMILES: CC(=O)N1CCN(c2ccc(CN3[C@@H](C)CCC(c4ccccc4)S3(=O)=O)c(F)c2)C[C@@H]1C#N] | (R)-1-Acetyl-4-[3-fluoro-4-((3S)-methyl-1,1-dioxo-6-phenyl-[1,2]thiazinan-2-ylmethyl)-phenyl]-piperazine-2-carbonitrile | $^1$H NMR (400 MHz, DMSO): δ 7.40-7.42 (m, 6 H); 6.81-6.85 (m, 2 H); 5.62 (s, 1 H); 4.40-4.42 (m, 3 H); 4.10 (dd, J = 12.2, 7.0 Hz, 1 H); 3.96 (d, J = 13.2 Hz, 2 H); 3.74 (d, J = 12.3 Hz, 1 H); 3.38 (t, J = 13.0 Hz, 1 H); 2.89 (d, J = 13.2 Hz, 1 H); 2.78 (t, J = 12.0 Hz, 1 H); 2.42 (dd, J = 14.7, 11.9 Hz, 1 H); 2.00-2.20 (m, 4 H); 1.80 (t, J = 13.1 Hz, 1 H); 1.65 (d, J = 14.1 Hz, 1 H); 1.09 (d, J = 6.9 Hz, 3 H). | 0.078 |
| 377 | 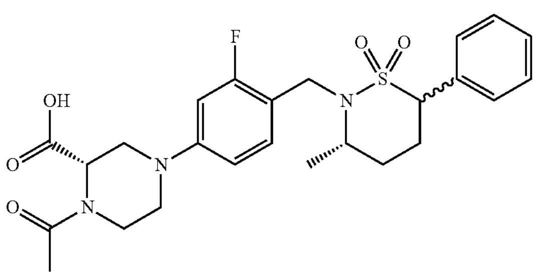 [SMILES: CC(=O)N1CCN(c2ccc(CN3[C@@H](C)CCC(c4ccccc4)S3(=O)=O)c(F)c2)C[C@H]1C(=O)O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid | | 1.36 |
| 378 | 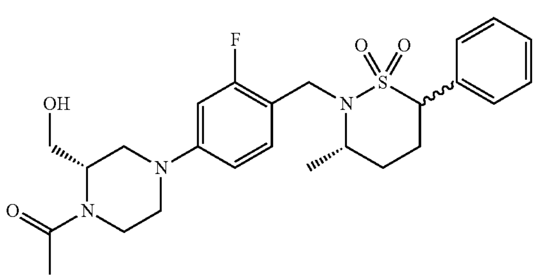 [SMILES: CC(=O)N1CCN(c2ccc(CN3[C@@H](C)CCC(c4ccccc4)S3(=O)=O)c(F)c2)C[C@H]1CO] | 1-{(S)-4-[3-Fluoro-4-((3S)-methyl-1,1-dioxo-6-phenyl-[1,2]thiazinan-2-ylmethyl)-phenyl]-2-hydroxymethyl-piperazin-1-yl}-ethanone | $^1$H NMR (400 MHz, DMSO): δ 7.37-7.39 (m, 6 H); 6.71-6.75 (m, 2 H); 4.91-4.93 (m, 1 H); 4.39-4.41 (m, 4 H); 4.02-4.10 (m, 2 H); 3.63-3.68 (m, 4 H); 2.77-2.82 (m, 2 H); 2.35-2.50 (m, 2 H); 2.05 (m, 4 H); 1.79-1.83 (m, 1 H); 1.64 (d, J = 14.1 Hz, 1 H); 1.08 (d, J = 6.9 Hz, 3 H). | 0.061 |
| 379 | 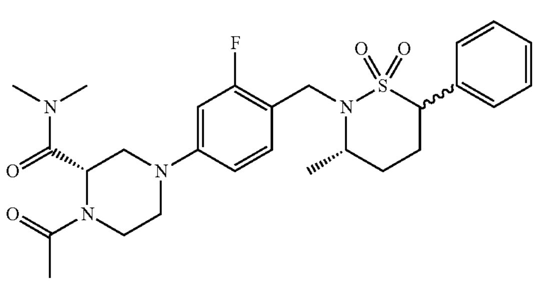 [SMILES: CC(=O)N1CCN(c2ccc(CN3[C@@H](C)CCC(c4ccccc4)S3(=O)=O)c(F)c2)C[C@H]1C(=O)N(C)C] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid dimethylamide | | 0.882 |

TABLE 4-continued

| | Structure | Name | Proton NMR | IC$_{50}$ |
|---|---|---|---|---|
| 380 | 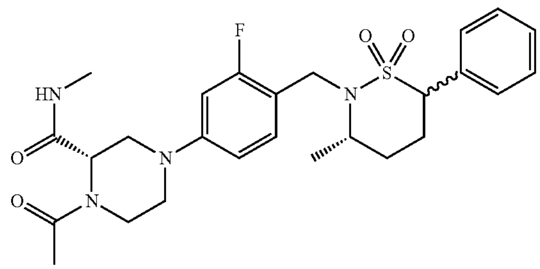 [SMILES: CNC(=O)[C@@H]1CN(c2ccc(CN3[C@@H](C)CCC(c4ccccc4)S3(=O)=O)c(F)c2)CCN1C(C)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid methylamide | | 0.138 |
| 381 | 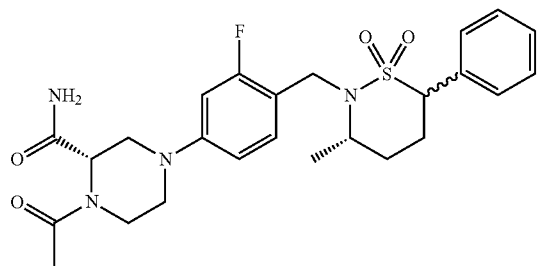 [SMILES: CC(=O)N1CCN(c2ccc(CN3[C@@H](C)CCC(c4ccccc4)S3(=O)=O)c(F)c2)C[C@H]1C(N)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid amide | | 0.522 |
| 382 | 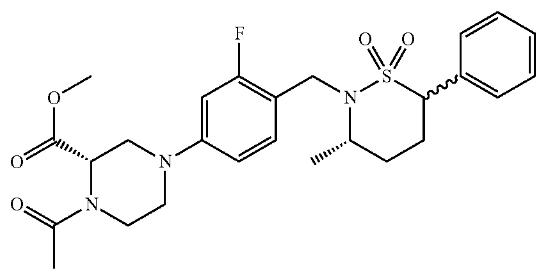 [SMILES: COC(=O)[C@@H]1CN(c2ccc(CN3[C@@H](C)CCC(c4ccccc4)S3(=O)=O)c(F)c2)CCN1C(C)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid methyl ester | $^1$H NMR (400 MHz, DMSO): δ 7.38-7.40 (m, 6 H); 6.74-6.76 (m, 2 H); 5.03 (d, J = 75.9 Hz, 1 H); 4.39-4.41 (m, 3 H); 4.10 (t, J = 13.3 Hz, 2 H); 3.60-3.80 (m, 5 H); 2.94-2.96 (m, 1 H); 2.76-2.79 (m, 1 H); 2.60-2.64 (m, 1 H); 2.41-2.43 (m, 1 H); 2.00-2.15 (m, 4 H); 1.69-1.74 (m, 2 H); 1.08 (d, J = 7.0 Hz, 3 H). | 0.034 |
| 383 | 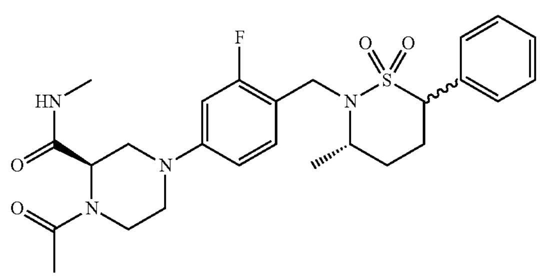 [SMILES: CNC(=O)[C@H]1CN(c2ccc(CN3[C@@H](C)CCC(c4ccccc4)S3(=O)=O)c(F)c2)CCN1C(C)=O] | (R)-1-Acetyl-4-[3-fluoro-4-((3S)-methyl-1,1-dioxo-6-phenyl-[1,2]thiazinan-2-ylmethyl)-phenyl]-piperazine-2-carboxylic acid methylamide | | 0.705 |
| 384 | 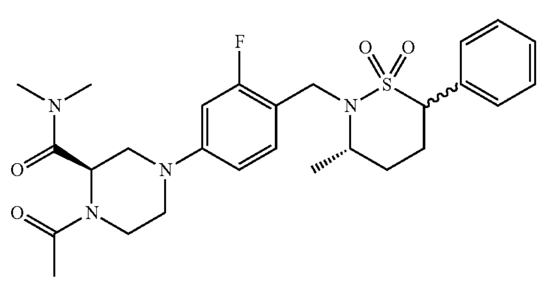 [SMILES: CC(=O)N1CCN(c2ccc(CN3[C@@H](C)CCC(c4ccccc4)S3(=O)=O)c(F)c2)C[C@@H]1C(=O)N(C)C] | (R)-1-Acetyl-4-[3-fluoro-4-((3S)-methyl-1,1-dioxo-6-phenyl-[1,2]thiazinan-2-ylmethyl)-phenyl]-piperazine-2-carboxylic acid dimethylamide | | 1.72 |

TABLE 4-continued

| | Structure | Name | Proton NMR | IC$_{50}$ |
|---|---|---|---|---|
| 385 | 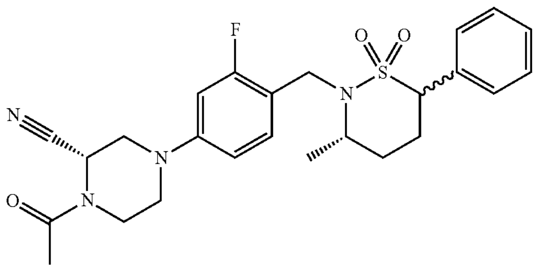 [SMILES: CC(=O)N1CCN(c2ccc(CN3[C@@H](C)CCC(c4ccccc4)S3(=O)=O)c(F)c2)C[C@H]1C#N] | (S)-1-Acetyl-4-[3-fluoro-4-((3S)-methyl-1,1-dioxo-6-phenyl-[1,2]thiazinan-2-ylmethyl)-phenyl]-piperazine-2-carbonitrile | | 0.24 |
| 386 | 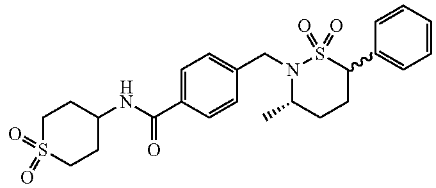 [SMILES: C[C@H]1CCC(c2ccccc2)S(=O)(=O)N1Cc1ccc(C(=O)NC2CCS(=O)(=O)CC2)cc1] | N-(1,1-Dioxo-hexahydro-1-thiopyran-4-yl)-4-((3S)-methyl-1,1-dioxo-6-phenyl-[1,2]thiazinan-2-ylmethyl)-benzamide | | 1.49 |
| 387 | 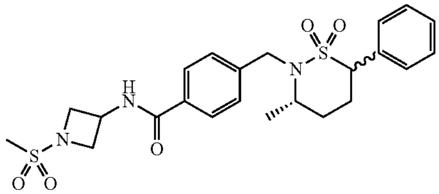 [SMILES: C[C@H]1CCC(c2ccccc2)S(=O)(=O)N1Cc1ccc(C(=O)NC2CN(S(C)(=O)=O)C2)cc1] | N-(1-Methanesulfonyl-azetidin-3-yl)-4-((3S)-methyl-1,1-dioxo-6-phenyl-[1,2]thiazinan-2-ylmethyl)-benzamide | | 0.607 |
| 388 | 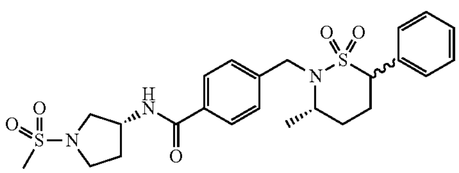 [SMILES: C[C@H]1CCC(c2ccccc2)S(=O)(=O)N1Cc1ccc(C(=O)N[C@@H]2CCN(S(C)(=O)=O)C2)cc1] | N-((R)-1-Methanesulfonyl-pyrrolidin-3-yl)-4-((3S)-methyl-1,1-dioxo-6-phenyl-[1,2]thiazinan-2-ylmethyl)-benzamide | | 3.52 |
| 389 | 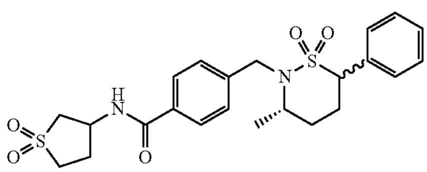 [SMILES: C[C@H]1CCC(c2ccccc2)S(=O)(=O)N1Cc1ccc(C(=O)NC2CCS(=O)(=O)C2)cc1] | N-(1,1-Dioxo-tetrahydro-6-thiophen-3-yl)-4-((3S)-methyl-1,1-dioxo-6-phenyl-[1,2]thiazinan-2-ylmethyl)-benzamide | | 3.22 |
| 390 | 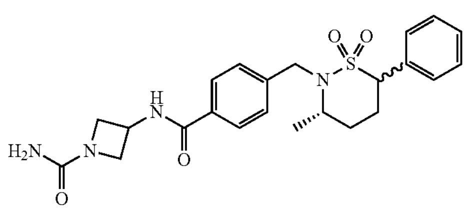 [SMILES: C[C@H]1CCC(c2ccccc2)S(=O)(=O)N1Cc1ccc(C(=O)NC2CN(C(N)=O)C2)cc1] | 3-[4-((3S)-Methyl-1,1-dioxo-6-phenyl-[1,2]thiazinan-2-ylmethyl)-benzoylamino]-azetidine-1-carboxylic acid amide | | 5.46 |
| 391 | 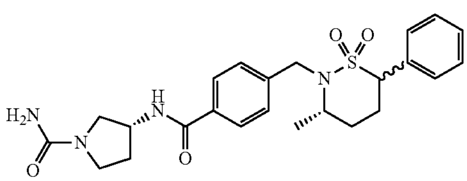 [SMILES: C[C@H]1CCC(c2ccccc2)S(=O)(=O)N1Cc1ccc(C(=O)N[C@@H]2CCN(C(N)=O)C2)cc1] | (R)-3-[4-((3S)-Methyl-1,1-dioxo-6-phenyl-[1,2]thiazinan-2-ylmethyl)-benzoylamino]-pyrrolidine-1-carboxylic acid amide | | 3.43 |

TABLE 4-continued

| | Structure | Name | Proton NMR | IC$_{50}$ |
|---|---|---|---|---|
| 392 | 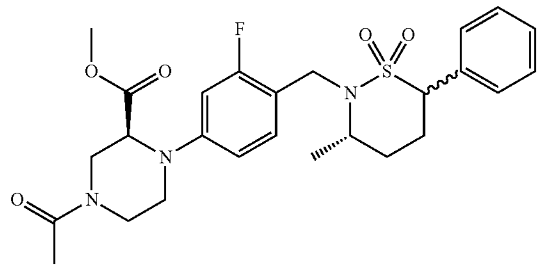 [SMILES: COC(=O)[C@@H]1CN(C(C)=O)CCN1c1ccc(CN2[C@@H](C)CCC(c3ccccc3)S2(=O)=O)c(F)c1] | (S)-4-Acetyl-1-[3-fluoro-4-((3S)-methyl-1,1-dioxo-6-phenyl-[1,2]thiazinan-2-ylmethyl)-phenyl]-piperazine-2-carboxylic acid methyl ester | $^1$H NMR (400 MHz, DMSO): δ 7.36-7.38 (m, 6 H); 6.72 (t, J = 15.3 Hz, 2 H); 4.79 (d, J = 46.6 Hz, 2 H); 4.37-4.39 (m, 4 H); 3.90-4.10 (m, 1 H); 3.53-3.55 (m, 5 H); 2.95-3.05 (m, 1 H); 2.60-2.80 (m, 1 H); 2.30-2.45 (m, 1 H); 2.00-2.10 (m, 1 H); 1.99 (d, J = 9.4 Hz, 3 H); 1.64-1.69 (m, 2 H); 1.07 (d, J = 6.9 Hz, 3 H). | 0.013 |
| 393 | 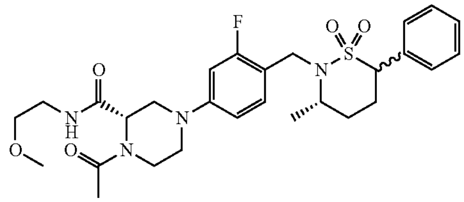 [SMILES: COCCNC(=O)[C@@H]1CN(c2ccc(CN3[C@@H](C)CCC(c4ccccc4)S3(=O)=O)c(F)c2)CCN1C(C)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid (2-methoxy-ethyl)-amide | | 0.697 |
| 394 | 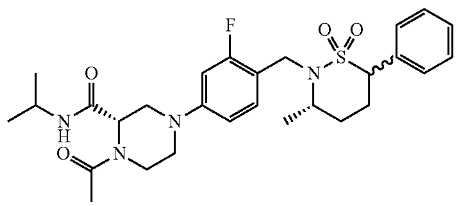 [SMILES: CC(=O)N1CCN(c2ccc(CN3[C@@H](C)CCC(c4ccccc4)S3(=O)=O)c(F)c2)C[C@H]1C(=O)NC(C)C] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid isopropylamide | | 3.18 |
| 395 | 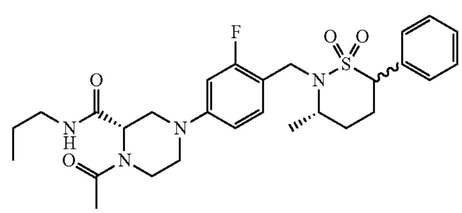 [SMILES: CCCNC(=O)[C@@H]1CN(c2ccc(CN3[C@@H](C)CCC(c4ccccc4)S3(=O)=O)c(F)c2)CCN1C(C)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid propylamide | | 0.287 |
| 396 | 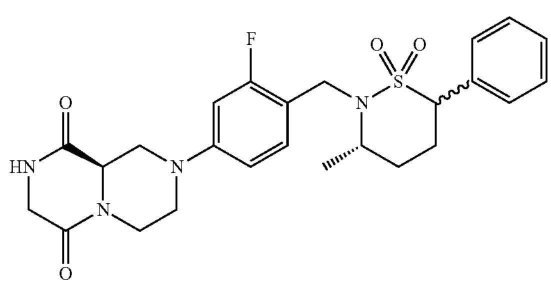 [SMILES: C[C@H]1CCC(c2ccccc2)S(=O)(=O)N1Cc1ccc(N2CCN3C(=O)CNC(=O)[C@H]3C2)cc1F] | (R)-8-[3-Fluoro-4-((3S)-methyl-1,1-dioxo-6-phenyl-[1,2]thiazinan-2-ylmethyl)-phenyl]-hexahydro-pyrazino[1,2-a]pyrazine-1,4-dione | | 3.25 |
| 397 | 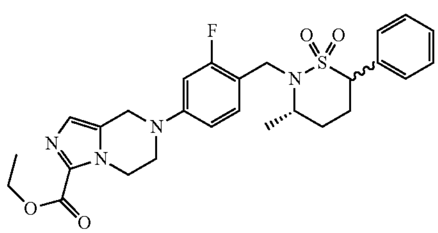 [SMILES: CCOC(=O)c1ncc2n1CCN(c1ccc(CN3[C@@H](C)CCC(c4ccccc4)S3(=O)=O)c(F)c1)C2] | 7-[3-Fluoro-4-((3S)-methyl-1,1-dioxo-6-phenyl-[1,2]thiazinan-2-ylmethyl)-phenyl]-5,6,7,8-tetrahydro-imidazo[1,5-a]pyrazine-3-carboxylic acid ethyl ester | | 0.872 |

TABLE 4-continued

| | Structure | Name | Proton NMR | IC$_{50}$ |
|---|---|---|---|---|
| 398 | 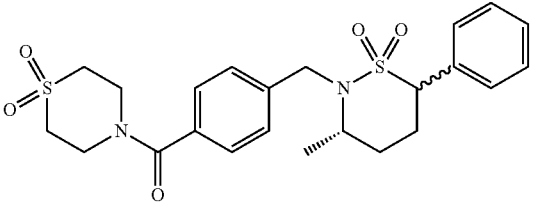 [SMILES: C[C@H]1CCC(c2ccccc2)S(=O)(=O)N1Cc1ccc(C(=O)N2CCS(=O)(=O)CC2)cc1] | (1,1-Dioxo-1-thiomorpholin-4-yl)-[4-((3S)-methyl-1,1-dioxo-6-phenyl-[1,2]thiazinan-2-ylmethyl)-phenyl]-methanone | | 5.71 |
| 399 | 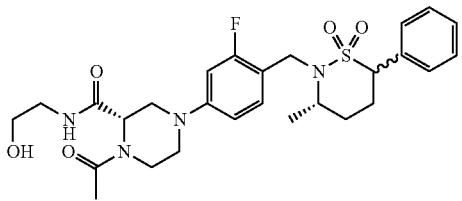 [SMILES: CC(=O)N1CCN(c2ccc(CN3[C@@H](C)CCC(c4ccccc4)S3(=O)=O)c(F)c2)C[C@H]1C(=O)NCCO] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid (2-hydroxy-ethyl)-amide | | 1.59 |
| 400 | 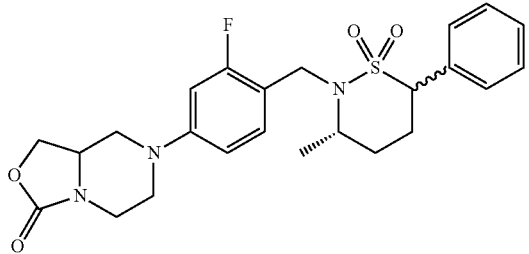 [SMILES: C[C@H]1CCC(c2ccccc2)S(=O)(=O)N1Cc1ccc(N2CCN3C(=O)OCC3C2)cc1F] | 7-[3-Fluoro-4-((3S)-methyl-1,1-dioxo-6-phenyl-[1,2]thiazinan-2-ylmethyl)-phenyl]-hexahydro-oxazolo[3,4-a]pyrazin-3-one | $^1$H NMR (400 MHz, DMSO): δ 7.37-7.39 (m, 6 H); 6.78-6.79 (m, 2 H); 4.39-4.41 (m, 4 H); 3.97-3.99 (m, 4 H); 3.70 (d, J = 12.8 Hz, 1 H); 3.61 (dd, J = 13.2, 3.4 Hz, 1 H); 3.10 (td, J = 12.6, 3.6 Hz, 1 H); 2.65-2.66 (m, 2 H); 2.41 (td, J = 13.2, 3.6 Hz, 1 H); 2.07-2.09 (m, 1 H); 1.78-1.82 (m, 1 H); 1.62-1.66 (m, 1 H); 1.07 (d, J = 6.8 Hz, 3 H). | 0.095 |
| 401 | 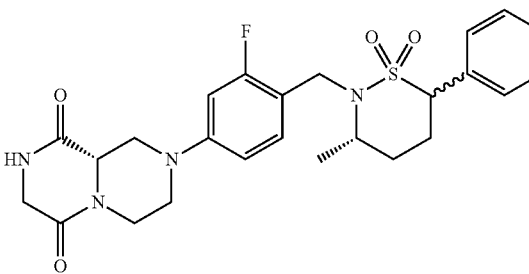 | (S)-8-[3-Fluoro-4-((3S)-methyl-1,1-dioxo-6-phenyl-[1,2]thiazinan-2-ylmethyl)-phenyl]-hexahydro-pyrazino[1,2-a]pyrazine-1,4-dione | | 2.79 |
| 402 | 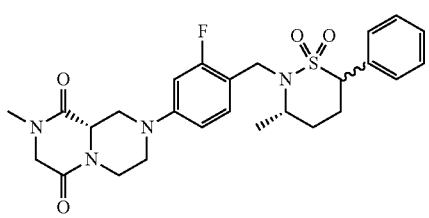 [SMILES: C[C@H]1CCC(c2ccccc2)S(=O)(=O)N1Cc1ccc(N2CCN3C(=O)CN(C)C(=O)[C@@H]3C2)cc1F] | (S)-8-[3-Fluoro-4-((3S)-methyl-1,1-dioxo-6-phenyl-[1,2]thiazinan-2-ylmethyl)-phenyl]-2-methyl-hexahydro-pyrazino[1,2-a]pyrazine-1,4-dione | | 3.54 |
| 403 | 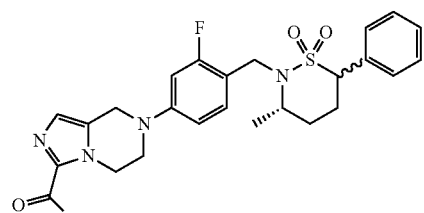 | 7-[3-Fluoro-4-((3S)-methyl-1,1-dioxo-6-phenyl-[1,2]thiazinan-2-ylmethyl)-phenyl]-5,6,7,8-tetrahydro-imidazo[1,5-a]pyrazine-3-carboxylic acid amide | | 0.346 |

TABLE 4-continued

| | Structure | Name | Proton NMR | IC$_{50}$ |
|---|---|---|---|---|
| 404 | 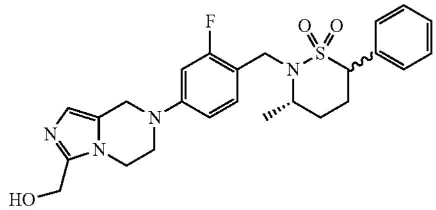 [SMILES: C[C@H]1CCC(c2ccccc2)S(=O)(=O)N1Cc1ccc(N2CCn3c(cnc3CO)C2)cc1F] | {7-[3-Fluoro-4-((3S)-methyl-1,1-dioxo-6-phenyl-[1,2]thiazinan-2-ylmethyl)-phenyl]-5,6,7,8-tetrahydro-imidazo[1,5-a]pyrazin-3-yl}-methanol | | 0.504 |
| | | 7-[3-Fluoro-4-((3S)-methyl-1,1-dioxo-6-phenyl-[1,2]thiazinan-2-ylmethyl)-phenyl]-5,6,7,8-tetrahydro-imidazo[1,5-a]pyrazine-3-carbonitrile | | 0.182 |
| | | 1-{1-[3-Fluoro-4-((3S)-methyl-1,1-dioxo-6-phenyl-[1,2]thiazinan-2-ylmethyl)-phenyl]-piperidin-4-yl}-pyrrolidin-2-one | | 0.878 |
| 407 | 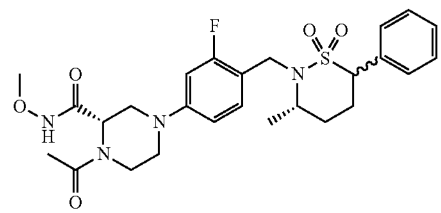 [SMILES: CONC(=O)[C@@H]1CN(c2ccc(CN3[C@@H](C)CCC(c4ccccc4)S3(=O)=O)c(F)c2)CCN1C(C)=O] | (S)-1-Acetyl-4-[3-fluoro-4-((3S)-methyl-1,1-dioxo-6-phenyl-[1,2]thiazinan-2-ylmethyl)-phenyl]-piperazine-2-carboxylic acid methoxy-amide | | 0.148 |
| 408 | Stereisomer A | N-(3-Hydroxy-cyclopentyl)-4-((3S)-methyl-1,1-dioxo-6-phenyl-[1,2]thiazinan-2-ylmethyl)-benzamide | | 3.52 |
| 409 | Stereisomer B | N-(3-Hydroxy-cyclopentyl)-4-((3S)-methyl-1,1-dioxo-6-phenyl-[1,2]thiazinan-2-ylmethyl)-benzamide | | 1.88 |

TABLE 4-continued

| | Structure | Name | Proton NMR | IC$_{50}$ |
|---|---|---|---|---|
| 410 | Stereisomer C | N-(3-Hydroxy-cyclopentyl)-4-((3S)-methyl-1,1-dioxo-6-phenyl-[1,2]thiazinan-2-ylmethyl)-benzamide | | 6.5 |
| 411 | Stereisomer D | N-(3-Hydroxy-cyclopentyl)-4-((3S)-methyl-1,1-dioxo-6-phenyl-[1,2]thiazinan-2-ylmethyl)-benzamide | | 3.52 |
| 412 | Stereisomer A | 2-[2-Fluoro-4-(4-methyl-4-[1,2,4]triazol-4-yl-piperidin-1-yl)-benzyl]-(3S)-methyl-6-phenyl-[1,2]thiazinane 1,1-dioxide | | 0.585 |
| 413 | Stereisomer B | 2-[2-Fluoro-4-(4-methyl-4-[1,2,4]triazol-4-yl-piperidin-1-yl)-benzyl]-(3S)-methyl-6-phenyl-[1,2]thiazinane 1,1-dioxide | | 0.032 |
| 414 | 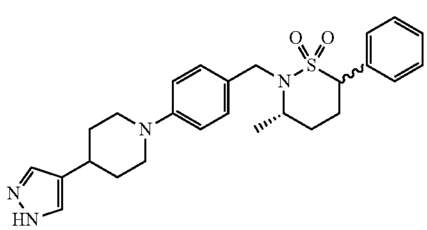 [SMILES: C[C@H]1CCC(c2ccccc2)S(=O)(=O)N1Cc1ccc(N2CCC(c3cn[nH]c3)CC2)cc1] | (3S)-Methyl-6-phenyl-2-{4-[4-(1H-pyrazol-4-yl)-piperidin-1-yl]-benzyl}-[1,2]thiazinane 1,1-dioxide | $^1$H NMR (400 MHz, DMSO) δ 12.64-12.41 (s, 1H), 7.48-7.44 (m, 3 H), 7.42-7.34 (m, 4H), 7.25-7.19 (m, 2H), 6.95-6.90 (m, 2H), 4.48-4.40 (m, 1H), 4.40-4.31 (m, 1H), 4.22-4.15 (m, 1H), 4.12-4.00 (m, 1H), 3.74-3.65 (m, 2H), 2.78-2.68 (m, 2H), 2.65-2.66 (m, 1H), 2.45-2.35 (m, 1H), 2.13-2.05 (m, 1H), 1.98-1.91 (m, 2H), 1.85-1.75 (m, 1H), 1.68-1.75 (m, 3H), 1.12-1.06 (d, J = 6.9 Hz, 3H). | 0.006 |

TABLE 4-continued

| | Structure | Name | Proton NMR | IC$_{50}$ |
|---|---|---|---|---|
| 415 | 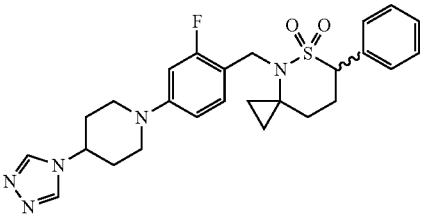 [SMILES: O=S1(=O)C(c2ccccc2)CCC2(CC2)N1Cc1ccc(N2CCC(n3cnnc3)CC2)cc1F]<br>Stereisomer A | (R)-4-[2-Fluoro-4-(4-[1,2,4]triazol-4-yl-piperidin-1-yl)-benzyl]-6-phenyl-5-thia-4-aza-spiro[2.5]octane 5,5-dioxide | 1H NMR (400 MHz, DMSO): δ 8.64 (s, 2 H); 7.48-7.37 (m, 5 H); 7.20 (t, J = 8.9 Hz, 1 H); 6.84-6.77 (m, 2 H); 4.60 (d, J = 15.6 Hz, 1 H); 4.50 (dd, J = 12.6, 3.3 Hz, 1 H); 4.35-4.37 (m, 2 H); 3.87 (d, J = 12.9 Hz, 2 H); 2.84 (t, J = 12.4 Hz, 2 H); 2.61 (d, J = 13.2 Hz, 1 H); 2.37-2.45 (m, 1 H); 2.06-2.13 (m, 3 H); 1.90-2.02 (m, 2 H); 1.00-1.07 (m, 2 H); 0.77-0.84 (m, 1 H); 0.51-0.63 (m, 2 H). | 0.037 |
| 416 | 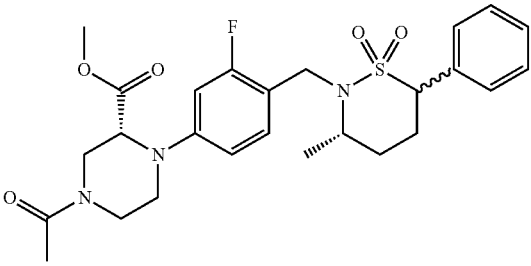 [SMILES: COC(=O)[C@H]1CN(C(C)=O)CCN1c1ccc(CN2[C@@H](C)CCC(c3ccccc3)S2(=O)=O)c(F)c1] | (R)-4-Acetyl-1-[3-fluoro-4-((3S)-methyl-1,1-dioxo-6-phenyl-[1,2]thiazinan-2-ylmethyl)-phenyl]-piperazine-2-carboxylic acid methyl ester | | 0.368 |
| 417 | 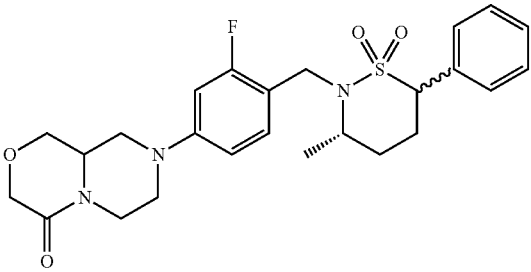 [SMILES: C[C@H]1CCC(c2ccccc2)S(=O)(=O)N1Cc1ccc(N2CCN3C(=O)COCC3C2)cc1F] | 8-[3-Fluoro-4-((3S)-methyl-1,1-dioxo-6-phenyl-[1,2]thiazinan-2-ylmethyl)-phenyl]-hexahydro-pyrazino[2,1-c][1,4]oxazin-4-one | | 0.231 |
| 418 | 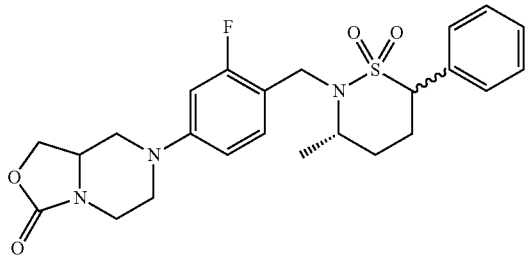 [SMILES: C[C@H]1CCC(c2ccccc2)S(=O)(=O)N1Cc1ccc(N2CCN3C(=O)OCC3C2)cc1F]<br>Stereisomer A | 7-[3-Fluoro-4-((3S)-methyl-1,1-dioxo-6-phenyl-[1,2]thiazinan-2-ylmethyl)-phenyl]-hexahydro-oxazolo[3,4-a]pyrazin-3-one | | 0.129 |
| 419 | 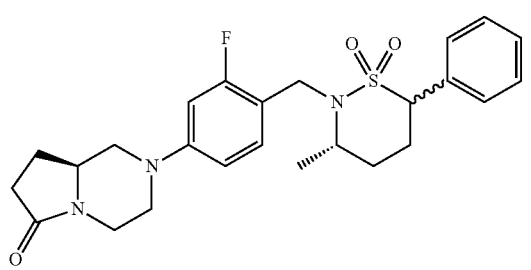 [SMILES: C[C@H]1CCC(c2ccccc2)S(=O)(=O)N1Cc1ccc(N2CCN3C(=O)CC[C@H]3C2)cc1F] | (S)-2-[3-Fluoro-4-((3S)-methyl-1,1-dioxo-6-phenyl-[1,2]thiazinan-2-ylmethyl)-phenyl]-hexahydro-pyrrolo[1,2-a]pyrazin-6-one | 1H NMR (400 MHz, DMSO): δ 7.30-7.47 (m, 6 H); 6.75-6.86 (m, 2 H); 4.23-4.48 (m, 3 H); 4.03-4.13 (m, 1 H); 3.81-3.89 (m, 2 H); 3.73 (d, J = 12.6 Hz, 1 H); 3.58-3.66 (m, 1 H); 2.83-2.92 (m, 1 H); 2.59 (td, J = 12.3, 3.6 Hz, 1 H); 2.37-2.47 (m, 2 H); 2.05-2.30 (m, 4 H); 1.75-1.85 (m, 1 H); 1.55-1.68 (m, 2 H); 1.08 (d, J = 6.9 Hz, 3 H). | 0.032 |

TABLE 4-continued

| | Structure | Name | Proton NMR | IC$_{50}$ |
|---|---|---|---|---|
| 420 | Stereisomer B | 7-[3-Fluoro-4-((3S)-methyl-1,1-dioxo-6-phenyl-[1,2]thiazinan-2-ylmethyl)-phenyl]-hexahydro-oxazolo[3,4-a]pyrazin-3-one | 1H NMR (400 MHz, DMSO): δ 7.30-7.48 (m, 6 H); 6.75-6.85 (m, 2 H); 4.25-4.50 (m, 4 H); 4.09 (dd, J = 12.0, 6.9 Hz, 1 H); 3.82-4.00 (m, 3 H); 3.71 (d, J = 12.8 Hz, 1 H); 3.62 (dd, J = 13.2, 3.4 Hz, 1 H); 3.11 (td, J = 12.6, 3.6 Hz, 1 H); 2.60-2.73 (m, 2 H); 2.40-2.44 (m, 1 H); 2.09 (dd, J = 13.8, 3.9 Hz, 1 H); 1.75-1.87 (m, 1 H); 1.64 (d, J = 14.1 Hz, 1 H); 1.08 (d, J = 6.9 Hz, 3 H). | 0.028 |
| 421 | Stereisomer B | (S)-4-[2-Fluoro-4-(4-[1,2,4]triazol-4-yl-piperidin-1-yl)-benzyl]-6-phenyl-5-thia-4-aza-spiro[2.5]octane 5,5-dioxide | | 0.289 |
| 422 | Stereisomer A | (3S)-Methyl-6-phenyl-2-[4-(4-tetrazol-1-yl-piperidin-1-yl)-benzyl]-[1,2]thiazinane 1,1-dioxide | | 0.070 |
| 423 | Stereisomer B | (3S)-Methyl-6-phenyl-2-[4-(4-tetrazol-2-yl-piperidin-1-yl)-benzyl]-[1,2]thiazinane 1,1-dioxide | $^1$H NMR (400 MHz, DMSO) δ 9.00-8.94 (s, 1H), 7.50-7.43 (m, 2H), 7.43-7.32 (m, 3H), 7.28-7.22 (m, 2H), 7.00-6.94 (m, 2H), 5.15-5.03 (m, 1H), 4.49-4.40 (m, 1H), 4.40-4.32 (m, 1H), 4.25-4.15 (m, 1H), 4.13-4.01 (m, 1H), 3.80-3.71 (m, 2H), 3.06-2.94 (m, 2H), 2.46-2.36 (m, 1H), 2.34-2.23 (m, 2H), 2.22-2.04 (m, 3H), 1.88-1.74 (m, 1H), 1.68-1.58 (m, 1H), 1.15-1.05 (d, J = 6.9 Hz, 3H). | 0.177 |
| 424 | Stereisomer A | 2-[3-Fluoro-4-((3S)-methyl-1,1-dioxo-6-phenyl-[1,2]thiazinan-2-ylmethyl)-phenyl]-6-[1,2,4]triazol-4-yl-2-aza-spiro[3.3]heptane | | 0.427 |

TABLE 4-continued

| | Structure | Name | Proton NMR | IC$_{50}$ |
|---|---|---|---|---|
| 425 | Stereisomer B | 2-[3-Fluoro-4-((3S)-methyl-1,1-dioxo-6-phenyl-[1,2]thiazinan-2-ylmethyl)-phenyl]-6-[1,2,4]triazol-4-yl-2-aza-spiro[3.3]heptane | | 1.01 |
| 426 | Stereisomer A | 1-[3-Fluoro-4-((3S)-methyl-1,1-dioxo-6-phenyl-[1,2]thiazinan-2-ylmethyl)-phenyl]-4-[1,2,4]triazol-4-yl-piperidine-4-carboxylic acid methyl ester | | 0.453 |
| 427 | Stereisomer B | 1-[3-Fluoro-4-((3S)-methyl-1,1-dioxo-6-phenyl-[1,2]thiazinan-2-ylmethyl)-phenyl]-4-[1,2,4]triazol-4-yl-piperidine-4-carboxylic acid methyl ester | | 0.447 |
| 428 | Stereisomer A | 2-[2-Fluoro-4-(3-[1,2,4]triazol-4-yl-azetidin-1-yl)-benzyl]-(3S)-methyl-6-phenyl-[1,2]thiazinane 1,1-dioxide | $^1$H NMR (400 MHz, DMSO) δ 8.78-8.74 (s, 2H), 7.48-7.43 (m, 2H), 7.43-7.30 (m, 4H), 6.41-6.35 (m, 1H), 6.35-6.30 (m, 1H), 5.35-5.25 (m, 1H), 4.49-4.36 (m, 2H), 4.35-4.23 (m, 3H), 4.15-4.06 (m, 1H), 4.06-3.99 (m, 2H), 2.47-2.34 (m, 1H), 2.14-2.05 (m, 1H), 1.88-1.73 (m, 1H), 1.68-1.59 (m, 1H), 1.15-1.05 (d, J = 6.8 Hz, 3H). | 0.088 |
| 429 | Stereoisomer B | 2-[2-Fluoro-4-(3-[1,2,4]triazol-4-yl-azetidin-1-yl)-benzyl]-(3S)-methyl-6-phenyl-[1,2]thiazinane 1,1-dioxide | | 0.316 |

TABLE 4-continued

| | Structure | Name | Proton NMR | IC$_{50}$ |
|---|---|---|---|---|
| 430 | 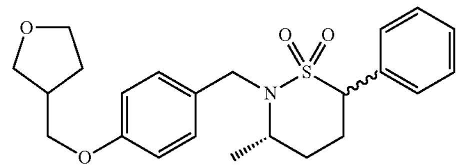 [SMILES: C[C@H]1CCC(c2ccccc2)S(=O)(=O)N1Cc1ccc(OCC2CCOC2)cc1] | (3S)-Methyl-6-phenyl-2-[4-(tetrahydro-furan-3-ylmethoxy)-benzyl]-[1,2]thiazinane 1,1-dioxide | | 0.559 |
| 431 | 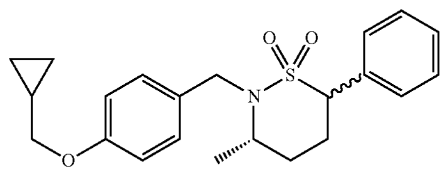 [SMILES: C[C@H]1CCC(c2ccccc2)S(=O)(=O)N1Cc1ccc(OCC2CC2)cc1] | 2-(4-Cyclopropylmethoxy-benzyl)-(3S)-methyl-6-phenyl-[1,2]thiazinane 1,1-dioxide | | 0.641 |
| 432 | 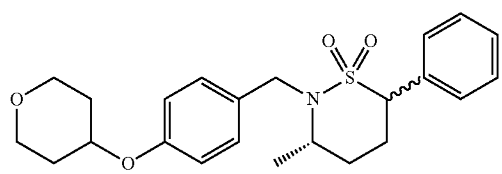 [SMILES: C[C@H]1CCC(c2ccccc2)S(=O)(=O)N1Cc1ccc(OC2CCOCC2)cc1] | (3S)-Methyl-6-phenyl-2-[4-(tetrahydro-pyran-4-yloxy)-benzyl]-[1,2]thiazinane 1,1-dioxide | | 1.11 |
| 433 | 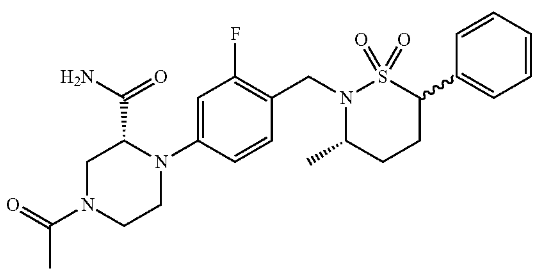 [SMILES: CC(=O)N1CCN(c2ccc(CN3[C@@H](C)CCC(c4ccccc4)S3(=O)=O)c(F)c2)[C@@H](C(N)=O)C1] | (R)-4-Acetyl-1-[3-fluoro-4-((3S)-methyl-1,1-dioxo-6-phenyl-[1,2]thiazinan-2-ylmethyl)-phenyl]-piperazine-2-carboxylic acid amide | | 0.228 |
| 434 | 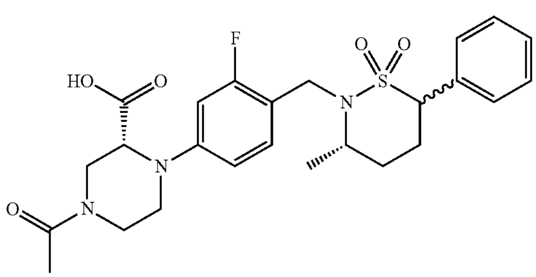 [SMILES: CC(=O)N1CCN(c2ccc(CN3[C@@H](C)CCC(c4ccccc4)S3(=O)=O)c(F)c2)[C@@H](C(=O)O)C1] | (R)-4-Acetyl-1-[3-fluoro-4-((3S)-methyl-1,1-dioxo-6-phenyl-[1,2]thiazinan-2-ylmethyl)-phenyl]-piperazine-2-carboxylic acid | | 1,13 |
| 435 | 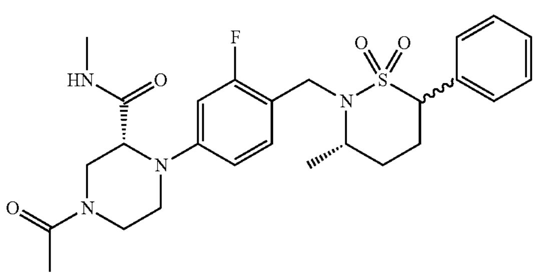 [SMILES: CNC(=O)[C@H]1CN(C(C)=O)CCN1c1ccc(CN2[C@@H](C)CCC(c3ccccc3)S2(=O)=O)c(F)c1] | (R)-4-Acetyl-1-[3-fluoro-4-((3S)-methyl-1,1-dioxo-6-phenyl-[1,2]thiazinan-2-ylmethyl)-phenyl]-piperazine-2-carboxylic acid methylamide | | 0.244 |

TABLE 4-continued

| | Structure | Name | Proton NMR | IC$_{50}$ |
|---|---|---|---|---|
| 436 | 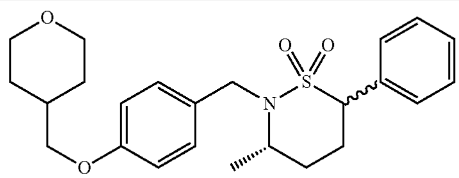 [SMILES: C[C@H]1CCC(c2ccccc2)S(=O)(=O)N1Cc1ccc(OCC2CCOCC2)cc1] | (3S)-Methyl-6-phenyl-2-[4-(tetrahydro-pyran-4-ylmethoxy)-benzyl]-[1,2]thiazinane 1,1-dioxide | $^1$H NMR (400 MHz, DMSO-d6) δ 7.50-7.43 (m, 2H), 7.43-7.33 (m, 3H), 7.33-7.24 (m, 2H), 6.94-6.85 (m, 2H), 4.46 (d, J = 16.6 Hz, 1H), 4.37 (dd, J = 12.7, 3.5 Hz, 1H), 4.22 (d, J = 16.5 Hz, 1H), 4.07 (ddd, J = 12.0, 7.0, 2.2 Hz, 1H), 3.92-3.83 (m, 2H), 3.81 (d, J = 6.5 Hz, 2H), 3.38-3.27 (m, 2H), 2.48-2.35 (m, 1H), 2.15-2.04 (m, 1H), 2.04-1.91 (m, 1H), 1.89-1.73 (m, 1H), 1.72-1.59 (m, 3H), 1.40-1.24 (m, 2H), 1.08 (d, J = 6.9 Hz, 3H). | 0.086 |
| 437 | 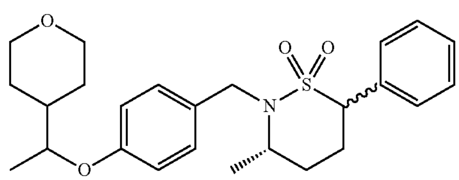 [SMILES: CC(Oc1ccc(CN2[C@@H](C)CCC(c3ccccc3)S2(=O)=O)cc1)C1CCOCC1] | (3S)-Methyl-6-phenyl-2-{4-[1-(tetrahydro-pyran-4-yl)-ethoxy]-benzyl}-[1,2]thiazinane 1,1-dioxide | $^1$H NMR (400 MHz, DMSO-d6) δ 7.50-7.43 (m, 2H), 7.43-7.31 (m, 3H), 7.32-7.24 (m, 2H), 6.93-6.84 (m, 2H), 4.50-4.33 (m, 2H), 4.26-4.15 (m, 2H), 4.13-4.00 (m, 1H), 3.87 (dd, J = 11.5, 4.3 Hz, 2H), 3.33-3.22 (m, 1H), 2.48-2.35 (m, 1H), 2.15-2.04 (m, 1H), 1.88-1.59 (m, 4H), 1.53 (d, J = 13.1 Hz, 1H), 1.43-1.23 (m, 2H), 1.18 (d, J = 6.1 Hz, 3H), 1.09 (d, J = 6.9 Hz, 3H). | 0.048 |
| 438 | 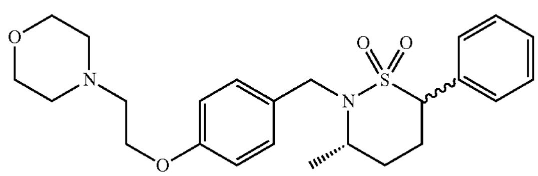 [SMILES: C[C@H]1CCC(c2ccccc2)S(=O)(=O)N1Cc1ccc(OCCN2CCOCC2)cc1] | 4-{2-[4-((3S)-Methyl-1,1-dioxo-6-phenyl-[1,2]thiazinan-2-ylmethyl)-phenoxy]-ethyl}-morpholine | | 0.665 |
| 439 | 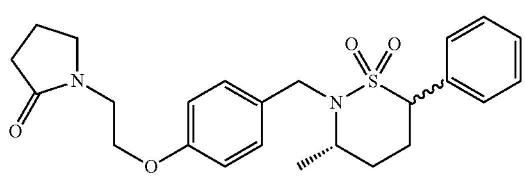 [SMILES: C[C@H]1CCC(c2ccccc2)S(=O)(=O)N1Cc1ccc(OCCN2CCCC2=O)cc1] | 1-{2-[4-((3S)-Methyl-1,1-dioxo-6-phenyl-[1,2]thiazinan-2-ylmethyl)-phenoxy]-ethyl}-pyrrolidin-2-one | | 0.325 |
| 440 | 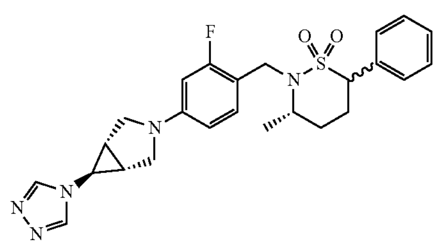 [SMILES: C[C@H]1CCC(c2ccccc2)S(=O)(=O)N1Cc1ccc(N2C[C@@H]3[C@H](C2)[C@H]3n2cnnc2)cc1F] | (1R,5S,6S)-3-[3-Fluoro-4-((3S)-methyl-1,1-dioxo-6-phenyl-[1,2]thiazinan-2-ylmethyl)-phenyl]-6-[1,2,4]triazol-4-yl-3-aza-bicyclo[3.1.0]hexane | $^1$H NMR (400 MHz, DMSO) δ 8.61-8.56 (s, 1H), 7.48-7.43 (m, 2H), 7.43-7.33 (m, 3H), 7.32-7.25 (m, 1H), 6.50-6.43 (m, 1H), 6.42-6.34 (m, 1H), 4.47-4.34 (m, 2H), 4.31-4.22 (m, 1H), 4.14-4.01 (m, 1H), 3.74-3.66 (m, 2H), 3.46-3.41 (m, 1H), 3.32-3.25 (m, 2H), 2.46-2.37 (m, 3H), 2.13-2.02 (m, 1H), 1.86-1.73 (m, 1H), 1.68-1.60 (m, 1H), 1.13-1.04 (d, J = 6.8 Hz, 3H). | 0.012 |
| 441 | 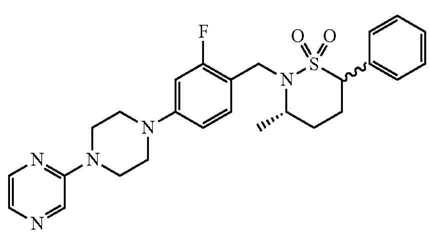 [SMILES: C[C@H]1CCC(c2ccccc2)S(=O)(=O)N1Cc1ccc(N2CCN(c3cnccn3)CC2)cc1F] | 4-[3-Fluoro-4-((3S)-methyl-1,1-dioxo-6-phenyl-[1,2]thiazinan-2-ylmethyl)-phenyl]-3,4,5,6-tetrahydro-2H-[1,2']bipyrazinyl | | 0.171 |

TABLE 4-continued

| | Structure | Name | Proton NMR | IC$_{50}$ |
|---|---|---|---|---|
| 442 | 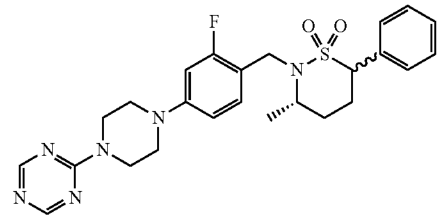 [SMILES: C[C@H]1CCC(c2ccccc2)S(=O)(=O)N1Cc1ccc(N2CCN(c3ncncn3)CC2)cc1F] | 2-{4-[3-Fluoro-4-((3S)-methyl-1,1-dioxo-6-phenyl-[1,2]thiazinan-2-ylmethyl)-phenyl]-piperazin-1-yl}-[1,3,5]triazine | | 0.037 |
| 443 | Stereoisomer A (mix of TRANS isomers) | 2-[2-Fluoro-4-((3S)-methyl-4-[1,2,4]triazol-4-yl-piperidin-1-yl)-benzyl]-3-methyl-6-phenyl-[1,2]thiazinane 1,1-dioxide | $^1$H NMR (400 MHz, DMSO) δ 8.64 (s, 2 H); 7.38-7.40 (m, 6 H); 6.81-6.82 (m, 2 H); 4.45-4.47 (m, 1 H); 4.31-4.33 (m, 2H); 4.02-4.05 (m, 2 H); 3.87 (t, J = 12.6 Hz, 2 H); 2.81 (t, J = 12.4 Hz, 1 H); 2.38-2.43 (m, 2 H); 2.03-2.09 (m, 4 H); 1.80 (t, J = 13.0 Hz, 1 H); 1.65 (d, J = 14.1 Hz, 1 H); 1.10 (d, J = 6.9 Hz, 3 H); 0.69 (d, J = 6.5 Hz, 3 H). | 0.015 |
| 444 | Stereoisomer B (mix of CIS isomers) | 2-[2-Fluoro-4-((3S)-methyl-4-[1,2,4]triazol-4-yl-piperidin-1-yl)-benzyl]-3-methyl-6-phenyl-[1,2]thiazinane 1,1-dioxide | $^1$H NMR (400 MHz, DMSO) δ 8.63 (s, 2 H); 7.38-7.40 (m, 6 H); 6.78-6.79 (m, 2 H); 4.49-4.51 (m, 2 H); 4.33-4.35 (m, 2H); 4.06-4.10 (m, 1 H); 3.72 (dd, J = 65.8, 12.8 Hz, 2 H); 3.01 (dd, J = 12.7, 3.0 Hz, 1 H); 2.83-2.86 (m, 1 H); 2.35-2.38 (m, 3 H); 2.07-2.10 (m, 1 H); 1.79-1.83 (m, 1 H); 1.65 (d, J = 14.0 Hz, 1 H); 1.09-1.10 (m, 4 H); 0.73 (d, J = 6.9 Hz, 3 H). | 0.015 |
| 445 | 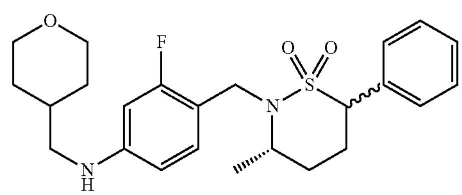 [SMILES: C[C@H]1CCC(c2ccccc2)S(=O)(=O)N1Cc1ccc(NCC2CCOCC2)cc1F] | [3-Fluoro-4-((3S)-methyl-1,1-dioxo-6-phenyl-[1,2]thiazinan-2-ylmethyl)-phenyl]-(tetrahydro-pyran-4-ylmethyl)-amine | $^1$H NMR (400 MHz, DMSO) δ 7.49-7.42 (m, 2H), 7.42-7.32 (m, 3H), 7.20-7.13 (m, 1H), 6.46-6.38 (dd, J = 8.6, 2.2 Hz, 1H), 6.33-6.25 (m, 1H), 5.95-5.87 (m, 1H), 4.46-4.37 (n, J = 12.9, 3.6 Hz, 1 H), 4.37-4.28 (m, 1H), 4.26-4.17 (m, 1H), 4.12-4.01 (m, 1H), 3.89-3.80 (m, 2H), 3.28-3.21 (m, 3H), 2.91-2.84 (m, 2H), 2.46-2.35 (m, 1H), 2.14-2.03 (m, 1H), 1.86-1.71 (m, 2H), 1.69-1.58 (m, 3H), 1.26-1.13 (m, 2H), 1.12-1.05 (d, J = 6.9 Hz, 3H). | 0.025 |
| 446 | 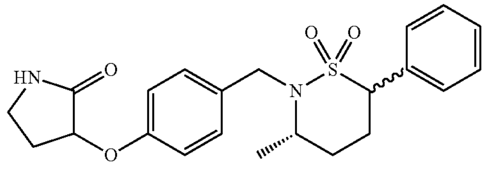 [SMILES: C[C@H]1CCC(c2ccccc2)S(=O)(=O)N1Cc1ccc(OC2CCNC2=O)cc1] | 3-[4-((3S)-Methyl-1,1-dioxo-6-phenyl-[1,2]thiazinan-2-ylmethyl)-phenoxy]-pyrrolidin-2-one | | 1.5 |
| 447 | 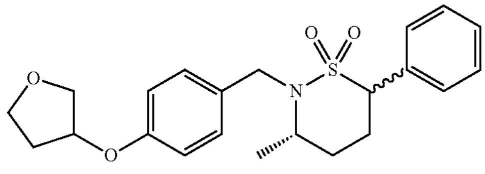 [SMILES: C[C@H]1CCC(c2ccccc2)S(=O)(=O)N1Cc1ccc(OC2CCOC2)cc1] | (3S)-Methyl-6-phenyl-2-[4-(tetrahydro-furan-3-yloxy)-benzyl]-[1,2]thiazinane 1,1-dioxide | | 0.268 |

TABLE 4-continued

| | Structure | Name | Proton NMR | IC$_{50}$ |
|---|---|---|---|---|
| 448 | 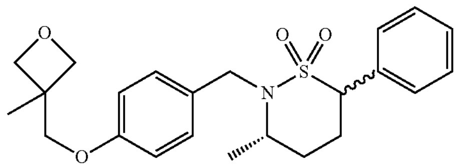 [SMILES: C[C@H]1CCC(c2ccccc2)S(=O)(=O)N1Cc1ccc(OCC2(C)COC2)cc1] | (3S)-Methyl-2-[4-(3-methyl-oxetan-3-ylmethoxy)-benzyl]-6-phenyl-[1,2]thiazinane 1,1-dioxide | | 0.656 |
| 449 | 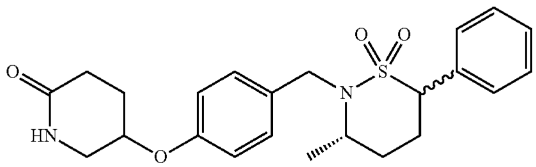 [SMILES: C[C@H]1CCC(c2ccccc2)S(=O)(=O)N1Cc1ccc(OC2CCC(=O)NC2)cc1] | 5-[4-((3S)-Methyl-1,1-dioxo-6-phenyl-[1,2]thiazinan-2-ylmethyl)-phenoxy]-piperidin-2-one | | 0.852 |
| 450 | 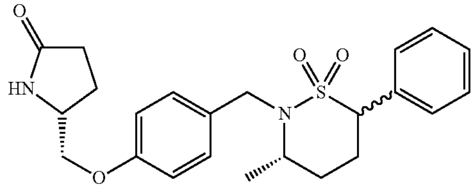 | (R)-5-[4-((3S)-Methyl-1,1-dioxo-6-phenyl-[1,2]thiazinan-2-ylmethyl)-phenoxymethyl]-pyrrolidin-2-one | | 1.05 |
| 451 | 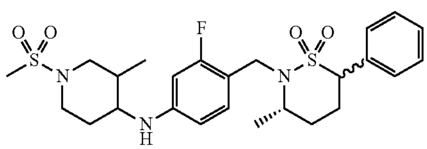 [SMILES: CC1CN(S(C)(=O)=O)CCC1Nc1ccc(CN2[C@@H](C)CCC(c3ccccc3)S2(=O)=O)c(F)c1] | [3-Fluoro-4-((3S)-methyl-1,1-dioxo-6-phenyl-[1,2]thiazinan-2-ylmethyl)-phenyl]-(1-methanesulfonyl-3-methyl-piperidin-4-yl)-amine | $^1$H NMR (400 MHz, DMSO) δ 7.40-7.42 (m, 5 H); 7.16 (t, J = 8.8 Hz, 1 H); 6.43 (dd, J = 8.6, 2.2 Hz, 1 H); 6.33 (dd, J = 13.6, 2.2 Hz, 1 H); 5.77 (d, J = 9.0 Hz, 1 H); 4.42 (dd, J = 12.7, 3.5 Hz, 1 H); 4.33 (d, J = 16.7 Hz, 1 H); 4.21 (d, J = 16.7 Hz, 1 H); 4.07 (dd, J = 12.1, 6.9 Hz, 1 H); 3.53 (d, J = 11.6 Hz, 2 H); 3.01 (m, 1 H); 2.80-2.9 (m, 4 H); 2.56 (d, J = 11.5 Hz, 1 H); 2.40-2.43 (m, 1 H); 2.03-2.07 (m, 2 H); 1.68-1.76 (m, 3 H); 1.24-1.29 (m, 1 H); 1.10 (d, J = 6.9 Hz, 3 H); 0.94 (d, J = 6.6 Hz, 3 H). | 0.012 |
| 452 | 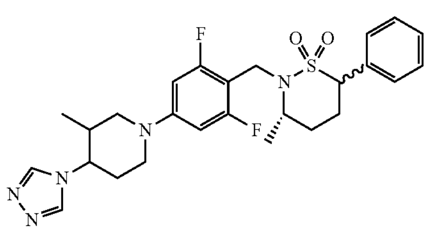 [SMILES: CC1CN(c2cc(F)c(CN3[C@@H](C)CCC(c4ccccc4)S3(=O)=O)c(F)c2)CCC1n1cnnc1] | 2-[2,6-Difluoro-4-(4-[1,2,4]triazol-4-yl-piperidin-1-yl)-benzyl]-(3S)-methyl-6-phenyl-[1,2]thiazinane 1,1-dioxide | | 0.055 |
| 453 | 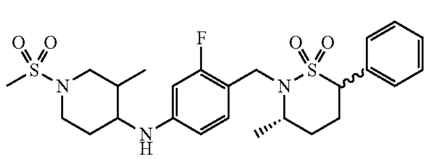 [SMILES: CC1CN(S(C)(=O)=O)CCC1Nc1ccc(CN2[C@@H](C)CCC(c3ccccc3)S2(=O)=O)c(F)c1] | [3-Fluoro-4-((3S)-methyl-1,1-dioxo-6-phenyl-[1,2]thiazinan-2-ylmethyl)-phenyl]-(1-methanesulfonyl-3-methyl-piperidin-4-yl)-amine | $^1$H NMR (400 MHz, DMSO) δ 7.41-7.43 (m, 5 H); 7.18 (t, J = 8.8 Hz, 1 H); 6.51 (dd, J = 8.6, 2.2 Hz, 1 H); 6.40 (dd, J = 13.7, 2.2 Hz, 1 H); 5.79 (d, J = 8.7 Hz, 1 H); 4.42 (dd, J = 12.7, 3.5 Hz, 1 H); 4.34 (d, J = 16.7 Hz, 1 H); 4.21 (d, J = 16.7 Hz, 1 H); 4.04-4.07 (m, 1 H); 3.49-3.56 (m, 1 H); 3.12-3.14 (m, 3 H); 2.85 (s, 3 H); 2.40-2.43 (m, 1 H); 2.08-2.14 (m, 2 H); 1.68-1.73 (m, 4 H); 1.08-1.09 (m, 4 H); 0.88 (d, J = 6.9 Hz, 3 H). | 0.009 |

TABLE 4-continued

| | Structure | Name | Proton NMR | IC$_{50}$ |
|---|---|---|---|---|
| 454 | 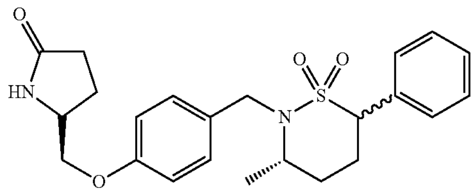 | (S)-5-[4-((3S)-Methyl-1,1-dioxo-6-phenyl-[1,2]thiazinan-2-ylmethyl)-phenoxymethyl]-pyrrolidin-2-one | | 0.62 |
| 455 | 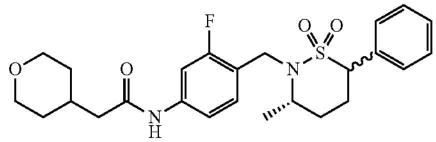 [SMILES: C[C@H]1CCC(c2ccccc2)S(=O)(=O)N1Cc1ccc(NC(=O)CC2CCOCC2)cc1F] | N-[3-Fluoro-4-((3S)-methyl-1,1-dioxo-6-phenyl-[1,2]thiazinan-2-ylmethyl)-phenyl]-2-(tetrahydro-pyran-4-yl)-acetamide | | 0.123 |
| 456 | 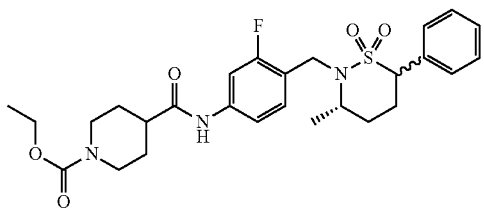 [SMILES: CCOC(=O)N1CCC(C(=O)Nc2ccc(CN3[C@@H](C)CCC(c4ccccc4)S3(=O)=O)c(F)c2)CC1] | 4-[3-Fluoro-4-((3S)-methyl-1,1-dioxo-6-phenyl-[1,2]thiazinan-2-ylmethyl)-phenylcarbamoyl]-piperidine-1-carboxylic acid ethyl ester | | 0.148 |
| 457 | 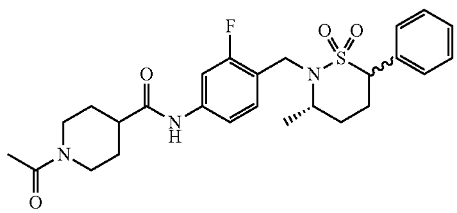 [SMILES: CC(=O)N1CCC(C(=O)Nc2ccc(CN3[C@@H](C)CCC(c4ccccc4)S3(=O)=O)c(F)c2)CC1] | 1-Acetyl-piperidine-4-carboxylic acid [3-fluoro-4-((3S)-methyl-1,1-dioxo-6-phenyl-[1,2]thiazinan-2-ylmethyl)-phenyl]-amide | | 0.437 |
| 458 | 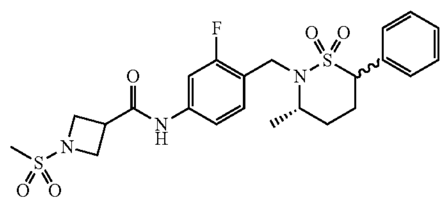 [SMILES: C[C@H]1CCC(c2ccccc2)S(=O)(=O)N1Cc1ccc(NC(=O)C2CN(S(C)(=O)=O)C2)cc1F] | 1-Methanesulfonyl-azetidine-3-carboxylic acid [3-fluoro-4-((3S)-methyl-1,1-dioxo-6-phenyl-[1,2]thiazinan-2-ylmethyl)-phenyl]-amide | $^1$H NMR (400 MHz, DMSO) δ 10.29-10.25 (s, 1 H), 7.67-7.61 (m, 1H), 7.49-7.42 (m, 3H), 7.42-7.34 (m, 3H), 7.29-7.24 (m, 1H), 4.53-4.44 (m, 2H), 4.37-4.31 (m, 1H), 4.16-4.06 (m, 1H), 4.06-3.97 (m, 4H), 3.59-3.49 (m, 1H), 3.05-2.99 (s, 3H), 2.48-2.38 (m, 1H), 2.15-2.06 (m, 1H), 1.88-1.76 (m, 1H), 1.70-1.62 (m, 1H), 1.10-1.05 (d, J = 6.8 Hz, 3H). | 0.098 |
| 459 | 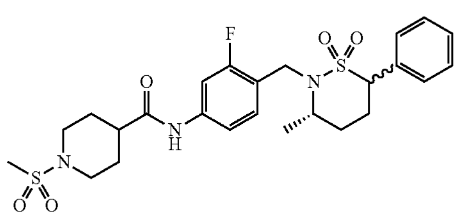 [SMILES: C[C@H]1CCC(c2ccccc2)S(=O)(=O)N1Cc1ccc(NC(=O)C2CCN(S(C)(=O)=O)CC2)cc1F] | 1-Methanesulfonyl-piperidine-4-carboxylic acid [3-fluoro-4-((3S)-methyl-1,1-dioxo-6-phenyl-[1,2]thiazinan-2-ylmethyl)-phenyl]-amide | $^1$H NMR (400 MHz, DMSO) δ 10.13-10.11 (s, 1 H), 7.66-7.61 (m, 1H), 7.48-7.34 (m, 6H), 7.29-7.25 (m, 1H), 4.52-4.43 (m, 2H), 4.37-4.30 (m, 1H), 4.15-4.05 (m, 1H), 3.65-3.57 (m, 2H), 2.91-2.87 (s, 3H), 2.81-2.70 (m, 2H), 2.47-2.38 (m, 2H), 2.15-2.05 (m, 1H), 1.95-1.86 (m, 2H), 1.86-1.76 (m, 1H), 1.70-1.62 (m, 3H), 1.11-1.04 (d, J = 6.8 Hz, 3H). | 0.074 |

Example 9

In Vitro RORc Ligand Binding Assay

This assay was used to determine a compound's potency in inhibiting activity of RORc by determining, $Ki_{app}$, $IC_{50}$, or percent inhibition values. Consumables used in this Example are shown in Table 5 below.

TABLE 5

Table 5

| Consumable | Supplier and product code |
| --- | --- |
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in *E. coli* |
| Plate seals | Perkin Elmer 6005185 |
| Microscint 0 | Perkin Elmer 6013611 |

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl, and 5 mM MgCl$_2$ was prepared to wash the filter plate. To prepare an assay buffer, BSA was added to the wash buffer to reach 0.01% and DTT was added to reach 1 mM.

Compounds

For $IC_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand 25-[$^3$H]Hydroxycholesterol) Preparation

25-[$^3$H]hydroxycholesterol was dilute in Assay Buffer to obtain 15 nM and vortex to mix. Add 20 uL to all wells to reach 6 nM final in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No R samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM MgCl$_2$; 0.01% BSA; 5% DMSO; 0.6 ug/mL RORc receptor; 6 nM 25-[$^3$H]hydroxycholesterol. For NSB wells, 1 uM 25-hydroxycholesterol was also present.

Example 10

Arthritis Mouse Model 8 to 10-week old male DBA/1 (DBA/1O1aHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of *M. tuberculosis* (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals receive two doses (a.m. and p.m.) of HRC-6 or 50 mg/kg OR-1050 p.o. (2.5 mls/kg). On weekends, a single dose of 100 mg/kg was administered (5 mls/kg).

The mice are observed daily for clinical symptoms of CIA based on the following qualitative scale. Each paw is examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score is calculated for each animal by totaling the sum of the daily hind paw measurements over several days.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

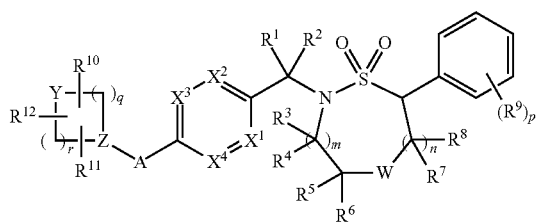

or a pharmaceutically acceptable salt thereof,
wherein:
  m is 0 or 1;
  n is 0 or 1;
  p is from 0 to 3;
  q is 0, 1 or 2;
  r is from 1 to 3;
  A is: a bond; $-(CR_jR_k)_t-$; $-C(O)-(CR_jR_k)_t-$; $-(CR_jR_k)_t-C(O)-$; $-NR^a-(CR_jR_k)_t-$; $-(CR_jR_k)_t-NR^a-$; $-C(O)NR^a-(CR_jR_k)_t-$; $-(CR_jR_k)_t-NR^aC(O)-$; $-O-(CR_jR_k)_t-$; $-(CR_jR_k)_t-O-$; $-S-(CR_jR_k)_t-$; $-(CR_jR_k)_t-S-$; $-SO_2-(CR_jR_k)_t-$; or $-(CR_jR_k)_t-SO_2-$;
  t is from 0 to 4;
  W is: $-CR^bR^c-$; $-O-$; $-S-$; $-SO_2-$; or $-NR^d-$;
  one of $X^1$, $X^2$, $X^3$ and $X^4$ is N and the others are $CR^e$; or two of $X^1$, $X^2$, $X^3$ and $X^4$ are N and the others are $CR^e$; or three of $X^1$, $X^2$, $X^3$ and $X^4$ are N and the other is $CR^e$; or each of $X^1$, $X^2$, $X^3$ and $X^4$ is $CR^e$;
  Y is: $-O-$; $-S-$; $SO_2-$; $-CR^fR^g-$; or $-NR^h-$;
  Z is: CH; or N;
  $R^1$, $R^2$, $R^3$, $R^4$, $R^5$, $R^6$, $R^7$ and $R^8$ each independently is: hydrogen; or $C_{1-6}$alkyl which may be unsubstituted or substituted one or more times with halo;
  or $R^3$ and $R^4$ together with the atom to which they are attached may form an ethylene group;
  or $R^3$ and $R^4$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  or $R^5$ and $R^6$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  or $R^7$ and $R^8$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  or one of $R^3$ and $R^4$ together with one of $R^5$ and $R^6$ and the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  or one of $R^5$ and $R^6$ together with one of $R^7$ and $R^8$ and the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  each $R^9$ is independently: $C_{1-6}$alkyl; halo; $C_{1-6}$alkoxy; or cyano; wherein the $C_{1-6}$alkyl moieties may be unsubstituted or substituted one or more times with halo;
  $R^{10}$ is: hydrogen; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; halo; or $C_{1-6}$alkyl which may be unsubstituted or substituted one or more times with halo or oxo;
  $R^{11}$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; $C_{1-6}$alkyl-sulfonylamino; $C_{1-6}$alkyl-sulfonylamino-$C_{1-6}$alkyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; or $C_{1-6}$alkyl which may be unsubstituted or substituted one or more times with halo or oxo;
  $R^{12}$ is: hydrogen; halo; carboxy; $C_{1-6}$alkyl-carbonyl; $C_{1-6}$alkoxy-carbonyl; oxo; hydroxy; aminocarbonyl; N—$C_{1-6}$alkyl-aminocarbonyl; N,N-di-$C_{1-6}$alkyl-aminocarbonyl; cyano; hydroxy-$C_{16}$alkyl; N—$C_{1-6}$alkoxy-$C_{1-6}$alkyl-aminocarbonyl; N-hydroxy-$C_{1-6}$alkyl-aminocarbonyl; N—$C_{1-6}$alkoxy-aminocarbonyl; or $C_{1-6}$alkyl which may be unsubstituted or substituted one or more times with halo or oxo;
  $R^a$, $R^b$, $R^c$ and $R^d$ each independent is: hydrogen; or $C_{1-6}$alkyl which may be unsubstituted or substituted one or more times with halo;
  or $R^b$ and $R^c$ together with the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;
  or one of $R^b$ and $R^c$ together with one of $R^7$ and $R^8$ and the atoms to which they are attached may form a three, four, five, six or seven membered saturated or partially saturated ring that may optionally include one or two heteroatoms selected from $-O-$, $-NR^a-$ or $-S-$, and which may be optionally substituted one or more times with $R^i$;

or one of $R^b$ and $R^c$ together with one of $R^5$ and $R^6$ and the atoms to which they are attached may form a three, four, five, six or seven membered saturated or partially saturated ring that may optionally include one or two heteroatoms selected from —O—, —NR$^a$- or —S—, and which may be optionally substituted one or more times with $R^i$;

each $R^e$ is independently: hydrogen; $C_{1-6}$alkyl; halo; $C_{1-6}$alkoxy; or cyano; wherein the $C_{1-6}$alkyl moieties may be unsubstituted or substituted one or more times with halo;

$R^f$ is: hydrogen; halo; or $C_{1-6}$alkyl which may be unsubstituted or substituted one or more times with halo;

$R^g$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; aminocarbonyl-$C_{1-6}$alkyl; N—$C_{1-6}$alkyl-aminocarbonyl-$C_{1-6}$alkyl; N,N-di-$C_{1-6}$alkyl-aminocarbonyl-$C_{1-6}$alkyl; $C_{1-6}$alkoxy-carbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N—$C_{1-6}$alkyl-sulfonylaminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; amino; N—$C_{1-6}$alkyl-amino; N,N-di-$C_{1-6}$alkyl-amino; halo-$C_{1-6}$alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;

or $R^f$ and $R^g$ together with the atoms to which they are attached may form a four, five, six or seven membered saturated or partially saturated ring that may optionally include one or two heteroatoms selected from —O—, —NR$^a$- or —S—, and which may be optionally substituted one or more times with $R^i$;

$R^h$ is: hydrogen; $C_{1-6}$alkyl; $C_{3-6}$cycloalkyl; $C_{3-6}$cycloalkenyl; $C_{3-6}$cycloalkyl-$C_{i-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkyl-sulfonylamino; sulfonylamino-$C_{1-6}$alkyl; N—($C_{1-6}$alkyl-sulfonyl)aminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; aminocarbonyl-$C_{1-6}$alkyl; N—$C_{1-6}$alkyl-aminocarbonyl-$C_{1-6}$alkyl; N,N-di-$C_{1-6}$alkyl-aminocarbonyl-$C_{1-6}$alkyl; $C_{1-6}$alkoxy-carbonyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;

or $R^h$ and one of $R^{10}$ and $R^{11}$ together with the atoms to which they are attached may form a four, five, six or seven membered aromatic, partially saturated or unsaturated ring that may optionally include one or two additional heteroatom selected from —O—, —NR$^a$- or —S—, and which may be optionally substituted one or more times with $R^i$—;

$R^i$ is: $C_{1-6}$alkyl; halo; oxo; hydroxy; acetyl; $C_{1-6}$alkyl-carbonyl; amino-carbonyl; hydroxy-$C_{1-6}$alkyl; cyano; heteroaryl; or $C_{1-6}$alkoxy; wherein the $C_{1-6}$alkyl moieties may be unsubstituted or substituted one or more times with halo; and $R^j$ and $R^k$ each independent is: hydrogen; or $C_{1-6}$alkyl which may be unsubstituted or substituted one or more times with halo.

2. The compound of claim 1, wherein m is 0.

3. The compound of claim 1, wherein n is 1.

4. The compound of claim 1, wherein p is 0 or 1.

5. The compound of claim 1, wherein q is 1 and r is 1.

6. The compound of claim 1, wherein q is 2 and r is 2.

7. The compound of claim 1, wherein A is a bond.

8. The compound of claim 1, wherein A is —O— or —NH—.

9. The compound of claim 1, wherein W is —CR$^b$R$^c$—.

10. The compound of claim 1, wherein $X^1$, $X^2$, $X^3$ and $X^4$ are CR$^e$.

11. The compound of claim 1, wherein each R$^e$ is independently: hydrogen; or halo.

12. The compound of claim 1, wherein Y is —SO$_2$—.

13. The compound of claim 1, wherein Y is —NR$^h$—.

14. The compound of claim 1, wherein Y is —CR$^f$R$^g$—.

15. The compound of claim 1, wherein Z is CH.

16. The compound of claim 1, wherein Z is N.

17. The compound of claim 1, wherein $R^1$ and $R^2$ are hydrogen.

18. The compound of claim 1, wherein $R^{10}$ and $R^{11}$ are hydrogen.

19. The compound of claim 1, wherein $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; or N,N-di-$C_{1-6}$alkyl-aminocarbonyl.

20. The compound of claim 1, wherein $R^h$ is: acetyl; methanesulfonyl; or cyclopropylcarbonyl.

21. A composition comprising:
(a) a pharmaceutically acceptable carrier; and
(b) a compound of claim 1.

\* \* \* \* \*